(12) United States Patent
Asbury et al.

(10) Patent No.: US 10,077,473 B2
(45) Date of Patent: *Sep. 18, 2018

(54) METHOD FOR GENOTYPING CLONOTYPE PROFILES USING SEQUENCE TAGS

(71) Applicant: Adaptive Biotechnologies Corp., Seattle, WA (US)

(72) Inventors: Thomas Asbury, San Francisco, CA (US); Kieran Hervold, San Francisco, CA (US); Chitra Kotwaliwale, Oakland, CA (US); Malek Faham, Pacifica, CA (US); Martin Moorhead, San Mateo, CA (US); Li Weng, Fremont, CA (US); Tobias Wittkop, San Mateo, CA (US); Jianbiao Zheng, Fremont, CA (US)

(73) Assignee: Adaptive Biotechnologies Corp., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/611,093

(22) Filed: Jun. 1, 2017

(65) Prior Publication Data

US 2017/0335390 A1 Nov. 23, 2017

Related U.S. Application Data

(63) Continuation of application No. 14/317,087, filed on Jun. 27, 2014, now Pat. No. 9,708,657.

(60) Provisional application No. 61/841,878, filed on Jul. 1, 2013, provisional application No. 62/001,580, filed on May 21, 2014.

(51) Int. Cl.
| | | |
|---|---|---|
| *C12P 19/34* | (2006.01) |
| *C12Q 1/6874* | (2018.01) |
| *C12Q 1/686* | (2018.01) |
| *C12Q 1/6886* | (2018.01) |
| *G06F 19/18* | (2011.01) |
| *G16H 50/30* | (2018.01) |
| *C12Q 1/6881* | (2018.01) |

(52) U.S. Cl.
CPC .......... *C12Q 1/6874* (2013.01); *C12Q 1/686* (2013.01); *C12Q 1/6886* (2013.01); *G06F 19/18* (2013.01); *G16H 50/30* (2018.01); *C12Q 1/6881* (2013.01); *C12Q 2600/112* (2013.01); *C12Q 2600/16* (2013.01); *Y02A 90/26* (2018.01)

(58) Field of Classification Search
None
See application file for complete search history.

(56) References Cited

U.S. PATENT DOCUMENTS

| | | |
|---|---|---|
| 3,270,960 A | 9/1966 | Phillips |
| 3,773,919 A | 11/1973 | Boswell et al. |
| 4,474,754 A | 10/1984 | Shimizu et al. |
| 4,683,195 A | 7/1987 | Mullis et al. |
| 4,683,202 A | 7/1987 | Mullis |
| 4,751,188 A | 6/1988 | Valet |
| 4,800,159 A | 1/1989 | Mullis et al. |
| 4,876,189 A | 10/1989 | Schetters |
| 4,942,124 A | 7/1990 | Church |
| 4,965,188 A | 10/1990 | Mullis et al. |
| 5,075,217 A | 12/1991 | Weber |
| 5,126,022 A | 6/1992 | Soane et al. |
| 5,149,625 A | 9/1992 | Church et al. |
| 5,168,038 A | 12/1992 | Tecott et al. |
| 5,189,147 A | 2/1993 | Saito et al. |
| 5,210,015 A | 5/1993 | Gelfand et al. |
| 5,213,960 A | 5/1993 | Chang |
| 5,231,012 A | 7/1993 | Mosmann et al. |
| 5,296,351 A | 3/1994 | Morley |
| 5,298,396 A | 3/1994 | Kotzin et al. |
| 5,326,696 A | 7/1994 | Chang |
| 5,336,598 A | 8/1994 | Kotzin et al. |
| 5,364,759 A | 11/1994 | Caskey et al. |
| 5,399,491 A | 3/1995 | Kacian et al. |
| 5,418,134 A | 5/1995 | Morley |
| 5,449,752 A | 9/1995 | Fujii et al. |

(Continued)

FOREIGN PATENT DOCUMENTS

| | | |
|---|---|---|
| CN | 101225441 A | 7/2008 |
| CN | 102272327 A | 12/2011 |

(Continued)

OTHER PUBLICATIONS

US 8,642,750, 2/2014, Faham et al. (withdrawn).

(Continued)

*Primary Examiner* — Kenneth R Horlick
(74) *Attorney, Agent, or Firm* — Cooley LLP

(57) ABSTRACT

The invention is directed to sequence-based profiling of populations of nucleic acids by multiplex amplification and attachment of one or more sequence tags to target nucleic acids and/or copies thereof followed by high-throughput sequencing of the amplification product. In some embodiments, the invention includes successive steps of primer extension, removal of unextended primers and addition of new primers either for amplification (for example by PCR) or for additional primer extensions. Some embodiments of the invention are directed to minimal residual disease (MRD) analysis of patients being treated for cancer. Sequence tags incorporated into sequence reads provide an efficient means for determining clonotypes and at the same time provide a convenient means for detecting carry-over contamination from other samples of the same patient or from samples of a different patient which were tested in the same laboratory.

16 Claims, 20 Drawing Sheets

Specification includes a Sequence Listing.

(56) References Cited

U.S. PATENT DOCUMENTS

| | | |
|---|---|---|
| 5,498,392 A | 3/1996 | Wilding et al. |
| 5,506,126 A | 4/1996 | Seed et al. |
| 5,587,128 A | 12/1996 | Wilding et al. |
| 5,627,037 A | 5/1997 | Ward |
| 5,627,052 A | 5/1997 | Schrader |
| 5,635,354 A | 6/1997 | Kourilsky et al. |
| 5,635,400 A | 6/1997 | Brenner |
| 5,667,967 A | 9/1997 | Steinman et al. |
| 5,698,396 A | 12/1997 | Pfreundschuh |
| 5,699,798 A | 12/1997 | Hochman et al. |
| 5,741,676 A | 4/1998 | Fuller |
| 5,776,708 A | 7/1998 | Kotzin et al. |
| 5,776,737 A | 7/1998 | Dunn |
| 5,837,447 A | 11/1998 | Gorski |
| 5,846,719 A | 12/1998 | Brenner et al. |
| 5,854,033 A | 12/1998 | Lizardi |
| 5,858,195 A | 1/1999 | Ramsey |
| 5,925,517 A | 7/1999 | Tyagi et al. |
| 5,935,793 A | 8/1999 | Wong |
| 5,969,108 A | 10/1999 | McCafferty et al. |
| 5,981,176 A | 11/1999 | Wallace |
| 5,981,179 A | 11/1999 | Lorinez et al. |
| 6,001,229 A | 12/1999 | Ramsey |
| 6,010,607 A | 1/2000 | Ramsey |
| 6,033,546 A | 3/2000 | Ramsey |
| 6,054,034 A | 4/2000 | Soane et al. |
| 6,087,096 A | 7/2000 | Dau et al. |
| 6,090,592 A | 7/2000 | Adams et al. |
| 6,091,000 A | 7/2000 | Haynes |
| 6,143,496 A | 11/2000 | Brown et al. |
| 6,172,214 B1 | 1/2001 | Brenner |
| 6,174,670 B1 | 1/2001 | Wittwer et al. |
| 6,228,589 B1 | 5/2001 | Brenner |
| 6,258,540 B1 | 7/2001 | Lo et al. |
| 6,258,568 B1 | 7/2001 | Nyren |
| 6,291,183 B1 | 9/2001 | Pirrung et al. |
| 6,300,070 B1 | 10/2001 | Boles et al. |
| 6,312,690 B1 | 11/2001 | Edelman et al. |
| 6,416,948 B1 | 7/2002 | Pilarski et al. |
| 6,440,706 B1 | 8/2002 | Vogelstein et al. |
| 6,458,530 B1 | 10/2002 | Morris et al. |
| 6,489,103 B1 | 12/2002 | Griffiths et al. |
| 6,524,829 B1 | 2/2003 | Seegar |
| 6,569,627 B2 | 5/2003 | Wittwer et al. |
| 6,596,492 B2 | 7/2003 | Avery et al. |
| 6,605,272 B2 | 8/2003 | Novak et al. |
| 6,613,525 B2 | 9/2003 | Nelson et al. |
| 6,667,159 B1 | 12/2003 | Walt |
| 6,753,147 B2 | 6/2004 | Vogelstein et al. |
| 6,787,308 B2 | 9/2004 | Balasubramanian et al. |
| 6,794,499 B2 | 9/2004 | Wengel et al. |
| 6,806,079 B1 | 10/2004 | McCafferty et al. |
| 6,858,412 B2 | 2/2005 | Willis et al. |
| 6,919,434 B1 | 7/2005 | Goto et al. |
| 6,964,850 B2 | 11/2005 | Bevilacqua |
| 7,068,874 B2 | 6/2006 | Wang et al. |
| 7,112,423 B2 | 9/2006 | Van Ness et al. |
| 7,115,400 B1 | 10/2006 | Adessi et al. |
| 7,148,040 B2 | 12/2006 | Meagher et al. |
| 7,157,228 B2 | 1/2007 | Hashmi et al. |
| 7,157,274 B2 | 1/2007 | Bohm et al. |
| 7,208,795 B2 | 4/2007 | Carver et al. |
| 7,232,653 B1 | 6/2007 | Austrup et al. |
| 7,306,906 B2 | 12/2007 | Maruyama et al. |
| 7,313,308 B2 | 12/2007 | Turner et al. |
| 7,323,305 B2 | 1/2008 | Leamon et al. |
| 7,323,306 B2 | 1/2008 | Dunn et al. |
| 7,329,731 B2 | 2/2008 | Jakobsen et al. |
| 7,351,578 B2 | 4/2008 | Cheo et al. |
| 7,365,179 B2 | 4/2008 | Brenner |
| 7,371,519 B2 | 5/2008 | Wolber |
| 7,375,211 B2 | 5/2008 | Kou |
| 7,393,665 B2 | 7/2008 | Brenner |
| 7,432,084 B2 | 10/2008 | Shoemaker |
| 7,537,897 B2 | 5/2009 | Brenner et al. |
| 7,544,473 B2 | 6/2009 | Brenner |
| 7,572,582 B2 | 8/2009 | Wengel et al. |
| 7,662,557 B2 | 2/2010 | McCafferty et al. |
| 7,666,604 B2 | 2/2010 | Jakobsen et al. |
| 7,691,994 B2 | 4/2010 | Brewer et al. |
| 7,700,323 B2 | 4/2010 | Willis et al. |
| 7,709,197 B2 | 5/2010 | Drmanac |
| 7,741,463 B2 | 6/2010 | Gormley et al. |
| 7,749,697 B2 | 7/2010 | Oleksiewicz et al. |
| 7,785,783 B2 | 8/2010 | Morley et al. |
| 7,833,716 B2 | 11/2010 | Becker et al. |
| 7,842,457 B2 | 11/2010 | Berka et al. |
| 7,862,999 B2 | 1/2011 | Zheng et al. |
| 7,879,324 B2 | 2/2011 | Saxon |
| 7,892,550 B2 | 2/2011 | Dennis et al. |
| 7,907,800 B2 | 3/2011 | Foquet et al. |
| 7,915,015 B2 | 3/2011 | Vogelstein et al. |
| 7,955,794 B2 | 6/2011 | Shen et al. |
| 7,956,043 B2 | 6/2011 | Krieg et al. |
| 7,960,116 B2 | 6/2011 | Eid et al. |
| 8,012,690 B2 | 9/2011 | Berka et al. |
| 8,021,842 B2 | 9/2011 | Brenner |
| 8,030,023 B2 | 10/2011 | Adams et al. |
| 8,048,627 B2 | 11/2011 | Dressman et al. |
| 8,053,188 B2 | 11/2011 | Gullberg et al. |
| 8,053,235 B2 | 11/2011 | Buckner et al. |
| 8,137,569 B2 | 3/2012 | Harnack et al. |
| 8,137,936 B2 | 3/2012 | Macevicz |
| 8,153,375 B2 | 4/2012 | Travers et al. |
| 8,158,359 B2 | 4/2012 | Leamon et al. |
| 8,236,503 B2 | 8/2012 | Faham et al. |
| 8,283,294 B2 | 10/2012 | Kastrup et al. |
| 8,309,312 B2 | 11/2012 | Lang et al. |
| 8,313,625 B2 | 11/2012 | Rothberg et al. |
| 8,318,433 B2 | 11/2012 | Brenner |
| 8,394,590 B2 | 3/2013 | Kwong et al. |
| 8,445,205 B2 | 5/2013 | Brenner |
| 8,481,292 B2 | 7/2013 | Casbon et al. |
| 8,507,205 B2 | 8/2013 | Faham |
| 8,628,927 B2 | 1/2014 | Faham |
| 8,685,678 B2 | 4/2014 | Casbon |
| 8,685,898 B2 | 4/2014 | Wiley |
| 8,691,510 B2 | 4/2014 | Faham |
| 8,699,361 B2 | 4/2014 | Jim et al. |
| 8,715,967 B2 | 5/2014 | Casbon |
| 8,722,368 B2 | 5/2014 | Casbon |
| 8,728,766 B2 | 5/2014 | Casbon |
| 8,741,606 B2 | 6/2014 | Casbon |
| 8,748,103 B2 | 6/2014 | Faham |
| 8,759,036 B2 | 6/2014 | Wang |
| 8,795,970 B2 | 8/2014 | Faham |
| 8,826,321 B2 | 9/2014 | Cronin et al. |
| 8,835,358 B2 | 9/2014 | Fodor |
| 9,012,148 B2 | 4/2015 | Han et al. |
| 9,043,160 B1 | 5/2015 | Moorhead et al. |
| 9,150,905 B2 | 10/2015 | Robins et al. |
| 9,217,176 B2 | 12/2015 | Faham et al. |
| 9,228,232 B2 | 1/2016 | Faham et al. |
| 9,371,558 B2 | 6/2016 | Robins et al. |
| 9,394,567 B2 | 7/2016 | Asbury et al. |
| 9,416,420 B2 | 8/2016 | Faham et al. |
| 9,506,119 B2 | 11/2016 | Faham et al. |
| 9,512,487 B2 | 12/2016 | Faham et al. |
| 9,708,657 B2 | 7/2017 | Asbury et al. |
| 9,809,813 B2 | 11/2017 | Robins et al. |
| 2002/0076725 A1 | 6/2002 | Toyosaki-Maeda et al. |
| 2002/0110807 A1 | 8/2002 | Pilarski et al. |
| 2003/0096277 A1 | 5/2003 | Chen |
| 2003/0120061 A1 | 6/2003 | Zhang |
| 2003/0162197 A1 | 8/2003 | Morley et al. |
| 2003/0207300 A1 | 11/2003 | Matray et al. |
| 2004/0018489 A1 | 1/2004 | Ma et al. |
| 2004/0033490 A1 | 2/2004 | Laird et al. |
| 2004/0121364 A1 | 6/2004 | Chee et al. |
| 2004/0132050 A1 | 7/2004 | Monforte |
| 2004/0146901 A1 | 7/2004 | Morris et al. |
| 2004/0170977 A1 | 9/2004 | Laird |
| 2004/0235061 A1 | 11/2004 | Wilkie et al. |
| 2004/0248172 A1 | 12/2004 | Samoszuk et al. |

(56) References Cited

U.S. PATENT DOCUMENTS

| | | |
|---|---|---|
| 2005/0037356 A1 | 2/2005 | Gullberg et al. |
| 2005/0064421 A1 | 3/2005 | Gehrmann et al. |
| 2005/0142577 A1 | 6/2005 | Jones et al. |
| 2005/0250147 A1 | 11/2005 | Macevicz |
| 2005/0255482 A1 | 11/2005 | Morley et al. |
| 2005/0260570 A1 | 11/2005 | Mao et al. |
| 2006/0019304 A1 | 1/2006 | Hardenbol et al. |
| 2006/0020397 A1 | 1/2006 | Kermani |
| 2006/0046258 A1 | 3/2006 | Lapidus et al. |
| 2006/0085139 A1 | 4/2006 | Collette et al. |
| 2006/0088876 A1 | 4/2006 | Bauer |
| 2006/0134125 A1 | 6/2006 | Luxembourg et al. |
| 2006/0147925 A1 | 7/2006 | Morley et al. |
| 2006/0199210 A1 | 9/2006 | Weichselbaum et al. |
| 2006/0211030 A1 | 9/2006 | Brenner |
| 2006/0216737 A1 | 9/2006 | Bodeau |
| 2006/0228350 A1 | 10/2006 | Wu et al. |
| 2006/0233812 A1 | 10/2006 | Burnie et al. |
| 2006/0234234 A1 | 10/2006 | Van Dongen et al. |
| 2006/0259248 A1 | 11/2006 | Collette et al. |
| 2006/0263789 A1 | 11/2006 | Kincaid |
| 2007/0020640 A1 | 1/2007 | McCloskey et al. |
| 2007/0020670 A1 | 1/2007 | Loken et al. |
| 2007/0105105 A1 | 5/2007 | Clelland et al. |
| 2007/0117134 A1 | 5/2007 | Kou |
| 2007/0160994 A1 | 7/2007 | Lim et al. |
| 2007/0161001 A1 | 7/2007 | Leshkowitz |
| 2007/0172873 A1 | 7/2007 | Brenner et al. |
| 2007/0238099 A1 | 10/2007 | Cohen et al. |
| 2007/0243564 A1 | 10/2007 | Lawson et al. |
| 2007/0264653 A1 | 11/2007 | Berlin et al. |
| 2007/0286849 A1 | 12/2007 | Chaturvedi |
| 2008/0050780 A1 | 2/2008 | Lee et al. |
| 2008/0069770 A1 | 3/2008 | Hercend et al. |
| 2008/0108509 A1 | 5/2008 | Haupl et al. |
| 2008/0166704 A1 | 7/2008 | Marche et al. |
| 2008/0166718 A1 | 7/2008 | Lim et al. |
| 2008/0199916 A1 | 8/2008 | Zheng et al. |
| 2008/0248484 A1 | 10/2008 | Bauer |
| 2008/0274904 A1 | 11/2008 | Gormley et al. |
| 2008/0280774 A1 | 11/2008 | Burczynski et al. |
| 2008/0286777 A1 | 11/2008 | Candeias et al. |
| 2009/0026082 A1 | 1/2009 | Rothberg et al. |
| 2009/0053184 A1 | 2/2009 | Morgan et al. |
| 2009/0098555 A1 | 4/2009 | Roth et al. |
| 2009/0105959 A1 | 4/2009 | Braverman et al. |
| 2009/0181859 A1 | 7/2009 | Muraguchi |
| 2009/0197257 A1 | 8/2009 | Harris |
| 2009/0208955 A1 | 8/2009 | Robins et al. |
| 2009/0226975 A1 | 9/2009 | Sabot et al. |
| 2009/0233301 A1 | 9/2009 | Lee |
| 2009/0233802 A1 | 9/2009 | Bignell et al. |
| 2009/0253581 A1 | 10/2009 | Van Eijk et al. |
| 2009/0264299 A1 | 10/2009 | Drmanac et al. |
| 2009/0280489 A1 | 11/2009 | Devinder et al. |
| 2009/0286237 A1 | 11/2009 | Fitzgerald et al. |
| 2009/0298060 A1 | 12/2009 | Lal et al. |
| 2010/0008920 A1 | 1/2010 | Schneck et al. |
| 2010/0021894 A1 | 1/2010 | Mirkin et al. |
| 2010/0021896 A1 | 1/2010 | Han |
| 2010/0021984 A1 | 1/2010 | Edd |
| 2010/0027896 A1 | 2/2010 | Geva et al. |
| 2010/0034834 A1 | 2/2010 | Robbins et al. |
| 2010/0035764 A1 | 2/2010 | Chen |
| 2010/0040606 A1 | 2/2010 | Lantto et al. |
| 2010/0042329 A1 | 2/2010 | Hood et al. |
| 2010/0105886 A1 | 4/2010 | Wondenberg |
| 2010/0129874 A1 | 5/2010 | Mitra et al. |
| 2010/0137143 A1 | 6/2010 | Rothberg et al. |
| 2010/0151471 A1 | 6/2010 | Faham et al. |
| 2010/0159456 A1 | 6/2010 | Albitar |
| 2010/0167353 A1 | 7/2010 | Walder et al. |
| 2010/0173394 A1 | 7/2010 | Colston, Jr. |
| 2010/0255471 A1 | 10/2010 | Clarke |
| 2010/0261204 A1 | 10/2010 | Goolsby et al. |
| 2010/0267043 A1 | 10/2010 | Braverman |
| 2010/0285975 A1 | 11/2010 | Mathies |
| 2010/0300895 A1 | 12/2010 | Nobile et al. |
| 2010/0304982 A1 | 12/2010 | Hinz et al. |
| 2010/0323348 A1 | 12/2010 | Hamady et al. |
| 2010/0323355 A1 | 12/2010 | Dittmer |
| 2010/0330571 A1 | 12/2010 | Robins et al. |
| 2011/0003291 A1 | 1/2011 | Pasqual et al. |
| 2011/0014659 A1 | 1/2011 | Balazs et al. |
| 2011/0097712 A1 | 4/2011 | Cantor et al. |
| 2011/0104671 A1 | 5/2011 | Dornan et al. |
| 2011/0105343 A1 | 5/2011 | Puledran et al. |
| 2011/0129830 A1 | 6/2011 | Ladner et al. |
| 2011/0160078 A1 | 6/2011 | Fodor et al. |
| 2011/0166034 A1 | 7/2011 | Kwong et al. |
| 2011/0183863 A1 | 7/2011 | Wagner et al. |
| 2011/0195253 A1 | 8/2011 | Hinz et al. |
| 2011/0207134 A1 | 8/2011 | Faham et al. |
| 2011/0207135 A1 | 8/2011 | Faham et al. |
| 2011/0207617 A1 | 8/2011 | Faham et al. |
| 2011/0251099 A1 | 10/2011 | Visvanathan et al. |
| 2012/0010096 A1 | 1/2012 | Wohlgemuth et al. |
| 2012/0035062 A1 | 2/2012 | Schultz et al. |
| 2012/0058902 A1 | 3/2012 | Livingston et al. |
| 2012/0071331 A1 | 3/2012 | Casbon et al. |
| 2012/0073667 A1 | 3/2012 | Schultz et al. |
| 2012/0122714 A1 | 5/2012 | Samuels |
| 2012/0135409 A1 | 5/2012 | Faham |
| 2012/0143531 A1 | 6/2012 | Davey et al. |
| 2012/0172241 A1 | 7/2012 | Rearick et al. |
| 2012/0173158 A1 | 7/2012 | Hubbell |
| 2012/0220466 A1 | 8/2012 | Fire et al. |
| 2012/0308999 A1 | 12/2012 | Sarma et al. |
| 2013/0005584 A1 | 1/2013 | Faham |
| 2013/0017957 A1 | 1/2013 | Faham et al. |
| 2013/0045221 A1 | 2/2013 | Stauss et al. |
| 2013/0065768 A1 | 3/2013 | Zheng |
| 2013/0116130 A1 | 5/2013 | Fu |
| 2013/0123120 A1 | 5/2013 | Zimmermann et al. |
| 2013/0136799 A1 | 5/2013 | Faham et al. |
| 2013/0137108 A1 | 5/2013 | Tripathi et al. |
| 2013/0150252 A1 | 6/2013 | Faham |
| 2013/0196328 A1 | 8/2013 | Pepin |
| 2013/0196861 A1 | 8/2013 | Quake |
| 2013/0202718 A1 | 8/2013 | Pepin |
| 2013/0236895 A1 | 9/2013 | Faham |
| 2013/0253842 A1 | 9/2013 | Sherwood et al. |
| 2013/0267427 A1 | 10/2013 | Faham |
| 2013/0273647 A1 | 10/2013 | Sahin et al. |
| 2013/0288237 A1 | 10/2013 | Robins et al. |
| 2013/0302801 A1 | 11/2013 | Asbury |
| 2013/0324422 A1 | 12/2013 | Faham et al. |
| 2013/0344066 A1 | 12/2013 | Faham |
| 2014/0057799 A1 | 2/2014 | Johnson et al. |
| 2014/0065629 A1 | 3/2014 | Barken et al. |
| 2014/0094376 A1 | 4/2014 | Han |
| 2014/0127699 A1 | 5/2014 | Han |
| 2014/0141982 A1 | 5/2014 | Jacobson et al. |
| 2014/0155277 A1 | 6/2014 | Wiley |
| 2014/0186848 A1 | 7/2014 | Robins et al. |
| 2014/0194295 A1 | 7/2014 | Robins et al. |
| 2014/0206548 A1 | 7/2014 | Robins et al. |
| 2014/0206549 A1 | 7/2014 | Robins et al. |
| 2014/0213463 A1 | 7/2014 | Robins et al. |
| 2014/0221220 A1 | 8/2014 | Robins et al. |
| 2014/0227705 A1 | 8/2014 | Vogelstein et al. |
| 2014/0234835 A1 | 8/2014 | Pepin |
| 2014/0235454 A1 | 8/2014 | Faham |
| 2014/0255929 A1 | 9/2014 | Zheng |
| 2014/0255944 A1 | 9/2014 | Carlton |
| 2014/0256567 A1 | 9/2014 | Robins et al. |
| 2014/0256592 A1 | 9/2014 | Faham |
| 2014/0315725 A1 | 10/2014 | Faham et al. |
| 2014/0322716 A1 | 10/2014 | Robins et al. |
| 2014/0336059 A1 | 11/2014 | Faham et al. |
| 2014/0342360 A1 | 11/2014 | Faham et al. |
| 2014/0342367 A1 | 11/2014 | Faham et al. |
| 2014/0349883 A1 | 11/2014 | Faham et al. |
| 2014/0356339 A1 | 12/2014 | Faham et al. |

(56) References Cited

U.S. PATENT DOCUMENTS

| | | |
|---|---|---|
| 2015/0017630 A1 | 1/2015 | Oved et al. |
| 2015/0017652 A1 | 1/2015 | Robins et al. |
| 2015/0031043 A1 | 1/2015 | Faham et al. |
| 2015/0031553 A1 | 1/2015 | Faham et al. |
| 2015/0031555 A1 | 1/2015 | Johnson et al. |
| 2015/0038346 A1 | 2/2015 | Faham et al. |
| 2015/0051089 A1 | 2/2015 | Robins et al. |
| 2015/0065352 A1 | 3/2015 | Faham et al. |
| 2015/0087535 A1 | 3/2015 | Patel et al. |
| 2015/0133317 A1 | 5/2015 | Robinson et al. |
| 2015/0154352 A1 | 6/2015 | Johnson et al. |
| 2015/0167080 A1 | 6/2015 | Moorhead et al. |
| 2015/0203897 A1 | 7/2015 | Robins et al. |
| 2015/0215062 A1 | 7/2015 | Li et al. |
| 2015/0218656 A1 | 8/2015 | Kirsch et al. |
| 2015/0232936 A1 | 8/2015 | Shoemaker et al. |
| 2015/0247182 A1 | 9/2015 | Faham et al. |
| 2015/0247198 A1 | 9/2015 | Klinger et al. |
| 2015/0247201 A1 | 9/2015 | Faham et al. |
| 2015/0252419 A1 | 9/2015 | Moorhead et al. |
| 2015/0252422 A1 | 9/2015 | Faham et al. |
| 2015/0259734 A1 | 9/2015 | Asbury et al. |
| 2015/0275296 A1 | 10/2015 | Klinger et al. |
| 2015/0275308 A1 | 10/2015 | Carlton et al. |
| 2015/0299785 A1 | 10/2015 | Livingston et al. |
| 2015/0299786 A1 | 10/2015 | Robins et al. |
| 2015/0299800 A1 | 10/2015 | Faham et al. |
| 2016/0024493 A1 | 1/2016 | Robins et al. |
| 2016/0115532 A1 | 4/2016 | Faham |
| 2016/0138011 A1 | 5/2016 | Dewitt et al. |
| 2016/0186260 A1 | 6/2016 | Klinger et al. |
| 2016/0201133 A1 | 7/2016 | Faham et al. |
| 2016/0251721 A1 | 9/2016 | Robins et al. |
| 2016/0251728 A1 | 9/2016 | Faham et al. |
| 2016/0258025 A1 | 9/2016 | Klinger et al. |
| 2016/0304956 A1 | 10/2016 | Robins et al. |
| 2016/0319340 A1 | 11/2016 | Robins et al. |
| 2017/0037469 A1 | 2/2017 | Robins et al. |
| 2017/0292149 A1 | 10/2017 | Emerson et al. |
| 2017/0335386 A1 | 11/2017 | Livingston et al. |
| 2017/0335390 A1 | 11/2017 | Asbury et al. |
| 2017/0335391 A1 | 11/2017 | Emerson et al. |
| 2017/0349954 A1 | 12/2017 | Faham et al. |
| 2018/0037953 A1 | 2/2018 | Emerson et al. |
| 2018/0073015 A1 | 3/2018 | Robins et al. |
| 2018/0080090 A1 | 3/2018 | Faham et al. |

FOREIGN PATENT DOCUMENTS

| | | |
|---|---|---|
| CN | 103097888 A | 5/2013 |
| EA | 007958 B1 | 2/2007 |
| EP | 0303459 A2 | 2/1989 |
| EP | 0799897 A1 | 10/1997 |
| EP | 1516929 A2 | 3/2005 |
| EP | 1544308 A1 | 6/2005 |
| EP | 1549764 B1 | 7/2005 |
| EP | 0972081 B1 | 6/2007 |
| EP | 1544308 B1 | 1/2009 |
| EP | 2062982 A1 | 5/2009 |
| EP | 2088432 A1 | 8/2009 |
| EP | 2418287 A2 | 2/2012 |
| EP | 2364368 B1 | 1/2014 |
| JP | 4262799 A | 9/1992 |
| JP | 2002-503954 A | 2/2001 |
| JP | 2005-245381 A | 9/2005 |
| JP | 2006-501842 A | 1/2006 |
| JP | 2007-515955 A | 6/2007 |
| JP | 2007-536939 A | 12/2007 |
| JP | 2008-099588 A | 5/2008 |
| JP | 2011-505123 A | 2/2011 |
| JP | 2012-508011 A | 4/2012 |
| JP | 2013-524848 A | 6/2013 |
| JP | 2013-524849 A | 6/2013 |
| WO | WO 1993/001838 A1 | 2/1993 |
| WO | WO 1995/028481 A1 | 10/1995 |
| WO | WO 1997/013868 A1 | 4/1997 |
| WO | WO 1997/013877 A1 | 4/1997 |
| WO | WO 1997/018330 A1 | 5/1997 |
| WO | WO 1997/046706 A1 | 12/1997 |
| WO | WO 1998/001738 A2 | 1/1998 |
| WO | WO 1998/044151 A1 | 10/1998 |
| WO | WO 1999/019717 A1 | 4/1999 |
| WO | WO 1999/020798 A1 | 4/1999 |
| WO | WO 2001/014424 A2 | 3/2001 |
| WO | WO 2002/024322 A2 | 3/2002 |
| WO | WO 2003/008624 A2 | 1/2003 |
| WO | WO 2003/044225 A2 | 5/2003 |
| WO | WO 2003/052101 A1 | 6/2003 |
| WO | WO 2003/059155 A2 | 7/2003 |
| WO | WO 2004/003820 A2 | 1/2004 |
| WO | WO 2004/033728 A2 | 4/2004 |
| WO | WO 2004/034031 A2 | 4/2004 |
| WO | WO 2004/044209 A1 | 5/2004 |
| WO | WO 2004/046098 A2 | 6/2004 |
| WO | WO 2004/063706 A2 | 7/2004 |
| WO | WO 2004/096985 A2 | 11/2004 |
| WO | WO 2005/003375 A2 | 1/2005 |
| WO | WO 2005/005651 A2 | 1/2005 |
| WO | WO 2005/010200 A2 | 2/2005 |
| WO | WO 2005/042774 A2 | 5/2005 |
| WO | WO 2005/053603 A2 | 6/2005 |
| WO | WO 2005/056828 A1 | 6/2005 |
| WO | WO 2005/059176 A1 | 6/2005 |
| WO | WO 2005/084134 A2 | 9/2005 |
| WO | WO 2005/111242 A2 | 11/2005 |
| WO | WO 2005/113803 A1 | 12/2005 |
| WO | WO 2006/076025 A2 | 7/2006 |
| WO | WO 2006/076205 A2 | 7/2006 |
| WO | WO 2006/110855 A2 | 10/2006 |
| WO | WO 2006/116155 A2 | 11/2006 |
| WO | WO 2006/138284 A2 | 12/2006 |
| WO | WO 2007/008759 A2 | 1/2007 |
| WO | WO 2007/134220 A2 | 11/2007 |
| WO | WO 2008/026927 A2 | 3/2008 |
| WO | WO 2008/039694 A2 | 4/2008 |
| WO | WO 2008/108803 A2 | 9/2008 |
| WO | WO 2008/147879 A1 | 12/2008 |
| WO | WO 2009/015296 A1 | 1/2009 |
| WO | WO 2009/017678 A2 | 2/2009 |
| WO | WO 2009/019657 A2 | 2/2009 |
| WO | WO 2009/021215 A1 | 2/2009 |
| WO | WO 2009/045898 A2 | 4/2009 |
| WO | WO 2009/070767 A2 | 6/2009 |
| WO | WO 2009/095567 A2 | 8/2009 |
| WO | WO 2009/108860 A2 | 9/2009 |
| WO | WO 2009/108866 A2 | 9/2009 |
| WO | WO 2009/137255 A2 | 11/2009 |
| WO | WO 2009/137832 A2 | 11/2009 |
| WO | WO 2009/145925 A1 | 12/2009 |
| WO | WO 2009/151628 A2 | 12/2009 |
| WO | WO 2009/152928 A2 | 12/2009 |
| WO | WO 2009/158521 A2 | 12/2009 |
| WO | WO 2010/011894 A1 | 1/2010 |
| WO | WO 2010/036352 A1 | 4/2010 |
| WO | WO 2010/053587 A2 | 5/2010 |
| WO | WO 2010/083456 A1 | 7/2010 |
| WO | WO 2010/151416 A1 | 12/2010 |
| WO | WO 2011/083296 A1 | 7/2011 |
| WO | WO 2011/083996 A2 | 7/2011 |
| WO | WO 2011/106738 A2 | 9/2011 |
| WO | WO 2011/107595 A1 | 9/2011 |
| WO | WO 2011/139371 A1 | 11/2011 |
| WO | WO 2011/139372 A1 | 11/2011 |
| WO | WO 2011/140433 A2 | 11/2011 |
| WO | WO 2012/012703 A2 | 1/2012 |
| WO | WO 2012/017081 A1 | 2/2012 |
| WO | WO 2012/027503 A2 | 3/2012 |
| WO | WO 2012/048340 A2 | 4/2012 |
| WO | WO 2012/048341 A1 | 4/2012 |
| WO | WO 2012/055929 A1 | 5/2012 |
| WO | WO 2012/061832 A1 | 5/2012 |
| WO | WO 2012/083069 A2 | 6/2012 |
| WO | WO 2012/083225 A2 | 6/2012 |
| WO | WO 2012/122484 A1 | 9/2012 |

(56) References Cited

FOREIGN PATENT DOCUMENTS

| | | |
|---|---|---|
| WO | WO 2012/142213 A2 | 10/2012 |
| WO | WO 2012/148497 A2 | 11/2012 |
| WO | WO 2012/159754 A2 | 11/2012 |
| WO | WO 2013/033721 A1 | 3/2013 |
| WO | WO 2013/036459 A2 | 3/2013 |
| WO | WO 2013/055595 A1 | 4/2013 |
| WO | WO 2013/059725 A1 | 4/2013 |
| WO | WO 2013/066726 A1 | 5/2013 |
| WO | WO 2013/085855 A1 | 6/2013 |
| WO | WO 2013/086450 A1 | 6/2013 |
| WO | WO 2013/086462 A1 | 6/2013 |
| WO | WO 2013/090390 A2 | 6/2013 |
| WO | WO 2013/090469 A1 | 6/2013 |
| WO | WO 2013/096480 A2 | 6/2013 |
| WO | WO 2013/123442 A1 | 8/2013 |
| WO | WO 2013/130512 A2 | 9/2013 |
| WO | WO 2013/131074 A1 | 9/2013 |
| WO | WO 2013/134162 A2 | 9/2013 |
| WO | WO 2013/134302 A1 | 9/2013 |
| WO | WO 2013/155119 A1 | 10/2013 |
| WO | WO 2013/158936 A1 | 10/2013 |
| WO | WO 2013/169957 A1 | 11/2013 |
| WO | WO 2013/181428 A2 | 12/2013 |
| WO | WO 2013/188471 A2 | 12/2013 |
| WO | WO 2013/188831 A1 | 12/2013 |
| WO | WO 2014/018460 A1 | 1/2014 |
| WO | WO 2014/026031 A1 | 2/2014 |
| WO | WO 2014/062945 A1 | 4/2014 |
| WO | WO 2014/062959 A1 | 4/2014 |
| WO | WO 2014/066184 A1 | 5/2014 |
| WO | WO 2014/130685 A1 | 8/2014 |
| WO | WO 2014/145992 A1 | 9/2014 |
| WO | WO 2015/002908 A1 | 1/2015 |
| WO | WO 2015/013461 A2 | 1/2015 |
| WO | WO 2015/058159 A1 | 4/2015 |
| WO | WO 2015/106161 A1 | 7/2015 |
| WO | WO 2015/134787 A2 | 9/2015 |
| WO | WO 2015/153788 A1 | 10/2015 |
| WO | WO 2015/160439 A2 | 10/2015 |
| WO | WO 2016/069886 A1 | 5/2016 |
| WO | WO 2016/138122 A1 | 9/2016 |
| WO | WO 2016/161273 A1 | 10/2016 |

OTHER PUBLICATIONS

Abath et al. "Single-tubed nested PCR using immobilized internal primers", *Biotechniques*, 33(6): 1210-1212, 1214 (2002).

Abbott, et al. "Design and use of signature primers to detect carry-over of amplified material", *J Virol Methods*, 46(1):51-59, Abstract Only (1994).

Ahmadzadeh et al. "FOXP3 expression accurately defines the population of intratumoral regulatory T cells that selectively accumulate in metastatic melanoma lesions", *Blood*, 112(13): 4953-4960 (2008).

Akatsuka, Y. et al., "Rapid screening of T-cell receptor (TCR) variable gene usage by multiplex PCR: Application for assessment of clonal composition", *Tissue Antigens*, 53(2):122-134 (1999).

Alatrakchi et al. "T-cell clonal expansion in patients with B-cell lymphoproliferative disorders", *Journal of Immunotherapy*, 21(5):363-370 (1998).

Alexandre, D. et al. "*H. sapiens* rearranged T-cell receptor gamma chain gene, V2-JP1", GenBank accession No. X57737, NCBI, Nov. 14, 2006, 8 pages [online] [retrieved on Jun. 26, 2013] Retrieved from the internet <URL:http://www.ncbi.nlm.nih.gov/nuccore/x57737>.

Alexandre, D. et al. "*H. sapiens* rearranged T-cell receptor gamma chain gene, V3RS-J1 (hybrid joint)", GenBank accession No. X57740, NCBI, Feb. 11, 1997, 8 pages [online] [retrieved on Jun. 26, 2013] Retrieved from the internet <URL:http://www.ncbi.nlm.nih.gov/nuccore/x57740>.

Al-Lazikani, B. et al., "Standard Conformations for the Canonical Structures of Immunoglobulins," *J. Mol. Biol.*, 273:927-948 (1997).

Altin et al. "The role of CD45 and CD45-associated molecules in T cell activation", *Immunology and Cell Biology*, 75: 430-445 (1997).

Altman, et al. "Phenotypic analysis of antigen-specific T lymphocytes", The *Journal of Immunology*, 187(1):7-9 (2011).

Altschul, et al. "Basic local alignment search tool", *J Mol Biol.*, 215(3):403-410 (1990).

Andreasson, et al. "The human IgE-encoding transcriptome to assess antibody repertoires and repertoire evolution", *J Mol Biol.*, 362(2):212-227 (2006). Epub Aug. 14, 2006.

Arnaout. "Specificity and overlap in gene segment-defined antibody repertoires", *BMC Genomics*, 6: 148 (2005).

Arden, et al. "Human T-cell receptor variable gene segment families", *Immunogenetics*, 42(6):455-500, Abstract Only (1995).

Armand, P. et al., "Detection of circulating tumour DNA in patients with aggressive B-cell non-Hodgkin lymphoma", *Brit. J. Haematol.*, vol. 163, pp. 123-126 (2013).

Arstila, T.P., et al., "A direct estimate of the human $\alpha\beta$ T cell receptor diversity," *Science*, 286(5441): 958-961 (1999).

Aslanzadeh. "Preventing PCR amplification carryover contamination in a clinical laboratory", *Ann Clin Lab Sci.*, 34(4):389-396 (2004).

Assaf, et al. "High Detection Rate of T-Cell Receptor Beta Chain Rearrangements in T-Cell Lymphoproliferations by Family Specific Polymerase Chain Reaction in Combination with the Genescan Technique and DNA Sequencing", *Blood*, 96(2): 640-646 (2000).

Ateya, et al. "The good, the bad, and the tiny: a review of microflow cytometry", *Anal Bioanal Chem.*, 391(5): 1485-1498 (2008). doi: 10.1007/s00216-007-1827-5. Epub Jan. 29, 2008.

Babrzadeh et al. "Development on High-throughput Sequencing Technology: emPCR Titration and Barcode Design", *Stanford School of Medicine*, 2 pages (2011).

Bagnara, et al. "IgV gene intraclonal diversification and clonal evolution in B-cell chronic lymphocytic leukaemia", *British Journal of Haematology*, 133(1):50-58 (2006).

Bahloul, M. et al., "Clinical impact of molecular diagnostics in low-grade lymphoma," Best Practice & Research Clinical Haematology, 18(1):97-111 (2005).

Baldauf, "Phylogeny for the faint of heart: a tutorial," Trends in Genetics, 19(6): 345-351 (2003).

Barbas, et al. "Assembly of combinatorial antibody libraries on phage surfaces: the gene III site", *PNAS*, 88(18): 7978-7982, Abstract Only (1991).

Barker, et al. "A second type II restriction endonuclease from Thermus aquaticus with an unusual sequence specificity", *Nucleic Acids Res.*, 12(14): 5567-5581 (1984).

Batzoglou, S. "The many faces of sequence alignment", *Briefings in Bioinformatics*, 6:6-22 (2005).

Baum and McCune et al. "Direct measurement of T-cell receptor repertoire diversity with AmpliCot", *Nat Methods*, 3(11): 895-901 (2006).

Becker-André and Hahlbrock. "Absolute mRNA quantification using the polymerase chain reaction (PCR). A novel approach by a PCR aided transcript titration assay (PATTY)", *Nucleic Acids Res.*, 17(22): 9437-9446 (1989).

Becton-Dickinson, CD marker handbook. bdbiosciences.com/go/mousecdmarkers, p. 1-47 (2010).

Becton-Dickinson T-Cell Research Tools, "Novel multicolor flow cytometry tools for the study of CD4+ T-cell differentiation and plasticity", 16 pages (2009).

Beishuizen, et al. "Analysis of Ig and T-cell receptor genes in 40 childhood acute lymphoblastic leukemias at diagnosis and subsequent relapse: implications for the detection of minimal residual disease by polymerase chain reaction analysis", *Blood*, 83(8):2238-2247 (1994).

Ben-Ezra, et al. Effect of fixation on the amplification of nucleic acids from paraffin-embedded material by the polymerase chain reaction, *The Journal of Histochemistry and Cytochemistry*, 39(3): 351-354 (1991).

Béné and Kaeda, "How and why minimal residual disease studies are necessary in leukemia: a review from WP10 and WP12 of the European LeukaemiaNet", *Haematologica*, 94(8):1135-1150 (2009).

(56) References Cited

OTHER PUBLICATIONS

Benecke. "DNA typing in forensic medicine and in criminal investigations: a current survey", *Naturwissenschaften*, 84(5): 181-188 (1997).

Benichou, J. et al., "Rep-Seq: uncovering the immunological repertoire through next-generation sequencing", *Immunology*, 135(3): 183-191 (2011).

Benichou, J. et al., "The restricted DH gene reading frame usage in the expressed human antibody repertoire is selected based upon its amino acid content", J Immunol., 190(11): 5567-77, 29 pages (2013).

Bentley, et al. "Accurate whole human genome sequencing using reversible terminator chemistry", *Nature*, 456(7218) :53-59 (2008). doi: 10.1038/nature07517.

Bereczki, et al. "Optimization of PCR amplification for B- and T-cell clonality analysis on formalin-fixed and paraffin-embedded samples", *Pathology Oncology Research*, 13(3): 209-214 (2007). Epub Oct. 7, 2007.

Berger, et al. "The clonotypic T cell receptor is a source of tumor-associated antigens in cutaneous T cell lymphoma", *Annals of the New York Academy of Sciences*, 941:106-122, Abstract Only (2001).

Berget, et al. "Detection of clonality in follicular lymphoma using formalin-fixed, paraffin-embedded tissue samples and BIOMED-2 immunoglobulin primers", J Clin Pathol., 64(1):37-41 (2011). doi: 10.1136/jcp.2010.081109. Epub Oct. 28, 2010.

Bernard et al. "Color multiplexing hybridization probes using the apolipoprotein E locus as a model system for genotyping", Anal Biochem., 273(2):221-228 (1999).

Bernardin, F. et al. "Estimate of the total number of CD8+ clonal expansions in healthy adults using a new DNA heteroduplex-tracking assay for CDR3 repertoire analysis", *Journal of Immunological Methods*, 274(I-2):159-175 (2003).

Berquam-Vrieze, K. et al., "Cell of origin strongly influences genetic selection in a mouse model of T-ALL", *Blood*, 118:4646-4656 (2011).

Bertness, et al. "T-Cell Receptor Gene Rearrangements as Clinical Markers of Human T-Cell Lymphomas", *The New England Journal of Medicine*, 313:534-538 (1985).

Berzofsky, et al. "Progress on new vaccine strategies for the immunotherapy and prevention of cancer", *J Clin Invest.*, 113(11): 1515-1525 (2004).

Biagi, et al. "Responses to human CD40 ligand/human interleukin-2 autologous cell vaccine in patients with B-cell chronic lymphocytic leukemia", *Clin Cancer Res.*, 11(19 Pt 1): 6916-6923 (2005).

Biggerstaff, et al. "Enumeration of leukocyte infiltration in solid tumors by confocal laser scanning microscopy", *BMC Immunol.*, 7:16, 13 pages (2006).

Blow, N., "PCR's next frontier," *Nature Methods*, 4(10):869-875 (2007).

Brochet et al. "IMGT/V-QUEST: the highly customized and integrated system for IG and TR standardized V-J and V-D-J sequence analysis", Nucleic Acids Research, vol. 36, Web Server issue W503-W508 (2008).

Bolotin, D.A. et al., "Next generation sequencing for TCR repertoire profiling: Platform-specific features and correction algorithms", *Eur. J. Immunol.*, 42:3073-3083 (2012).

Bonarius, H.P.J. et al. "Monitoring the T-Cell Receptor Repertoire at Single-Clone Resolution", *PLOS One*, 1(e55):1-10 (2006).

Bonner et al. "Fluorescence activated cell sorting", Rev Sci Instrum., 43(3):404-409, Abstract Only (1972).

Boria, et al. "Primer sets for cloning the human repertoire of T cell receptor variable regions", *BMC Immunology*, 9:50, 9 pages (2008).

Borst, et al. "False-positive results and contamination in nucleic acid amplification assays: suggestions for a prevent and destroy strategy", Eur J Clin Microbiol Infect Dis., 23(4):289-299, Abstract Only (2004). Epub Mar. 10, 2004.

Boudinot et al. "New perspectives for large-scale repertoire analysis of immune receptors", *Molecular Immunology*, 45: 2437-2445 (2008).

Bousso. "Generation of MHC-peptide tetramers: a new opportunity for dissecting T-cell immune responses", Microbes Infect., 2(4):425-429, Abstract Only (2000).

Boyce, et al. "Human regulatory T-cell isolation and measurement of function", *BD Biosciences*, pp. 1-20 (2010).

Boyd, S.D. et al., "Individual Variation in the Germline Ig Gene Repertoire Inferred from Variable Region Gene Rearrangements", *The Journal of Immunology*, 184(12): 6986-6992 (2010). Epub 2010.

Boyd, S.D. et al., "Measurement and Clinical Monitoring of Human Lymphocyte Clonality by Massively Parallel V-D-J Pyrosequencing," *Science Translational Medicine*, 1:12ra23, 40 pages, including Supplementary Materials (2009).

Bradfield, et al. "Graft-versus-leukemia effect in acute lymphoblastic leukemia: the importance of tumor burden and early detection", Leukemia, 18(6): 1156-1158 (2004).

Bravo and Irizarry. "Model-Based Quality Assessment and Base-Calling for Second-Generation Sequencing Data", Biometrics, 66(3): 665-674 (2010).

Brehm-Stecher and Johnson. "Single-cell microbiology: tools, technologies, and applications", *Microbiology and Molecular Biology Reviews*, 68(3):538-559 (2004).

Brenan, C. et al., "High throughput, nanoliter quantitative PCR," *Drug Discovery Today: Technologies*, 2(3):247-253 (2005).

Brenner, et al. "In vitro cloning of complex mixtures of DNA on microbeads: physical separation of differentially expressed cDNAs", *PNAS*, 97(4): 1665-1670 (2000).

Brennan et al. "Predictable αβ T-cell receptor selection toward an HLA-B*3501-restricted human cytomegalovirus epitope", J. Virol., 81(13): 7269-7273 (2007).

Brentjens, et al. "CD19-targeted T cells rapidly induce molecular remissions in adults with chemotherapy-refractory acute lymphoblastic leukemia", Sci Transl Med., 5(177): 177ra38 (2013). doi: 10.1126/scitranslmed.3005930.

Brisco, et al. "Determining the repertoire of IGH gene rearrangements to develop molecular markers for minimal residual disease in B-lineage acute lymphoblastic leukemia", *J Mol Diagn.*, 11(3):194-200 (2009).

Brisco, et al. "Outcome prediction in childhood acute lymphoblastic leukaemia by molecular quantification of residual disease at the end of induction", *Lancet*, 343:196-200 (1994).

Brockman et al, "Quality scores and SNP detection in sequencing-by-synthesis systems," Genome Research, 18: 763-770 (2008).

Brody, et al. "Active and passive immunotherapy for lymphoma: proving principles and improving results", J Clin Oncol., 29(14):1864-1875, Abstract Only (2011). doi: 10.1200/JCO.2010.33.4623. Epub Apr. 11, 2011.

Brody, et al., "Immunotransplant for mantle cell lymphoma: Phase I/II study preliminary results", *Journal of Clinical Oncology*, ASCO Annual Meeting Abstracts Part 1, Suppl; abstr 2509: vol. 29, No. 15, 1 page (2011).

Brody, et al. "Lymphoma immunotherapy: vaccines, adoptive cell transfer and immunotransplant", *Immunotherapy*, 1(5): 809-824 (2009). doi: 10.2217/imt.09.50.

Brown, et al. "Current techniques for single-cell lysis", *J. R. Soc. Interface*, 5:S131-S138 (2008).

Brownie et al. "The elimination of primer-dimer accumulation in PCR", Nucleic Acids Research, 25(16): 3235-3241 (1997).

Brüggemann, et al. "Clinical significance of minimal residual disease quantification in adult patients with standard-risk acute lymphoblastic leukemia", *Blood*, 107(3):1116-1123 (2006). Epub Sep. 29, 2005.

Brüggemann, et al. "Rearranged T-cell receptor beta genes represent powerful targets for quantification of minimal residual disease in childhood and adult T-cell acute lymphoblastic leukemia", *Leukemia*, 18(4): 709-719 (2004).

Brüggemann, et al. "Standardized MRD quantification in European ALL trials: proceedings of the Second International Symposium on MRD assessment in Kiel, Germany, Sep. 18-20, 2008", *Leukemia*, 24(3):521-535 (2010). doi: 10.1038/leu.2009.268. Epub Dec. 24, 2009.

Buck, G.A. et al. "Design Strategies and Performance of Custom DNA Sequencing Primers", *Biotechniques*, 27(3):528-536 (1999).

(56) References Cited

OTHER PUBLICATIONS

Buccisano, et al. "Prognostic and therapeutic implications of minimal residual disease detection in acute myeloid leukemia", Blood, 119(2):332-341 (2012). doi: 10.1182/blood-2011-08-363291. Epub Oct. 28, 2011.
Buccisano, et al. "Monitoring of minimal residual disease in acute myeloid leukemia", Curr Opin Oncol., 21(6):582-588, Abstract Only (2009). doi: 10.1097/CCO.0b013e3283311856.
Butkus, B. "Hutch Team Uses ddPCR to Quantify T-Cell Response in Tumors; Adaptive Biotech Eyes Market", PCR Insider, Dec. 12, 2013, 3 pages http://www.genomeweb.com/print/1323296.
Bystrykh. "Generalized DNA Barcode Design Based on Hamming Codes", PLoS ONE, 7(5): e36852, 1-8 (2012).
Campana, D., "Progress of Minimal Residual Disease Studies in Childhood Acute Leukemia," Curr Hematol Malig Rep, 5:169-176 (2010).
Campana. "Minimal residual disease in acute lymphoblastic leukemia", Semin Hematol., 46(1):100-106 (2009).
Campana, et al. "Role of minimal residual disease monitoring in adult and pediatric acute lymphoblastic leukemia", Hematol Oncol Clin North Am., 23(5): 1083-1098 (2009). doi: 10.1016/j.hoc.2009.07.010.
Campbell et al. "Subclonal phylogenetic structures in cancer revealed by ultra-deep sequencing," PNAS, 105(35):13081-13086 (2008).
Caporaso, J.G. et al. "Global patterns of 16S rRNA diversity at a depth of millions of sequences per sample", PNAS, 108(Suppl. 1):4516-4522 (2010).
Carlotti, et al. "Transformation of follicular lymphoma to diffuse large B-cell lymphoma may occur by divergent evolution from a common progenitor cell or by direct evolution from the follicular lymphoma clone", Blood, 113(15): 3553-3557 (2009). doi: 10.1182/blood-2008-08-174839. Epub Feb. 6, 2009.
Carlson et al. "Profiling the repertoire of TCRB usage in induced and natural Treg cells", The Journal of Immunology, 186: 62.5, Abstract (2011).
Carlson, et al. "Immune Profiling Suggests an IGH Signaling-Dependent Subtype of Aggressive B-ALL", Blood, 120: 1428, Abstract (2012).
Carlson, et al. "Deep sequencing of the human TCRγ and TCRβ repertoires provides evidence that TCRβ rearranges after αβ, γδT cell commitment". Presented at the ASHG 2011 Conference. Oct. 2011. Poster. 1 page.
Carlson, et al. "Detection of tumor tagging clones in multiple myeloma via high throughput sequencing is robust to significant levels of SHM", Presented for the 2014 ASH Annual Meeting. Poster. 1 page. Dec. 5-9, 2014.
Carlson, C.S. et al. "Using synthetic templates to design an unbiased multiplex PCR assay", Nature Communications, 4:2680, pp. 1-9 (2013).
Casali, et al. "Human monoclonals from antigen-specific selection of B lymphocytes and transformation by EBV", Science, 234(4775): 476-479, Abstract Only (1986).
Casbon et al. "A method for counting PCR template molecules with application to next-generation sequencing", Nucleic Acids Research, 39(12): e81, 8 pages (2011).
Catherwood, M.A. et al., "Improved clonality assessment in germinal centre/post germinal centre non-Hodgkin's lymphomas with high rates of somatic hypermutation", J. Clin. Pathol., 60:524-528, Abstract (2007).
Cavé, H. et al., "Clinical Significance of minimal residual disease in childhood acute lymphoblastic leukemia," The New England Journal of Medicine, 339:591-598 (1998).
Cha et al., "Improved Survival with T Cell Clonotype Stability After Anti-CTLA-4 Treatment in Cancer Patients." Sci Transl Med (2014); 6(238): 238ra70.
Chan et al. "Evaluation of Nanofluidics Technology for High-Throughput SNP Genotyping in a Clinical Setting", The Journal of Molecular Diagnostics, 13(3): 305-312 (2011).

Chattopadhyay, et al. "A live-cell assay to detect antigen-specific CD4+ T cells with diverse cytokine profiles", Nat Med., 11(10): 1113-1117 (2005). Epub Sep. 25, 2005.
Chen et al. "A novel approach for the analysis of T-cell reconstitution by using a T-cell receptor β-based oligonucleotide microarray in hematopoietic stem cell transplantation", Exp Hematol., 35(5):831-841 (2007).
Chen et al. "Identification of racehorse and sample contamination by novel 24-plex STR system", Forensic Science International: Genetics, 4:158-167 (2010).
Chen, et al. "Microfluidic cell sorter with integrated piezoelectric actuator", Biomed Microdevices, 11(6): 1223-1231 (2009). doi: 10.1007/s10544-009-9341-5.
Chen, Y. et al., "T-cell receptor gene expression in tumour-infiltrating lymphocytes and peripheral blood lymphocytes of patients with nasopharyngeal carcinoma", British Journal of Cancer, 72(1): 117-22 (1995).
Chen, et al. "Total Gene Synthesis: Novel Single-Step and Convergent Strategies Applied to the Construction of a 779 Base Pair Bacteriorhodopsis", Gene. J. Am. Chem Soc., 116: 8799-8800, Abstract Only (1994).
Chinese Application No. 201380042163.X, Search Report dated Apr. 12, 2016 (English translation), 2 pages.
Chinese Patent Application No. 2014800254909, Search Report and English translation, dated May 25, 2017, mailed by the Chinese Patent Office dated Jun. 6, 2017, 5 pages.
Chiu, et al. "Non-invasive prenatal assessment of trisomy 21 by multiplexed maternal plasma DNA sequencing: large scale validity study", BMJ, 342:c7401, 9 pages (2011). doi: 10.1136/bmj.c7401.
Choi, et al. "Relapse in children with acute lymphoblastic leukemia involving selection of a preexisting drug-resistant subclone", Blood, 110(2):632-639 (2007).
Choi, et al. "Clonal evolution in B-lineage acute lymphoblastic leukemia by contemporaneous $V_H$-$V_H$ gene replacements and $V_H$-$DJ_H$ gene rearrangements", Blood, 87(6):2506-2512 (1996).
Chothia, C. et al. "Canonical structures for the hypervariable regions of immunoglobulins," J. Mol. Biol., 196:901-917, Abstract only (1987).
Chothia, C. et al. "Conformations of immunoglobulin hypervariable regions," Nature, 342:877-883 (1989).
Churchill and Waterman. "The Accuracy of DNA Sequences: Estimating Sequence Quality", Genomics, 14:89-98 (1992).
Chute, et al. "Detection of immunoglobulin heavy chain gene rearrangements in classic Hodgkin lymphoma using commercially available BIOMED-2 primers", Diagn Mol Pathol., 17(2): 65-72 (2008). doi: 10.1097/PDM.0b013e318150d695.
Citri et al. "Comprehensive qPCR profiling of gene expression in single neuronal cells", Nature Protocols, 7(1): 118-127 (2012).
Ciudad, J. et al. "Detection of abnormalities in B-cell differentiation pattern is a useful tool to predict relapse in precursor-B-ALL", British Journal of Haematology, 104:695-705 (1999).
Cleary, et al. "Production of complex nucleic acid libraries using highly parallel in situ oligonucleotide synthesis", Nat Methods, 1(3): 241-248 (2004). Epub Nov. 18, 2004.
Clemente, et al. "Deep sequencing of the T-cell receptor repertoire in CD8+ T-large granular lymphocyte leukemia identifies signature landscapes", Blood, 122(25): 4077-85 (2013). doi: 10.1182/blood-2013-05-506386. Epub Oct. 22, 2013.
Cooper, et al. "BRAF inhibition is associated with increased clonality in tumor infiltrating lymphocytes", Oncoimmunology, 2(10):e26615 (2013). Epub Oct. 15, 2013.
Costabile, et al. "Molecular approaches in the diagnosis of primary immunodeficiency diseases", Human Mutation, 27(12):1163-1173 (2006).
Coustan-Smith, E. et al., "Clinical importance of minimal residual disease in childhood acute lymphoblastic leukemia," Blood, 96(8):2691-2696 (2000).
Coustan-Smith, E. et al., "Early T-cell precursor leukaemia: a subtype of very high-risk acute lymphoblastic leukaemia," Lancet Oncology, 10:147-156 (2009).
Coustan-Smith, E. et al., "Prognostic importance of measuring early clearance of leukemic cells by flow cytometry in childhood acute lymphoblastic leukemia", Blood, 100(1):52-58 (2002).

(56) References Cited

OTHER PUBLICATIONS

Craig et al. "Identification of genetic variants using bar-coded multiplex sequencing", Nature Methods, 5(10): 887-893 (2008) and Supplemental Materials.

Cronin, et al. "Comprehensive next-generation cancer genome sequencing in the era of targeted therapy and personalized oncology", Biomark Med., 5(3):293-305 (2011). (Abstract only). doi: 10.2217/bmm.11.37.

Cronn et al. "Multiplex sequencing of plant chloroplast genomes using Solexa sequencing-by-synthesis technology", Nucleic Acids Research, 36(19):e122, 1-11 (2008).

Curran et al. "Nucleotide sequencing of psoriatic arthritis tissue before and during methotrexate administration reveals a complex inflammatory T cell infiltrate with very few clones exhibiting features that suggest they drive the inflammatory process by recognizing autoantigens", The Journal of Immunology, 172:1935-1944 (2004).

Curran-Everett, D., "Multiple comparisons: philosophies and illustrations", Am J Physiol Regulatory Integrative Comp Physiol., 279:R1-R8 (2000).

Currier and Robinson. "Spectratype/immunoscope analysis of the expressed TCR repertoire", Current Protocols in Immunology, Supplement 38:10.28.1-10.28.24 (2000).

Dahl et al. "Multiplex amplification enabled by selective circularization of large sets of genomic DNA fragments", Nucleic Acids Res., 33(8): e71 (2005).

Damle et al. "B-cell chronic lymphocytic leukemia cells express a surface membrane phenotype of activated, antigen-experienced B lymphocytes", Blood, 99(11): 4087-93 (2002).

Dash, P. et al., "Paired analysis of TCR[alpha] and TCR[beta] chains at the single-cell level in mice", Journal of Clinical Investigation, 121(1):288-295 (2011).

Davi, et al. "Lymphocytic progenitor cell origin and clonal evolution of human B-lineage acute lymphoblastic leukemia", Blood, 88(2):609-621 (1996).

Davila, et al. Efficacy and toxicity management of 19-28z CART cell therapy in B cell acute lymphoblastic leukemia, Sci Transl Med., 6(224):224ra25 (2014). doi: 10.1126/scitranslmed.3008226.

Davis, et al. "Interrogating the repertoire: broadening the scope of peptide-MHC multimer analysis", Nat Rev Immunol., 11(8):551-558 (2011). doi: 10.1038/nri3020.

Davis, et al. "Staining of cell surface human CD4 with 2'-F-pyrimidine-containing RNA aptamers for flow cytometry", Nucleic Acids Research, 26(17):3915-3924 (1998).

De Bona et al. "Optimal spliced alignments of short sequence reads", Bioinformatics, 9(Suppl 10):O7, 2 pages (2008).

De Jonge, H.J.M., et al. "Evidence Based Selection of Housekeeping Genes," PLoS One, 9(e898):1-5 (2007).

Dean, et al. "Rapid amplification of plasmid and phage DNA using Phi 29 DNA polymerase and multiply-primed rolling circle amplification", Genome Res., 11(6): 1095-1099 (2001).

Decoste et al. "Relative and Absolute Quantitative Real-Time PCR-Based Quantifications of hcnC and phlD Gene Transcripts in Natural Soil Spiked with Pseudomonas sp. Strain LBUM300", Applied and Environmental Microbiology, 77(1): 41-47 (2011).

Dedhia, et al. "Evaluation of DNA extraction methods and real time PCR optimization on formalin-fixed paraffin-embedded tissues", Asian Pac J Cancer Prev., 8(1): 55-59 (2007).

Deiman, et al. "Characteristics and applications of nucleic acid sequence-based amplification (NASBA)", Mol Biotechnol., 20(2): 163-179, Abstract Only (2002).

DeKosky et al. "High-throughput sequencing of the paired human immunoglobulin heavy and light chain repertoire", Nature Biotechnology, 31(2): 166-169 (2013).

Delaney, et al. "Evolution and Clinical Implications of the T cell Repertoire Following Cord Blood Transplant", Biology of Blood and Marrow Transplant, vol. 19, Issue 2, S201-S202. Published Feb. 2013.

Deng et al. "Gene profiling involved in immature CD4+ T lymphocyte responsible for systemic lupus erythematosus", Molecular Immunology, 43:1497-1507 (2006).

DeNucci, C.C. et al. "Integrin function in T-cell homing to lymphoid and nonlymphoid sites: getting there and staying there," Critical Reviews in Immunology, 29(2):87-109 (2009).

Deschoolmeester, et al. "Tumor infiltrating lymphocytes: an intriguing player in the survival of colorectal cancer patients", BMC Immunology, 11:19, 12 pages (2010). doi: 10.1186/1471-2172-11-19.

Desmarais, et al. "Deep profiling of the mouse TCRβ CDR3 region in thymus and spleen". Oct. 2010. Poster. 1 page.

Desmarais, et al. High-throughput sequencing of memory and naïve T cell receptor repertoires at the RNA and DNA levels reveals differences in relative expression of expanded TCR clones. Adaptive Technologies. Seattle W A. Poster, 1 page. Presented May 5, 2012.

Desmarais and Robins. "High-throughput sequencing of memory and naïve T cell receptor repertoires at the RNA and DNA levels reveals differences in relative expression of expanded TCR clones", The Journal of Immunology, 182: 178.12 (2012).

Dheda, K., et al. "Validation of housekeeping genes for normalizing RNA expression in real-time PCR," Bio Techniques, 37:112-119 (2004).

Dictor et al. "Resolving T-cell receptor clonality in two and genotype in four multiplex polymerase chain reactions", Haematologica, 90(11): 1524-1532 (2005).

Diederichsen, et al. "Prognostic value of the CD4+/CD8+ ratio of tumour infiltrating lymphocytes in colorectal cancer and HLA-DR expression on tumour cells", Cancer Immunol Immunother., 52(7):423-428 (2003). Epub Apr. 15, 2013.

Diehl, et al. "BEAMing: single-molecule PCR on microparticles in water-in-oil emulsions", Nat Methods, 3(7):551-559, Abstract Only (2006).

Dik, W., et al. "New insights on human T cell development by quantitative T cell receptor gene rearrangement studies and gene expression profiling," JEM, 201(11):1715-1723 (2005).

Diluvio et al. "Identical TCRβ-chain rearrangements in streptococcal angina and skin lesions of patients with psoriasis vulgaris", J Immunol., 176(11 ): 7104-11 (2006).

Ding, et al. "Clonal evolution in relapsed acute myeloid leukaemia revealed by whole-genome sequencing", Nature, 481(7382):506-510 (2012). doi: 10.1038/nature10738.

Diviacco, et al. "A novel procedure for quantitative polymerase chain reaction by coamplification of competitive templates", Gene, 122(2):313-320 (1992).

Do and Batzoglou. "What is the expectation maximization algorithm?", Nature Biotechnology, 26(8): 897-899 (2008).

Dobosy, J. et al. "RNase H-dependent PCR (rhPCR): improved specificity and single nucleotide polymorphism detection using blocked cleavable primers", BMC Biotechnology, 11(80):1-18 (2011).

Dohm, et al. "Substantial biases in ultra-short read data sets from high throughput DNA sequencing", Nucleic Acids Research, 36:e105, 10 pages (2008).

Dou, et al. "Analysis of T cell receptor $V_\beta$ gene usage during the course of disease in patients with chronic hepatitis B", Journal of Biomedical Science, 5(6):428-434 (1998).

Dressman, et al. "Transforming single DNA molecules into fluorescent magnetic particles for detection and enumeration of genetic variations", PNAS, 100(15):8817-8822 (2003). Epub Jul. 11, 2003.

Drmanac, et al. "Human genome sequencing using unchained base reads on self-assembling DNA nanoarrays", Science, 327(5961):78-81 (2010). doi: 10.1126/science.1181498. Epub Nov. 5, 2009.

Droege, et al. "The Genome Sequencer FLX System—longer reads, more applications, straight forward bioinformatics and more complete data sets", J Biotechnol., 136(1-2):3-10 (2008). doi: 10.1016/j.jbiotec.2008.03.021. Epub Jun. 21, 2008.

Droese, J., et al. "Validation of BIOMED-2 multiplex PCR tubes for detection of TCRB gene rearrangements in T-cell malignancies," Leukemia, 18:1531-1538 (2004).

Drossman, et al. "High-speed separations of DNA sequencing reactions by capillary electrophoresis", Anal Chem., 62(9): 900-903 (1990).

(56) References Cited

OTHER PUBLICATIONS

Du et al. "TCR spectratyping revealed T lymphocytes associated with graft-versus-host disease after allogeneic hematopoietic stem cell transplantation", *Leukemia & Lymphoma*, 48(8):1618-1627 (2007).
Duby, A.D. et al., "Human T-cell receptor aberrantly rearranged beta-chain J1.5-Dx-J2.1 gene," PNAS, GenBank accession No. M13574.1, bases 1 to 100, 4 pages (1986).
Dudgeon, et al. "The evolution of thymic lymphomas in p53 knockout mice", Genes Dev., 28(23): 2613-20 (2014). doi: 10.1101/gad.252148.114.
Dueñas, M., et al. "In vitro immunization of naive human B cells yields high affinity immunoglobulin G antibodies as illustrated by phage display." Immunology (1996); 89.1: 1-7.
Dunn, et al. "Focus on TILs: Prognostic significance of tumor infiltrating lymphocytes in human glioma", *Cancer Immun.*, 7:12, 16 pages (2007).
Eason et al. "Characterization of synthetic DNA bar codes in *Saccharomyces cerevisiae* gene-deletion strains," PNAS, 101(30): 11046-11051 (2004).
Edd et al. "Controlled encapsulation of single cells into monodisperse picoliter drops", *Lab Chip*, 8(8):1262-1264 (2008).
Edwards and Gibbs, "Multiplex PCR: advantages, development, and applications," Genome Research, 3:S65-S75 (1994).
Eichler, et al. "Haplotype and interspersion analysis of the FMR1 CGG repeat identifies two different mutational pathways for the origin of the fragile X syndrome", *Hum Mol Genet.*, 5(3):319-330 (1996).
Eichler, et al. "Length of uninterrupted CGG repeats determines instability in the FMR1 gene", *Nat Genet.*, 8(1):88-94, Abstract Only (1994).
Eid et al. "Real-time DNA sequencing from single polymerase molecules", *Science*, 323(5910):133-138 (2009). doi: 10.1126/science.1162986. Epub Nov. 20, 2008.
Eis, et al. "An invasive cleavage assay for direct quantitation of specific RNAs", *Nat Biotechnol.*, 19(7):673-676, Abstract Only (2001).
Eisenstein. "Personalized, sequencing-based immune profiling spurs startups", Nat Biotechnol., 31(3):184-186 (2013). doi: 10.1038/nbt0313-184b.
Elkord et al. "T regulatory cells in cancer: recent advances and therapeutic potential", *Expert Opinion on Biological Therapy*, 10(11): 1573-1586 (2010).
Elnifro, E.M., et al. "Multiplex PCR: Optimization and Application in Diagnostic Virology", *Clinical Microbiology Reviews*, 13(4):559-570 (2000).
Emerson, et al. "Correlation of TCR diversity with immune reconstitution after cord blood transplant", Presented at the American Society of Clinical Oncology's annual meeting. May 2012. Poster. 1 page.
Emerson et al. "Defining the Alloreactive T Cell Repertoire Using High-Throughput Sequencing of Mixed Lymphocyte Reaction Culture", *PLoS One*, 9(11): e111943 (2014).
Emerson, R.O. et al. "High-throughput sequencing of T-cell receptors reveals a homogeneous repertoire of tumour-infiltrating lymphocytes in ovarian cancer", *Journal of Pathology*, 231: 433-440 (2013).
Emerson, et al. "CD4+ and CD8+ T cell β antigen receptors have different and predictable V and J gene usage and CDR3 lengths", Presented at the Annual Meeting of The American Association of Immunologists 2012 in Boston, MA May 2012. Poster.
Emerson, et al. "Estimating the ratio of CD4+ to CD8+ T cells using high-throughput sequence data", J Immunol Methods, 391(1-2):14-21 (2013). doi: 10.1016/j.jim.2013.02.002. Epub Feb. 18, 2013.
Emerson, et al. TCR repertoire diversity assessed with immunosequencing is associated with patient mortality following cord blood transplant. Presented for the 2014 ASH Annual Meeting. Poster. 1 page. Dec. 5-9, 2014.
Estorninho, et al. "A novel approach to tracking antigen-experienced CD4 T cells into functional compartments via tandem deep and shallow TCR clonotyping", J Immunol., 191(11): 5430-5440 (2013). doi: 10.4049/jimmunol.I300622. Epub Oct. 25, 2013.
Erlich, et al. "Alta-Cyclic: a self-optimizing base caller for next-generation sequencing", *Nat Methods.*, 5(8): 679-682 (2008). doi: 10.1038/nmeth.1230. Epub Jul. 6, 2008.
European Application No. 09764927.1, Notice of Opposition dated Oct. 14, 2014, Reference# 547-7.
European Application No. 09764927.1, Notice of Opposition dated Oct. 14, 2014, Reference# BR0-0001EP.
European Application No. 09764927.1, European Opposition dated Oct. 15, 2014 (in French only).
Esendagli et al. "Malignant and non-malignant lung tissue areas are differentially populated by natural killer cells and regulatory T cells in non-small cell lung cancer", *Lung Cancer*, 59(1): 32-40 (2008).
European Application No. 10732172.1, Extended European Search Report dated May 29, 2012, 5 pages.
European Application No. 16162568.6, Extended European Search Report dated Jul. 20, 2016, 6 pages.
European Patent Application No. 13195379.6, European Search Report and Opinion dated Mar. 13, 2014, 6 pages.
European Patent Application No. 11777704.5, European Search Report dated Jul. 26, 2013, 6 pages.
European Patent Application No. 16183402.3, Extended European Search Report dated Feb. 21, 2017, 8 pages.
European Patent Application No. 13828563.0, Extended European Search Report dated Feb. 12, 2016, 10 pages.
European Patent Application No. 13804085.2, Extended European Search Report dated Nov. 16, 2015, 10 pages.
European Patent Application No. 14819680.1, Extended European Search Report dated Feb. 10, 2017, 10 pages.
European Patent Application No. 13775514.6, Extended European Search Report dated Dec. 1, 2015, 12 pages.
European Patent Application No. 13757482.8, Extended European Search Report dated Jun. 6, 2016, 5 pages.
European Patent Application No. 16165939.6, Extended European Search Report dated Oct. 7, 2016, 9 pages.
European Patent Application No. 09764927.1, EPO's Communication of Notices of Opposition, dated Nov. 21, 2014.
European Patent Application No. 09764927.1, Patentee's Observations/Response dated May 27, 2015.
European Patent Application No. 09764927.1, Opponent's Response to Submission of the Patentee dated Nov. 23, 2015.
European Patent Application No. 15772627.4, Extended European Search Report dated Jul. 19, 2017, 8 pages.
Ewing and Green, "Base-calling of automated sequencer traces using Phred. I. Accuracy Assessment," Genome Research, 8: 175-185 (1998).
Faham, M. et al. "Deep-sequencing approach for minimal residual disease detection in acute lymphoblastic leukemia", *Blood*, 120(26): 5173-5180 (2012).
Felsenstein, et al. "Evolutionary Trees from DNA Sequences: A Maximum Likelihood Approach", J Mol Evol, 17:368-376 (1981).
Ferradini et al. "Analysis of T Cell Receptor Variability in Tumor-infiltrating Lymphocytes from a Human Regressive Melanoma", *J. Clin. Invest.*, pp. 1183-1190 (1993).
Ferrero, et al. "Multiple myeloma shows no intra-disease clustering of immunoglobulin heavy chain genes", *Haematologica*, 97(6): 849-853 (2012). doi: 10.3324/haematol.2011.052852. Epub Dec. 29, 2011.
Fisher et al. "The Relation Between the Number of Species and the Number of Individuals in a Random Sample of an Animal Population", *Journal of Animal Ecology*, 12(1): 42-58 (1943).
Flaherty et al. "Ultrasensitive detection of rare mutations using next-generation targeted resequencing", *Nucleic Acids Research*, 40(1): e2, 12 pages (2012).
Flicek and Birney, "Sense from sequence reads: methods for alignment and assembly," Nature Methods Supplement, 6(11s): S6-S12 (2009).
Flohr, T., et al. "Minimal residual disease-directed risk stratification using real-time quantitative PCT analysis of immunoglobulin and T-cell receptor gene rearrangements in the international multicenter trial AIEOP-BFM ALL 2000 for childhood acute lymphoblastic leukemia", *Leukemia*, 22:771-782 (2008).

(56) References Cited

OTHER PUBLICATIONS

Frampton, et al. "Development and validation of a clinical cancer genomic profiling test based on massively parallel DNA sequencing", Nat Biotechnol., 31(11): 1023-1031 (2013). doi: 10.1038/nbt.2696. Epub Oct. 20, 2013.
Frank. "BARCRAWL and BARTAB: software tools for the design and implementation of barcoded primers for highly multiplexed DNA sequencing," BMC Bioinformatics, 10: 362 (2009).
Frederiksson et al., "Multiplex amplification of all coding sequences within 10 cancer genes by Gene-Collector", Nucleic Acids Research, 35(7): e47 (2007).
Freeman, et al. "Quantitative RT-PCR: Pitfalls and Potential", Biotechniques, 6(1): 112-125 (1999).
Freeman, J.D., et al. "Profiling the T-Cell Receptor Beta-Chain Repertoire by Massively Parallel Sequencing", Genome Research, 19(10):1817-1824 (2009). Epub Jun. 18, 2009.
Fridman, et al. "Prognostic and predictive impact of intra- and peritumoral immune infiltrates", Cancer Research, 71(17): 5601-5605 (2011). doi: 10.1158/0008-5472.CAN-11-1316. Epub Aug. 16, 2011.
Fritz et al. "Alterations in the spinal cord T cell repertoire during relapsing experimental autoimmune encephalomyelitis," J Immunol, 164:6662-6668 (2000).
Fu et al. "Counting individual DNA molecules by the stochastic attachment of diverse labels", PNAS, 108(22): 9026-9031 and Supporting Materials, 8 pages (2011).
Fuller, et al. "The challenges of sequencing by synthesis", Nat Biotechnol., 7(11): 1013-1023 (2009) (Abstract only). doi: 10.1038/nbt.1585. Epub Nov. 6, 2009.
Furmanski, et al. "Public T cell receptor β-chains are not advantaged during positive selection", The Journal of Immunology, 180(2): 1029-1039 (2008).
García-Castillo and Núñez, et al. "Detection of clonal immunoglobulin and T-cell receptor gene recombination in hematological malignancies: monitoring minimal residual disease", Cardiovascular & Haematological Disorders—Drug Targets, 9:124-135 (2009).
Gauss, et al. "Mechanistic constraints on diversity in human V(D)J recombination", Mol Cell Biol., 16(1):258-269 (1996).
Gawad, et al. "Massive evolution of the immunoglobulin heavy chain locus in children with B precursor acute lymphoblastic leukemia", Blood, 120(22):4407-4417 (2012). doi: 10.1182/blood-2012-05-429811. Epub Aug. 28, 2012.
Gerlinger and Swanton. "How Darwinian models inform therapeutic failure initiated by clonal heterogeneity in cancer medicine", British Journal of Cancer, 103(8):1139-1143 (2010). doi: 10.1038/sj.bjc.6605912. Epub Sep. 28, 2010.
Gerlinger, M. et al. "Ultra deep T cell receptor sequencing reveals the complexity and intratumour heterogeneity of T cell clones in renal cell carcinomas", Journal of Pathology, 231:424-432 (2013).
Germano, et al. "Clonality profile in relapsed precursor-B-ALL children by GeneScan and sequencing analyses. Consequences on minimal residual disease monitoring", Leukemia, 17(8):1573-1582 (2003).
Giannoni, et al. Allelic exclusion and peripheral reconstitution by TCR transgenic T cells arising from transduced human hematopoietic stem/progenitor cells, Mol Ther., 21(5):1044-1054 (2013). doi: 10.1038/mt.2013.8. Epub Feb. 5, 2013.
GIGA—Roche 454 FLX technology how it works. Fiche technique du Centre Interdisciplinaire de Genoproteomique Appliquee (Universite de Liege, Belgique). Accessed Oct. 15, 2014.
Gilbert, et al. "The isolation of nucleic acids from fixed, paraffin-embedded tissues—which methods are useful when?", PLoS One, 2(6):e537, 12 pages (2007).
Giuggio, et al. "Evolution of the intrahepatic T cell repertoire during chronic hepatitis C virus infection", Viral Immunology, 18(1):179-189 (2005).
Gloor et al. "Microbiome profiling by Illumina sequencing of combinatorial sequence-tagged PCR products," PLoS ONE, 5(10): e15406, 15 pages (2010).
Godelaine, et al. "Polyclonal CTL responses observed in melanoma patients vaccinated with dendritic cells pulsed with a MAGE-3.A1 peptide", J Immunol., 171(9):4893-4897 (2003).
Golembowski, et al. "Clonal evolution in a primary cutaneous follicle center B cell lymphoma revealed by single cell analysis in sequential biopsies", Immunobiology, 201(5):631-644 (2000).
Gomes, et al. "Single-tube nested PCR using immobilized internal primers for the identification of dengue virus serotypes", J Virol Methods., 145(1):76-9 (2007). Epub Jun. 15, 2007.
Gonzalez, et al. "Incomplete DJH rearrangements of the IgH gene are frequent in multiple myeloma patients: immunobiological characteristics and clinical implications", Leukemia, 17:1398-1403 (2003).
Gonzalez et al., "Incomplete DJH rearrangements as a novel tumor target for minimal residual disease quantitation in multiple myeloma using real-time PCR", Leukemia, 17:1051-1057 (2003).
Gonzalez, S.F., et al. "Trafficking of B Cell Antigen in Lymph Nodes", Ann. Rev. Immunol., 29: 215-233 (2011).
Gopalakrishnan, et al. "Unifying model for molecular determinants of the preselection Vβ repertoire", Proc Natl Acad Sci USA, 110(34):E3206-15 (2013). doi: 10.1073/pnas.1304048110. Epub Aug. 5, 2013.
Gorski, et al. "Circulating T cell repertoire complexity in normal individuals and bone marrow recipients analyzed by CDR3 size spectratyping. Correlation with immune status", J Immunol., 152(10):5109-5119 (1994).
Gottenberg, et al. "Markers of B-lymphocyte activation are elevated in patients with early rheumatoid arthritis and correlated with disease activity in the ESPOIR cohort", Arthritis Res Ther., 11(4): R114 (2009). doi: 10.1186/ar2773. Epub Jul. 23, 2009.
Gratama and Kern. "Flow cytometric enumeration of antigen-specific T lymphocytes", Cytometry A, 58(1): 79-86 (2004).
Gratama, et al. "Measuring antigen-specific immune responses", 2008 update. Cytometry A., 73(11): 971-974 (2008). doi: 10.1002/cyto.a.20655.
Green, et al. "Clonal diversity of Ig and T-cell-receptor gene rearrangements identifies a subset of childhood B-precursor acute lymphoblastic leukemia with increased risk of relapse", Blood, 92(3):952-958 (1998).
Greenberg, et al. "Profile of immunoglobulin heavy chain variable gene repertoires and highly selective detection of malignant clonotypes in acute lymphoblastic leukemia" J Leukoc Biol., 57(6):856-864 (1995).
Greenman, et al. "Patterns of somatic mutation in human cancer genomes", Nature, 446(7132): 153-158 (2007).
Gribben, JG. "Stem cell transplantation in chronic lymphocytic leukemia", Biol. Blood Marrow Transplant., 15(1 Suppl): 53-58 (2009). doi: 10.1016/j.bbmt.2008.10.022.
Grupp, et al. "Chimeric antigen receptor-modified T cells for acute lymphoid leukemia", N Engl J Med., 368(16):1509-1518 (2013). doi: 10.1056/NEJMoa1215134. Epub Mar. 25, 2013.
Grupp, et al. "Adoptive transfer of autologous T cells improves T-cell repertoire diversity and long-term B-cell function in pediatric patients with neuroblastoma", Clin Cancer Res., 18(24):6732-6741 (2012). doi: 10.1158/1078-0432.CCR-12-1432. Epub Oct. 23, 2012.
Gulliksen, et al. "Real-time nucleic acid sequence-based amplification in nanoliter volumes", Anal Chem., 76(1): 9-14, Abstract Only (2004).
Gunderson et al. "Decoding Randomly Ordered DNA Arrays", Genome Research, 14: 870-877 (2004).
Guo, et al. "Sequence changes at the V-D junction of the $V_H1$ heavy chain of anti-phosphocholine antibodies alter binding to and protection against Streptococcus pneumoniae", Int Immunol., 9(5):665-677 (1997).
Gupta, Pushpendra K. "Single-molecule DNA sequencing technologies for future genomics research", Trends Biotechnol., 26(11): 602-611 (2008). doi: 10.1016/j.tibtech.2008.07.003. Epub Aug. 21, 2008.
Gurrieri, et al. "Chronic lymphocytic leukemia B cells can undergo somatic hypermutation and intraclonal immunoglobulin $V_HDJ_H$ gene diversification", J Exp Med., 196(5):629-639 (2002).

(56) References Cited

OTHER PUBLICATIONS

Hadrup, et al. "Parallel detection of antigen-specific T-cell responses by multidimensional encoding of MHC multimers", *Nat Methods*, 6(7): 520-526 (2009) (Abstract Only). doi: 10.1038/nmeth.1345. Epub Jun. 21, 2009.
Halldórsdóttir, et al. "Application of BIOMED-2 clonality assays to formalin-fixed paraffin embedded follicular lymphoma specimens: superior performance of the IGK assays compared to IGH for suboptimal specimens", *Leukemia & Lymphoma*, 48(7): 1338-1343 (2007).
Hamady, et al. "Error-correcting barcoded primers for pyrosequencing hundreds of samples in multiplex", *Nature Methods*, 5(3):235-237 (2008). doi: 10.1038/nmeth.1184. Epub Feb. 10, 2008.
Han et al. "Immunorepertoire analysis by multiplex PCR amplification and high throughput sequencing", *The Journal of Immunology*, 182:42.6, 1 page (2009).
Hanahan, et al. "Hallmarks of cancer: the next generation", *Cell*, 144(5): 646-674 (2011). doi: 10.1016/j.cell.2011.02.013.
Harismendy et al. "Evaluation of next generation sequencing platforms for population targeted sequencing studies", *Genome Biology*, 10:R32, 13 pages (2009).
Harris et al. "Single-Molecule DNA Sequencing of a Viral Genome", *Science*, 320: 106-109 (2008).
Hathcock, et al. "ATM influences the efficiency of TCRβ rearrangement, subsequent TCRβ-dependent T cell development, and generation of the pre-selection TCRβ CDR3 repertoire", PLoS One, 8(4):e62188 (2013). doi: 10.1371/journal.pone.0062188. Print 2013.
Hawkins, et al. "Whole genome amplification—applications and advances", *Curr Opin Biotechnol.*, 13(1): 65-67 (2002).
He, et al. "IgH gene rearrangements as plasma biomarkers in Non-Hodgkin's lymphoma patients", *Oncotarget*, 2(3): 178-185 (2011).
Heger, M. "Studies Highlight Challenges of Immune Repertoire Sequencing's Clinical Applicability", available at http://www.genomeweb.com/sequencing/studies-highlight-challenges-immune-repertoire-sequencings-clinical-applicabilit?hq_e=el&hq_m=966798&hq_l=10&hq_v=2357e2f0b3. Accessed Apr. 6, 2011.
Heger. "Roche's 454 Eyes Immune Repertoire Sequencing as Key Application for Long-Read Platform". Feb. 2, 2010. 4 pages. http://www.genomeweb.com/print/932624.
Henegariu, O. et al., "Multiplex PCR: Critical Parameters and Step-By-Step Protocol," Biotechniques, Informa HealthCare, 23(3):504-511 (1997).
Hensel et al. "Simultaneous identification of bacterial virulence genes by negative selection", *Science*, 269(5222): 400-403 (1995).
Hill, et al. "Using ecological diversity measures with bacterial communities", *FEMS Microbiol Ecol.*, 43(1):1-11 (2003). doi: 10.1111/j.1574-6941.2003.tb01040.x.
Hirohata, et al. "Regulation of human B cell function by sulfasalazine and its metabolites", *Int Immunopharmacol.*, 2(5): 631-640, Abstract Only (2002).
Hodges, E. et al. "Diagnostic role of tests for T cell receptor (TCR) genes", *J Clin Pathol.*, 56(1): 1-11 (2003).
Holder and Lewis. "Phylogeny estimation: traditional and bayesian approaches", Nat Rev Genet., 4(4): 275-84 (2009).
Holt. "Q &A: BC cancer agency's Robert Halt on sequencing the immune repertoire in immune reconstitution," *Genome Web* (www.genomeweb.com) Jun. 30, 2009.
Holt and Jones. "The new paradigm of flow cell sequencing", *Genome Research*, 18:839-846 (2008).
Hoogenboom, et al. "Multi-subunit proteins on the surface of filamentous phage: methodologies for displaying antibody (Fab) heavy and light chains", *Nucleic Acids Res.*, 19(15): 4133-4137 (1991).
Hoogendoorn, et al. "Primary allogeneic T-cell responses against mantle cell lymphoma antigen-presenting cells for adoptive immunotherapy after stem cell transplantation", *Clin Cancer Res.*, 11(14): 5310-5318 (2005).
Hoos, et al. "Improved endpoints for cancer immunotherapy trials", *J Natl Cancer Inst.*, 102(18): 1388-1397 (2010). doi: 10.1093/jnci/djq310. Epub Sep. 8, 2010.
Hoover and Lubkowski. "DNAWorks: an automated method for designing oligonucleotides for PCR-based gene synthesis", *Nucleic Acids Res.*, 30(10): e43, 7 pages (2002).
Hosono, et al. "Unbiased whole-genome amplification directly from clinical samples", *Genome Res.*, 13(5): 954-964 (2003). Epub Apr. 14, 2003.
Hoven, et al. "Detection and isolation of antigen-specific B cells by the fluorescence activated cell sorter (FACS)", *J Immunol Methods*, 117(2): 275-284, Abstract Only, 2 pages (1989).
Howe, et al. "T cell receptor clonotype analysis of T cell responses: Diagnostic application of a clonotypic database", *Blood*, 102:Abstract 3918 (2003).
Huang, et al. "Isolation of cell-free DNA from maternal plasma using manual and automated systems", *Methods Mol Biol.*, 444: 203-208, Abstract Only (2008). doi: 10.1007/978-1-59745-066-9_15.
Huh, et al. "Microfluidics for flow cytometric analysis of cells and particles", *Physiol Meas.*, 26(3): R73-98, Abstract Only (2005). Epub Feb. 1, 2005.
Huijsmans, et al. "Comparative analysis of four methods to extract DNA from paraffin-embedded tissues: effect on downstream molecular applications", *BMC Res Notes*, 3:239, 9 pages (2010). doi: 10.1186/1756-0500-3-239.
Huse, et al. "Generation of a large combinatorial library of the immunoglobulin repertoire in phage lambda", *Science*, 246(4935): 1275-1281, Abstract Only (1989).
Huse et al. "Accuracy and quality of massively parallel DNA pyrosequencing", *Genome Biology*, 8: R143 (2007).
Hwang, H.Y. et al. "Identification of a Commonly used CDR3 Region of Infiltrating T Cells Expressing Vβ13 and Vβ15 Derived from Psoriasis Patients", *The Journal of Investigative Dermatology*, 120(3):359-364 (2003).
Iancu, et al. "Profile of a serial killer: cellular and molecular approaches to study individual cytotoxic T-cells following therapeutic vaccination", *J Biomed Biotechnol.*, 2011: 452606 (2011). doi: 10.1155/2011/452606. Epub Nov. 14, 2010.
Ilakovac, V., "Statistical hypothesis testing and some pitfalls." Biochemia Medica (2009); 19(1): 10-16, 4 pages. [online]. [Retrieved on Apr. 12, 2016]. Retrieved from the Internet: <URL:http://www.biochemia-medica.com/contentlstatistical-hypothesis-testing-and-some-pitfalls>PDF.
Illumina. Genome analyzer pipeline software version 1.0 user guide. Part #1004759, 176 pages (2008).
Illumina. Data Sheet: Sequencing. Genomic Sequencing. Pub. No. 770.2008-016 Reference states: "Current as of Jan. 30, 2009", 6 pages, Copyright 2010.
Illumina. Data Sheet, "TruSeq™ exome enrichment kit", 5 pages (2011).
Illumina Systems & Software, Technology Spotlight, DNA Sequencing with Solexa® Technology, Illumina, Inc., Pub. No. 770-2007-002, 4 pages (2007).
Illumina. "Technical Note: Systems and Software. Calling sequencing SNPs", 3 pages (2010).
Illumina. TruSeq Sample Preparation Kit and Data Sheet. Illumina, Inc., San Diego, CA, 4 pages (2011).
Ishii et al. "Isolation and expression profiling of genes upregulated in the peripheral blood cells of systemic lupus erythematosus patients," *DNA Research*, 12:429-439 (2005).
Jabara et al. "Accurate sampling and deep sequencing of the HIV-1 protease gene using a Primer ID", *PNAS*, 108(50): 20166-20171 (2011).
Jacobi et al. "Activated memory B cell subsets correlate with disease activity in systemic lupus erythematosus: delineation by expression of CD27, IgD, and CD95", *Arthritis & Rheumatism*, 58(6):1762-1773 (2008).
Jacobi et al. "Correlation between circulating CD27$^{high}$ plasma cells and disease activity in patients with systemic lupus erythematosus" *Arthritis & Rheumatism*, 48(5):1332-1342 (2003).

(56) References Cited

OTHER PUBLICATIONS

Jaffe, et al. "Classification of lymphoid neoplasms: the microscope as a tool for disease discovery", *Blood*, 112(12): 4384-4399 (2008). doi: 10.1182/blood-2008-07-077982.

Jalla, et al. "Enumeration of lymphocyte subsets using flow cytometry: Effect of storage before and after staining in a developing country setting", *Indian J Clin Biochem.*, 19(2): 95-99 (2004). doi: 10.1007/BF02894264.

Jena, et al. "Amplification of genes, single transcripts and cDNA libraries from one cell and direct sequence analysis of amplified products derived from one molecule", *J. Immunol. Methods*, 190:199-213 (1996).

Jochems and Schlom. "Tumor-infiltrating immune cells and prognosis: the potential link between conventional cancer therapy and immunity", *Exp Biol Med* (Maywood), 236(5): 567-579 (2011). doi: 10.1258/ebm.2011.011007. Epub Apr. 12, 2011.

Jones, et al. "Human autoimmunity after lymphocyte depletion is caused by homeostatic T-cell proliferation", Proc Natl Acad Sci USA, 110(50) :20200-20205 (2013). doi: 10.1073/pnas.1313654110. Epub Nov. 26, 2013.

Jung, et al. "Unraveling V(D)J recombination; insights into gene regulation", *Cell*, 116(2): 299-311 (2004).

Jurkat, Clone 6-1 (ATCC TIB-152) Webpage retrievable from the ATCC under http://www.lgcstandards-atcc.org/Products/All MB-152.aspx#characteristics. Accessed Oct. 14, 2014.

Kalinina, O. et al. "Nanoliter scale PCR with TaqMan detection", *Nucleic Acids Research*, 25(10):1999-2004 (1997).

Kalos, M. et al. "T Cells with Chimeric Antigen Receptors Have Potent Antitumor Effects and Can Establish Memory in Patients with Advanced Leukemia", *Science Translational Medicine*, 3(95ra73): 1-11 (2011).

Kanda, et al. "Immune recovery in adult patients after myeloablative dual umbilical cord blood, matched sibling, and matched unrelated donor hematopoietic cell transplantation", Biol Blood Marrow Transplant, 18(11):1664-1676 (2012). doi: 10.1016/j.bbmt.2012.06.005. Epub Jun. 12, 2012.

Kaplinski and Remm. "MultiPLX Automatic Grouping and Evaluation of PCR Primers", *Methods in Molecular Biology*, 402(PCR Primer Design):287-303 (2004).

Kato et al. "Analysis of accumulated T cell clonotypes in patients with systemic lupus erythematosus," *Arthritis & Rheumatism*, 43(12):2712-2721 (2000).

Katz, S.C. et al. "T Cell Infiltrate Predicts Long-Term Survival Following Resection of Colorectal Cancer Liver Metastases," Ann. Surg. Oncol., 16:2524-2530 (2009).

Kedzierska, et al. "Tracking phenotypically and functionally distinct T cell subsets via T cell repertoire diversity", *Mol Immunol.*, 45(3): 607-618 (2008). Epub Aug. 24, 2007.

Kehrl, J.H. et al. "Chemoattractant Receptor Signaling and Its Role in Lymphocyte Motility and Trafficking", *Current Topics in Microbiology and Immunology*, 334:107-127 (2009).

Kiianitsa, et al., "Development of Tools for T-Cell Repertoire Analysis (TCRB Spectratyping) for the Canine Model of Hematopoietic Cell Transplantation", *Blood*, ASH—Annual Meeting Abstracts, 110:Abstract 4873, 2 pages (2007).

Kim, et al. "An efficient and reliable DNA extraction method for preimplantation genetic diagnosis: a comparison of allele drop out and amplification rates using different single cell lysis methods", *Fertility and Sterility*, 92: 814-818 (2009).

Kim, et al. "Polony multiplex analysis of gene expression (PMAGE) in mouse hypertrophic cardiomyopathy", *Science*, 316(5830):1481-1484 (2007).

Kinde et al. "Detection and quantification of rare mutations with massively parallel sequencing," *PNAS*, 108(23): 9530-9535 and Supporting Information, 16 pages (2011).

Kircher, et al. "Improved base calling for the Illumine Genome Analyzer using machine learning strategies", *Genome Biol.*, 10(8): R83, 9 pages (2009). doi: 10.1186/gb-2009-10-8-r83. Epub Aug. 14, 2009.

Kirsch, et al. "Defining immunoglobulin somatic hypermutation in de novo diffuse large b-cell lymphoma patients: potential application prognosis and risk stratification", Presented for the 2014 ASH Annual Meeting. Poster. 1 page. Dec. 5-9, 2014.

Kirsch, et al. "High-throughput TCR sequencing provides added value in the diagnosis of cutaneous T-cell lymphoma", Presented for the 2014 ASH Annual meeting. Poster. 1 page. Dec. 5-9, 2014.

Kita, et al. "T cell receptor clonotypes in skin lesions from patients with systemic lupus erythematosus", *Journal of Investigative Dermatology*,110(1): 41-46 (1988).

Kivioja et al. "Counting absolute numbers of molecules using unique molecular identifiers," *Nature Methods*, 9(1): 72-76 (2012).

Klarenbeek, P.L. et al. "Deep sequencing of antiviral T-cell responses to HCMV and EBV in humans reveals a stable repertoire that is maintained for many years." PLoS Pathogens (2012); 8.9: e1002889.

Klarenbeek, P.L. et al. "Human T-cell memory consists mainly of unexpanded clones", *Immunology Letters*, 133: 42-48 (2010).

Klinger et al. "Combining next-generation sequencing and immune assays: a novel method for identification of antigen-specific T cells", PLoS One, 8(9): e74231, 1-9 (2013).

Klebanoff, et al. "Therapeutic cancer vaccines: are we there yet?", *Immunol Rev.*, 239(1): 27-44 (2011). doi: 10.1111/j.1600-065X.2010.00979.x.

Klenerman, et al. "Tracking T cells with tetramers: new tales from new tools", *Nat Rev Immunol.*, 2(4):263-272 (2002).

Kneba, M., et al. "Analysis of Rearranged T-cell Receptor β-Chain Genes by Polymerase Chain Reaction (PCR) DNA Sequencing and Automated High Resolution PCR Fragment Analysis", *Blood*, 86:3930-3937 (1995).

Kneba, et al. "Characterization of clone-specific rearrangement T-cell receptor gamma-chain genes in lymphomas and leukemias by the polymerase chain reaction and DNA sequencing", *Blood*, 84(2):574-581 (1994).

Kobari, et al. "T cells accumulating in the inflamed joints of a spontaneous murine model of rheumatoid arthritis become restricted to common clonotypes during disease progression", *Int Immunol.*, 16(1):131-138 (2004).

Koboldt et al., "VarScan: variant detection in massively parallel sequencing of individual and pooled samples", Bioinformatics, 25(17): 2283-2285 (2009).

Koch, et al. "Tumor infiltrating T lymphocytes in colorectal cancer: Tumor-selective activation and cytotoxic activity in situ," *Ann Surg.*, 244(6): 986-992; discussion 992-993 (2006).

Kojima et al. "PCR amplification from single DNA molecules on magnetic beads in emulsion: application for high-throughput screening of transcription factor targets", *Nucleic Acids Research*, 33: 17, e150, 9 pages (2005).

Kohlmann, et al. "Integration of next-generation sequencing into clinical practice: are we there yet?", *Semin Oncol.*, 39(1): 26-36, Abstract Only (2012). doi: 10.1053/j.seminoncol.2011.11.008.

Kou, et al. "T-Cell receptor Vbeta repertoire CDR3 length diversity differs within CD45RA and CD45RO T-cell subsets in healthy and human immunodeficiency virus-infected children", *Clin Diagn Lab Immunol.*, 7(6):953-9 (2000).

Krause et al. "Epitope-Specific Human Influenza Antibody Repertoires Diversify by B Cell Intraclonal Sequence Divergence and Interclonal Convergence", *The Journal of Immunology*, 187: 3704-3711 (2011).

Krueger, et al. "Large scale loss of data in low-diversity illumina sequencing libraries can be recovered by deferred cluster calling", *PLoS One*, 6(1): e16607, 7 pages (2011). doi: 10.1371/journal.pone.0016607.

Ku, et al. "Exome sequencing: dual role as a discovery and diagnostic tool", *Ann Neurol.*, 71(1):5-14, Abstract Only (2012). doi: 10.1002/ana.22647.

Kumar, et al. "PEG-labeled nucleotides and nanopore detection for single molecule DNA sequencing by synthesis", *Sci Rep.*, 2:684, 8 pages (2012). Epub Sep. 21, 2012.

Kwak, et al. "Induction of immune responses in patients with B-cell lymphoma against the surface-immunoglobulin idiotype expressed by their tumors", *N Engl J Med.*, 327(17):1209-1215 (1992).

(56) References Cited

OTHER PUBLICATIONS

Kyu et al. "Frequencies of human influenza-specific antibody secreting cells or plasmablasts post vaccination from fresh and frozen peripheral blood mononuclear cells", *Journal of Immunological Methods*, 340: 42-47 (2009).
Ladányi, A., et al. "Prognostic impact of B-cell density in cutaneous melanoma", *Cancer Immunol. Immunother*, 60(12): 1729-1738 (2011).
Ladetto, et al., "Next-generation sequencing and real-time quantitative PCR for minimal residual disease (MRD) detection using the immunoglobulin heavy chain variable region: A methodical comparison in acute lymphoblastic leukemia (ALL), mantle cell lymphoma (MCL) and multiple myeloma (MM)", *Blood*, vol. 120, No. 21, Abstract 788 (Conference Abstract), Entire Abstract (2012).
Ladetto, M. et al. "Real-time polymerase chain reaction in multiple myeloma: Quantitative analysis of tumor contamination of stem cell harvests", *Experimental Hematology*, 30:529-536 (2002).
Ladetto, M. et al. "Real-Time Polymerase Chain Reaction of Immunoglobulin Rearrangements for Quantitative Evaluation of Minimal Residual Disease in Multiple Myeloma", *American Society for Blood and Marrow Transplantation*, 6(3):241-253 (2000).
Landwehr-Kenzel, et al. "Novel GMP-compatible protocol employing an allogeneic B cell bank for clonal expansion of allospecific natural regulatory T cells", Am J Transplant., 14(3):594-606 (2014). doi: 10.1111/ajt.12629. Epub Jan. 27, 2014.
Langerak, et al. "Immunoglobulin/T-cell receptor clonality diagnostics", *Expert Opin. Med. Diagn.*, 1(3):451-461 (2007).
Langerak, et al. "Polymerase chain reaction-based clonality testing in tissue samples with reactive lymphoproliferations: usefulness and pitfalls. A report of the BIOMED-2 Concerted Action BMH4-CT98-3936", *Leukemia*, 21(2):222-229 (2007).
Laplaud et al. "Blood T-cell receptor β chain transcriptome in multiple sclerosis. Characterization of the T cells with altered CDR3 length distribution", *Brain*, 127:981-995 (2004).
Laplaud et al. "Serial blood T cell repertoire alterations in multiple sclerosis patients; correlation with clinical and MRI parameters", *Journal of Neuroimmunology*, 177(1-2):151-160 (2006).
Larimore, K., et al. "Shaping of Human Germline IgH Repertoires Revealed by Deep Sequencing", *The Journal of Immunology*, 189(6): 3221-3230 (2012).
Lassmann, et al. "Application of BIOMED-2 primers in fixed and decalcified bone marrow biopsies: analysis of immunoglobulin H receptor rearrangements in B-cell non-Hodgkin's lymphomas", *J Mol Diagn.*, 7(5): 582-591 (2005).
Lazareva-Ulitsky et al, "On the quality of tree-based protein classification," Bioinformatics, 21(9): 1876-1890 (2005).
Lee, et al. "Characterization of circulating T cells specific for tumor-associated antigens in melanoma patients", *Nat Med.*, 5(6): 677-685, Abstract Only (1999).
Lee, et al. "Prognostic implications of type and density of tumour-infiltrating lymphocytes in gastric cancer", *Br J Cancer*, 99(10): 1704-1711 (2008). doi: 10.1038/sj.bjc.6604738. Epub Oct. 21, 2008.
Lefranc. "IMGT, the international ImMunoGeneTics database", *Nucleic Acids Res.*, 31(1):307-310 (2003).
Leiden, J.M. et al. "The Complete Primary Structure of the T-Cell Receptor Genes From an Alloreactive Cytotoxic Human T-Lymphocyte Clone", Immunogenetics, 24(1): 17-23 (1986).
Leisner, et al. "One-pot, mix-and-read peptide-MHC tetramers", *PLoS One*, 3(2):e1678, 11 pages (2008). doi: 10.1371/journal.pone.0001678.
Lennon, et al. "A scalable, fully automated process for construction of sequence-ready barcoded libraries for 454", *Genome Biol.*, 11(2):R15, 9 pages (2010). doi: 10.1186/gb-2010-11-2-r15. Epub Feb. 5, 2010.
Leary, et al. "Development of personalized tumor biomarkers using massively parallel sequencing", Sci Transl Med., 2(20): 20ra14 (2010). doi: 10.1126/scitranslmed.3000702.
Leone, et al. "Molecular beacon probes combined with amplification by NASBA enable homogeneous, real-time detection of RNA", *Nucleic Acids Research*, 26(9): 2150-2155 (1998).
Leproust, et al. "Synthesis of high-quality libraries of long (150mer) oligonucleotides by a novel depurination controlled process", *Nucleic Acids Res.*, 38(8): 2522-2540 (2010). doi: 10.1093/nar/gkq163. Epub Mar. 22, 2010.
Lessin, et al. "Molecular diagnosis of cutaneous T-cell lymphoma: polymerase chain reaction amplification of T-cell antigen receptor beta-chain gene rearrangements", *J Invest Dermatol.*, 96(3): 299-302 (1991).
Li, et al. "Utilization of Ig heavy chain variable, diversity, and joining gene segments in children with B-lineage acute lymphoblastic leukemia: implications for the mechanisms of VDJ recombination and for pathogenesis", *Blood*, 103(12):4602-4609 (2004).
Li, et al. "An improved one-tube RT-PCR protocol for analyzing single-cell gene expression in individual mammalian cells", *Anal. Bioanal. Chem.*, 397: 1853-1859 (2010).
Li, et al. "β cell-specific CD4+ T cell clonotypes in peripheral blood and the pancreatic islets are distinct", *J Immunol.*, 183(11): 7585-7591 (2009). doi: 10.4049/jimmunol.0901587. Epub Nov. 16, 2009.
Li, et al. "Clonal rearrangements in childhood and adult precursor B acute lymphoblastic leukemia: a comparative polymerase chain reaction study using multiple sets of primers", *Eur J Haematol.*, 63(4):211-218 (1999).
Li, et al. "Detailed clonality analysis of relapsing precursor B acute lymphoblastic leukemia: implications for minimal residual disease detection", *Leukemia Research*, 25:1033-1045 (2001).
Li et al, "Mapping short DNA sequencing reads and calling variants using mapping quality scores," Genome Research, 18: 1851-1858 (2008).
Li, et al. "Sequence analysis of clonal immunoglobulin and T-cell receptor gene rearrangements in children with acute lymphoblastic leukemia at diagnosis and at relapse: implications for pathogenesis and for the clinical utility of PCR-based methods of minimal residual disease detection", *Blood*, 102:4520-4526 (2003).
Liedtke, et al. "A comparison of methods for RNA extraction from lymphocytes for RT-PCR", *PCR Methods and Applications*, 4(3): 185-187 (1994).
Lin, et al. "Multiplex genotype determination at a large number of gene loci", *Proc Natl Acad Sci USA*, 93(6): 2582-2587 (1996).
Liu, et al. "CD127 expression inversely correlates with FoxP3 and suppressive function of human CD4+ T reg cells", *J Exp Med.*, 203(7): 1701-1711 (2006). Epub Jul. 3, 2006.
Lo, et al. "T cell immunodominance is dictated by the positively selecting self-peptide", Elife, 3:e01457 (2014). doi: 10.7554/eLife.01457. Epub Jan. 14, 2014.
Logan, et al., "High-throughput immunoglobulin gene sequencing quantifies minimal residual disease in CLL with 10e-6 sensitivity and strongly predicts relapse after allogeneic hematopoietic cell transplantation", *Blood*, vol. 118 (21), Abstract 2542 (2011).
Logan, A.C. et al. "High-throughput VDJ sequencing for quantification of minimal residual disease in chronic lymphocytic leukemia and immune reconstitution assessment", *PNAS*, 108(52): 21194-21199 (2011). Epub Dec. 12, 2011.
Logan, et al., "Massively parallel immunoglobulin gene sequencing provides ultra-sensitive minimal residual disease detection and predicts post-transplant relapse in acute lymphoblastic leukemia by three to six months", *Blood*, vol. 118 (21), Abstract 4104 (2011).
Lorimer, I. A., and Pastan, Ira. "Random recombination of antibody single chain Fv sequences after fragmentation with DNaseI in the presence of Mn2+." Nucleic Acids Research (1995); 23.15: 3067-3068.
Lossos, et al. "Transformation of follicular lymphoma to diffuse large-cell lymphoma: alternative patterns with increased or decreased expression of c-myc and its regulated genes", *PNAS*, 99(13): 8886-8891 (2002). Epub Jun. 19, 2002.
Lovisa, et al. "IGH and IGK gene rearrangements as PCR targets for pediatric Burkitt's lymphoma and mature B-ALL MRD analysis", *Lab Invest.*, 89(10):1182-1186 (2009).
Lowe, T., et al., "A computer program for selection of oligonucleotide primers for polymerase chain reactions," Nucleic Acids Research, 18(7):1757-1761 (1990).
Lowman, et al. "Monovalent phage display: a method for selecting variant proteins from random libraries", *Methods: A Companion to Methods in Enzymology*, 3: 205-216, Abstract Only (1991).

(56) References Cited

OTHER PUBLICATIONS

Lúcio, P. et al. "Flow cytometric analysis of normal B cell differentiation: a frame of reference for the detection of minimal residual disease in precursor-B-ALL", Leukemia, 13:419-427 (1999).
Lyamichev, et al. "Polymorphism identification and quantitative detection of genomic DNA by invasive cleavage of oligonucleotide probes", Nat Biotechnol., 17(3): 292-396 (1999).
Luo et al. "Analysis of the interindividual conservation of T cell receptor α- and β-chain variable regions gene in the peripheral blood of patients with systemic lupus erythematosus", Clinical & Experimental Immunology, 154(3):316-324 (2008).
Mackay, et al. "Real-time PCR in virology", Nucleic Acids Res., 30(6): 1292-1305 (2002).
Mahmoud, S.M.A. et al. "Tumor-Infiltrating CD8+ Lymphocytes Predict Clinical Outcome in Breast Cancer", Journal of Clinical Oncology, 29(15): 1949-1955 (2011).
Maldonado, et al. "Intramuscular therapeutic vaccination targeting HPV16 induces T cell responses that localize in mucosal lesions", Sci Transl Med., 6(221): 221ra13 (2014). doi: 10.1126/scitranslmed. 3007323.
Malyguine, et al. "ELISPOT Assay for Monitoring Cytotoxic T Lymphocytes (CTL) Activity in Cancer Vaccine Clinical Trials", Cells, 1(2): 111-126 (2012). doi: 10.3390/cells1020111.
Manion et al., "Reducing Error in Next Generation Sequencing Data with NextGENe Software's Condensation Tool™", Mar. 2009, pp. 1-3.
Manrao, et al. "Reading DNA at single-nucleotide resolution with a mutant MspA nanopore and phi29 DNA polymerase", Nat Biotechnol., 30(4): 349-353 (2012). doi: 10.1038/nbt.2171.
Mar et al. "Inferring steady state single-cell gene expression distributions from analysis of mesoscopic samples", Genome Biology, 7(12): R119, 12 pages (2006).
Mardis. "Next-generation DNA sequencing methods", Annu. Rev. Genomics Hum. Genet., 9:387-402 (2008). doi: 10.1146/annurev. genom.9.081307.164359.
Marelli-Berg, F.M., et al. "Memory T-cell trafficking: new directions for busy commuters", Immunology, 130:158-165 (2010).
Margulies, et al. "Genome sequencing in microfabricated high-density picolitre reactors", Nature, 437(7057):376-380 (2005). Epub Jul. 31, 2005.
Mariani, S. et al., "Comprehensive assessment of the TCRBV repertoire in small T-cell samples by means of an improved and convenient multiplex PCR method" Experimental Hematology, 37(6):728-738 (2009).
Markoulatos, P. et al., "Multiplex Polymerase Chain Reaction: A Practical Approach", Journal of Clinical Laboratory Analysis, 16:47-51 (2002).
Marrero, et al. "High-throughput sequencing of islet-infiltrating memory CD4+T cells reveals a similar pattern of TCR Vβ usage in prediabetic and diabetic NOD mice", PLoS One, 8(10):e76546 (2013). doi: 10.1371/journal.pone.0076546. eCollection 2013.
Martin-Jimenez, et al. "Molecular characterization of heavy chain immunoglobulin gene rearrangements in Waldenström's macroglobulinemia and IgM monoclonal gammopathy of undetermined significance", Haematologica, 92(5): 635-642 (2007).
Mary et al. "Analysis of gene expression at the single-cell level using microdroplet-based microfluidic technology", Biomicrofluidics, 5: 024109-1-024109-10 (2011).
Maryanski, J.L. et al., "A quantitative, single-cell PCR analysis of an antigen-specific TCR repertoire 8 selected during an in vivo CD8 response: direct evidence for a wide range of clone sizes with uniform tissue distribution", Molecular Immunology, 36:745-753 (1999).
Maślanka, K. et al., "Molecular Analysis of T-Cell Repertoires: Spectratypes Generated by Multiplex Polymerase Chain Reaction and Evaluated by Radioactivity or Fluorescence", Human Technology, 44(1):28-34 (1995).
Mato et al. "Correlation of clonal T cell expansion with disease activity in systemic lupus erythematosus", Int Immunol., 9(4):547-554 (1997).

Matolcsy, et al. "Clonal evolution of B cells in transformation from low- to high-grade lymphoma", Eur. J. Immunol.,29(4):1253-1264 (1999).
Matsubara, et al. "Microchamber array based DNA quantification and specific sequence detection from a single copy via PCR in nanoliter volumes", Biosens Bioelectron, 20(8): 1482-1490, Abstract Only (2005).
Matsumoto et al. "CDR3 spectratyping analysis of the TCR repertoire in Myasthenia Gravis", The Journal of Immunology, 176:5100-5107 (2006).
Matsumoto et al. "Complementarity-determining region 3 spectratyping analysis of the TCR repertoire in multiple sclerosis", The Journal of Immunology, 170:4846-4853 (2003).
Mazor et al. "Antibody internalization studied using a novel IgG binding toxin fusion", Journal of Immunological Methods, 321: 41-59 (2007).
Mazumder, et al., "Detection of multiple myeloma cells in peripheral blood using high-throughput sequencing assay" Blood, vol. 120, No. 21, Abstract 321 (Conference Abstract), Entire Abstract (2012).
McCloskey et al. "Encoding PCR products with batch-stamps and barcodes," Biochem. Genet., 45: 761-767 (2007).
McGoldrick, et al. "Cytomegalovirus-specific T cells are primed early after cord blood transplant but fail to control virus in vivo", Blood, 121(14): 2796-803 (2013). doi: 10.1182/blood-2012-09-453720. Epub Feb. 14, 2013.
McLean et al. "Recognition of human cytomegalovirus by human primary immunoglobulins identifies an innate foundation to an adaptive immune response", J. Immunol., 174(8): 4768-4778 (2005).
Mei et al. "Blood-borne human plasma cells in steady state are derived from mucosal immune responses", Blood, 113(11): 2461-2469 (2009).
Meijer et al. "Isolation of Human Antibody Repertoires with Preservation of the Natural Heavy and Light Chain Pairing", J. Mol. Biol., 358: 764-772 (2006).
Meier, et al. "Fractal organization of the human T cell repertoire in health and after stem cell transplantation", Biol Blood Marrow Transplant., 19(3):366-77 (2013). doi: 10.1016/j.bbmt.2012.12.004. Epub Jan. 11, 2013.
Meier et al. "Simultaneous evaluation of T-cell and B-cell clonality, t(11;14) and t(14;18), in a single reaction by a four-color multiplex polymerase chain reaction assay and automated High-Resolution fragment analysis", American Journal of Pathology, 159(6): 2031-2043 (2001).
Meier, et al. "The influence of different stimulation conditions on the assessment of antigen-induced CD154 expression on CD4+ T cells", Cytometry A., (11):1035-1042 (2008). doi: 10.1002/cyto.a. 20640.
Meleshko, et al. "Rearrangements of IgH, TCRD and TCRG genes as clonality marker of childhood acute lymphoblastic leukemia", Experimental Oncology, 27(4):319-324 (2005).
Menezes et al. "A public T cell clonotype within a heterogeneous autoreactive repertoire is dominant in driving EAE", J Clin Invest, 117(8):2176-2185 (2007).
Merriam-Webster, 2 pages, (definition of "e.g.," accessed Apr. 25, 2014).
Merriam-Webster, 4 pages (definition of "substantial," accessed Apr. 25, 2014).
Metzker, "Sequencing Technologies—The Next Generation", Nature Reviews, Genetics, 11:31-46 (2010).
Meyer et al. "Targeted high-throughput sequencing of tagged nucleic acid samples", Nucleic Acids Research, 35(15): e97, 5 pages (2007).
Miceli and Parnes. "The roles of CD4 and CD8 in T cell activation", Seminars in Immunology, 3(3): 133-141 (1991). Abstract only.
Michálek, et al. "Detection and long-term in vivo monitoring of individual tumor-specific T cell clones in patients with metastatic melanoma", J Immunol., 178(11):6789-6795 (2007).
Michálek, et al. "Identification and monitoring of graft-versus-host specific T-cell clone in stem cell transplantation", The Lancet, 361(9364): 1183-1185 (2003).
Miller, et al., "Assembly algorithms for next-generation sequencing data", Genomics, 95(6): 315-327 (2010).

(56) References Cited

OTHER PUBLICATIONS

Miltenyi, et al. "High gradient magnetic cell separation with MACS", *Cytometry*, 11(2): 231-238 (1990).

Miner et al. "Molecular barcodes detect redundancy and contamination in hairpin-bisulfite PCR", *Nucleic Acids Research*, 32(17): e135, 4 pages (2004).

Miqueu, P. et al. "Statistical analysis of CDR3 length distributions for the assessment of T and B cell repertoire biases", *Molecular Immunology*, 44:1057-1064 (2007).

Mitra, et al. "Fluorescent in situ sequencing on polymerase colonies", *Anal Biochem.*, 320(1): 55-65, Abstract Only (2003).

Mittelstadl, et al. "Thymocyte responsiveness to endogenous glucocorticoids is required for immunological fitness", J Clin Invest., 122(7):2384-94 (2012). doi: 10.1172/JCI63067. Epub Jun. 1, 2012.

Miyashita, et al. "N-Methyl substituted 2',4'-BNANC: a highly nuclease-resistant nucleic acid analogue with high-affinity RNA selective hybridization", *Chem Commun* (Camb), (36): 3765-3767, Abstract Only (2007). Epub Jul. 9, 2007.

Moen, et al. "Immunoglobulin G and A antibody responses to Bacteroides forsyth and Prevotella intermedia in sera and synovial fluids of arthritis patients", *Clin Diagn Lab Immunol.*, 10(6): 1043-1050 (2003).

Molloy, et al. "Soluble T cell receptors: novel immunotherapies", *Curr Opin Pharmacol.*, 5(4): 438-443 (2005) (Abstract Only).

Monod, M.Y. et al. "IMGT/JunctionAnalysis: the first tool for the analysis of the immunogloblulin and T cell receptor complex V-J and V-D-J JUNCTIONs", *Bioinformatics*, 20(Suppl 1):i379-385 (2004).

Moody, et al. "Antigen-specific B cell detection reagents: use and quality control", *Cytometry A.*, 73(11): 1086-1092 (2008). doi: 10.1002/cyto.a.20599.

Morgan, et al. "Cancer regression in patients after transfer of genetically engineered lymphocytes", *Science*, 314(5796): 126-129 (2006). Epub Aug. 31, 2006.

Morozova et al. "Applications of New Sequencing Technologies for Transcriptome Analysis", *Annu. Rev. Genomics Hum. Genet.*, 10: 135-151 (2009).

Morrissy et al. "Next-generation tag sequencing for cancer gene expression profiling", *Genome Research*, 19: 1825-1835 (2009).

Moss, et al. "The human T cell receptor in health and disease", *Annu. Rev. Immunol.*, 10:71-96 (1992).

Moura, et al. "Alterations on peripheral blood B-cell subpopulations in very early arthritis patients", *Rheumatology* (Oxford), 49(6): 1082-1092 (2010). doi: 10.1093/rheumatology/keq029. Epub Mar. 7, 2010.

Mueller, et al. "Human Treg responses allow sustained recombinant adeno-associated virus-mediated transgene expression", J Clin Invest., 123(12): 5310-5318 (2013). doi: 10.1172/JCI70314. Epub Nov. 15, 2013.

Muraro et al. "Molecular tracking of antigen-specific T cell clones in neurological immune-mediated disorders", *Brain*, 126(Pt 1):20-31 (2003).

Muraro, et al. "T cell repertoire following autologous stem cell transplantation for multiple sclerosis", J Clin Invest, 124(3): 1168-1172 (2014). doi: 10.1172/JCI71691. Epub Feb. 17, 2014.

Murugan, et al. "Statistical inference of the generation probability of T-cell receptors from sequence repertoires", *PNAS*, 109(40): 16161-16166 (2012). doi: 10.1073/pnas.1212755109. Epub Sep. 17, 2012.

Naito, et al. "CD8+ T cells infiltrated within cancer cell nests as a prognostic factor in human colorectal cancer", *Cancer Research*, 58(16): 3491-3494 (1998).

Nakano, et al. "Single-molecule PCR using water-in-oil emulsion", *J Biotechnol.*, 102(2): 117-124, Abstract Only (2003).

Nardi, et al. "Quantitative monitoring by polymerase colony assay of known mutations resistant to ABL kinase inhibitors", *Oncogene*, 27(6):775-782 (2008). Epub Aug. 6, 2007, 1-8.

Navarrete, et al. "Upfront immunization with autologous recombinant idiotype Fab fragment without prior cytoreduction in indolent B-cell lymphoma", *Blood*, 117(5): 1483-1491 (2011). doi: 10.1182/blood-2010-06-292342. Epub Nov. 2, 2010.

Neale, et al. "Comparative analysis of flow cytometry and polymerase chain reaction for the detection of minimal residual disease in childhood acute lymphoblastic leukemia", *Leukemia*, 18(5):934-938 (2004).

Needleman and Wunsch. "A general method applicable to the search for similarities in the amino acid sequence of two proteins", *J Mol Biol.*, 48(3): 443-453 (1970).

Neller, et al. "High frequency of herpesvirus-specific clonotypes in the human T cell repertoire can remain stable over decades with minimal turnover", J Virol., 87(1): 697-700 (2013). doi: 10.1128/NI.02180-12. Epub Oct. 17, 2012.

Nelson. "CD20+ B cells: the other tumor-infiltrating lymphocytes", *The Journal of Immunology*, 185(9): 4977-4982 (2010). doi: 10.4049/jimmuno1.1001323.

Newman, et al. "Identification of an antigen-specific B cell population", *J Immunol Methods*, 272(1-2): 177-187, Abstract Only (2003).

Nguyen et al. "Identification of errors introduced during high throughput sequencing of the T cell receptor repertoire" *BMC Genomics*, 12: 106, 13 pages (2011).

Nicot, N. et al. "Housekeeping gene selection for real-time RT-PCR normalization in potato during biotic and abiotic stress", *Journal of Experimental Botany*, 56(421):2907-2914 (2005).

Nie, et al. "Optical detection of single molecules", *Annu. Rev. Biophys. Biomol. Struct.*, 26: 567-596 (1997).

Nielsen, et al. "Peptide nucleic acid (PNA). A DNA mimic with a pseudopeptide backbone", *Chem. Soc. Rev.*, 26:73-78, Abstract Only (1997).

Nolan, T. et al. "Quantification of mRNA using real-time RT-PCR", *Nature Protocols*, 1(3):1559-1582 (2006).

Nosho, et al. "Tumour-infiltrating T-cell subsets, molecular changes in colorectal cancer, and prognosis: cohort study and literature review", *J Pathol.*, 222(4): 350-366 (2010). doi: 10.1002/path.2774.

Novak, et al. "Single Cell Multiplex Gene Detection and Sequencing Using Microfluidically-Generated Agarose Emulsions", *Angew Chem Int Ed Engl.*, 50(2): 390-395, with supplemental materials (2011).

Nucleis product webpage, "Exonuclease I-Shrimp alkaline phosphatase clean up of PCR products," (Published on webpage 2013) Downloaded Dec. 15, 2015.

Oble, et al. "Focus on TILs: prognostic significance of tumor infiltrating lymphocytes in human melanoma", *Cancer Immunity*, 9: 3, 20 pages (2009).

O'Brian et al., "Sorting out mix-ups. The provenance of tissue sections may be confirmed by PCR using microsatellite markers", Am. J. Clin. Pathol., 106(6): 758-764 (1996). (Abstract Only).

Oelke, et al. "Ex vivo induction and expansion of antigen-specific cytotoxic T cells by HLA-Ig-coated artificial antigen-presenting cells", *Nat Med.*, 9(5): 619-624 (2003). Epub Apr. 21, 2003.

Ogle, et al. "Direct measurement of lymphocyte receptor diversity", *Nucleic Acids Research*, 31(22):e139, 6 pages (2003).

Ohlin, Mats, et al. "Light chain shuffling of a high affinity antibody results in a drift in epitope recognition." Molecular Immunology (1996); 33.1: 47-56.

Ohtani. "Focus on TILs: prognostic significance of tumor infiltrating lymphocytes in human colorectal cancer", *Cancer Immunity*, 7: 4, 9 pages (2007).

Okajima et al. "Analysis of T cell receptor Vβ diversity in peripheral $CD4^+$ and $CD8^+$ T lymphocytes in patients with autoimmune thyroid diseases", *Clinical & Experimental Immunology*, 155:166-172 (2008).

Okello et al. "Comparison of methods in the recovery of nucleic acids from archival formalin-fixed paraffin-embedded autopsy tissues", *Anal Biochem.*, 400(1): 110-117 (2010). doi: 10.1016/j.ab.2010.01.014. Epub Jan. 15, 2010.

Ottensmeier, et al. "Analysis of VH genes in follicular and diffuse lymphoma shows ongoing somatic mutation and multiple isotype transcripts in early disease with changes during disease progression", *Blood*, 91(11): 4292-4299 (1998).

(56) References Cited

OTHER PUBLICATIONS

Packer and Muraro. "Optimized clonotypic analysis of T-cell receptor repertoire in immune reconstitution", *Experimental Hematology,* 35(3):516-521 (2007).
Pagès, Franck. Tumor-associated immune parameters for personalized patient care. Sci Transl Med., 5(214):214fs42 (2013). doi: 10.1126/scitranslmed.3007942.
Palmowski, et al. "The use of HLA class I tetramers to design a vaccination strategy for melanoma patients", *Immunol Rev.,* 188: 155-163 (2002) (Abstract Only).
Palomaki, et al. "DNA sequencing of maternal plasma reliably identifies trisomy 18 and trisomy 13 as well as Down syndrome: an international collaborative study", *Genet. Med.,* 14(3): 296-305 (2012). doi: 10.1038/gim.2011.73. Epub Feb. 2, 2012.
Pan, et al. "A new FACS approach isolates hESC derived endoderm using transcription factors", *PLoS One,* 6(3): e17536, 9 pages (2011). doi: 10.1371/journal.pone.0017536.
Panzer-Grümayer et al. "Immunogenotype changes prevail in relapses of young children with TEL-AML1-positive acute lymphoblastic leukemia and derive mainly from clonal selection", *Clin Cancer Research,* 11(21):7720-7727 (2005).
Parameswaran et al. "A pyrosequencing-tailored nucleotide barcode design unveils opportunities for large-scale sample multiplexing", *Nucleic Acids Research,* 35(19): e130, 9 pages (2007).
Parmigiani, et al. "Design and analysis issues in genome-wide somatic mutation studies of cancer", *Genomics,* 93(1): 17-21 (2009). doi: 10.1016/j.ygeno.2008.07.005. Epub Aug. 23, 2008.
Pasqual et al. "Quantitative and qualitative changes in V-J alpha rearrangements during mouse thymocytes differentiation: implication for a limited T cell receptor alpha chain repertoire", *Journal of Experimental Medicine,* 196(9): 1163-1173 (2002). XP002322207 ISSN: 0022-1007.
Paszkiewicz et al, "De novo assembly of short sequence reads," Briefings in Bioinformatics, 11(5): 457-472 (2010).
Payne, et al. "Peripheral blood mononuclear cells of patients with breast cancer can be reprogrammed to enhance anti-HER-2/neu reactivity and overcome myeloid-derived suppressor cells", Breast Cancer Res Treat., 142(1):45-57 (2013). doi: 10.1007/s10549-013-2733-5. Epub Oct. 25, 2013.
Peet. "The Measurement of Species Diversity", *Annual Review of Ecology and Systematics,* 5: 285-307, Abstract Only (1974).
Petrosino, et al. "Metagenomic pyrosequencing and microbial identification", *Clin Chem.,* 55(5): 856-866 (2009). doi: 10.1373/clinchem. 2008.107565. Epub Mar. 5, 2009.
PCT/US2009/006053, International Search Report dated Jun. 15, 2010, 6 pages.
PCT/US2009/006053, Written Opinion dated Jun. 15, 2010, 4 pages.
PCT/US2009/006053, International Preliminary Report on Patentability dated May 10, 2011, 5 pages.
PCT/US2010/021264, International Search Report and Written Opinion dated Apr. 14, 2010, 7 pages.
PCT/US2010/021264, International Preliminary Report on Patentability dated Jul. 19, 2011, 5 pages.
PCT/US2016/019343, International Search Report and Written Opinion dated Jul. 22, 2016, 23 pages.
PCT/US2016/025535, International Search Report and Written Opinion dated Jul. 11, 2016, 9 pages.
PCT/US2010/037477, International Search Report and Written Opinion dated Sep. 24, 2010, 10 pages.
PCT/US2010/037477, International Preliminary Report on Patentability dated Jan. 4, 2012, 7 pages.
PCT/US2011/000791, International Search Report and Written Opinion dated Sep. 22, 2011, 13 pages.
PCT/US2011/000791, International Preliminary Report on Patentability dated Nov. 6, 2012, 10 pages.
PCT/US2011/049012, International Search Report and Written Opinion dated Apr. 10, 2012, 9 pages.
PCT/US2011/049012, International Preliminary Report on Patentability dated Feb. 26, 2013, 5 pages.
PCT/US2013/028942, International Search Report and Written Opinion dated May 9, 2013, 10 pages.
PCT/US2013/028942, International Preliminary Report on Patentability dated May 5, 2015, 9 pages.
PCT/US2013/054189, International Search Report and Written Opinion dated Oct. 21, 2013, 10 pages.
PCT/US2013/054189, International Preliminary Report on Patentability dated Feb. 10, 2015, 7 pages.
PCT/US2013/035857, International Search Report and Written Opinion dated Aug. 7, 2013, 10 pages.
PCT/US2013/035857, International Preliminary Report on Patentability dated Oct. 14, 2014, 8 pages.
PCT/US2013/040221, International Search Report and Written Opinion dated Sep. 23, 2013, 15 pages.
PCT/US2013/040221, International Preliminary Report on Patentability dated Apr. 24, 2014, 41 pages.
PCT/US2013/045276, International Search Report and Written Opinion dated Jan. 29, 2014, 11 pages.
PCT/US2013/045276, International Preliminary Report on Patentability dated Dec. 16, 2014, 2014, 7 pages.
PCT/US2013/045994, International Search Report and Written Opinion dated Oct. 25, 2013, 15 pages.
PCT/US2013/045994, International Preliminary Report on Patentability dated Dec. 16, 2014, 10 pages.
PCT/US2013/051539, International Search Report and Written Opinion dated Nov. 27, 2013, 9 pages.
PCT/US2013/051539, International Preliminary Report on Patentability dated Jan. 27, 2015, 7 pages.
PCT/US2014/030859, International Search Report and Written Opinion dated Jul. 18, 2014, 14 pages.
PCT/US2014/030859, International Preliminary Report on Patentability dated Sep. 15, 2015, 8 pages.
PCT/US2014/044971, International Search Report and Written Opinion dated Oct. 30, 2014, 14 pages.
PCT/US2014/044971, International Preliminary Examination Report dated Jan. 6, 2016, 12 pages.
PCT/US2015/018967, International Search Report and Written Opinion dated Jul. 30, 2015, 17 pages.
PCT/US2015/018967, International Preliminary Report on Patentability dated Oct. 18, 2016, 11 pages.
PCT/US2015/019029, International Search Report and Written Opinion dated Sep. 15, 2015, 19 pages.
PCT/US2015/019029, International Preliminary Report on Patentability dated Sep. 6, 2016, 14 pages.
PCT/US2015/023915, International Search Report and Written Opinion dated Aug. 26, 2015, 11 pages.
PCT/US2015/023915, International Preliminary Report on Patentability dated Oct. 4, 2016, 7 pages.
PCT/US2015/058035, International Search Report and Written Opinion dated Jan. 29, 2016, 14 pages.
PCT/US2015/058035, International Preliminary Report on Patentability dated May 2, 2017, 8 pages.
Pekin, D. et al. "Quantitative and sensitive detection of rare mutations using droplet-based microfluidics", *Lab Chip,* 11(3): 2156-2166 (2011).
Pels et al. "Clonal evolution as pathogenetic mechanism in relapse of primary CNS lymphoma", *Neurology,* 63(1):167-169 (2004).
Perkel, J. "Overcoming the Challenges of Multiplex PCR", *Biocompare Editorial Article,* Oct. 23, 2012, 6 Pages, can be retrieved at URL:http://www.biocompare.com/Editorial-Articles/117895-Multiplex-PCR/>.
Pira et al. "Human naive CD4 T-cell clones specific for HIV envelope persist for years in vivo in the absence of antigenic challenge", *J Acquir Immune Defic Syndr.,* 40(2):132-139 (2005).
Plasilova et al. "Application of the Molecular Analysis of the T-Cell Receptor Repertoire in the Study of Immune-Mediated Hematologic Diseases", *Hematology,* 8(3): 173-181 (2003).
Pohl, G. and Shih. "Principle and applications of digital PCR", *Expert Rev. Mol. Diagn.,* 4(1):41-47 (2004).
Polstra, et al. "Development of real-time NASBA assays with molecular beacon detection to quantify mRNA coding for HHV-8 lytic and latent genes", *BMC Infect Dis.,* 2: 18 (2002). Epub Sep. 4, 2002.

(56) References Cited

OTHER PUBLICATIONS

Pop and Salzberg. "Bioinformatics challenges of new sequencing technology", *NIH, Trends Genet.*, 24(3): 142-149 (2008).
Pourmand, et al. "Direct electrical detection of DNA synthesis", *PNAS*, 103(17): 6466-6470 (2006). Epub Apr. 13, 2006.
Polz and Cavanaugh. "Bias in Template-to-Product Ratios in Multitemplate PCR", *Applied and Environmental Microbiology*, 64(10): 3724-3730 (1998).
Porter, et al. "Chimeric antigen receptor-modified T cells in chronic lymphoid leukemia", *N Engl J Med.*, 365(8):725-33 (2011). doi: 10.1056/NEJMoa1103849. Epub Aug. 10, 2011.
Prabakaran et al. "454 antibody sequencing—error characterization and correction", *BMC Research Notes*, 4: 404 (2011).
Puisieux, I. et al., "Oligoclonality of Tumor-Infiltrating Lymphocytes from Human Melanomas," The Journal of Immunology, 153:2807-2818 (1994).
Putnam, et al. "Clinical grade manufacturing of human alloantigen-reactive regulatory T cells for use in transplantation", Am J Transplant., 13(11): 3010-3020 (2013). doi: 10.1111/ajt.12433. EpubSep. 18, 2013.
Qiu et al. "DNA sequence-based "bar codes" for tracking the origins of expressed sequence tags from a maize cDNA library constructed using multiple mRNA sources", *Plant Physiology*, 133(2): 475-481 (2003).
Qu et al. "Efficient frequency-based de novo short-read clustering for error trimming in next-generation sequencing", *Genome Research*, 19: 1309-1315 (2009).
Quick. SOLiD System—a next-gen DNA sequencing platform announced, Gizmag online magazine, http://www.mizmag.com/go/8248, pp. 1-5, Oct. 2007.
Quince et al. "Removing Noise From Pyrosequenced Amplicons", *BMC Informatics*, 12: 38 (2011).
Ramesh, et al. "Clonal and constricted T cell repertoire in Common Variable Immune Deficiency", Clin Immunol., pii: S1521-6616(15)00004-2 (2015). doi: 10.1016/j.clim.2015.01.002. [Epub ahead of print].
Ramsden, et al. "V(D)J recombination: Born to be wild", *Semin Cancer Biol.*, 20(4): 254-260 (2010). doi: 10.1016/j.semcancer.2010.06.002. Epub Jul. 1, 2010.
Rasmussen, T. et al. "Quantitation of minimal residual disease in multiple myeloma using an allele-specific real-time PCR assay", *Experimental Hematology*, 28:1039-1045 (2000).
Ray, et al. "Single cell multiplex PCR amplification of five dystrophin gene exons combined with gender determination", *Molecular Human Reproduction*, 7(5): 489-494 (2001).
Reddy, et al. "Monoclonal antibodies isolated without screening by analyzing the variable-gene repertoire of plasma cells", *Nature Biotechnology*, 28(9): 965-969 (2010). doi: 10.1038/nbt.1673. Epub Aug. 29, 2010.
Reddy and Georgiou. "Systems analysis of adaptive immunity by utilization of high-throughput technologies", *Current Opinion in Biotechnology*, 22(4): 584-589 (2011).
Reinartz et al. "Massively parallel signature sequencing (MPSS) as a tool for in-depth quantitative gene expression profiling in all organisms", *Brief Funct Genomic Proteomic.*, 1(1):95-104 (2002).
Reischl and Kochanowski. "Quantitative PCR. A Survey of the Present Technology", *Molecular Biotechnology*, 3:55-71 (1995).
Ria, et al. "Collagen-specific T-cell repertoire in blood and synovial fluid varies with disease activity in early rheumatoid arthritis", *Arthritis Res Ther.*, 10(6):R135, 18 pages (2008). Epub Nov. 17, 2008.
Rickinson and Moss. "Human cytotoxic T lymphocyte responses to Epstein-Barr virus infection", *Annu Rev Immunol.*, 15:405-431 (1997).
Rieder, et al. "A normalization procedure for removal of residual multiplex PCR amplification bias from ultra-deep sequencing of the TCR repertoire", (Program #530W). Presented at the 62nd Annual Meeting of the American Society of Human Genetics, Nov. 7, 2012 in San Francisco, California. 2 pages.
Rieder, et al. "A normalization procedure for removal of residual multiplex PCR amplification bias from ultra-deep sequencing of the TCR repertoire", Presented at the Annual Meeting of the American Society of Hematology 2012 in Atlanta, Georgia Dec. 8-11, 2012. Poster. 1 page.
Risitano et al. "In-vivo dominant immune responses in aplastic anaemia: molecular tracking of putatively pathogenetic T-cell clones by TCRβ-CDR3 sequencing", *Lancet*, 364:355-364 (2004).
Robert, et al. "CTLA4 blockade broadens the peripheral T-cell receptor repertoire", Clin Cancer Res., 20(9):2424-32 (2014). doi: 10.1158/1078-0432.CCR-13/2648. Epub Feb. 28, 2014.
Robins, H. et al. "Ultra-sensitive detection of rare T cell clones", *Journal of Immunological Methods*, 375(1-2): 14-19 (2012). Epub Sep. 10, 2011.
Robins, et al. "CD4+ and CD8+ T cell β antigen receptors have different and predictable V and J gene usage and CDR3 lengths", *J. Immunol.*, 188: 115.10, Abstract (2012).
Robins et al. "Detecting and monitoring lymphoma with high-throughput sequencing" *Oncotarget*, 2:287-288 (2011).
Robins, H. et al. "Digital Genomic Quantification of Tumor Infiltrating Lymphocytes", *Science Translational Medicine*, 5:214ra169, 19 pages, Supplementary Materials (2013).
Robins, H. et al. "Comprehensive assessment of T-cell receptor β-chain diversity in αβ T cells", *Blood*, 114(19):4099-4107 (and Supplemental Materials) (2009).
Robins, et al. "Effects of aging on the human adaptive immune system revealed by high-throughput DNA sequencing of T cell receptors", *J Immunol.*, 188: 47.16, Abstract (2012).
Robins, et al. "High-throughput sequencing of T -cell receptors." Sep. 2010. Poster. 1 page.
Robins, et al. "Immune profiling with high-throughput sequencing." Presented for the ASHI 2011 conference. Oct. 2011. Poster. 1 page.
Robins, et al. "Immunosequencing: applications of immune repertoire deep sequencing", *Curr Opin Immunol.*, 25(5): 646-652 (2013). doi: 10.1016/j.coi.2013.09.017. Epub Oct. 16, 2013.
Robins, H. et al. "Overlap and Effective Size of the Human CD8+T Cell Receptor Repertoire", *Science Transitional Medicine*, 2(47, 47ra64):17 pages, Supplemental Materials (2010).
Robins, et al. "Overlap of the human CD8+ T cell receptor repertoire." Oct. 2010. Poster. 1 page.
Robins. "Overlap and effective size of the human CD8+ T cell repertoire", Keystone Symposia held Oct. 27, 2010 to Nov. 1, 2010. Immunological Mechanisms of Vaccination (Abstract). Available online Sep. 27, 2010, 1 page.
Robins, H. et al. "The Computational Detection of Functional Nucleotide Sequence Motifs in the Coding Regions of Organisms", *Exp Biol Med*, 233(6): 665-673 (2008).
Rock, E.P. et al. "CDR3 Length in Antigen-specific Immune Receptors", *J. Exp. Med.*, 179:323-328 (1994).
Ronaghi, et al. "A sequencing method based on real-time pyrophosphate", *Science*, 281(5375): 363, 365, 5 pages (1998).
Rosenberg, S.A. et al. "New Approach to the Adoptive Immunotherapy of Cancer with Tumor-Infiltrating Lymphocytes", *Science*, 233(4770): 1318-1321 (1986).
Rosenquist, et al. "Clonal evolution as judged by immunoglobulin heavy chain gene rearrangements in relapsing precursor-B acute lymphoblastic leukemia", *Eur J Haematol.*, 63(3):171-179 (1999).
Roshal, M. et al. "Immaturity Associated Antigens Are Lost During Induction for T Cell Lymphoblastic Leukemia: Implications for Minimal Residual Disease Detection", *Cytometry Part B (Clinical Cytometry)*, 78:139-146 (2010).
Rothberg, et al. "An integrated semiconductor device enabling non-optical genome sequencing", *Nature*, 475(7356): 348-352 (2011). doi: 10.1038/nature10242.
Rothberg et al. "The development and impact of 454 sequencing", *Nature Biotechnology*, 26(10): 1117-1124 (2008).
Rougemont, et al. "Probabilistic base calling of Solexa sequencing data", *BMC Bioinformatics*, 9:431, 12 pages (2008).
Rozen, S. et al. "Primer3 on the WWW for General Users and for Biologist Programmers", *Methods in Molecular Biology, Bioinformatics Methods and Protocols*, 132:365-386 (2000).
Ryan et al. "Clonal evolution of lymphoblastoid cell lines", *Laboratory Investigation*, 86(11):1193-1200 (2006). Epub Oct. 2, 2006.

(56) References Cited

OTHER PUBLICATIONS

Saada, R. et al. "Models for antigen receptor gene rearrangement: CDR3 length", *Immunology and Cell Biology*, 85:323-332 (2007).

Salzberg. "Mind the gaps", *Nature Methods*, 7(2): 105-106 (2010).

Sanchez-Freire et al. "Microfluidic single-cell real-time PCR for comparative analysis of gene expression patterns", *Nature Protocols*, 7(5): 829-838 (2012).

Sandberg et al. "BIOMED-2 Multiplex Immunoglobulin/T-Cell Receptor Polymerase Chain Reaction Protocols Can Reliably Replace Southern Blot Analysis in Routine Clonality Diagnostics", *J. Molecular Diagnostics*, 7(4): 495-503 (2005).

Sandberg, et al. "Capturing whole-genome characteristics in short sequences using a naïve Bayesian classifier", *Genome Res.*, 11(8): 1404-9 (2001).

Santalucia, Jr., J. "Physical Principles and Visual-OMP Software for Optimal PCR Design," *Methods in Molecular Biology*, 402(PCR Primer Design):3-33, 40 pages (2007).

Santamaria, P. et al. "Beta-Cell-Cytotoxic CD8 T Cells from Nonobese Diabetic Mice Use Highly Homologous T Cell Receptor a-Chain CDR3 Sequences", *The Journal of Immunology*, 154(5):2494-2503 (1995).

Sartorius Stedim Biotech product brochure, "Primer removal after a PCR reaction with Vivacon® 2", (2010).

Sato et al. "Intraepithelial CD8+ tumor-infiltrating lymphocytes and a high CD8+/regulatory T cell ratio are associated with favorable prognosis in ovarian cancer", *PNAS*, 102(51): 18538-18543 (2005). Epub Dec. 12, 2005.

Satoh et al. "Pretreatment with restriction enzyme or bovine serum albumin for effective PCR amplification of Epstein-Barr virus DNA in DNA extracted from paraffin-embedded gastric carcinoma tissue", *J Clin Microbiol.*, 36(11): 3423-3425 (1998).

Schaufelberger et al. "An uneven expression of T cell receptor V genes in the arterial wall and peripheral blood in giant cell arteritis", *Inflammation*, 31(6):372-383 (2008).

Schlissel, M.S. et al. "Leukemia and lymphoma: a cost of doing business for adaptive immunity", *Genes Dev.*, 20(12): 1539-1544 (2006).

Schloss, PD et al. Reducing the Effects of PCR Amplification and Sequencing Artifacts on 16S Rrna-Based Studies. PLoS One. Dec. 14, 2011, vol. 6, No. 12; e27310; DOI: 1 0.1371/journal.pone.0027310.

Schmitt et al. "Detection of ultra-rare mutations by next-generation sequencing," *PNAS*, 109(36): 14508-14513 and Supporting Information, 9 pages (2012).

Schøller et al. "Analysis of T cell receptor αβ variability in lymphocytes infiltrating melanoma primary tumours and metastatic lesions", *Cancer Immunol Immunother.* 39(4):239-248 (1994).

Schrappe, M. et al. "Late MRD response determines relapse risk overall and in subsets of childhood T-cell ALL: results of the AIEOP-BFM-ALL 2000 study", *Blood*, 118(8): 2077-2084 (2011).

Schreiber et al. "Cancer immunoediting: integrating immunity's roles in cancer suppression and promotion", *Science*, 331(6024): 1565-1570 (2011). doi: 10.1126/science.1203486.

Schwab et al. "CD8+ T-cell clones dominate brain infiltrates in Rasmussen encephalitis and persist in the periphery", *Brain*, 132:1236-1246 (2009).

Schwartzman, Armin. "Empirical null and false discovery rate inference for exponential families." The Annals of Applied Statistics (2008); 2(4): 1332-1359.

Schweiger et al. "Genome-wide massively parallel sequencing of formaldehyde fixed-paraffin embedded (FFPE) tumor tissues for copy-number- and mutation-analysis", *PLoS One*, 4(5): e5548, 7 pages (2009). doi: 10.1371/journal.pone.0005548. Epub May 14, 2009.

Chinese Patent Application No. 201510054401.X, Search Report dated Jul. 14, 2016, 2 pages.

Sebastian, E. et al., "Molecular Characterization of immunoglobulin gene rearrangements in diffuse large B-cell lymphoma", *Am. J. Pathol.*, 181: 1879-1888, Abstract (2012). (Epub: Sep. 28, 2012).

Sehouli et al. "Epigenetic quantification of tumor-infiltrating T-lymphocytes" *Epigenetics*, 6(2): 236-246 (2011). Epub Feb. 1, 2011.

Seitz, et al. "Reconstitution of paired T cell receptor α- and β-chains from microdissected single cells of human inflammatory tissues", *PNAS*, 103: 12057-12062 (2006).

Seo, et al. "Four-color DNA sequencing by synthesis on a chip using photocleavable fluorescent nucleotides", *PNAS*, 102(17): 5926-5931 (2005). Epub Apr. 13, 2005.

Sequenta and iRepertoire Join Forces on Blood Cancer Testing. Business Wire. Aug. 8, 2013. http://www.businesswire.com/news/home/20130808005363/en/SequentaiRepertoire-Join-Forces-Blo . . . #.VGTT9W dOyUk. 2 pages.

Sfanos et al. "Human Prostate-Infiltrating CD8+ T Lymphocytes are Oligoclonal and PD-1+", *The Prostate*, 69(15): 1694-1703 (2009).

Sfanos et al. "Phenotypic analysis of prostate-infiltrating lymphocytes reveals TH17 and Treg skewing", *Clinical Cancer Research*, 14(11):3254-3261 (2008). doi: 10.1158/1078-0432.CCR-07-5164.

Shen et al. "Comparing platforms for C. elegans mutant identification using high-throughput whole-genome sequencing", *PLoS One*, 3(12):e4012, 6 pages (2008).

Shendure, et al. "Accurate multiplex polony sequencing of an evolved bacterial genome", *Science*, 309(5741): 1728-1732, Abstract Only (2005). Epub Aug. 4, 2005.

Shendure, et al. "Advanced sequencing technologies: methods and goals", *Nat Rev Genet.*, 5(5): 335-344 (2004).

Shendure and Ji. "Next-generation DNA sequencing", *Nature Biotechnology*, 26(10):1135-1145 (2008).

Sherwood, A. et al. "Deep Sequencing of the Human TCRγ and TCRβ Repertoires Suggests that TCR β Rearranges After αβ and γδ T Cell Commitment", Science Translational Medicine, *Sci. Transl. Med.*, 3(90): 1-7 (2011).

Sherwood, et al. "New Technologies for Measurements of Tumor Infiltrating Lymphocytes", Presented Nov. 7, 2012 Moscone Center, Exhibit Halls ABC.

Sherwood, et al. "Tumor-infiltrating lymphocytes in colorectal tumors display a diversity of T cell receptor sequences that differ from the T cells in adjacent mucosal tissue", Cancer Immunol Immunother., 62(9):1453-61 (2013). doi: 10.1007/s00262-013-1446-2. Epub Jun. 16, 2013.

Shino, et al. "Usefulness of immune monitoring in lung transplantation using adenosine triphosphate production in activated lymphocytes", *The Journal of Heart and Lung Transplant*, 31: 996-1002 (2012).

Shiroguchi et al. "Digital RNA sequencing minimizes sequence-dependent bias and amplification noise with optimized single-molecule barcodes", *PNAS*, 109(4): 1347-1352 (2012).

Shoemaker et al. "Quantitative phenotypic analysis of yeast deletion mutants using a highly parallel molecular bar-coding strategy," *Nature Genetics*, 14(4): 450-456 (1996).

Shumaker, et al. "Mutation detection by solid phase primer extension", *Hum Mutat.*, 7(4): 346-354, Abstract Only (1996).

Sia, et al. "Microfluidic devices fabricated in poly(dimethylsiloxane) for biological studies", *Electrophoresis*, 24(21): 3563-3576, Abstract Only (2003).

Silver, N. et al. "Selection of housekeeping genes for gene expression studies in human reticulocytes using real-time PCR", *BMC Molecular Biology*, 7(33):1-9 (2006).

Sims, et al. "Fluorogenic DNA sequencing in PDMS microreactors", *Nat Methods*, 8(7): 575-580 (2011). doi: 10.1038/nmeth.1629.

Sims, et al. "MHC-peptide tetramers for the analysis of antigen-specific T cells", *Expert Rev Vaccines*, 9(7): 765-774 (2010). doi: 10.1586/erv.10.66.

Sing et al. "A molecular comparison of T Lymphocyte populations infiltrating the liver and circulating in the blood of patients with chronic hepatitis B: evidence for antigen-driven selection of a public complementarity-determining region 3 (CDR3) motif", *Hepatology*, 33(5):1288-1298 (2001).

Singapore Application No. 11201407888R, Written Opinion dated Aug. 14, 2015, 12 pages.

Singapore Application No. 11201500313Y, Search Report and Written Opinion dated Dec. 9, 2015, 11 pages.

(56) References Cited

OTHER PUBLICATIONS

Sint, D., et al. "Advances in multiplex PCR: balancing primer efficiencies and improving detection success", *Methods in Ecology and Evolution*, 3(5): 898-905 (2012).
Skulina et al. "Multiple Sclerosis: Brain-infiltrating CD8+ T cells persist as clonal expansions in the cerebrospinal fluid and blood", *PNAS*, 101(8):2428-2433 (2004).
Slightom, J.L. et al. "*Homo sapiens* germline beta T-cell receptor locus", NCBI Accession No. L36092 NCBI, 254 pages (2009) Retrieved from the Internet: <URL:http://www.ncbi.nlm.nih.gov/nuccore/L36092>.
Smith, et al. "Comparison of biosequences", *Advances in Applied Mathematics*, 2: 482-489 (1981).
Smith et al. "Rapid generation of fully human monoclonal antibodies specific to a vaccinating antigen", *Nature Protocols*, 4(3): 372-384 and CORRIGENDA (2009).
Smith et al. "Rapid whole-genome mutational profiling using next-generation sequencing technologies", *Genome Research*, 18: 1638-1642 (2008).
Smith et al. "Quantitative phenotyping via deep barcode sequencing", *Genome Research*, 19: 1836-1842 (2009).
Smith et al, "Using quality scores and longer reads improves accuracy of Solexa read mapping," BMC Bioinformatics, 9: 128 (2008).
Sobrino, et al. "SNPs in forensic genetics: a review on SNP typing methodologies", *Forensic Sci Int.*, 154(2-3): 181-194, Abstract Only (2005). Epub Jan. 11, 2005.
Spreafico, et al. "A circulating reservoir of pathogenic-like CD4+ T cells shares a genetic and phenotypic signature with the inflamed synovial micro-environment", *Ann Rheum Dis.*, 0: 1-7 (2014). doi: 10.1136/annrheumdis-2014-206226. [Epub ahead of print].
Sramkova, et al. "Detectable minimal residual disease before allogeneic hematopoietic stem cell transplantation predicts extremely poor prognosis in children with acute lymphoblastic leukemia", *Pediatr. Blood Cancer*, 48(1):93-100 (2007).
Srinivasan et al. "Effect of fixatives and tissue processing on the content and integrity of nucleic acids", *Am J Pathol.*, 161(6): 1961-1971 (2002).
Srivastava and Robins. "Palindromic nucleotide analysis in human T cell receptor rearrangements", PLoS One, 7(12):e52250 (2012). doi: 10.1371/journal.pone.0052250. Epub Dec. 21, 2012.
Standard Sequencing Primers, Max Planck Genome Center Cologne, Jan. 15, 2011, 2 pages, downloaded from https://genomecentre.mpipz.mpg.de/SeqOrderDB/export/sequencing-primers.html.
Stanley. Essentials of Immunology & Serology, Delmar, Thomson Learning, Chapter 7, T cells, p. 95 (2002).
Steenbergen, et al. "Distinct ongoing Ig heavy chain rearrangement processes in childhood B-precursor acute lymphoblastic leukemia", *Blood*, 82(2):581-589 (1993).
Steenbergen, et al. "Frequent ongoing T-cell receptor rearrangements in childhood B-precursor acute lymphoblastic leukemia: implications for monitoring minimal residual disease", *Blood*, 86(2): 692-702, Abstract Only (1995).
Stein and Nombela-Arrieta. "Chemokine control of lymphocyte trafficking: a general overview", *Immunology*, 116(10):1-12 (2005).
Steinmetz, O.M. et al. "Chemokines and B cells in renal inflammation and allograft rejection", *Frontiers in Bioscience (Schol. Ed.)*, 1:13-22 (2009).
Stemmer, et al. "Single-step assembly of a gene and entire plasmid from large numbers of oligodeoxyribonucleotides", *Gene*, 164(1): 49-53 (1995).
Steward et al. "A polymerase chain reaction study of the stability of Ig heavy-chain and T-cell receptor delta gene rearrangements between presentation and relapse of childhood B-lineage acute lymphoblastic leukemia", *Blood*, 83(5):1355-1362 (1994).
Stewart and Schwartz. "Immunoglobulin V regions and the B cell", *Blood*, 83(7): 1717-1730 (1994).
Stickler, et al. "An in vitro human cell-based assay to rank the relative immunogenicity of proteins", *Toxicol Sci.*, 77(2): 280-289 (2004). Epub Dec. 22, 2003.

Stiller et al. "Direct multiplex sequencing (DMPS)—a novel method for targeted high-throughput sequencing of ancient and highly degraded DNA", *Genome Research*, 19: 1843-849 (2009).
Straten, Per thor, et al. "T-cell clonotypes in cancer", *Journal of Translational Medicine*, 2(1): 11, 10 pages (2004).
Stratton. "Exploring the genomes of cancer cells: progress and promise", *Science*, 331(6024): 1553-1558 (2011). doi: 10.1126/science.1204040.
Striebich, et al. "Selective Accumulation of Related CD41 T Cell Clones in the Synovial Fluid of Patients with Rheumatoid Arthritis", *J Immunol.*, 161(8): 4428-4436 (1998).
Struyk et al. "T cell receptors in rheumatoid arthritis", *Arthritis & Rheumatism*, 38(5):577-589 (1995).
Sumida et al. "T cell receptor repertoire of infiltrating T cells in lips of Sjögren's syndrome patients", *J Clin Invest.*, 89:681-685 (1992).
Sumida et al. "T cell receptor Vα repertoire of infiltrating T cells in labial salivary glands from patients with Sjögren's syndrome", *J Rheumatol.*, 21:1655-1661 (1994).
Swarup and Rajeswari. "Circulating (cell-free) nucleic acids—a promising, non-invasive tool for early detection of several human diseases", *FEBS Letters*, 581(5): 795-799 (2007). Epub Feb. 2, 2007.
Szczepanski et al. "Comparative analysis of Ig and TCR gene rearrangements at diagnosis and at relapse of childhood precursor-B-ALL provides improved strategies for selection of stable PCR targets for monitoring of minimal residual disease", *Blood*, 99(7):2315-2323 (2002).
Szczepanski, T. et al. "Minimal residual disease in leukemia patients", *Lancet Oncology*, 2:409-417 (2001).
Szczepanski et al. "Why and how to quantify minimal residual disease in acute lymphoblastic leukemia?", *Leukemia*, 21(4):622-626 (2007). Epub Feb. 15, 2007.
Tackenberg et al. "Clonal expansions of CD4+ β helper T cells in autoimmune myasthenia gravis", *European Journal of Immunology*, 37(3):849-863 (2007).
Tajiri et al. "Cell-microarray analysis of antigen-specific B-cells: single cell analysis of antigen receptor expression and specificity", *Cytometry Part A*, 71A: 961-967 (2007).
Takamatsu , et al., "A comparison between next-generation sequencing and ASO-qPCR for minimal residual disease detection in multiple myeloma", *J. Clin. Oncol.*, 31(Supplement 1): Abstract 8601 (Conference Abstract), Entire Abstract (2013).
Tam, James P. "Synthetic peptide vaccine design: synthesis and properties of a high-density multiple antigenic peptide system." Proceedings of the National Academy of Sciences (1988); 85.15: 5409-5413.
Tanaka et al. "Single-Cell Analysis of T-Cell Receptor Repertoire of HTLV-1 Tax-Specific Cytotoxic T Cells in Allogeneic Transplant Recipients with Adult T-Cell Leukemia/Lymphoma", *Cancer Research*, 70: 6181-6192 (2010).
Taubenheim et al. "High Rate of Antibody Secretion Is not Integral to Plasma Cell Differentiation as Revealed by XBP-1 Deficiency", *The Journal of Immunology*, 189: 3328-3338 (2012).
Tautz, et al. "Cryptic simplicity in DNA is a major source of genetic variation", *Nature*, 322(6080): 652-656 (1986).
Tawfik, et al. "Man-made cell-like compartments for molecular evolution", *Nat Biotechnol.*, 16(7): 652-656, Abstract Only (1998).
ten Bosch et al. "Keeping Up With the Next Generation Massively Parallel Sequencing in Clinical Diagnostics", *Journal of Molecular Diagnostics*, 10(6): 484-492 (2008).
Tewhey, R. et al. "Corrigendum: Microdroplet-based PCR enrichment for large-scale targeted sequencing", *Nature Biotechnology*, 28(2):178, 1 page (2010).
Tewhey, R. et al. "Microdroplet-based PCR enrichment for large-scale targeted sequencing," *Nature Biotechnology*, 27(11):1025-1031 (2009).
Thiel, et al. "Antigen-specific cytometry—new tools arrived!", *Clin Immunol.*, 111(2): 155-161, Abstract Only (2004).
Thornhill et al. "A comparison of different lysis buffers to assess allele dropout from single cells for preimplantation genetic diagnosis", *Prenatal Diagnosis*, 21:490-497 (2001).
Tokimitsu et al. "Single lymphocyte analysis with a microwell array chip", *Cytometry Part A*, 71A:1003-1010 (2007).

(56) References Cited

OTHER PUBLICATIONS

Toriello et al. "Integrated microfluidic bioprocessor for single-cell gene expression analysis", PNAS, 105(51): 20173-20178 (2008).
Triebel, F. et al. "A Unique V-J-C-Rearranged Gene Encodes A γ Protein Expressed on the Majority of CD3+ T Cell Receptor-a/fr Circulating Lymphocytes", J. Exp. Med., 167:694-699 (1988).
Tsai et al. "Discovery of rare mutations in populations: TILLING by sequencing", Plant Physiology, 156(3): 1257-1268 (and Supplemental Data) (2011).
Tsankova, et al. "Peripheral T-cell lymphoma emerging in a patient with aggressive polymyositis: molecular evidence for neoplastic transformation of an oligo clonal T-cell infiltrate", Acta Neuropathol., 126(4):595-601 (2013). doi: 10.1007/s00401-013-1164-z. Epub Aug. 13, 2013.
Tschumper, et al. "Comprehensive assessment of potential multiple myeloma immunoglobulin heavy chain V-D-J intraclonal variation using massively parallel pyrosequencing", Oncotarget, 3(4): 502-513 (2012).
Turcotte and Rosenberg. "Immunotherapy for metastatic solid cancers", Adv Surg., 45: 341-360 (2011).
UK combined search and examination report dated Mar. 20, 2013 for GB 1300533.5.
UK Combined Search Report and Office action dated Jun. 29, 2012 for UK application No. GB1209668.1.
UK Combined Search Report and Office action dated May 27, 2011 for UK application No. GB1105068.9.
UK Search Report and office action dated Jan. 13, 2012 for UK application No. GB1120209.0.
UK Search Report and office action dated Jul. 7, 2010 for UK application No. GB1009641.0.
Umibe et al. "Clonal expansion of T cells infiltrating in the airways of non-atopic asthmatics", Clinical & Experimental Immunology, 119(3):390-397 (2000).
Unrau and Deugau. "Non-cloning amplification of specific DNA fragments from whole genomic DNA digests using DNA 'indexers'", Gene., 145(2): 163-169, Abstract Only, 2 pages (1994).
Uppaluri et al. "Focus on TILs: prognostic significance of tumor infiltrating lymphocytes in head and neck cancers", Cancer Immunity, 8:16, 10 pages (2008).
Urban, et al. "A systematic and quantitative analysis of PCR template contamination", J Forensic Sci., 45(6): 1307-1311 (2000).
Urquhart, et al. "Rate-controlled delivery systems in drug and hormone research", Annu Rev Pharmacol Toxicol., 24: 199-236, Abstract Only (1984).
Van Der Velden, V.H.J., et al. "Analysis of minimal residual disease by Ig/TCR gene rearrangements: guidelines for interpretation of real-time quantitative PCR data," Leukemia, 21:604-611 (2007).
Van Der Velden, V.H.J., et al. "Detection of minimal residual disease in hematologic malignancies by realtime quantitative PCR: principles, approaches, and laboratory aspects," Leukemia, 17:1013-1034 (2003).
Van Der Velden, V.H.J., et al. "Optimization of PCR-based minimal residual disease diagnostics for childhood acute lymphoblastic leukemia in a multi-center setting," Leukemia, 21:706-713 (2007).
Van Der Velden, V.H.J., et al. "Real-time quantitative PCR for detection of minimal residual disease before allogeneic stem cell transplantation predicts outcome in children with acute lymphoblastic leukemia", Leukemia, 15:1485-1487 (2001).
Van Dongen, J.J.M. et al. "Design and standardization of PCR primers and protocols for detection of clonal immunoglobulin and I-cell receptor gene recombinations in suspect lymphoproliferations: Report of the BIOMED-2 Concerted Action BMHC-CT98-3936", Leukemia, 17:2257-2317 (2003).
Van Dongen, J.J.M. et al. "Prognostic value of minimal residual disease in acute lymphoblastic leukaemia in childhood", The Lancet, 352:1731-1738 (1998).
Van Heijst, J.W.J., et al., "Quantitative assessment of T-cell repertoire recovery after hematopoietic stem cell transplantation." Nat Med. (2013); 19(3): 372-377.

Vanderborght, et al. "Dynamic T cell receptor clonotype changes in synovial tissue of patients with early rheumatoid arthritis: effects of treatment with cyclosporin A (Neoral)", J Rheumatol., 29(3): 416-426 (2002).
Varley and Mitra. "Nested patch PCR enables highly multiplexed mutation discovery in candidate genes", Genome Research, 18: 1844-1850 (2008).
Venturi, et al. "A mechanism for TCR sharing between T cell subsets and individuals revealed by pyrosequencing", J Immunol., 186(7): 4285-4294 (2011). doi: 10.4049/jimmunol.1003898. Epub Mar. 7, 2011.
Venturi, V. et al. "TCR β-Chain Sharing in Human CD8+ T Cell Responses to Cytomegalovirus and EBV", The Journal of Immunology, 181:7853-7862 (2008).
Venturi, V. et al. "The molecular basis for public T-cell responses?", Nature Reviews, 8:231-238 (2008).
Verhagen, O.J.H.M., et al. "Application of germline IGH probes in real-time quantitative PCR for the detection of minimal residual disease in acute lymphoblastic leukemia", Leukemia, 14:1426-1435 (2000).
Vester, et al. "LNA (locked nucleic acid): high-affinity targeting of complementary RNA and DNA", Biochemistry, 43(42): 13233-13241, Abstract Only (2004).
Vlassov, et al. "Circulating nucleic acids as a potential source for cancer biomarkers", Curr Mol Med., 10(2): 142-165 (2010).
Vogelstein et al. "Cancer genome landscapes", Science, 339(6127): 1546-1558 (2013). doi: 10.1126/science.1235122.
Vogelstein and Kinzler. "Digital PCR," Genetics, PNAS, 96:9236-9241 (1999).
Wälchli, et al. "A practical approach to T-cell receptor cloning and expression", PLoS One, 6(11): e27930, 11 pages (2011). doi: 10.1371/journal.pone.0027930. Epub Nov. 21, 2011.
Wang, et al. "Balanced-PCR amplification allows unbiased identification of genomic copy changes in minute cell and tissue samples", Nucleic Acids Research, 32(9): e76, 10 pages (2004).
Wang, et al. "High throughput sequencing reveals a complex pattern of dynamic interrelationships among human T cell subsets", PNAS, 107(4): 1518-1528 (2010).
Wang, et al. "HIV integration site selection: Analysis by massively parallel pyrosequencing reveals association with epigenetic modifications", Genome Research, 17(8): 1186-1194 (2007). EpubJun. 1, 2007.
Wang et al. "Immunorepertoire analysis by multiplex PCR amplification and high throughput sequencing", Poster-Program 42.6, The 96th Annual Meeting of the America Association of Immunologists, Seattle, USA, May 8-12, 2009, 1 page.
Wang, X. et al. "Quantitative Measurement of Pathogen Specific Human Memory T Cell Repertoire Diversity using a CDR3 B-Specific Microarray", BMC Genomics, 8(329): 1-13 (2007).
Ward and Marelli-Berg. "Mechanisms of chemokine and antigen-dependent T-lymphocyte navigation", Biochem. J., 418:13-27 (2009).
Warren et al. "Exhaustive T-cell repertoire sequencing of human peripheral blood samples reveals signatures of antigen selection and a directly measured repertoire size of at least 1 million clonotypes", Genome Res., 21(5): 790-797 (2011). Epub Feb. 24, 2011.
Warren et al. "Profiling model T-cell metagenomes with short reads", Bioinformatics, 25(4):458-464 (2009).
Weinstein, J.A. et al. "High-Throughput Sequencing of the Zebrafish Antibody Repertoire", Science, 324(5928): 807-810 (2009).
Weinstein, J.A. et al. "High-Throughput Sequencing of the Zebrafish Antibody Repertoire", Science, 324(5928): 807-810, Supporting/Supplementary Materials (2009).
Weiss et al. "Clonal Rearrangements of T-Cell Receptor Genes in Mycosis Fungoides and Dermatopathic Lymphadenopathy", The New England Journal of Medicine, 313(9):539-544 (1985).
Welch and Link. "Genomics of AML: clinical applications of next-generation sequencing", American Society of Hematology, 2011: 30-35 (2011). doi: 10.1182/asheducation-2011.1.30.
Wells, et al. "Rapid evolution of peptide and protein binding properties in vitro", Curr Opin Biotechnol., 3(4): 355-362, Abstract Only (1992).

(56) References Cited

OTHER PUBLICATIONS

Wells, et al. "Strategies for preimplantation genetic diagnosis of single gene disorders by DNA amplification", *Prenatal Diagnosis*, 18(13):1389-1401 (1998).
Weng, et al. "Minimal residual disease monitoring with high-throughput sequencing of T cell receptors in cutaneous T cell lymphoma", *Sci Transl Med.*, 5(214):214ra171 (2013). doi: 10.1126/scitranslmed.3007420.
Westermann and Pabst. "Distribution of lymphocyte subsets and natural killer cells in the human body", *Clin Investig.*, 70(7): 539-544 (1992).
Wetmur and Chen. "An emulsion polymerase chain reaction-based method for molecular haplotyping", *Methods in Molecular Biology*, 410: 351-361 (1996).
Wetmur and Chen. "Linking emulsion PCR haplotype analysis", chapter 11, Park, D.J. (ed.), *PCR Protocols, Methods in Molecular Biology*, 687: 165-175 (2011).
Wetmur et al. "Molecular haplotyping by linking emulsion PCR: analysis of paraoxonase 1 haplotypes and phenotypes", *Nucleic Acids Research*, 33(8):2615-2619 (2005).
Weusten, et al. "Principles of quantitation of viral loads using nucleic acid sequence-based amplification in combination with homogeneo detection using molecular beacons", Nucleic Acids Res., 30(6): e26, 7 pages (2002).
White et al. "High-throughput microfluidic single-cell RT-qPCR", *PNAS*, 108(34): 13999-14004 (2011).
Whiteford, et al. "Swift: primary data analysis for the Illumina Solexa sequencing platform", *Bioinformatics*, 25(17): 2194-2199 (2009). doi: 10.1093/bioinformatics/btp383. Epub Jun. 23, 2009.
Wilson-Lingardo et al., "Deconvolution of Combinatorial Libraries for Drug Discovery: Experimental Comparison of Pooling Strategies." J. Med. Chem., (1996); 39 (14): 2720-2726.
Williams, et al. "Amplification of complex gene libraries by emulsion PCR", *Nat Methods*, 3(7): 545-550 (2006).
Wlodarski et al. "Molecular strategies for detection and quantitation of clonal cytotoxic T-cell responses in aplastic anemia and myelodysplastic syndrome", *Blood*, 108(8):2632-2641 (2006).
Wlodarski et al. "Pathologic clonal cytotoxic T-cell responses: nonrandom nature of the T-cell-receptor restriction in large granular lymphocyte leukemia", *Blood*, 106:2769-2779 (2005).
Wolda. "Similarity Indices, Sample Size and Diversity", *Oecologia* (Berl), 50:296-302 (1981).
Wolfl, et al. "Activation-induced expression of CD137 permits detection, isolation, and expansion of the full repertoire of CD8+ T cells responding to antigen without requiring knowledge of epitope specificities", *Blood*, 110(1): 201-210 (2007). Epub Mar. 19, 2007.
Wolfl, et al. "Use of CD137 to study the full repertoire of CD8+ T cells without the need to know epitope specificities", *Cytometry A.*, 73(11): 1043-1049 (2008). doi: 10.1002/cyto.a.20594.
Wood, B. "9-Color and 10-Color Flow Cytometry in the Clinical Laboratory", *Arch Pathol Lab Med*, 130:680-690 (2006).
Wood, et al. "Using next-generation sequencing for high resolution multiplex analysis of copy number variation from nanogram quantities of DNA from formalin-fixed paraffin-embedded specimens", *Nucleic Acids Research*, 38(14): e151, 11 pages (2010). doi: 10.1093/nar/gkq510. Epub Jun. 4, 2010.
Woodsworth, Daniel J., et al., "Sequence analysis of T-cell repertoires in health and disease." Genome Medicine (2013); 5: 98, 13 pages.
Wrammert et al. "Rapid cloning of high-affinity human monoclonal antibodies against influenza virus", *Nature*, 453: 667-672 (2008).
Wu, et al. "High-throughput sequencing detects minimal residual disease in acute T lymphoblastic leukemia", Sci Transl Med., 4(134):134ra63 (2012). doi: 10.1126/scitranslmed.3003656.
Wu, et al. "High-throughput sequencing of T-cell receptor gene loci for minimal residual disease monitoring in T Lymphoblastic Leukemia", Blood, 118: 2545 (Abstr) (2011).
Wu, Y-C. et al. "High-throughput immunoglobulin repertoire analysis distinguishes between human IgM memory and switched memory B-cell populations", *Blood Journal*, 116(7): 1070-1078, 22 pages (2010).
Wu et al. "Focused Evolution of HIV-1 Neutralizing Antibodies Revealed by Structures and Deep Sequencing", *Science*, 333: 1593-1602 (2011).
Wu, H.D. et al. "The Lymphocytic Infiltration in Calcific Aortic Stenosis Predominantly Consists of Clonally Expanded T Cells", *The Journal of Immunology*, 178(8): 5329-5339 (2007).
Xie, Yang, et al., "A note on using permutation-based false discovery rate estimates to compare different analysis methods for microarray data." Bioinformatics (2005); 21.23: 4280-4288.
Xiong, et al. "Chemical gene synthesis: strategies, softwares, error corrections, and applications", *FEMS Microbiol Rev.*, 32(3): 522-540 (2008). doi: 10.1111/j.1574-6976.2008.00109.x. Epub Apr. 2, 2008.
Xiong, et al. "Non-polymerase-cycling-assembly-based chemical gene synthesis: strategies, methods, and progress", *Biotechnol Adv.*, 26(2): 121-134, Abstract Only (2008). Epub Nov. 7, 2007.
Xu, W. et al. "A Novel Universal Primer-Multiplex-PCR Method with Sequencing Gel Electrophoresis Analysis", *PLoS One*, 7(1): e22900, 10 pages (2012).
Xu, et al. "Simultaneous isolation of DNA and RNA from the same cell population obtained by laser capture microdissection for genome and transcriptome profiling", *J Mol Diagn.*, 10(2):129-134 (2008). doi: 10.2353/jmoldx.2008.070131. Epub Feb. 7, 2008.
Yao, et al. "Analysis of the CDR3 length repertoire and the diversity of TCRα chain in human peripheral blood T Lymphocytes", Cell Mol Immunol., 4(3): 215-220 (2007).
Yeh, et al. "Regulating DNA translocation through functionalized soft nanopores", *Nanoscale*, 4(8): 2685-4693, Abstract Only (2012). doi: 10.1039/c2nr30102d. Epub Mar. 15, 2012.
Yassai, M.B. et al. "A clonotype nomenclature for T cell receptors", *Immunogenetics*, 61:493-502 (2009).
Yin et al. "Antiretroviral therapy restores diversity in the T-cell receptor Vβ repertoire of CD4 T-cell subpopulations among human immunodeficiency virus type 1-infected children and adolescents", *Clinical and Vaccine Immunology*, 16(9):1293-1301 (2009).
Yon and Fried. "Precise gene fusion by PCR", *Nucleic Acids Research*, 17(12):4895, 1 page (1989).
York, et al. "Highly parallel oligonucleotide purification and functionalization using reversible chemistry", *Nucleic Acids Res.*, 40(1): e4, 7 pages (2012). doi: 10.1093/nar/gkr910. Epub Oct. 29, 2011.
Yu and Fu. "Tumor-infiltrating T lymphocytes: friends or foes?", *Lab Invest.*, 86(3): 231-245 (2006).
Zagnoni, et al. "Droplet Microfluidics for High-throughput Analysis of Cells and Particles", *Methods in Cell Biology*, Chapter 2, 102: 23-48 (2011).
Zaliova, et al. "Quantification of fusion transcript reveals a subgroup with distinct biological properties and predicts relapse in BCR/ABL-positive ALL: implications for residual disease monitoring", *Leukemia*,23(5):944-951 (2009).
Zehentner et al. "Minimal Disease Detection and Confirmation in Hematologic Malignancies: Combining Cell Sorting with Clonality Profiling", *Clinical Chemistry*, 52(3): 430-437 (2006).
Zeng et al. "High-performance single cell genetic analysis using microfluidic emulsion generator arrays", *Anal. Chem.*, 82(8):3183-3190 (2010).
Zhong, Q. et al. "Multiplex digital PCR: breaking the one target per color barrier of quantitative PCR", Lab Chip, 11:2167-2174 (2011).
Zhou et al. "High throughput analysis of TCR-β rearrangement and gene expression in single cells", *Laboratory Investigation*, 86: 314-321 (2006).
Zhou et al. "Isolation of purified and live Foxp3+ regulatory T cells using FACS sorting on scatter plot", *J Mol Cell Biol*, 2(3): 164-169 (2010). doi: 10.1093/jmcb/mjq007. Epub Apr. 29, 2010.
Zhu, et al. "Immune surveillance by CD8αα+ skin-resident T cells in human herpes virus infection", Nature, 497(7450):494-7 and Corrigendum (2013). doi: 10.1038/nature12110. Epub May 8, 2013.
Zimmerman and Mannhalter. "Technical aspects of quantitative competitive PCR", *Biotechniques*, 21: 268-279 (1996).

(56) References Cited

OTHER PUBLICATIONS

European Patent Application No. 15779750.7, Extended European Search Report dated Aug. 9, 2017, 9 pages.
European Patent Application No. 15758762.7, Extended European Search Report dated Sep. 22, 2017, 12 pages.
European Patent Application No. 15854358.7, Extended European Search Report dated Mar. 12, 2018, 12 pages.
Födinger et al., "Multiplex PCR for rapid detection of T-cell receptor-gamma chain gene rearrangements in patients with lymphoproliferative diseases." British Journal of Haematology (1996); 94(1): 136-139.
Howie, et al., "High throughput pairing of T cell receptor α and β sequences." Science Translational Medicine (2015); 7(301): 301ra131, and supplementary materials, 19 pages.
Panzara, et al., "Analysis of the T cell repertoire using the PCR and specific oligonucleotide primers." Biotechniques (1992); 12(5): 728-735.
PCT/US2016/019343, International Preliminary Report on Patentability dated Aug. 29, 2017, 14 pages.
PCT/US2016/025535, International Preliminary Report on Patentability dated Oct. 3, 2017, 7 pages.
Sotomayor, et al., "Conversion of tumor-specific $CD4^+$ T-cell tolerance to T-cell priming through in vivo ligation of CD40." Nature Medicine (1999); 5(7): 780-787.
Szczepek, et al., "A high frequency of circulating B cells share clonotypic Ig heavy-chain VDJ rearrangements with autologous bone marrow plasma cells in multiple myeloma, as measured by single-cell and in situ reverse transcriptase-polymerase chain reaction." Blood (1998); 92(8): 2844-2855.
Willenbrock, et al., "Analysis of T-Cell Subpopulations in T-Cell Non-Hodgkin's Lymphoma of Angioimmunoblastic Lymphadenopathy with Dysproteinemia Type by Single Target Gene Amplification of T Cell Receptor-β Gene Rearrangements." Am J Pathol. (2001); 158(5): 1851-1857.
Yagi, et al., "Detection of clonotypic IGH and TCR rearrangements in the neonatal blood spots of infants and children with B-cell precursor acute lymphoblastic leukemia." Blood (2000); 96(1): 264-268.

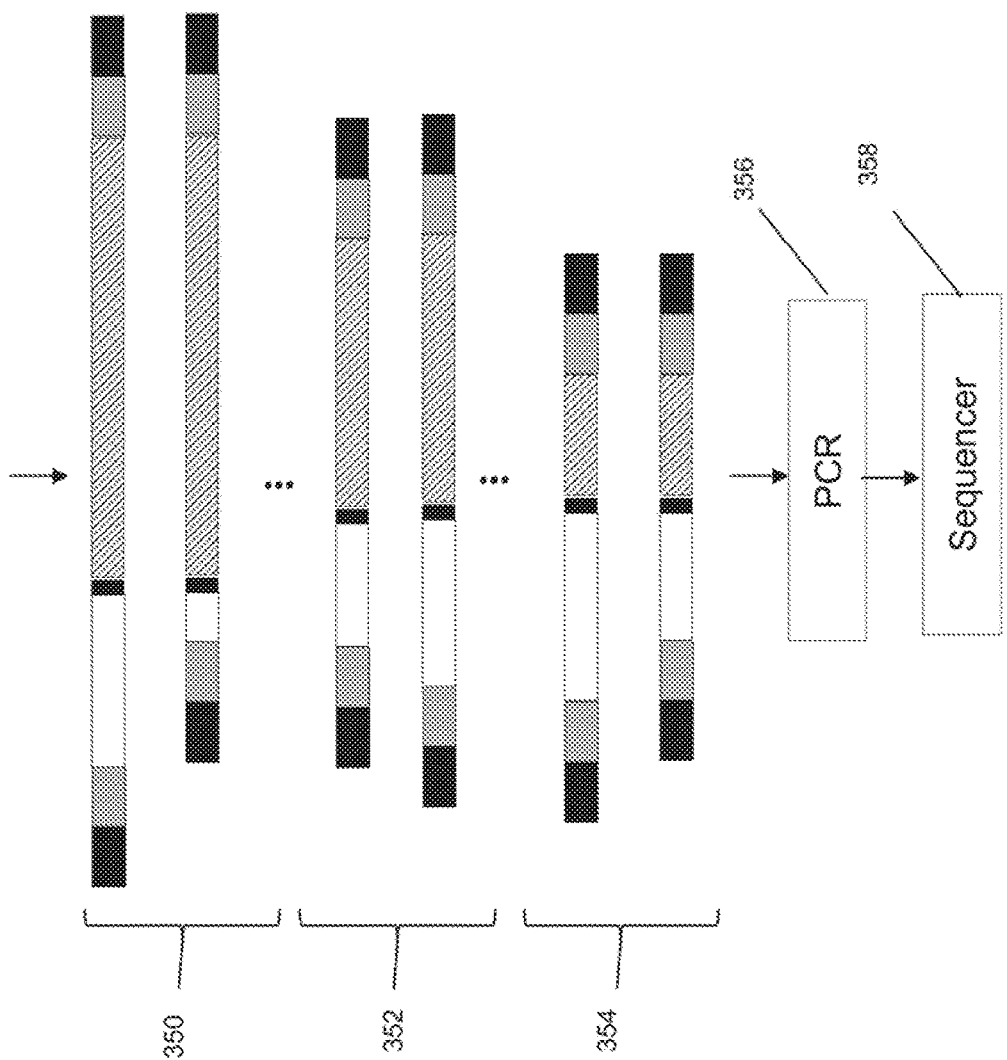

METHOD FOR GENOTYPING CLONOTYPE PROFILES USING SEQUENCE TAGS

CROSS-REFERENCE TO RELATED APPLICATIONS

This application is a continuation of U.S. application Ser. No. 14/317,087, filed Jun. 27, 2014, now U.S. Pat. No. 9,708,657, issued Jul. 18, 2017, which claims priority from U.S. provisional application Ser. No. 61/841,878 filed 1 Jul. 2013 and Ser. No. 62/001,580 filed 21 May 2014, each of which are incorporated herein by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ADBS_062_03US_SeqList_ST25.txt, date recorded: Jun. 1, 2017, file size 1.61 kilobytes).

BACKGROUND OF THE INVENTION

Large-scale DNA sequencing in diagnostic and prognostic applications has expanded rapidly as its speed and convenience has increased and its per-base cost has decreased, e.g. Ding et al, Nature, 481(7382): 506-510 (2012); Chiu et al, Brit. Med. J., 342: c7401 (2011); Ku et al, Annals of Neurology, 71(1): 5-14 (2012); and the like. In particular, profiles of nucleic acids encoding immune molecules, such as T cell or B cell receptors, or their components, contain a wealth of information on the state of health or disease of an organism, so that the use of such profiles as diagnostic or prognostic indicators has been proposed for a wide variety of conditions, e.g. Faham and Willis, U.S. Pat. Nos. 8,236,503 and 8,628,927; Freeman et al, Genome Research, 19: 1817-1824 (2009); Han et al, J. Immunol, 182 (1001):42.6 (2009); Boyd et al, Sci. Transl. Med., 1(12): 12ra23 (2009); He et al, Oncotarget (Mar. 8, 2011).

For example, patients treated for many cancers often retain a minimal residual disease (MRD) related to the cancer. That is even though a patient may have by clinical measures a complete remission of the disease in response to treatment, a small fraction of the cancer cells may remain that have, for one reason or another, escaped destruction. The type and size of this residual population is an important prognostic factor for the patient's continued treatment, e.g. Campana. Hematol. Oncol. Clin. North Am., 23(5): 1083-1098 (2009); Buccisano et al, Blood, 119(2): 332-341 (2012). Consequently, several techniques for assessing this population have been developed, including techniques based on flow cytometry, in situ hybridization, cytogenetics, amplification of nucleic acid markers, and the like, e.g. Buccisano et al, Current Opinion in Oncology, 21: 582-588 (2009); van Dongen et al, Leukemia, 17(12): 2257-2317 (2003); and the like. The amplification of recombined nucleic acids encoding segments of immune receptors (i.e. clonotypes) from T cells and/or B cells have been particularly useful in assessing MRD in leukemias and lymphomas, because such clonotypes typically have unique sequences which may serve as molecular tags for their associated cancer cells. Such measurements are usually made by amplifying and sequencing nucleic acids encoding a single receptor chain, in part, because such amplifications are highly multiplexed and are difficult to develop. As the scale of multiplexing increases, several problems are encountered, including increased probability of spurious amplifications due to mis-hybridizations, primer-dimer formation, variable rates of amplification leading to biased sequence representation, and the like, e.g. Elnifro et al, Clinical Microbiology Reviews, 13(4): 559-570 (2000). Furthermore, the similarity of the target sequences and the incorporation of sequence tags into amplified sequences, either for sequence analysis, sample tracking, contamination detection, or the like, can exacerbate the above difficulties associated with large-scale amplifications. These challenges have prevented the development of large-scale one-reaction amplifications of multiple immune receptor chains, which would he highly beneficial for reducing the number of separate assays required for measuring nucleic acid sequences correlated with a minimal disease.

In view of the foregoing, it would be highly advantageous if more efficient methods were available for assessing selected nucleic acids in a single reaction, such as exons of cancer genes or clonotypes encoding sets of immune receptor chains.

SUMMARY OF THE INVENTION

The present invention is directed to methods of large-scale amplification in a single reaction, particularly by a polymerase chain reaction (PCR), of a population of target polynucleotides, such as recombined nucleic acids encoding immune receptor chains, followed by their identification using large-scale DNA sequencing. The invention includes the application of the foregoing methods for monitoring minimal residual disease of a cancer. The invention is exemplified in a number of implementations and applications, some of which are summarized below and throughout the specification.

In some embodiments, the invention is directed to methods of generating profiles of nucleic acids that encode a population of biomolecules of interest, such as immune receptor molecules. In one aspect, methods of the invention comprise attaching sequence tags to a selected population of nucleic acids in a sample to form tag-nucleic acid conjugates, amplifying the tag-nucleic acid conjugates, and sequencing amplified tag-nucleic acid conjugates to provide sequence reads each comprising both a tag sequence and a nucleic acid sequence, for which a profile of the nucleic acids is generated. In some embodiments, attaching sequence tags is enabled by one or more successive steps of primer extension and pruner removal, after which the resulting product may be further amplified without bias by common forward and reverse primers.

In some embodiments, the invention is directed to methods for detecting and measuring contamination, such as carry-over contamination, in a sample from material originating from a different sample. In one embodiment, such method for detecting contamination in an individual being monitored for a minimal residual disease may comprise the following steps: (a) obtaining from an individual a tissue sample; (b) attaching sequence tags to cancer gene molecules or recombined nucleic acids to form tag-nucleic acid conjugates, wherein at least one nucleic acid or copies thereof have different sequence tags attached and wherein the cancer gene molecules are characteristic of a cancer of the individual; (c) amplifying the tag-nucleic acid conjugates; (d) sequencing a sample of the tag-nucleic acid conjugates to provide sequence reads having error rates and comprising a tag sequence and a cancer gene sequence or recombined nucleic acid sequence; (e) comparing tag sequences to separately determined tag sequences from other tissue samples; and (f) determining the presence, absence and/or level of contamination by the identity of one or more tag sequences with any separately determined tag sequences from other tissue samples.

In another aspect, the invention is directed to a method as described above for generating clonotype profiles based on at least two chains of a B cell receptor, which method comprises amplifying in a single reaction target nucleic acids encoding two or more chains of a B cell receptor. In another aspect, such methods are employed to monitor minimal residual disease in a B cell cancer.

In another aspect, the invention is directed to a method as described above generating clonotype profiles based on at least two chains of a T cell receptor, which method comprises amplifying in a single reaction target nucleic acids encoding two or more chains of a T cell receptor. In another aspect, such methods are employed to monitor minimal residual disease in a T cell cancer.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the invention.

BRIEF DESCRIPTION OF THE DRAWINGS

The novel features of the invention are set forth with particularity in the appended claims. A better understanding of the features and advantages of the present invention is obtained by reference to the following detailed description that sets forth illustrative embodiments, in which the principles of the invention are utilized, and the accompanying drawings of which:

FIGS. 3A and 3B illustrate diagrammatically an aspect of the invention for generating clonotype profiles from nucleic acid sequences encoding IgH chains.

DETAILED DESCRIPTION OF THE INVENTION

Figure 1A:
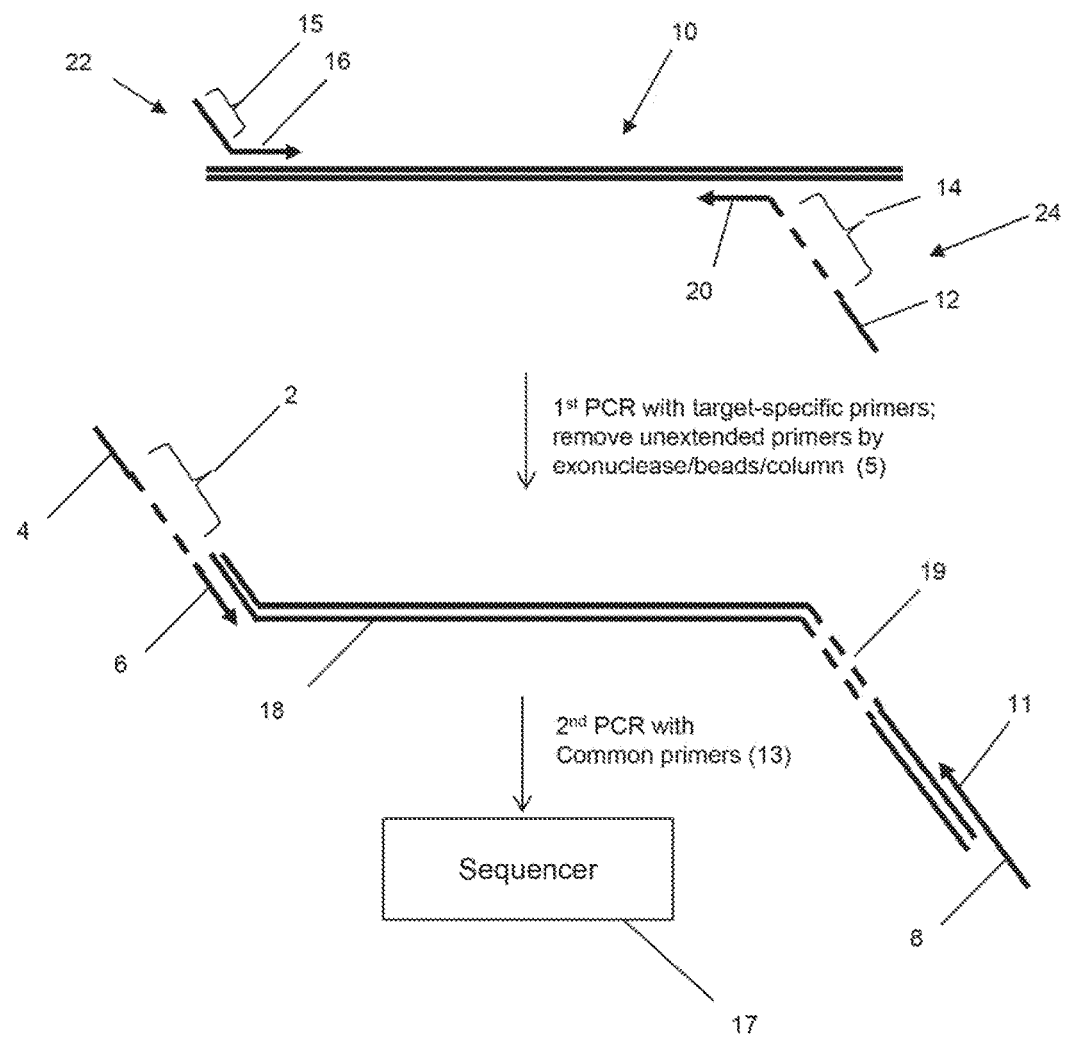
FIGS. 1A through 1C illustrate diagrammatically various embodiments of the invention.

The practice or the present invention may employ, unless otherwise indicated, conventional techniques and descriptions of molecular biology (including recombinant techniques), bioinformatics, cell biology, and biochemistry, which are within the skill of the art. Such conventional techniques include, but are not limited to, sampling and analysis of blood cells, nucleic acid sequencing and analysis, and the like. Specific illustrations of suitable technique can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV); *PCR Primer: A Laboratory Manual; and Molecular Cloning: A Laboratory Manual* (all from Cold Spring Harbor Laboratory Press) and the like.

In one aspect the invention is directed to methods for producing clonotype profiles of multiple immune receptor chains by large-scale multiplex amplification of nucleic acids encoding such chains followed by high-throughput sequencing of the amplification product, or amplicon. In some embodiments, the invention overcomes common drawbacks of multiplex amplification by including successive steps of primer extension, removal of unextended, or unincorporated, primers and addition of new primers either for amplification (for example by PCR) or for additional primer extensions. Such steps also enable the use of sequence tags which otherwise would contribute to nonspecific or spurious amplifications. In another aspect, sequence tags are employed in embodiments with clinical applications, particularly minimal residual disease (MRD) analysis, for example, of samples from a patient being treated for a cancer. Sequence tags incorporated into sequence reads provide an efficient means for determining clonotypes and at the same time provide a convenient means for detecting carry-over contamination by detecting the presence or absence of sequence tags from previous assays, either from samples of the same patient or from samples of a different patient which were tested in the same laboratory. Of particular interest are methods for generating sequence-based clonotype profiles of recombined nucleic acids encoding a plurality of B cell receptor (BCR) chains by using a single amplification reaction followed by high throughput next-generation sequencing. Also of particular interest are methods for generating sequence-based clonotype profiles of recombined nucleic acids encoding a plurality of T cell receptor (TCR) chains by using a single amplification reaction followed by high throughput next generation sequencing. Methods of the invention may also be applied other large-scale amplification and sequencing of other sets of nucleic acids of interest, including, for example, sets of exons of cancer genes. In these aspects, sequence tags permit both monitoring of carry over contamination and more sensitive determination of nucleotide sequences of target polynucleotides in view of error-prone sequencing methodologies. Also in these aspects, a set of sequence tags (as discussed more fully below) is typically much larger than the number of target polynucleotides in a sample and the sequence difference among sequence tags attached to target polynucleotides is large enough so that effectively a sequence of one tag could not be transformed into another by sequencing error.

One embodiment of the invention is illustrated in FIG. 1A. In a reaction mixture, primers (22) from a first set (each primer of the first set having receptor-specific portion (16) and 5'-non-complementary portion (15) comprising a first primer binding site) anneal to one end of target polynucleotides (10) (after melting target polynucleotide (10)) and primers (24) from as second set (each primer of the second set having receptor-specific portion (20) and 5'-non-complementary portion comprising sequence tag (14) and second primer binding site (12)) anneal to another end of target polynucleotides (10). In some embodiments, as noted below, non-complementary portion (15) of primer (22) may also comprise a sequence tag. In some circumstance, two shorter sequence tags may be more advantageous than a single longer sequence tag of equivalent diversity. Thus, for example, two 8-mer random-nucleotide sequence tags may be less likely to cause spurious priming, primer-dimers, and the like, than a single 16-mer random nucleotide sequence tag. Target polynucleotides (10) are typically somatically recombined nucleic acids from T cells or B cells which encoded chains or portions of chains of T cell receptors (TCRs) or B cell receptors (e.g., portions of IgH chains or IgK chains). Thus, in some embodiments, the receptor-specific portions of primers (22) and (24) may be specific for V region sequences and J region sequences, respectively, or in other embodiments, vice versa.

In some embodiments, target polynucleotides (10) may comprise complex mixtures of nucleic acids whose sequence profiles are desired, including but not limited to, recombined nucleic acids encoding portions of immune receptor molecules, 16S rDNAs of microbial communities, metagenomic amplifications of genes encoding proteins of industrial or medical importance (such as, enzymes), human or animal genes and/or exons related to specific diseases, such as cancer, infectious disease, or the like. In embodiments relating to recombined nucleic acids encoding immune receptors, usually at least portions of a V, D or J region are present between the two binding locations of the first and second sets of primers. In some embodiments, between the two binding locations of the first and second sets of primers there is at least a portion of a VDJ rearrangement of IgH, a DJ rearrangement of IgH, at VJ rearrangement of IgK, a VJ rearrangement of IgL, a VDJ rearrangement of TCR β, a DJ rearrangement of TCR β, a VJ rearrangement of TCR α, a VJ rearrangement of TCR γ, a VDJ rearrangement of TCR δ, or a VD rearrangement of TCR δ. In some embodiments, between the two binding locations of the first and second sets of primers there is at least a portion of a VDJ rearrangement of IgH, a DJ rearrangement of IgH, a VJ rearrangement of IgK, or a VJ rearrangement of IgL. In some embodiments, between the two binding locations of the first and second sets of primers there is at least a portion of a VDJ rearrangement of TCR β, as DJ rearrangement of TCR β, a VJ rearrangement of TCR α, a VJ rearrangement of TCR γ, a VDJ rearrangement of TCR δ, or a VD rearrangement of TCR δ. In still other embodiments, between the two binding locations of the first and second sets of primers there is at least as portion of a VDJ rearrangement of IgH, a DJ rearrangement of IgH, and a VJ rearrangement of IgK. And in other embodiments, between the two binding locations of the first and second sets of primers there is at least a portion of a VDJ rearrangement of TCR β, a VJ rearrangement of TCR γ, and a VDJ rearrangement of TCR δ or a VD rearrangement of TCR δ. In some embodiments, at least a portion of a VDJ rearrangement comprises the complete D or NDN portion and parts of the V and J segments sufficient for their identification. In some embodiments, at least a portion of a VDJ rearrangement comprises at least a 50 nucleotide segment comprising the complete D or NDN portion and parts of the V and J segments. In some embodiments, at least a portion of a VDJ rearrangement comprises at least a 70 nucleotide segment comprising the complete D or NDN portion and parts of the V and J segments.

In some embodiments, a first set comprises one or more primers that are each specific for a J segment or a C segment. Primers from such a first set are annealed to their target sequences and are extended, after which non-extended primers of the first set are removed. Primers from a second set that are each specific for a V segment are annealed to their target sequences and are extended. In other embodiments, a first set comprises primers that are each specific for a V segment and primers of such first set are annealed to their target sequences, and are extended, after which non-extended primers of the first set are removed, primers of a second set that are each specific for a J segment or a C segment are annealed to their target sequences and are extended. In alternatives of both of these embodiments, first and second sets may each contain a plurality of primers and each primer may be specific for a different immune receptor segment.

Returning to FIG. 1A, in some embodiments, primers of the first and second sets are extended (5) by carrying out in alternative embodiments, 1-10, or 2-10, or 3-10, or 4-10, or 5-10 cycles of melting, annealing and extension, after which nonextended primers are removed from the reaction mixture using conventional techniques. In other embodiments, primers of the first and second sets are extended (5) by carrying out in alternative embodiments, 2-5, or 3-5, or 4-5 cycles of melting, annealing and extension, after which nonextended primers are removed from the reaction mixture using conventional techniques. In still another embodiment, primers of the first and second sets are extended by carrying out two cycles of melting, annealing and extending. For example, nonextended primers may be removed by exonuclease digestion, hybridization to complementary sequences on magnetic beads, size exclusion chromatography, commercially available spin columns (e.g. Qiagen QIAquick PCR Purification Kit), or the like. In one embodiment, unextended, or unincorporated, primers are removed, for example, by digestion with an exonuclease I. Double stranded DNAs (18), which are products of extensions (5), have common first and second primer binding sites at each end, to which (in some embodiments) forward and reverse primers, with complementary sequences (6 and 11), may be added for later generation of clusters by bridge PCR. In some embodiments, double stranded DNA also has sequence tag (19) and forward or reverse primer may include sample tag (2) for identifying or tracking or associating DNA (18) with a sample or patient. In some embodiments, sequence tag (19) is substantially unique for each different recombined nucleic acid in a sample. As explained more fully below, sequence tag (19) may be used for coalescing sequence reads into clonotypes well as used for detecting and tracking sample contamination. Forward and reverse primers may also include primer binding sites (4) and (8) for implementing (13) bridge PCR for certain sequencing protocols, e.g. on a Genome Analyzer (Illumina, San Diego) (17). In other embodiments, in which more than one extensions are carried out with sequence tag-containing primers, each different recombined nucleic acid in a sample may have copies with different sequence tags attached; thus, for example, if four separate cycles of melting, annealing and extension are carried out on target polynucleotides in accordance with the embodiment of FIG. 1A, and if the sample contains recombined nucleic acid, Si, then at the completion of amplification (13) with common primers, the copies of Si will have up to four different sequence tags. Therefore, sequence reads of Si will have up to four different sequence tags. As explained more fully below, in such embodiments, clonotypes may be determined by a combination of aligning sequence tags and coalescing sequence reads within each subset defined by a common sequence tag.

Figure 1B:
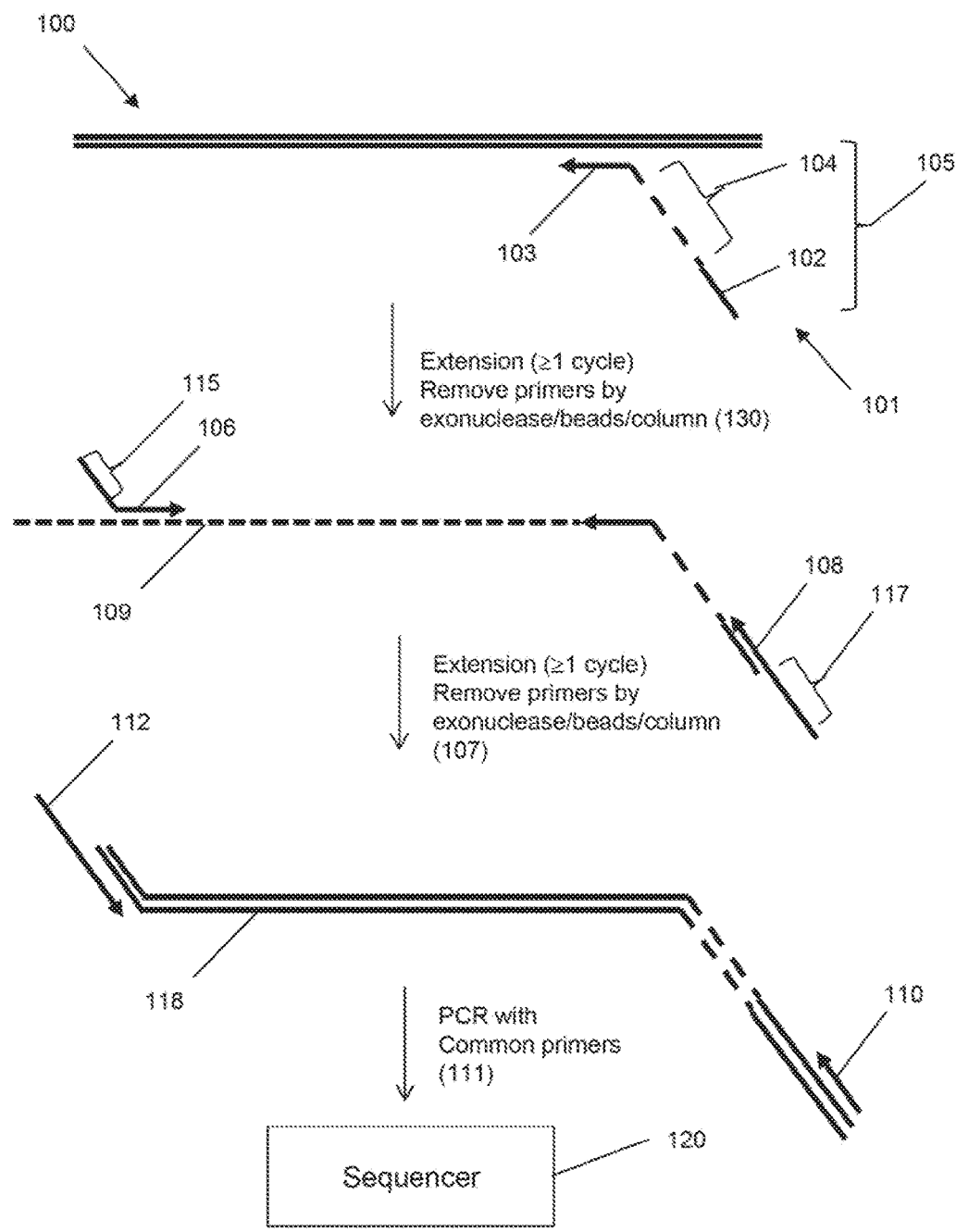

In another embodiment, at least two extensions and two steps to remove unincorporated primers are implemented prior to PCR with common primers. As illustrated in FIG. 1B, primers (101) are annealed to one end of target polynucleotides (100), such as recombined nucleic acids encoding immune receptor chains, and extended, e.g. with a DNA polymerase. Primers (101) may each include receptor-specific portion (103) and 5' non complementary portion (105) which, in turn, comprises sequence tag (104) and first primer binding site (102). After extension and removal of unincorporated primers (130), as described above, to first extension product (109) in the reaction mixture is added (a) primers (125), wherein each primer comprises receptor-specific portion (106) and 5'-non-complementary portion (115) (that contains a primer binding site), and (b) primers (127), comprising portion (108) specific for first primer binding site (102) and 5' non-complementary portion (117). After primers (125) and (127) anneal to their primer binding sites, they are extended (107) to form second extension product (118), after which non-extended primers are removed. To second extension product (118) common forward primers (112) and reverse primers (110) are added and a PCR is implemented (111), after which the resulting amplicon is sequenced (120). As above with the embodiment of FIG. 1A, whenever more than one extension step is performed in the presence of sequence tag-containing primers (such as (101)), copies of the same target polynucleotide (100) may be labeled with a plurality of different sequence tags.

Figure 1C:
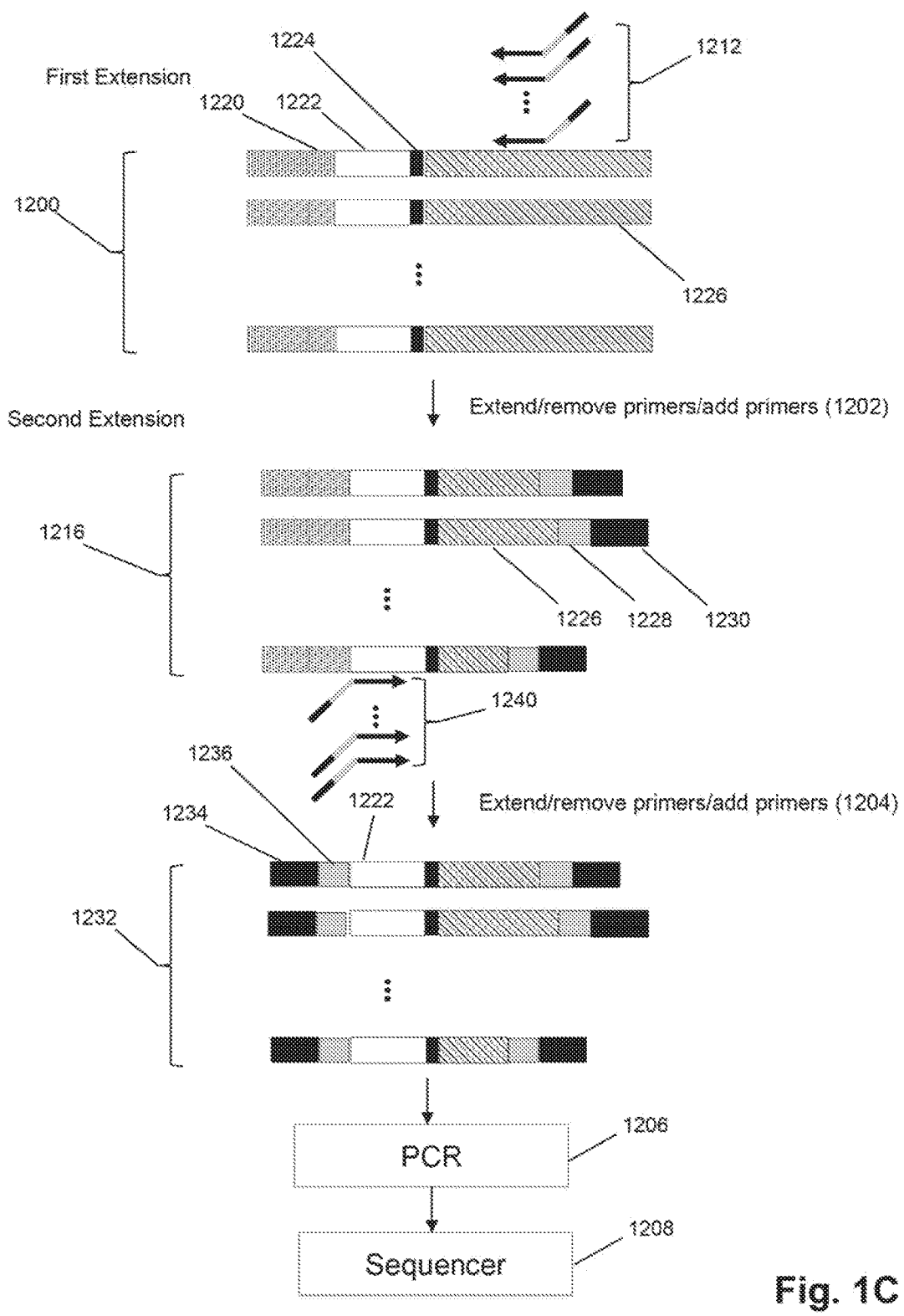

FIG. 1C illustrates another embodiment with V, D and J regions shown explicitly. In a reaction mixture under primer annealing conditions, to recombined nucleic acids (1200) encoding immune receptors, such as TCRs, primers (1212), a first set of primers specific to V region (1226), is added. Each primer of the first set (1212) includes a receptor-specific portion and a 5'-non-complementary portion which, in turn, comprises optionally a sequence tag and a first primer binding site (e.g., 102, 103 and 104 in FIG. 1B). Primers of first set (1212) anneal to V regions (1226) of recombined nucleic acids (1200) and primers of first set (1212) are extended (1202) through D region (1224) into at least J region (1222) and optionally to C region (1220) to form first extension products (1216) that includes optional sequence tag (1228) and first primer binding site (1230). After removing nonextended primers of first set (1212), primers of second set (1240) are added to the reaction mixture tinder annealing conditions so that they anneal to their respective target J regions (1222), after which they are extended (1204) to form second extension products (1232), each of which comprises sequence tag (1236) (optional) and second primer binding site (1234). Second extension products (1232) may comprise a single sequence tag located, for example, adjacent to V regions (1226), as shown by sequence tag (1228), or adjacent to J regions (1222), as shown by sequence tag (1236), or second extension products (1232) may comprise two sequence tags located in both positions. In one embodiment, second extension products (1232) comprise a single sequence tag (1228) adjacent to V regions (1226). In another embodiment, second extension products (1232) comprise a single sequence tag (1236) adjacent to J regions (1222). In some embodiments, sequence tags (1228) and/or (1236) are mosaic tags described below. After nonextended primers of second set (1240) are removed, common forward and reverse primers are added which are specific for first and second primer binding sites (1230) and (1234), respectively, and a PCR is carried out (1206). A sample of the resulting amplicon is sequenced (1208) to generate sequence reads for constructing clonotypes and clonotype profiles.

Figure 1D:
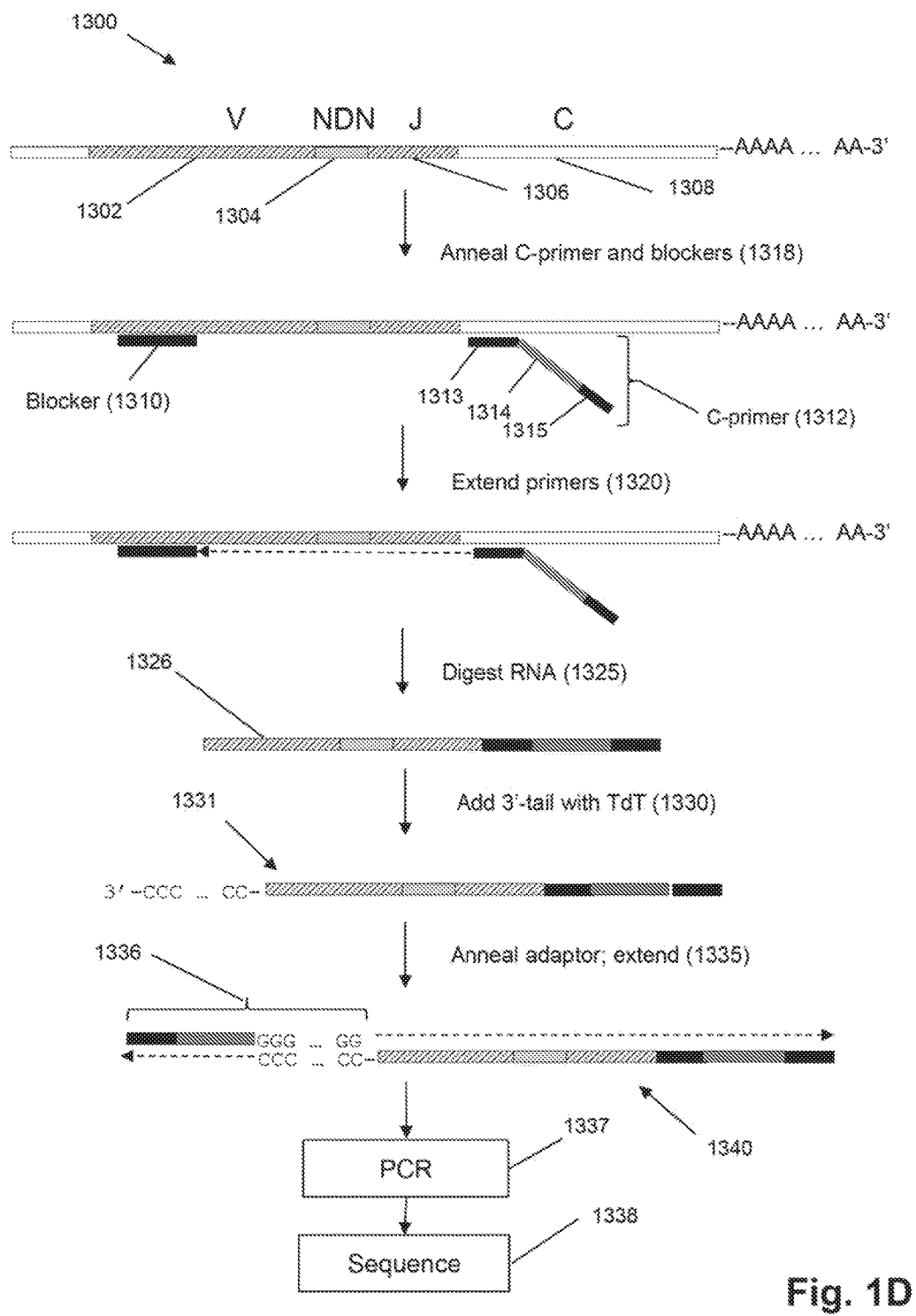
FIG. 1D illustrates a method of generating (with or without sequence tags) templates of recombined nucleic acids having a predetermined length.

FIG. 1D illustrates a method of generating templates of a defined length and for attaching one or two sequence tags thereto. The embodiment of FIG. 1D shows messenger RNA (mRNA) as the starting material, but the method may be used with either DNA or RNA samples. To mRNA (1300) containing a VDJ region, one or more primers (1312) specific for C region (1308) ("C primers") are annealed to mRNA (1300). Usually only a single C primer is used. Alternatively, one or more primers (having a similar structure) specific for J region may be used. C primer (1312) comprises target specific segment (1313), sequence tag segment (1314) and common primer binding site (1315). Also annealed to target mRNAs (1300) are polymerase blockers (1310), which may be oligonucleotides specific for V regions (1302). In some embodiments, blockers (1310) may be a natural oligonucleotide so long as a polymerase used to extend primer (1312) does not have either strand displacement activity or 5'→-3' exonuclease activity and so long as the oligonucleotide is non-extendable, e.g. it has a 3'-dideoxynucleotide. Usually, blockers (1310) are oligonucleotide analogs with enhanced binding activity and nuclease resistance, such as antisense compounds. In some embodiments, blockers (1310) may be locked nucleic acids (LNAs) or peptide nucleic acids (PNAs) or bridged nucleic acids (BNAs), which are disclosed in the following references. Wengel et al, U.S. Pat. Nos. 6,794,499; 7,572,582; Vester et al, Biochemistry, 43(42): 13233-13241 (2004); and the like, and Kazuyuki et al, Chem. Comm., 3765-3767 (2007); Nielson et al, Chem. Soc. Rev., 26: 73-78 (1997); and the like. Sequences of blockers (1310) are selected so that the extension of primer(s) (1312) are halted at a predetermined location on V region (1302). In some embodiments, blockers (1310) are designed so that only enough of V region (1302) is copied in the extension step so that the V region can be identified from the copied sequence. In some embodiments, obtaining blockers (1310) specific for each V region is unnecessary, as consensus sequences may be selected that permit some mismatches, so long as the progression of a polymerase is stopped. The lengths of blockers (1310) may vary widely depending on the kind of oligonucleotide or analog used. In some embodiments, blockers (1310) have lengths in the range of from 10 to 25 monomers. In some embodiments, blockers (1310) may anneal to different locations on different V region sequences.

Returning to FIG. 1D, primers (1312) are extended to blockers (1310) making a cDNA copy of a portion of VDJ region of target (1300) that has a predetermined length. In some embodiments, the predetermined length (or equivalently the binding sites of blockers (1310)) are selected so that a desired portion of the VDJ region may be covered by one or more sequence reads of the sequence technique used in the method. After extension is completed, RNA template (1300) is digested (1325) using conventional techniques, e.g. digestion with an RNAse, such as RNAse H and/or RNAse A, to give single stranded cDNA (1326). To this cDNA is added a 3' mononucleotide tail, such as a polyC tail, using terminal deoxynucleotide transferase (TdT) in a conventional protocol. To tailed cDNA (1331), adaptor (1336) having a complementary overhang to the mononucleotide tail of cDNA (1331), after which it is extended to produce double stranded DNA (1340), which may be amplified, e.g. by PCR (1337), and the resulting amplicon sequenced (1338).

Figure 3A:
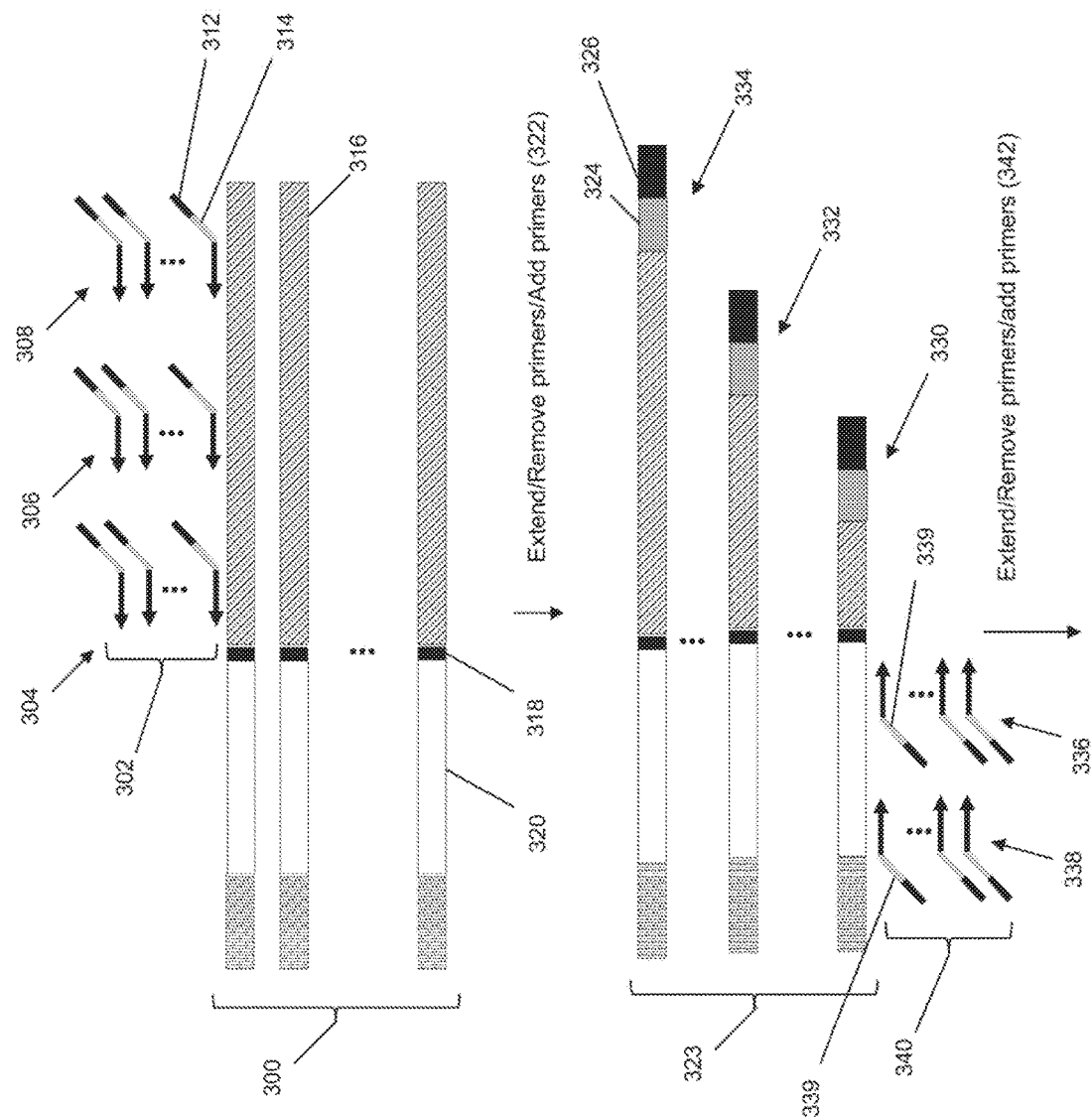

Recombined nucleic acids that undergo hypermutation, such as IgH-encoding nucleic acids, may be amplified using sets of primers that include primers that bind to different primer binding sites on the same recombined nucleic acid; that is, such sets may include primers that bind to one or more nonoverlapping primer binding sites on the same recombined nucleic acid encoding a receptor chain. Such set may comprise one or both first set of primers and second set of primers. In some embodiments, recombined nucleic acids subject to hypermutation are amplified with a first set of primers and a second set of primers wherein at least one of the two sets comprises primers specific for a plurality of nonoverlapping primer binding sites, for example, one set may contain for each different V segment a plurality of primers each specific for a different nonoverlapping primer binding on the different V segments. An embodiment applicable to amplification of recombined nucleic acids undergoing hypermutation is illustrated in FIGS. 3A-3B, where nested sets of primers are employed to ensure amplification of each recombined nucleic acid in a sample under conditions, for example, of somatic hypermutation, clonal evolution, or the like. Recombined nucleic acids, e.g. encoding IgH molecules, are combined in a reaction mixture under annealing conditions with first nested set (302) of primers, comprising in this example groups (304), (306) and (308) of primers specific for different sites along V region (316) of recombined nucleic acids (300). In this embodiment, the first nested set comprises a plurality of groups of primers, each specific for a different site or location of the V region, wherein the different members of a group are specific for different variants of the region at the site. In some embodiments, the plurality of groups is in the range of 2-4; in other embodiments, the plurality is 2 or 3. In some embodiments, each primer of first nested set (302) may have a unique sequence tag (314) and first primer binding site (312) in a 5' noncomplementary tail. Primers of first nested set (302) anneal to their target recombined nucleic acids and are extended through D region (318) and at least a portion of J region (320) to form first amplicon (323) which comprises three components (330), (332) and (334) corresponding to the three subsets or primers (304), (306) and (308), respectively. Each member of first amplicon (323) incorporates sequence tag (324) and primer binding site (326).

After nonextended primers are removed (322), second nested set of primers (340) is added the reaction mixture under annealing conditions. As illustrated in FIG. 3A, primers of second nested set (340) comprise subsets (336) and (338) a primers which anneal at different nonoverlapping positions on J region (320) of members of first amplicon (323). In some embodiments, the second nested set of primers may contain only a single group of primers. Primers of second nested set (340) are extended to form second extension product (360) which comprises subsets (350), (352) and (354) which, in turn, each comprise two further subsets (subsubsets) corresponding to primers (336) and (338). In some embodiments, second nested set of primers (340) contain primers specific to only a single primer binding site and first nested set of primers (302) contain primers specific to at least two non-overlapping primer binding sites. After removing nonextended primers (342), common forward and reverse primers may be added to carry out PCR (356) and a sample of the resulting amplicon may be sequenced (358). In various embodiments, primers of both the first nested set and the second nested set may include sequence tags (339); primers of the first nested set but not the second nested set may include sequence tags; and primers of the second nested set but not the first nested set may include sequence tags. In some embodiments, primers of the first nested set are extended first after which non-extended primers are removed or destroyed and primers of the second nested set are annealed and extended (as illustrated in FIGS. 3A-3B). In other embodiments, the order of the annealing, extending and removing steps are reversed; that is, primers of the second nested set are extended first after which non-extended primers are removed or destroyed and primers of the first nested set are annealed and extended.

In some embodiments of the above method, more than one extension step, either (322) or (342), may be implemented, for example, in order to attach sequence tags to a greater fraction of target polynucleotides in a sample. In such embodiments, more than one distinct sequence tag may be attached to a target polynucleotide and/or copies thereof. That is, a plurality of different sequence tags may be attached to a target polynucleotide and its progeny from an amplification reaction, such as PCR; thus, copies of an original target polynucleotide may be labeled with more than one sequence tag. As explained more fully below, such pluralities of sequence tags are still useful in tracking carry over contamination and in permitting more sensitive determination of target polynucleotide sequences.

Some of the embodiments described above may be carried out with the following steps. For example, a method of generating clonotype profiles from multiple, or a plurality of, T cell receptor chains may comprise the steps of: (a) combining in a reaction mixture under primer extension conditions a first set of primers with a sample of recombined nucleic acids from T-cells, wherein each primer of the first set has a receptor-specific portion with a length such that the receptor-specific portion anneals to a different recombined nucleic acid at a predetermined location or site one the target recombined nucleic acid and is extended to form a first extension product, and wherein each primer of the first set has a 5'-non-complementary end containing a first primer binding site; (b)) removing from the reaction mixture non-extended primers of the first set; (c) adding to the reaction mixture under primer extension conditions it second set of primers, wherein each primer of the second set has a receptor-specific portion such that the receptor-specific portion anneals to the first extension product at a predetermined location or site and has a 5'-non-complementary end containing a second primer binding site, primers of the first set and/or primers of the second set comprising a sequence tag disposed between the receptor-specific portion and the first or second primer binding site, respectively, and wherein each primer of the second set is extended to form a second extension product, such that each second extension product comprises a first primer binding site, a second primer binding site, at least one sequence tag, and either (i) a portion of a Vβ segment and a portion of a Jβ segment of a T cell receptor chain, (ii) a portion of a Vδ segment and a portion of a J δ segment of a T cell receptor chain, or (iii) a portion of a Vγ segment and a portion of a Jγ segment or a T cell receptor chain; (d) performing a polymerase chain reaction in the reaction mixture to form an amplicon, the polymerase chain reaction using forward primers specific for the first primer binding site and reverse primers specific for the second primer binding site; and (e) sequencing the nucleic acids of the amplicon to form a clonotype profile of multiple T cell receptor chains. As used herein, "primer extension conditions" in a reaction mixture includes conditions in which substantially all primer binding sites are in a single stranded state. In some embodiments, such conditions are obtained by melting double stranded target nucleic acids so that primer binding sites are in single stranded form so that primers can anneal to them to form substrates for polymerase extension.

The predetermined locations or sites at which primers of the first and second sets bind may be determined by conventional methods known to those of ordinary skill in the art of multiplex nucleic acid amplifications, such as multiplex PCRs, as exemplified in the references cited below. For example, in the case of target polynucleotides being recombined nucleic acids encoding immune receptor molecules, Faham and Willis (cited above), Van Dongen et al, Leukemia, 17: 2257-2317 (2003), and like references provide guidance for selecting primer binding sites for multiplex amplification of such target polynucleotides. In some embodiments, selecting such predetermined locations or sites depends of several factors including (i) their effect on amplification efficiency (it is desirable that frequencies of different copies in an amplicon faithfully represent frequencies of target polynucleotides in a sample), (ii) their effect on the lengths of copies in an amplicon correspond to requirements of the DNA sequencing chemistry being employed, (iii) whether the selected primers span a portion of the recombined nucleic acids with desired diversity, e.g. a VDJ region, and the like. In relation to this aspect, in part the invention includes an appreciation and recognition that primer cross-reactivity with different target polynucleotides does not effect results of methods of the invention as compared to, for example, in methods based solely on analog readouts of PCR amplifications, spectratyping, and the like), because a set of sequences is the readout rather than an analog signal.

In some embodiments, the step or sequencing includes the following steps: (i) providing a plurality of sequence reads each having an error rate and each comprising a nucleotide sequence and a tag sequence, and (ii) aligning groups of sequence reads having like tag sequences, after which base calls are made based on sequence reads within the groups to determine the nucleotide sequence. Such group-level nucleotide sequences may then be coalesced into the same or different clonotypes as described below. In some embodiments, in the PCR steps, the lengths of the receptor-specific portions of the primers of the first and second sets are selected so that relative levels of different recombined nucleic acids in the amplicon are substantially the same as those of recombined nucleic acids in the sample. In implementing such selection of primers the positions and lengths of the binding sites of the primers on their respective target polynucleotides may be varied. In some embodiments, sequence tags are selected from a set of sequence tags which is much larger than the number of distinct target polynucleotides in a sample, so that substantially every distinct target polynucleotide in the sample and copies thereof will have a different sequence tag (for example, in accordance with the "labeling by sampling" methodology described in Brenner, U.S. Pat. No. 7,537,897). In some embodiments, the number of sequence tags in such a set is at least 100 times the size of the population of target polynucleotides in a sample. Further, in some embodiments where substantially every original target polynucleotide and copies thereof are labeled with the same unique sequence tag, the step of sequencing includes generating sequence reads of nucleic acids of the amplicon and aligning sequence reads having the same sequence tags to determine sequence reads corresponding to the same clonotypes the sample. Further, in some embodiments, the step of aligning further includes determining a nucleotide sequence of each clonotype by determining a majority nucleotide at each nucleotide position of the sequence reads having the same sequence tag. Further, in some embodiments, steps of removing the non-extended primers may be carried out by digesting single stranded nucleic acids in the reaction mixture using a nuclease having 3'→5' single strand exonuclease activity (which may be provided by, for example, *E. coli* exonuclease 1, which may be conveniently inactivated by heat). In further embodiments, the above methods may be used to generate clonotype profiles for diagnosing and/or monitoring minimal residual disease of a cancer patient, such as a myeloma, lymphoma or leukemia patient. Such diagnosing and/or monitoring may be implemented with the following additional step after the above method steps: determining from the clonotype profile a presence, absence and/or level of one or more patient-specific clonotypes correlated with the cancer. Methods of this embodiment may further include steps or determining sequences of each of one or more sequence tags and comparing such sequences with sequences of sequence tags of previously determined clonotype profiles to determine a presence, absence and/or level of contaminating sequences. In some embodiments, such step of comparing includes comparing the sequences of one of more sequence tags to sequence tags of a clonotype database containing clonotypes from at least one individual other than the patient.

In still another embodiment, a method of amplifying in one reaction a plurality of recombined nucleic acids encoding β, δ and γ T cell receptor components may comprise the steps of: (a) combining in a reaction mixture under primer extension conditions a first set of primers with a sample of recombined nucleic acids from T-cells, wherein each of the recombined nucleic acids comprises at first end at least a portion of a Jβ, Jδ or Jγ segment of a T cell receptor, and wherein each primer of the first set each has a receptor-specific portion with a length, which receptor-specific portion anneals to the first end of a different recombined nucleic acid and is extended to form a first extension product, and wherein each primer of the first set has a 5'-non-complementary end containing in a 3'→5' ordering a sequence tag and a first primer binding site, the sequence tag being different for substantially every primer of the first set; (b) removing from the reaction mixture non-extended primers of the first set; (c) adding to the reaction mixture under primer extension conditions a second set of primers, each primer of the second set having a receptor-specific portion with a length, which anneals to the first extension product and is extended to form a second extension product, wherein each second extension product comprises at least a portion of a Vβ, Vδ or Vγ segment of a T cell receptor, and wherein each primer of the second set has a 5'-non-complementary end containing a second primer binding site; and (d) performing polymerase chain reaction in the reaction mixture to form an amplicon, the polymerase chain reaction using a forward primer specific for the first primer binding site and a reverse primer specific for the second primer binding site. The above method may further include a step of sequencing a sample of sequences of the amplicon. Typically such sample as a "representative sample" in that it is large enough to that different clonotypes are present in the sample in approximately the same frequencies as in the original sample of biological material. In some embodiments, the step of sequencing includes providing a plurality of sequence reads each having an error rate and each comprising a nucleotide sequence and a tag sequence, and aligning sequence reads having like tag sequences to determine sequence reads corresponding to the same clonotype. Such sequence reads may be processed in further step of coalescing, as described more fully below, whenever multiple sequence tags are attached to original target polynucleotides or copies thereof.

In to another embodiment, a method of generating clonotype profiles from multiple T cell receptor chains may comprise the steps of: (a) combining in a reaction mixture under primer extension conditions a first set of primers with a sample of recombined nucleic acids from T-cells, wherein each primer of the first set has a receptor-specific portion with a length such that the receptor-specific portion anneals to a different recombined nucleic acid at a predetermined location and is extended to form a first extension product, and wherein each primer of the first set has a 5'-non-complementary end containing a first primer binding site; (b) removing from the reaction mixture non-extended primers of the first set; (c) adding to the reaction mixture a second set of primers, wherein each primer of the second set has a receptor-specific portion with a length, the receptor-specific portion being specific for the first extension product at a predetermined location and having a 5'-non-complementary end containing a second primer binding site, primers of the first set and/or primers of the second set comprising a sequence tag disposed between the receptor-specific portion and the first or second primer binding site, respectively; (d) performing a first polymerase chain reaction to form a first amplicon, the first polymerase chain reaction using forward primers specific for the first primer binding site and primers of the second set, wherein each nucleotide sequence of the first amplicon comprises a first primer binding site, a second primer binding site, at least one sequence tag, and either a portion of a Vβ segment and a portion of a Jβ segment of a T cell receptor chain, a portion of a Vδ segment and a portion of a Jδ segment of a T cell receptor chain, or a portion of a Vγ segment and a portion of a Jγ segment of a T cell receptor chain, and wherein the lengths of the receptor-specific portions of the primers of the first and second sets are selected so that relative levels of different recombined nucleic acids in the amplicon are substantially the same as those of different recombined nucleic acids in the sample; (e) adding reverse primers specific for the second primer binding site; (f) performing a second polymerase chain reaction in the reaction mixture to form a second amplicon, the polymerase chain reaction using forward primers specific for the first primer binding site and reverse primers specific for the second primer binding site; (g) sequencing the nucleic acids of the second amplicon to form a clonotype profile of multiple cell receptor chains. In some embodiments, the step of sequencing includes providing a plurality of sequence reads each having an error rate and each comprising a nucleotide sequence and a to sequence, and aligning sequence reads having like tag sequences to determine sequence reads corresponding to the same clonotype. In further embodiments where target polynucleotides and/or copies thereof are labeled with more than one sequence tag, after aligning like sequence tags, sequence reads may be processed in a further step of coalescing, as described more fully below.

In another example, a method of generating clonotype profiles from multiple B cell receptor chains may be carried out by the steps of: (a) combining in a reaction mixture under primer extension conditions a first nested set of primers with a sample of recombined nucleic acids from B-cells, the first nested set comprising one or more groups of primers, wherein each primer of each group has a receptor-specific portion with a length such that the receptor-specific portion of each primer from a different group anneals to a different recombined nucleic acid at a predetermined site that does not overlap a predetermined site of any other primer of the first nested set, and wherein each primer of each group has a 5'-non-complementary end containing a first primer binding site; (b) extending primers of the first nested set to form a first extension product; (c) removing from the reaction mixture non-extended primers of the first nested set; (d) adding to the reaction mixture under primer extension conditions a second nested set of primers, the second nested set comprising one or more groups of primers, wherein each primer of each group has a receptor-specific portion with a length such that the receptor-specific portion of each primer from a different group anneals to the first extension product at a predetermined site that does not overlap a predetermined site of any other primer of the second nested set, and wherein each primer of each group has a 5'-non-complementary end containing a second primer binding site, and wherein primers of the first nested set and/or primers of the second nested set comprise a sequence tag disposed between its receptor-specific portion and its first or second primer binding site, respectively; (e) extending primers of the second nested set to form a second extension product, such that each second extension product comprising a first primer binding site, a second primer binding site, at least one sequence tag, and either (i) a portion of a V segment and a portion of a J segment of a B cell receptor heavy chain, or (ii) a portion of a V segment and a portion of a J segment of a B cell receptor kappa light chain; (f) performing a polymerase chain reaction in the reaction mixture to form an amplicon, the polymerase chain reaction using forward primers specific for the first primer binding site and reverse primers specific for the second primer binding site and (g) sequencing the nucleic acids of the amplicon to form a clonotype profile of multiple B cell receptor chains.

In some embodiments, more than one cycles of annealing and extending primers (after melting the extension product) may be implemented in steps (b) and/or (e), in which case copies of the original recombined nucleic acids in the sample may be labeled with one or more sequence tags. In these embodiments, sequencing step (g) may include further steps of aligning and coalescing as described below for determining clonotypes and clonotype profiles. In some embodiments, for example, where only single extensions are made in steps (b) and (e), the step of sequencing includes providing a plurality of sequence reads each having an error rate and each comprising a nucleotide sequence and a tag sequence, and aligning sequence reads having like tag sequences to determine sequence reads corresponding to the same clonotype. As above, in some embodiments, in the PCR the positions and the lengths of the receptor-specific portions of the primers of the first and second sets are selected so that relative levels of different recombined nucleic acids in the amplicon are substantially the same as those of different recombined nucleic acids in the sample.

In some of the embodiments, sequence tags are attached to a target polynucleotide or a copy thereof in a step of primer extension, wherein substantially every different target polynucleotide and copy thereof is labeled with the same sequence tag. In other embodiments, target polynucleotides of a sample or copies thereof may be labeled with more than one different sequence tags. As explained further below, in some embodiments, multiple extensions or multiple cycles of a PCR may be carried out in the presence of sequence tag-containing primers (either a first set of primers or a second set of primers), which may result in different sequence tags being attached to the same target polynucleotide and/or its copies.

Sequence Tags in Clonotype Analysis

In one aspect, the invention is directed to a method for obtaining and analyzing sequence data from a repertoire of immune molecules, such as T cell receptors (TCRs) or B cell receptors (BCRs) or defined fragments thereof, to rapidly and efficiently determine a clonotype profile. Sequence data typically comprises a large collection of sequence reads, i.e. sequences of base calls and associated quality scores, from a DNA sequencer used to analyze the immune molecules. A key challenge in constructing clonotype profiles is to rapidly and accurately distinguish sequence reads that contain genuine differences from those that contain errors from non-biological sources, such as the extraction steps, sequencing chemistry, amplification chemistry, or the like. An aspect of the invention includes attaching a unique sequence tag to each target polynucleotide, for example, recombined nucleic acid, in a sample to assist in determining whether sequence reads of such conjugates are derived from the same original target polynucleotide. In accordance with one aspect of the invention, sequence tags are attached to the somatically recombined nucleic acid molecules to form tag-molecule conjugates wherein each recombined nucleic acid of such a conjugate has a unique sequence tag. Usually such attachment is made after nucleic acid molecules are extracted from a sample containing T cells and/or B cells and/or cell-free DNA. Preferably, such unique sequence tags differ as greatly as possible from one another as determined by conventional distance measures for sequences, such as a Hamming distance, or the like. By maximizing the distance between sequence tags in tag-molecule conjugates, even with a high rate of sequencing and amplification errors, a sequence tag of a conjugate remains far closer to its ancestral tag sequence than to that of any other tag sequence of a different conjugate. For example, if 16-mer sequence tags are employed and each such tag on a set of clonotypes has a Hamming distance of at least fifty percent, or eight nucleotides, from every other sequence tag on the clonotypes, then at least eight sequencing or amplification errors would be necessary to transform one such tag into another for a miss-read of a sequence tag (and the incorrect grouping of a sequence read of a clonotype with the wrong sequence tag). In one embodiment, sequence tags are selected so that after attachment to recombined nucleic acids molecules to form tag-molecule conjugates, the Hamming distance between tags of the tag-molecule conjugates is a number at least twenty-five percent of the total length of such sequence tags (that is, each sequence tag differs in sequence from every other such tag in at least 25 percent of its nucleotides); in another embodiment, the Hamming, distance between such sequence tags is a number at least 50 percent of the total length of such sequence tags.

In one aspect, the invention is implemented by the following steps: (a) obtaining a sample from an individual comprising T-cells and/or B-cells and/or cell-free DNA; (b) attaching sequence tags to molecules of recombined nucleic acids of T-cell receptor genes or immunoglobulin genes in the sample to form tag-molecule conjugates, wherein substantially every molecule of the tag-molecule conjugates has a unique sequence tag; (c) amplifying the tag-molecule conjugates; (d) sequencing the tag-molecule conjugates; and (e) aligning sequence reads of like sequence tags to determine sequence reads corresponding to the same recombined nucleic acid in the sample. Samples containing B-cells or T-cells are obtained using conventional techniques. In the step of attaching sequence tags, preferably sequence tags are not only unique but also are sufficiently different from one another that the likelihood of even a large number of sequencing or amplification errors transforming one sequence tag into another would be close to zero. After attaching sequence tags, amplification of the tag-molecule conjugate is necessary for most sequencing technologies; however, whenever single-molecule sequencing technologies are employed an amplification step is optional. Single molecule sequencing technologies include, but are not limited to, single molecule real-time (SMRT) sequencing, nanopore sequencing, or the like, e.g. U.S. Pat. Nos. 7,313,308; 8,153,375; 7,907,800; 7,960,116; 8,137,569; Manrao et al, Nature Biotechnology, 4(8): 2685-2693 (2012); and the like.

In another aspect, the invention includes a method for determining the number of lymphocytes in a sample by counting unique sequence tags. Even without sequence tags, clonotypes of TCRβ or IgH genes, particularly those including the V(D)J regions, provide for a lymphocyte and its clones a unique marker. Whenever recombined nucleic acids are obtained from genomic DNA, then a count of lymphocytes in a sample may be estimated by the number of unique clonotypes that are counted after sequencing. This approach breaks down whenever there are significant clonal populations of identical lymphocytes associated with the same clonotype (or when recombined nucleic acids are obtained from mRNA of a sample, whose quantity of individual sequences may reflect, or depend on, expression rate as well as call number). The use of sequence tags overcomes this short coming and is especially useful for providing counts of lymphocytes in patients suffering from many lymphoid disorders, such as lymphomas or leukemias. In accordance with one aspect of the invention, sequence tags may be used to obtain an absolute count of lymphocytes in a sample regardless of whether there is a large dominant clone present, such as with leukemia. Such a method may be implemented with the steps: (a) obtaining a sample from an individual comprising lymphocytes; (b) attaching sequence tags to molecules of recombined nucleic acids of T-cell receptor genes or of immunoglobulin genes of the lymphocytes to form tag-molecule conjugates, wherein substantially every molecule of the tag-molecule conjugates has a unique sequence tag; (c) amplifying the tag-molecule conjugates: (d) sequencing the tag-molecule conjugates; and (e) counting the number of distinct sequence tags to determine the number of lymphocytes in the sample. In some embodiments, the molecules of recombined nucleic acids are from genomic DNA.

In one embodiment of the invention, sequence tags are attached to recombined nucleic acid molecules of a sample by labeling by sampling, e.g. as disclosed by Brenner et al, U.S. Pat. No. 5,846,719; Brenner et al, U.S. Pat. No. 7,537,897; Macevicz, International patent publication WO 2005/111242; and the like, which are incorporated herein by reference. In labeling by sampling, polynucleotides of a population to be labeled (or uniquely tagged) are used to sample (by attachment, linking, or the like) sequence tags of a much larger population. That is, if the population of polynucleotides has K members (including replicates of the same polynucleotide) and the population of sequence tags has N members, then N>>K. In one embodiment, the size of a population of sequence tags used with the invention is at least 10 times the size of the population of clonotypes in a sample; in another embodiment, the size of a population of sequence tags used with the invention is at least 100 times the size of the population of clonotypes in a sample; and in another embodiment, the size of a population of sequence tags used with the invention is at least 1000 times the size of the population of clonotypes in a sample. In other embodiments, a size of sequence tag population is selected so that substantially every clonotype in a sample will have a unique sequence tag whenever such clonotypes are combined with such sequence tag population, e.g. in an attachment reaction, such as a ligation reaction, amplification reaction, or the like. In some embodiments, substantially every clonotype means at least 90 percent of such clonotypes will have a unique sequence tag; in other embodiments, substantially every clonotype means at least 99 percent of such clonotypes will have a unique sequence tag; in other embodiments, substantially every clonotype means at least 99.9 percent of such clonotypes will have a unique sequence tag. In many tissue samples or biopsies the number of T cells or B cells may be up to or about 1 million cells; thus, in some embodiments of the invention employing such samples, the number of unique sequence tags employed in labeling by sampling is at least $10^8$ or in other embodiments at least $10^9$.

In such embodiments, in which up to 1 million clonotypes are labeled by sampling, large sets of sequence tags may be efficiently produced by combinatorial synthesis by reacting a mixture of all four nucleotide precursors at each addition step of a synthesis reaction, e.g. as disclosed in Church, U.S. Pat. No. 5,149,625, which is incorporated by reference. The result is a set of sequence tags hiving a structure of "$N_1 N_2 \ldots N_8$" where each $N_i$=A, C, G or T and k is the number of nucleotides in the tags. The number of sequence tags in a set of sequence tags made by such combinatorial synthesis is $4^k$. Thus, a set of such sequence tags with k at least 14, or k in the range of about 14 to 18, is appropriate for attaching sequence tags to a $10^6$-member population of molecules by labeling by sampling. Sets of sequence tags with the above structure include many sequences that may introduce difficulties or errors while implementing the methods of the invention. For example, the above combinatorially synthesized set of sequence tags includes many member tags with homopolymers segments that some sequencing approaches, such as sequencing-by-synthesis approaches, have difficulty determining with accuracy above a certain length. Therefore, the invention includes combinatorially synthesized sequence tags having structures that are efficient for particular method steps, such as sequencing. For example, several sequence tag structures efficient for sequencing-by-synthesis chemistries may be made by dividing the four natural nucleotides into disjoint subsets which are used alternatively in combinatorial synthesis, thereby preventing homopolymer segments above a given length. For example, let z be either A or C and x be either G or T, to give a sequence tag structure of $$[(z)_1(z)_2 \ldots (z)_j][(x)_1(x)_2 \ldots (x)_j] \ldots$$

where i and j, which may be the same or different, are selected to limit the size of any homopolymer segment. In one embodiment, i and j are in the range of from 1 to 6. In such embodiments, sequence tags may have lengths in the range of from 12 to 36 nucleotides; and in other embodiments, such sequence tags may have lengths in the range of from 12 to 24 nucleotides. In other embodiments other pairing of nucleotides may be used, for example, z is A or T and x is G or C; or z is A or G and x is T or C. Alternatively, let $z^2$ be any combination of three of the four natural nucleotides and let x' be whatever nucleotide is not a z' (for example, z' is A, C or G, and x' is T). This gives a sequence tag structure as follows:

$$[(z')_1(z')_2 \ldots (z')_i]x'[(z')_1(z')_2 \ldots (z')_i]x' \ldots$$

where i is selected as above and the occurrence of x' serves as a punctuation to terminate any undesired homopolymers.

Further Sequence Tags

The invention uses methods of labeling nucleic acids, such as fragments of genomic DNA, with unique sequence tags, which may include "mosaic tags," prior to amplification and sequencing. Such sequence tags are useful for identifying amplification and sequencing errors. Mosaic tags minimize sequencing and amplification artifacts due to inappropriate annealing, priming, hairpin formation, or the like, that may occur with completely random sequence tags of the prior art. In one aspect, mosaic tags are sequence tags that comprise alternating constant regions and variable regions, wherein each constant region has a position in the mosaic tag and comprises a predetermined sequence of nucleotides and each variable region has a position in the mosaic tag and comprises a predetermined number of randomly selected nucleotides. By way of illustration, a 22-mer mosaic tag (SEQ ID NO: 1) may have the following form:

| 1 2 3 | 4 5 6 7 8 | 9 | 10 11 | 12 13 14 | 15 16 17 |
|---|---|---|---|---|---|
| N N N | b b b b b | N | b b | N N N | b b b |
| 1 | 2 | 3 | 4 | 5 | 6 |

| 18 19 | 20 | 21 22 |
|---|---|---|
| N N | b | N N |
| 7 | 8 | 9 |

Region Position

There are nine constant and variable regions, with regions 1 (nucleotides 1-3), 3 (nucleotide 9), 5 (nucleotides 12-14), 7 (nucleotides 18-19) and 9 (nucleotides 21-22) being variable (double underlined nucleotides) and regions 2 (nucleotides 4-8), 4 (nucleotides 10-11), 6 (nucleotides 15-17), and 8 (nucleotide 20) being constant. N represents a randomly selected nucleotide from the set of A, C, G or T; thus, the number of mosaic tags of this example is $4^{11}$=4,194,304 tags. b represents a predetermined nucleotide at the indicated position. In some embodiments, the sequence of b's, "***bbbbb*bb*bbbb**", is selected to minimize the likelihood of having a perfect match in a genome of the organism making up the sample.

In one aspect, for mosaic tags of a particular embodiment of the method of the invention, all constant regions with the same position have the same length and all variable regions with the same position have the same length. This allows mosaic tags to be synthesized using partial combinatorial synthesis with conventional chemistries and instruments.

In one aspect, mosaic tags comprise from 10 to 100 nucleotides, or 12 to 80 nucleotides, or from 15 to 60 nucleotides. In some embodiments, mosaic tags comprise at least eight nucleotide positions with randomly selected nucleotides; in other embodiments, whenever mosaic tags have a length of at least 15 nucleotides, they comprise at least 12 nucleotide positions with randomly selected nucleotides. In another aspect, no variable region within a mosaic tag may have a length that is greater than seven nucleotides.

In another aspect, mosaic tags may be used in the following steps: (i) preparing DNA templates from nucleic acids in a sample; (ii) labeling by sampling the DNA templates to form a multiplicity tag-template conjugates, wherein substantially every DNA template or a tag-template conjugate has a unique mosaic tag comprising alternating constant regions and variable regions, each constant region having a position in the mosaic tag and a length of from 1 to 10 nucleotides of a predetermined sequence and each variable region having a position in the mosaic tag and a length of from 1 to 10 randomly selected nucleotides, such that constant regions having the same positions have the same lengths and variable region having the same positions have the same lengths; (iii) amplifying the multiplicity of tag-template conjugates; (iv) generating a plurality of sequence reads for each of the amplified tag-template conjugates; and (v) determining a nucleotide sequence of each of the nucleic acids by determining a consensus nucleotide at each nucleotide position of each plurality of sequence reads having identical mosaic tags. In another aspect, mosaic tags may be used in the following steps: (a) preparing single stranded DNA templates from nucleic acids in a sample; (b) labeling by sampling the single stranded DNA templates to form tag-template conjugates, wherein substantially every single stranded DNA template of a tag-template conjugate has a unique sequence tag (that is, a mosaic tag) having a length of at least 15 nucleotides and having the following form:

$$[(N_1N_2 \ldots N_{Kj})(b_1b_2 \ldots b_{ij})]_M$$

wherein each $N_i$ for $i=1, 2, \ldots K_j$, is a nucleotide randomly selected from the group consisting of A, C, G and T; $K_j$ is an integer in the range of from 1 to 10 for each j less than or equal to M (that is, regions $N_1N_2 \ldots N_{Kj}$ are variable regions); each $b_i$, for $i=1, 2, \ldots L_j$, is a nucleotide; $L_j$ is an integer in the range of from 1 to 10 for each j less than or equal to M; such that every sequence tag (i) has the same Kj for every j and (ii) has the same sequences $b_1b_2 \ldots b_{Tj}$ for every j (that is, regions $b_1b_2 \ldots b_{ij}$ are constant regions); and M is an integer greater than or equal to 2; (c) amplifying the tag-template conjugates; (d) generating as plurality of sequence reads for each or the amplified tag-template conjugates; and (e) determining a nucleotide sequence of each of the nucleic acids by determining a consensus nucleotide at each nucleotide position of each plurality of sequence reads having identical sequence tags. In some embodiments, the plurality of sequence reads is at least $10^4$; in other embodiments, the plurality of sequence reads is at least $10^5$; in still other embodiments, the plurality or sequence reads is at least $10^6$. In some embodiments, the total length of the above sequence tag is in the range of from 15 to 80 nucleotides.

Attaching Sequence Tags

A variety of different attachment reactions may be used to attach unique tags to substantially every clonotype in a sample in addition to those illustrated above. Many techniques for capturing subsets of sample nucleic acids, for example, to reduce sample complexity in microarray or genome sequencing technology, may be used with routine modification in the present invention to attached sequence tags to recombined nucleic acids. Exemplary techniques for capturing diverse sets of target nucleic acids for subsequent manipulation, including attaching sequence tags, sequencing, and the like, include the following: Willis et al, U.S. Pat. No. 7,700,323: Jones et al, U.S. patent publication 2005/0142577; Gullberg et al, U.S. patent publication 2005/0037356; Porreca et al, Nature Methods, 4(11): 931-936 (2007); Turner et al, Nature Methods, 6(5): 315-316 (2009); Church, U.S. Pat. No. 5,149,625; Macevicz, U.S. Pat. No. 8,137,936; and the like.

In one embodiment, such attachment is accomplished by combining a sample containing recombined nucleic acid molecules (which, in turn, comprise clonotype sequences) with a population or library of sequence tags so that members of the two populations of molecules can randomly combine and become associated or linked, e.g. covalently. For example, such random combining may occur in a bimolecular reaction wherein a tag-containing primer anneals to a target nucleic acid and is extended or wherein a tag-containing adaptor is ligated to the end of target nucleic acid. In some embodiments, the method of attaching, tags may depend in part on the DNA sequencing approach. For example, in sequencing methods that produce relatively long accurate sequence reads, such as 454 sequencing, a cDNA library may be made from mRNA comprising recombined nucleic acids using conventional techniques, e.g. 5'-RACE, such as disclosed in Freeman et al, Genome Research, 19: 1817-1824 (2009), after which sequence tags may be attached by ligating sequence-tag-containing adapters to one or both ends. In other embodiments, when sequencing methods, such as "Illumina" sequencing or "Ion Torrent" sequencing, are used that produce relatively short and error-prone sequence reads, further steps may be required so that amplicons for sequencing have lengths that are covered by sequence reads generated from the techniques. In such tag attachment reactions, clonotype sequences comprise linear single or double stranded polynucleotides and sequence tags are carried by reagents such as amplification primers, such as PCR primers, ligation adapters, circularizable probes, plasmids, or the like. Several such reagents capable of carrying sequence tag populations are disclosed in Macevicz, U.S. Pat. No. 8,137,936; Faham et al, U.S. Pat. No. 7,862,999; Landegren et al, U.S. Pat. No. 8,053,188; Unrau and Deugau, Gene, 145: 163-169 (1994); Church, U.S. Pat. No. 5,149,625; and the like, which are incorporated herein by reference.

Figure 2A:
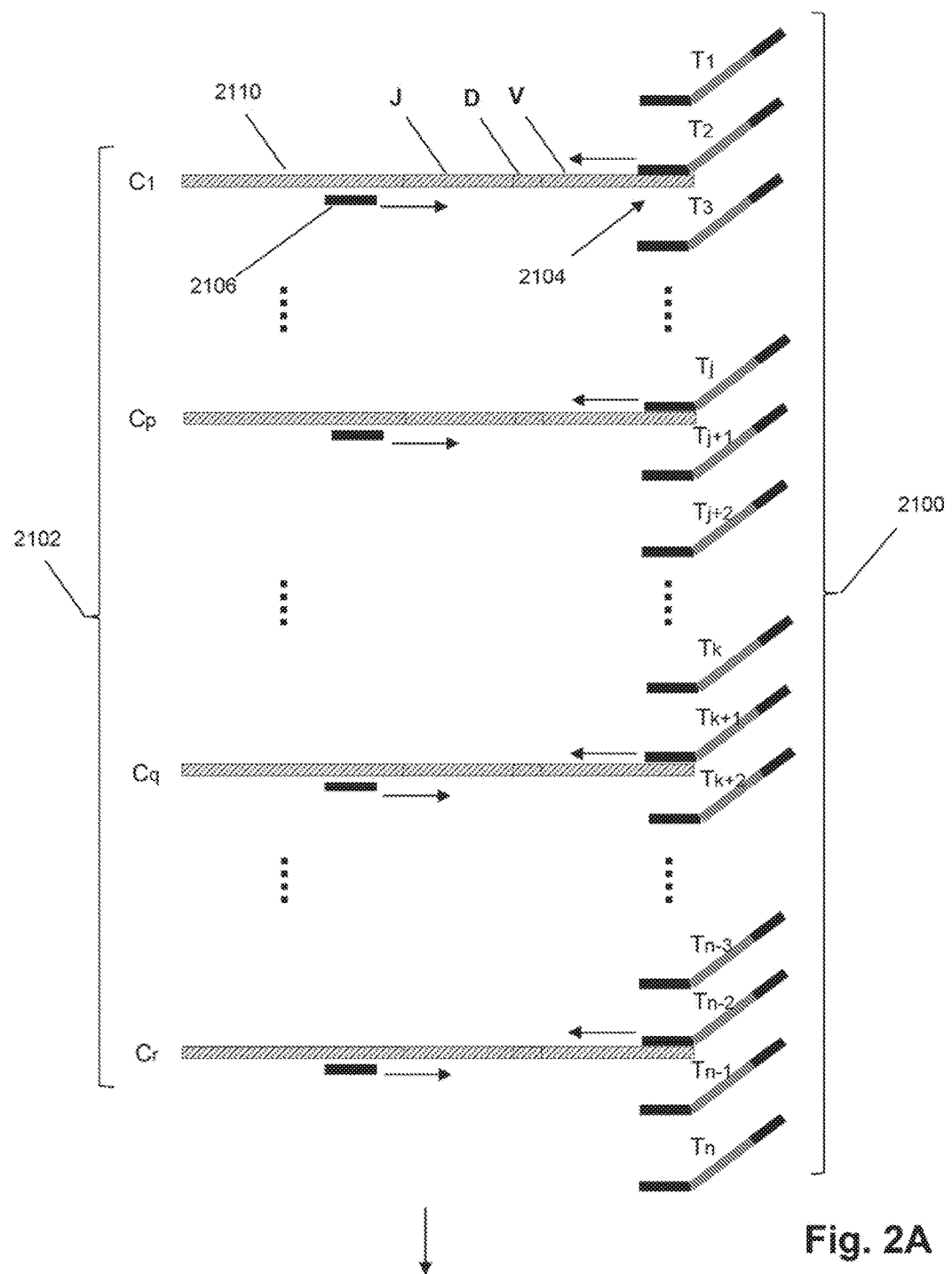
FIGS. 2A through 2G illustrate various methods for attaching unique sequence tags to substantially every target sequence in a sample.
Figure 2B:
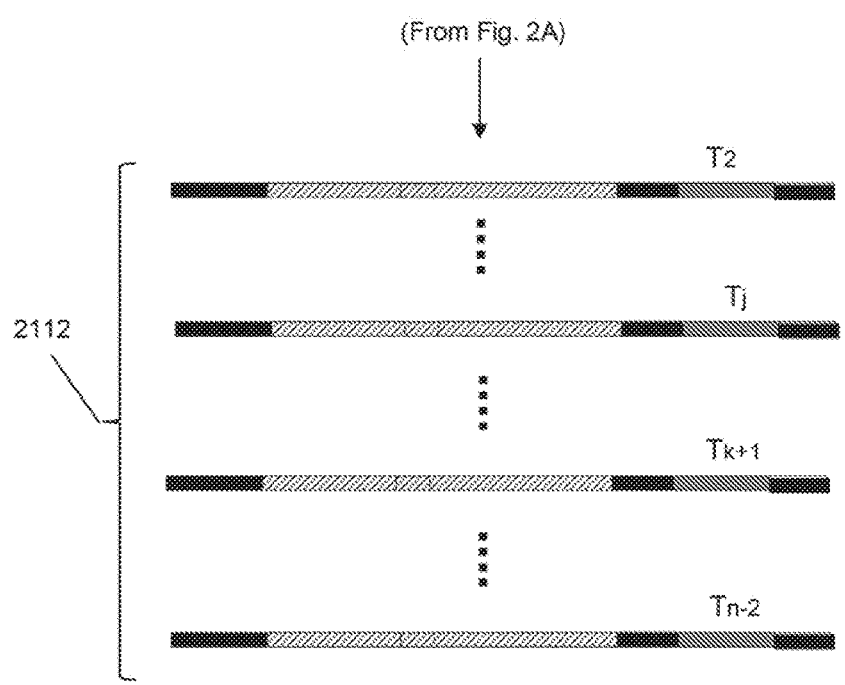

FIGS. 2A and 2B illustrate an attachment reaction comprising a PCR in which is population of sequence tags ($T_1, T_2, T_3 \ldots T_j, T_{j+1} \ldots T_k, T_{k+1} \ldots T_{n+1}, T_n$) is incorporated into primers (2100). The population of sequence tags has a much greater size than that of recombined nucleic acid molecules (2102). The sequence rags are attached to the recombined nucleic acid molecules by annealing the primers to the nucleic acid molecules and extending the primers with a DNA polymerase in the first cycle of a PCR. The figure depicts how the recombined nucleic acid molecules select, or sample, a small fraction of the total population of sequence tags by randomly annealing to the primers by way of their common primer binding regions (2104), for example, in V region (2108). Since the primers (an therefore sequence tags) combine with the recombined nucleic acid sequence molecules randomly, there is a small possibility that the same sequence tag may be attached to different nucleic acid molecules; however, if the population of sequence tags is large as taught herein, then such possibility will be negligibly small so that substantially every recombined nucleic acid molecule will have a unique sequence tag attached. The other primer (2106) of the forward and reverse primer pair anneals to C region (2110) so that after multiple cycles of annealing, extending and melting, amplicon (2112) is formed, thereby attaching unique sequence tags to the V(D)J regions comprising the clonotypes of population (2102). That is amplicon (2112) comprises the tag-molecule conjugates from the attachment reaction.

Figure 2C:
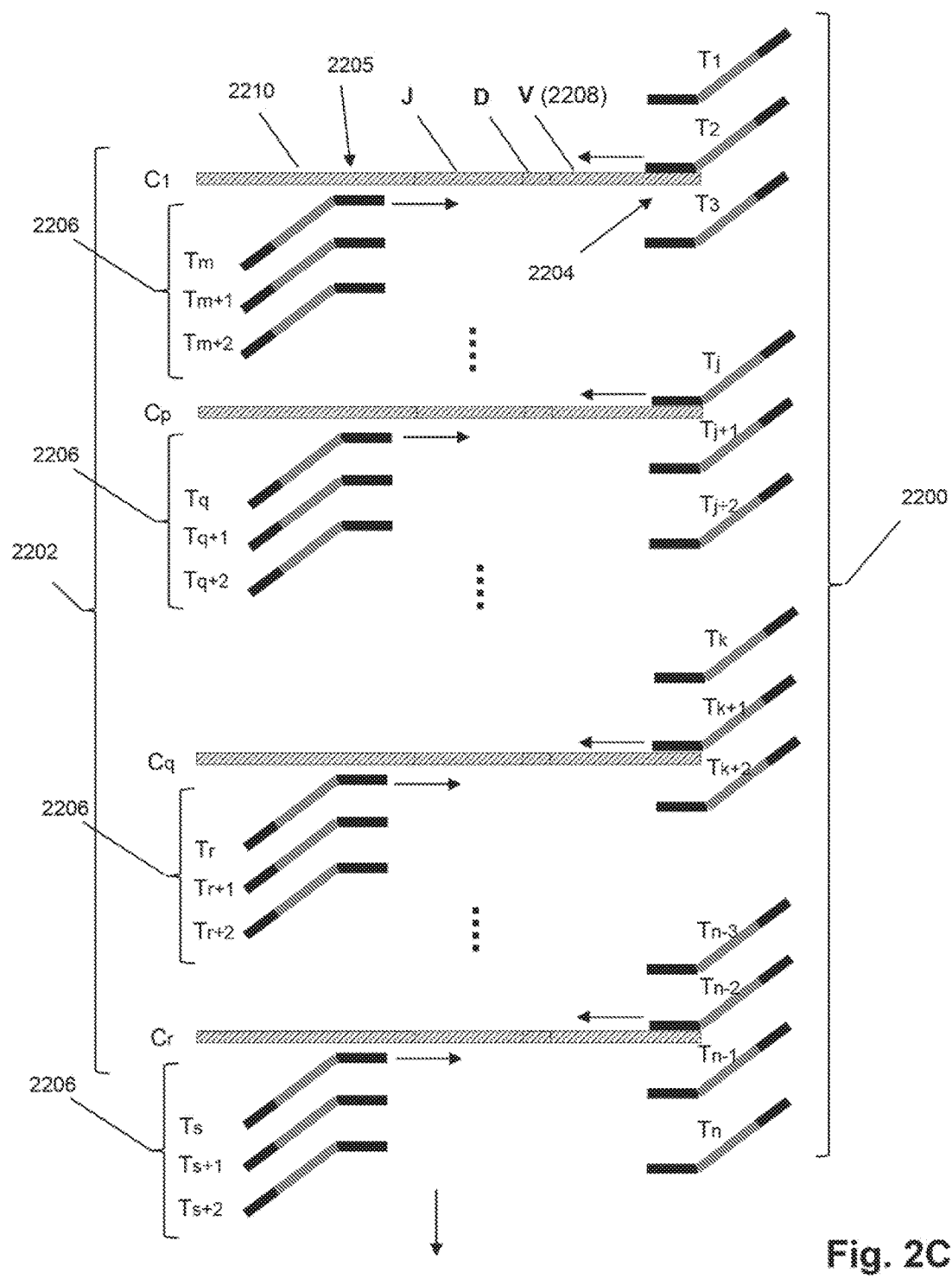
Figure 2D:
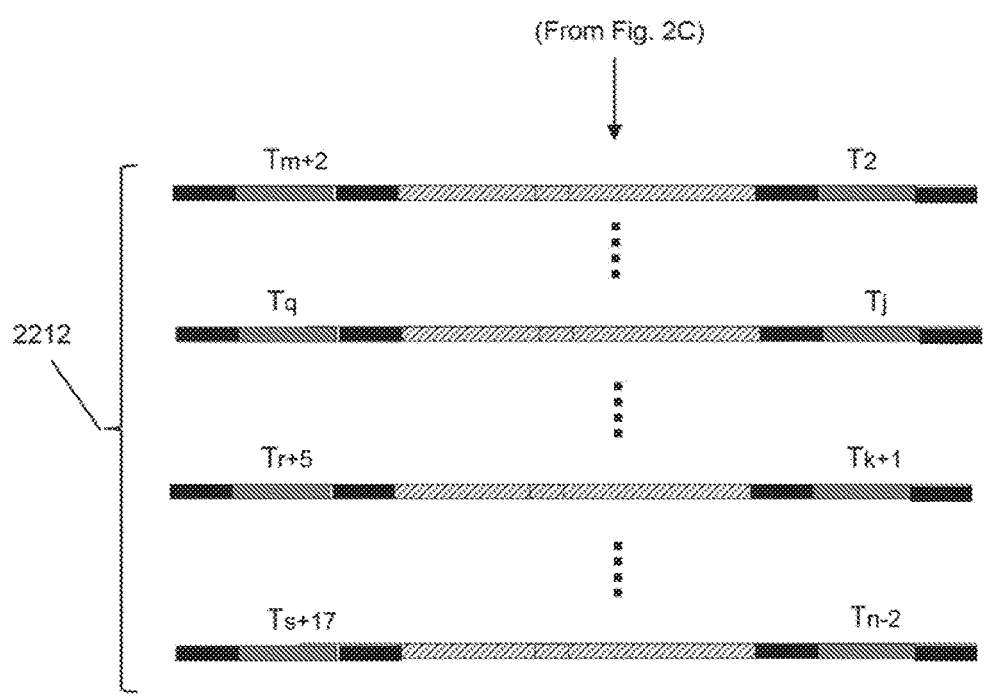

FIGS. 2C and 2D illustrate a method for attaching a pair of sequence lags to each, or substantially each, recombined nucleic acid in a sample. As in the method of FIGS. 2A and 2B, primers (2200) carrying sequence tags ($T_1, T_2, T_3 \ldots T_j, T_{j+1} \ldots T_k, T_{k+1} \ldots T_{n+1}, T_n$) are used as downstream primers and additionally, replacing common primer (2106), primers (2206) carrying sequence tags (Tm, Tm+1, Tm+2 ... Tq, Tq+1, Tq+2, ... Tr, Tr+1, Tr+2, ... Ts, Ts+1, Ts+2 ... ) are used as upstream primers. As with the downstream set of primers, the number of different sequence tags carried by upstream primers (2206) may be large compared to the number of recombined nucleic acid molecules (2202) so that substantially every recombined nucleic acid (2202) will have a unique tag after amplification. In some embodiments, each set of sequence tags in primers (2206) and (2200) need not be as large as the set of sequence tags in the embodiment of FIGS. 2A and 2B. Since each recombined nucleic acid is uniquely labeled by a pair of sequence tags, sharing one sequence tag of the pair with a difference recombined nucleic acid will not detract from the substantial uniqueness to a pair of sequence tags labelling a single recombined nucleic acid. Thus, in the embodiment of FIGS. 2C and 2D, sequence tags of each primer set (2200) and (2206) may be less diverse than the sequence tags of primer set (2100). For example, if random sequence tags are employed and primers (2100) contain 16-mer sequence tags, then primers (2200) and (2206) may each contain 8-mer sequence tags to provide the same total sequence tag diversity. Otherwise, the embodiment of FIGS. 2C and 2D operates similarly to that of FIGS. 2A and 2B. Sequence tags are attached to the recombined nucleic acid molecules by annealing the primers to the nucleic acid molecules and extending the primers with a DNA polymerase in the first cycle of a PCR. As above, FIG. 2C depicts how the recombined, nucleic acid molecules select, or sample, a small fraction of the total population of pairs of sequence tags by randomly annealing to the primers by way of their common primer binding regions (2204) and (2205), for example, in V region (2208) and C region (2210), respectively. Since the primers (an therefore sequence tags) combine with the recombined nucleic acid sequence molecules randomly, there is a small possibility that the same pair of sequence tags may be attached to different nucleic acid molecules; however, if the population of sequence tags is large as taught herein, then such possibility will be negligibly small so that substantially every recombined nucleic acid molecule will have a unique pair of sequence tags attached. After multiple cycles of annealing, extending and melting, amplicon (2212) is formed, thereby attaching unique pairs of sequence tags to the V(D)J regions comprising the clonotypes of population (2202). That is amplicon (2212) comprises the tag-molecule conjugates from the attachment reaction.

Figure 2E:
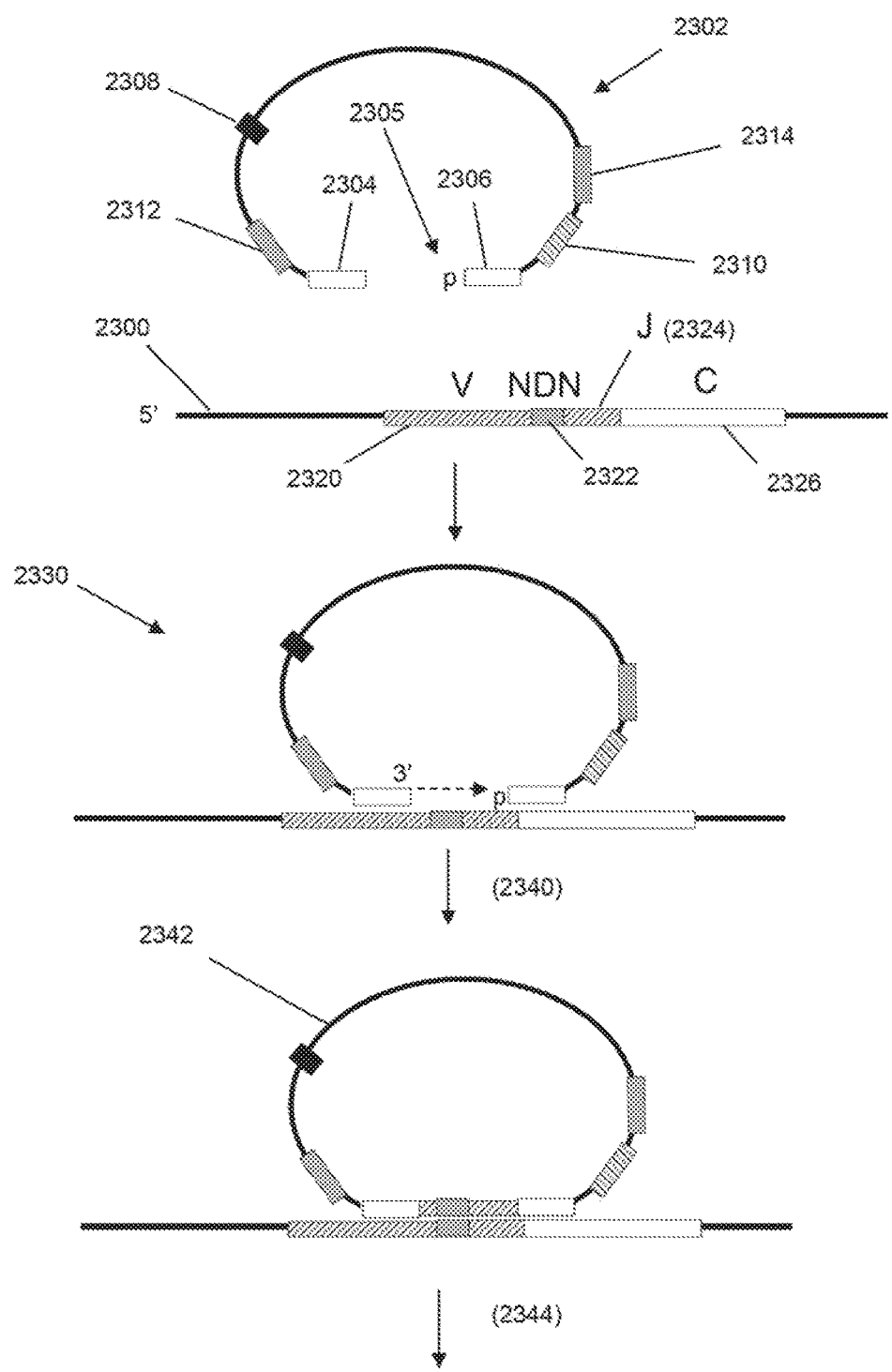
Figure 2F:
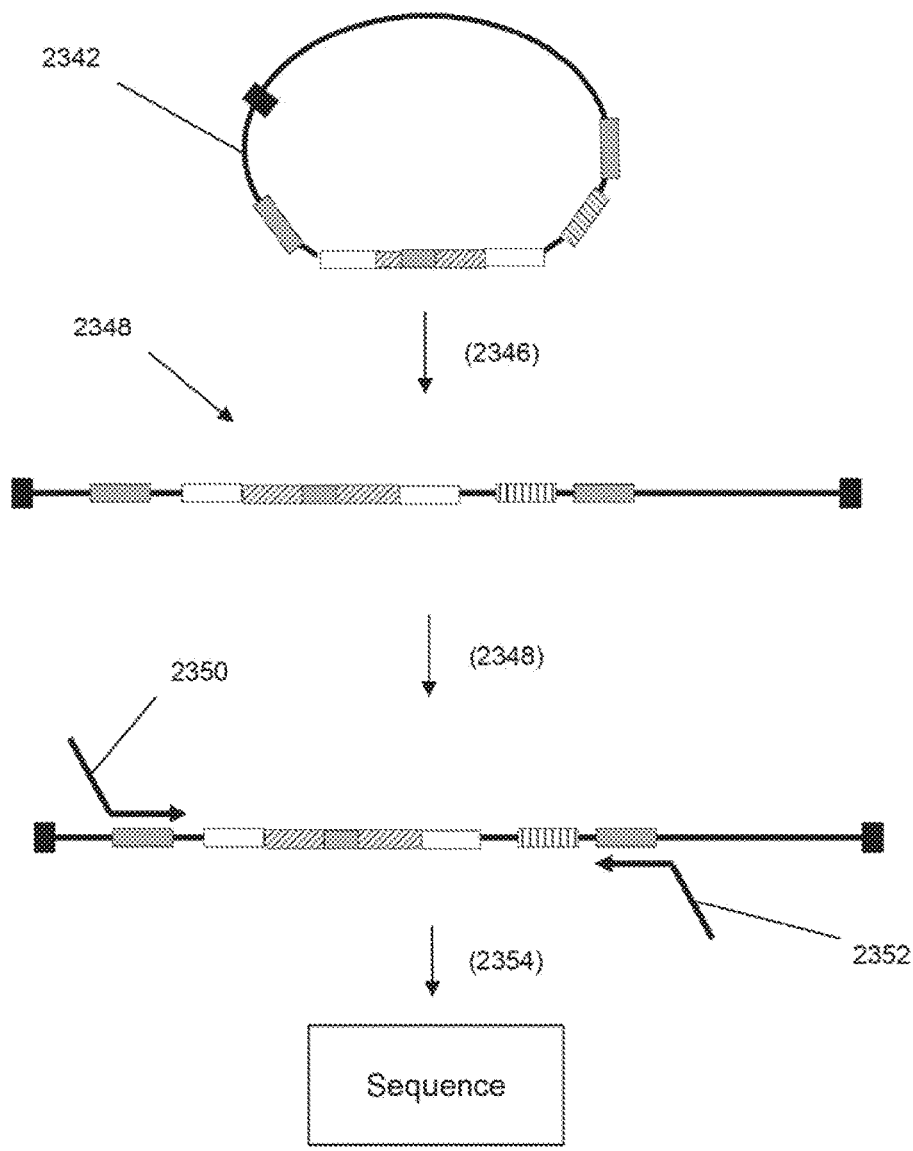

In some embodiments, circularizable probes may be used to capture and attach sequence tags to desired recombined nucleic acids, for example, with routine modification of techniques disclosed by Porreca et al (cited above); Willis et al (cited above); or like references. As illustrated in FIGS. 2E and 2F, circularizable probe (2302) is provided comprising the following elements: upstream target binding segment (2304), downstream target binding segment (2306) that has 5'-phosphorylated end (2305); sequence tag (2310); second common primer binding site (2314); optional cleavage site (2308); and first common primer binding site (2312). Circularizable probe (2302) is combined in a reaction mixture under annealing conditions with a sample containing target polynucleotides (2300), which may be, for example, first or second strands of a cDNA prepared from mRNAs using conventional techniques. As shown, target polynucleotides comprise V, NDN, J and C regions of recombined nucleic acids encoding IgHs or TCRβ chains. In some embodiments, sequences of upstream and downstream target binding segments (2304) and (2306), respectively, are selected so that they span a portion of the VDJ region of the target polynucleotides. Circularizable probe (2302) and target polynucleotides (2300) form complex (2330) in the reaction mixture upon annealing of upstream and downstream target binding segments (2304 and 2306). In the presence of a DNA polymerase and dNTPs, upstream target binding segment (2304) is extended (2340) to downstream target binding segment (2306) copying (and thereby capturing) a portion of the VDJ region of the target polynucleotide. In the presence of a ligase activity, the extended upstream target binding segment is ligated to downstream target binding segment (2306), thereby forming a closed single stranded DNA circle (2342). The reaction mixture optionally may then be treated (2344) with an exonuclease to remove unreacted probe and target polynucleotides. In some embodiments, single stranded circles (2342) are linearized by cleaving cleavage site (2308), which may be, for example, a rare-cutting endonuclease recognition site, or inserting an RNA monomer in the probe and cleaving with RNase H, or the like, after which VDJ-tag inserts of the linearized probes (2348) may be amplified by primers (2350) and (2352). Primers (2350) and (2352) may include noncomplementary regions for adding elements to permit later DNA sequencing (2354). Alternatively, single stranded circle may be used to generate nanoball templates for direct sequencing, e.g. Drmanac et al, Science, 327(5961); 78-81 (2010); U.S. Pat. No. 8,445,196; and the like.

Figure 2G:
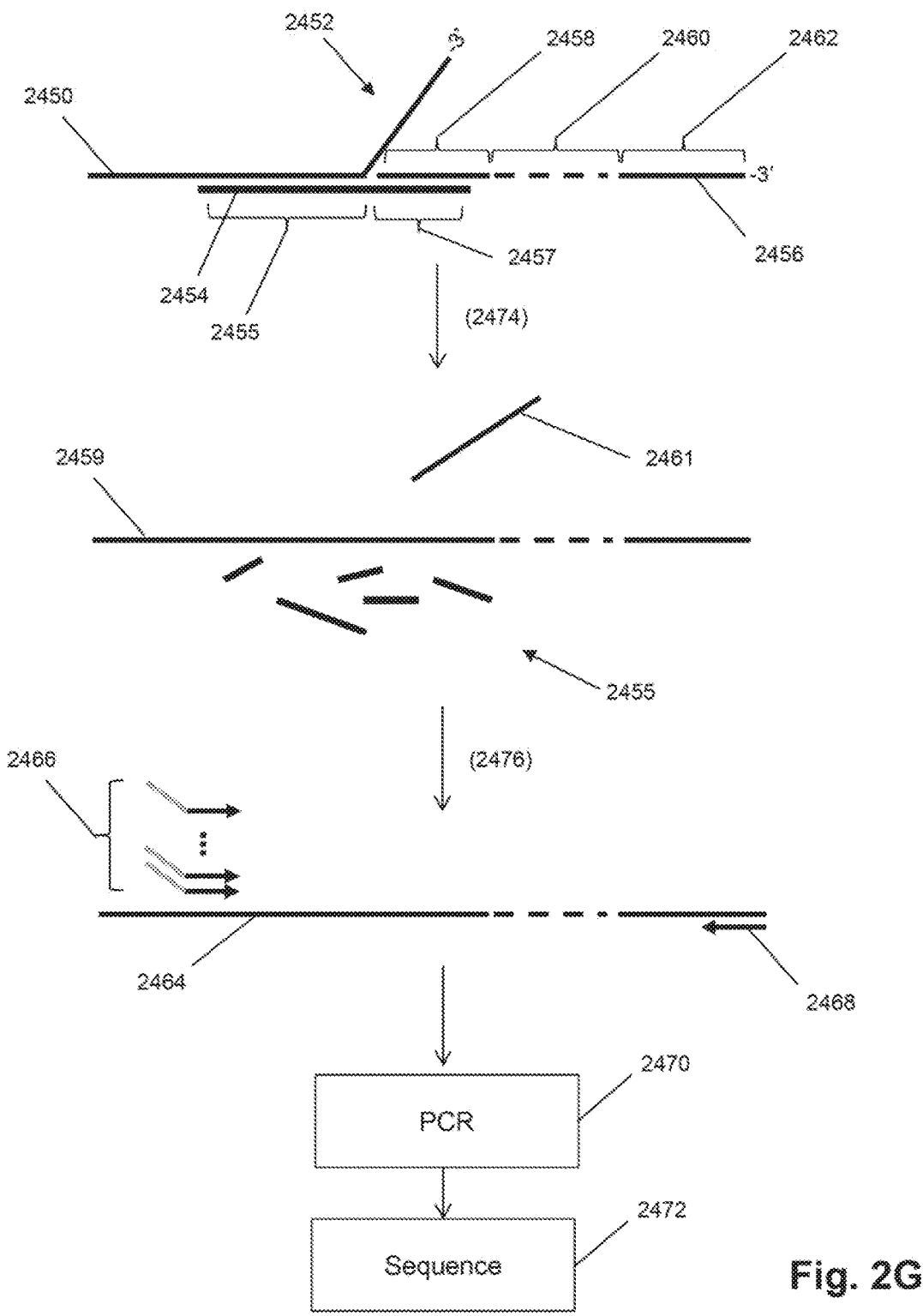

FIG. 2G illustrates another embodiment for attaching a sequence tag to a recombined nucleic acid encoding an immune receptor molecule. Guidance for implementing this embodiment may be found in Faham and Zheng, U.S. Pat. No. 7,208,295, which is incorporated herein by reference. Recombined nucleic acids (2450) are combined in a reaction mixture under annealing conditions for probes (2454) and adapters (2456). Probes (2454) comprise receptor-specific portion (2455) and adaptor-specific portion (2457). For example, probes (2454) may comprise a mixture of probes wherein different probes have receptor-specific portions specific for different J regions, or in other embodiments, specific for different V regions. Adapters (2456), which are 5'-phosphorylated, comprise probe-specific portion (2458) at its 5' end, sequence tag (2460) and first primer binding site (2462). The locations, sequences, and lengths of receptor-specific portion (2455) and adaptor-specific portion (2457) of probe (2454) and probe-specific portion (2458) are selected so that they hybridize with one another to form structures (2452). After structure (2452) forms, single stranded portion (2461) is cleaved from recombined nucleic acid (2450) and the free 3' end of recombined nucleic acid (2450) is ligated to the 5' phosphorylated end of adaptor (2456) to form first extension product (2459), after which probe (2454) is removed (2474). Cleavage of (2461) may be effected by a single stranded nuclease, as described in Faham and Zheng. In one embodiment, probe (2454) is synthesized with thymidines replaced with uracils, e.g. in a PCR with dUTPs in place of dTTps, and it is removed by treating with uracil-DNA glycosylase (UDG), e.g. as taught by Faham et al, U.S. Pat. No. 7,208,295, which is incorporated by reference. UDG treatment cleaves probe (2454) at uracils to give fragments (2455). After free probe, adaptors and flaps are removed (2476), forward primers (2466) and reverse primers (2468) are added to extension product (2464) and PCR (2470) is carried out, after which a sample of the resulting amplicon is sequenced (2472).

In a similar embodiment to that of FIG. 2G, similar probes and adaptors may be used to attached sequence tags at predetermined sites of a target polynucleotide, wherein a flap endonuclease, such as FEN-1, is used to cleave a single stranded portion corresponding to (2461). In this embodiment besides using a different nuclease, the polarity of the probe and adaptor sequences are reversed; namely, a substrate for a flap endonuclease requires that the 3' end of the adaptor corresponding to (2454) be annealed to target sequence (2450) and that the single stranded portion corresponding to (2452) be a 5' end of the target sequence. After cleavage and removal of the probe sequence, the remaining steps are substantially the same. Guidance for using flap endonucleases in detection assays may be found in the following references: Lyamichev et al, Nature Biotechnology, 17: 292-296 (1999); Eis et al, Nature Biotechnology, 19: 673-676 (2001); and like references.

In some embodiments, recombined nucleic acids encode immune receptor molecule chains that typically form an immune repertoire which may comprise a very large set of very similar polynucleotides (e.g. >1000, but more than 10,000, and still more usually from 100,000 to 1,000,000, or more) which may have a length of less than 500 nucleotides, or in other embodiments, less than 400 nucleotides, or in still other embodiments, less than 300 nucleotides. In one aspect of the invention, the inventors recognized and appreciated that these characteristics permitted the use of highly dissimilar sequence tags to efficiently compare sequence reads of highly similar clonotypes to determine whether they are derived from the same original sequence or not.

Samples

The term "sample" refers to a quantity of biological material, which in some embodiments is obtained from a patient, and which contains cells and/or cell-free DNA; that is, the term is used interchangeably with the term "specimen," or "tissue sample." The term "sample" also sometime used in a statistical sense of obtaining a subset, or portion, of a larger set or quantity, respectively, of, for example, recombined nucleic acids; in particular, the statistical usage of the term "sample" may also be understood to mean "representative sample," in that such a sample is understood to reflect, or approximate, the relative frequencies of different nucleic acids in a tissue (for example). One skilled in the art is able to distinguish the proper usage from the context of the terms.

Clonotype profiles may be obtained from samples of immune cells or fluids, such as blood, containing cell-free nucleic acids encoding immune receptor chains. For example, immune cells can include T-cells and/or B-cells. T-cells (T lymphocytes) include, for example, cells that express T cell receptors. T-cells include helper T cells (effector T cells or Th cells), cytotoxic T cells (CTLs), memory T cells, and regulatory T cells. In one aspect a sample of T cells includes at least 1,000 T cells; but more typically, a sample includes at least 10,000 T cells, and more typically, at least 100,000 T cells. In another aspect, a sample includes a number of T cells in the range of from 1000 to 1,000,000 cells. A sample of immune cells may also comprise B cells, include, for example, plasma B cells, memory B cells, B1 cells, B2 cells, marginal-zone B cells, and follicular B cells. B-cells can express immunoglobulins (antibodies, B cell receptor). As above, in one aspect a sample of B cells includes at least 1,000 B cells; but more typically, a sample includes at least 10,000 B cells, and more typically, at least 100,000 B cells. In another aspect, a sample includes a number of B cells in the range of from 1000 to 1,000,000 B cells.

Samples used in the methods of the invention can come from a variety of tissues, including, for example, tumor tissue, blood and blood plasma, lymph fluid, cerebrospinal fluid surrounding the brain and the spinal cord, synovial fluid surrounding bone joints, and the like. In one embodiment, the sample is a blood sample. The blood sample can be about 0.1, 0.2, 0.3, 0.4, 0.5, 0.6, 0.7, 0.8. 0.9, 1.0, 1.5, 2.0, 2.5, 3.0, 3.5, 4.0, 4.5, or 5.0 mL. The sample can be a tumor biopsy. The biopsy can be from, for example, from a tumor of the brain, liver, lung, heart, colon, kidney, or bone marrow. Any biopsy technique used by those skilled in the art can be used for isolating a sample from a subject. For example, a biopsy can be an open biopsy, in which general anesthesia is used. The biopsy can be a closed biopsy, in which a smaller cut is made than in an open biopsy. The biopsy can be a core or incisional biopsy, in which part of the tissue is removed. The biopsy can be an excisional biopsy, in which attempts to remove an entire lesion are made. The biopsy can be a fine needle aspiration biopsy, in which a sample of tissue or fluid is removed with a needle.

In some embodiments, clonotype profiles for methods of the invention are generated from a tumor or peripheral blood in the case of diagnostic samples or from peripheral blood in the case of samples for monitoring residual disease. One or more clonotypes correlated with a disease, such as a lymphoid or myeloid proliferative disorder, are determined from a diagnostic sample. Usually the one or more clonotypes correlated with a lymphoid or myeloid proliferative disorder are those present in a clonotype profile with the highest frequencies. In some cases, there may be a single correlated clonotype and in other cases there may be multiple clonotypes correlated with a lymphoid or myeloid proliferative disorder. Tumor samples may be taken from any tissue affected by such a disorder, which includes lymph nodes or other tissues outside of the lymphatic system. As mentioned above, clonotype profiles for monitoring residual disease may be generated from a sample of nucleic acids extracted from peripheral blood. The nucleic acids of the sample may from B-cells from a cell-containing fraction of the peripheral blood or from a cell free fraction of the peripheral blood, such as plasma or serum. In one embodiment, a peripheral blood sample includes at least 1,000 B cells; but more typically, such a sample includes at least 10,000 B cells and more typically, at least 100,000 B cells. In another aspect, a sample, includes a number of B cells in the range of from 1000 to 1,000,000 B cells. In some embodiments, the number of cells in a sample sets a limit on the sensitivity of a measurement. That is, greater sensitivity of detecting a residual disease is achieved by using a larger sample of peripheral blood. For example, in a sample containing 1,000 B cells, the lowest frequency of clonotype detectable is $\frac{1}{1000}$ or 0.001, regardless of how many sequencing reads are obtained when the DNA of such cells is analyzed by sequencing. The nucleic acids of the sample may from T-cells from a cell-containing fraction of the peripheral blood or from a cell free fraction of the peripheral blood, such as plasma or serum. In one embodiment, a peripheral blood sample includes at least 1,000 T cells; but more typically, such a sample includes at least 10,000 T cells, and more typically, at least 100,000 T cells. In another aspect, a sample includes a number of T cells in the range of from 1000 to 1,000,000 T cells. In some embodiments, the number of cells in a sample sets a limit on the sensitivity of a measurement. That is, greater sensitivity of detecting a residual disease is achieved by using a larger sample of peripheral blood. For example, in a sample containing 1,000 T cells, the lowest frequency of clonotype detectable is $\frac{1}{1000}$ or 0.001, regardless of how many sequencing reads are obtained when the DNA of such cells is analyzed by sequencing.

A sample for use with the invention can include DNA (e.g., genomic DNA) or RNA (e.g., messenger RNA). The nucleic acid can be cell-free DNA or RNA, e.g. extracted from the circulatory system, Vlassov et al, Curr. Mol. Med., 10: 142-165 (2010); Swarup et al, FEBS Lett., 581: 795-799 (2007). In the methods of the provided invention, the amount of RNA or DNA from a subject that can be analyzed includes, for example, as low as a single cell in some applications (e.g., a calibration test with other cell selection criteria, e.g., morphological criteria) and as many as 10 million of cells or more, which translates into a quantity of DNA in the range of from 6 pg-60 ug, and a quantity of RNA in the range of from 1 pg-10 ug. In some embodiments, a nucleic acid sample is a DNA sample of from 6 pg to 60 ug. In other embodiments, a nucleic acid sample is a DNA sample from 100 µL to 10 mL of peripheral blood; in other embodiments, a nucleic acid sample is a DNA sample from a cell free fraction of from 100 µL to 10 mL of peripheral blood.

In some embodiments, a sample of lymphocytes or cell free nucleic acid is sufficiently large so that substantially every B cell or T cell with a distinct clonotype is represented therein, thereby forming a "repertoire" of clonotypes. In one embodiment, to achieve substantial representation of every distinct clonotype, a sample is taken that contains with a probability of ninety-nine percent every clonotype of a population present at a frequency of 0.001 percent or greater. In another embodiment, a sample is taken that contains with a probability of ninety-nine percent every clonotype of a population present at a frequency of 0.0001 percent or greater. And in another embodiment, a sample is taken that contains with a probability of ninety-nine percent every clonotype of a population present at a frequency of 0.00001 percent or greater. In one embodiment, a sample of B cells or T cells includes at least one half million cells, and in another embodiment such sample includes at least one million cells.

Nucleic acid samples may be obtained from peripheral blood using conventional techniques, e.g., Innis et al, editors, PCR Protocols (Academic Press, 1990); or the like. For example, white blood cells may be separated from blood samples using convention techniques, e.g. RosetteSep kit (Stem Cell Technologies, Vancouver, Canada). Blood samples may range in volume from 100 µL to 10 mL; in one aspect, blood sample volumes are in the range of from 100 µL to 2 mL. DNA and/or RNA may then be extracted from such blood sample using conventional techniques for use in methods of the invention, e.g. DNeasy Blood & Tissue Kit (Qiagen, Valencia, Calif.). Optionally, subsets of white blood cells, e.g. lymphocytes, may be further isolated using conventional techniques, e.g. fluorescently activated cell sorting (FACS)(Becton Dickinson, San Jose, Calif.), magnetically activated cell sorting (MACS)(Miltenyi Biotec, Auburn, Calif.), or the like. For example, memory B cells may be isolated by way of surface markers CD19 and CD27.

Cell-free DNA may also be extracted from peripheral blood samples using conventional techniques, e.g. Lo et al, U.S. Pat. No. 6,258,540; Huang et al, Methods Mol. Biol., 444: 203-208 (2008); and the like, which are incorporated herein by reference. By way of nonlimiting example, peripheral blood may be collected in EDTA tubes, after which it may be fractionated into plasma, white blood cell, and red blood cell components by centrifugation. DNA from the cell free plasma fraction (e.g. from 0.5 to 2.0 mL) may be extracted using a QIAamp DNA Blood Mini Kit (Qiagen, Valencia, Calif.), or like kit, in accordance with the manufacturer's protocol.

In one aspect, a sample of lymphocytes for generating a clonotype profile is sufficiently large that substantially every T cell or B cell with a distinct clonotype is represented therein. In one embodiment, a sample is taken that contains with a probability of ninety-nine percent every clonotype of a population present at a frequency of 0.001 percent or greater. In another embodiment, a sample is taken that contains with a probability of ninety-nine percent every clonotype or a population present at a frequency of 0.0001 percent or greater. In another embodiment, a sample is taken that contains with a probability of ninety-nine percent every clonotype a population present at a frequency of 0.00001 percent or greater. In other embodiments, a sample is taken that contains with a probability of ninety-five percent every clonotype of a population present at a frequency of 0.001 percent or greater. In another embodiment, a sample is taken that contains with a probability of ninety-five percent every clonotype of a population present at a frequency of 0.0001 percent or greater. In another embodiment, a sample is taken that contains with a probability of ninety-five percent every clonotype of a population present at a frequency of 0.00001 percent or greater. In still another embodiment, a sample of B cells or T cells includes at least a half million cells, and in another embodiment such sample includes at least one million cells.

Whenever a source of Material from which a sample is taken is scarce, such as, clinical study samples, or the like, DNA from the material may be amplified by a non-biasing technique, such as whole genome amplification (WGA), multiple displacement amplification (MDA); or like technique, e.g. Hawkins et al, Curr. Opin. Biotech., 13: 65-67 (2002); Dean et al, Genome Research, 11: 1095-1099 (2001); Wang et al, Nucleic Acids Research, 32: e76 (2004); Hosono et al, Genome Research, 13: 954-964 (2003); and the like.

Blood samples are of particular interest and may be obtained using conventional techniques, e.g. Innis et al, editors, PCR Protocols (Academic Press, 1990); or the like. For example, white blood cells may be separated from blood samples using convention techniques, e.g. RosetteSep kit (Stem Cell Technologies, Vancouver, Canada). Blood samples may range in volume from 100 µL to 10 mL; in one aspect, blood sample volumes are in the range of from 100 µL to 2 mL. DNA and/or RNA may then be extracted from such blood sample using conventional techniques for use in methods of the invention, e.g. DNeasy Blood & Tissue Kit (Qiagen, Valencia, Calif.). Optionally, subsets of white blood cells, e.g. lymphocytes, may be further isolated using conventional techniques, e.g. fluorescently activated cell sorting (FACS)(Becton Dickinson, San Jose, Calif.), magnetically activated cell sorting (MACS)(Miltenyi Biotec, Auburn, Calif.), or the like.

Since the identifying recombinations are present in the DNA of each individual's adaptive immunity cells as well as their associated RNA transcripts, either RNA or DNA can be sequenced in the methods of the provided invention. A recombined sequence from a T-cell or B-cell encoding a chain of a T cell receptor or immunoglobulin molecule, or a portion thereof, is referred to as a clonotype. The DNA or RNA can correspond to sequences from T-cell receptor (TCR) genes or immunoglobulin (Ig) genes that encode antibodies. For example, the DNA and RNA can correspond to sequences encoding α, β, γ, or δ chains of a TCR. In a majority of T-cells, the TCR is a heterodimer consisting of an α-chain and β-chain. The TCRα chain is generated by VJ recombination, and the β chain receptor is generated by V(D)J recombination. For the TCRβ chain, in humans there are 48 V segments, 2D segments, and 13 J segments. Several bases may be deleted and others added (called N and P nucleotides) at each of the two junctions. In a minority of T-cells, the TCRs consist of γ and δ delta chains. The TCR γ chain is generated by VJ recombination, and the TCR δ chain is generated by V(D)J recombination (Kenneth Murphy, Paul Travers, and Mark Walport, *Janeway's Immunology* 7th edition, Garland Science, 2007, which is herein incorporated by reference in its entirety).

The DNA and RNA analyzed in the methods of the invention can correspond to sequences encoding heavy chain immunoglobulins (IgH) with constant regions (α, δ, ε, γ, or μ) or light chain immunoglobulins (IgK or IgL) with constant regions λ or κ. Each antibody has two identical light chains and two identical heavy chains. Each chain is composed of a constant (C) and a variable region. For the heavy chain, the variable region is composed of a variable (V), diversity (D), and joining (J) segments. Several distinct sequences coding for each type of these segments are present in the genome. A specific VDJ recombination event occurs during the development of a B-cell, marking that cell to generate a specific heavy chain. Diversity in the light chain is generated in a similar fashion except that there is no D region so there is only VJ recombination. Somatic mutation often occurs close to the site of the recombination, causing the addition or deletion of several nucleotides, further increasing the diversity of heavy and light chains generated by B-cells. The possible diversity of the antibodies generated by a B-cell is then the product of the different heavy and light chains. The variable regions of the heavy and light chains contribute to form the antigen recognition (or binding) region or site. Added to this diversity is a process of somatic hypermutation which can occur after a specific response is mounted against some epitope.

As mentioned above, in accordance with the invention, primers may be selected to generate amplicons containing portions of recombined nucleic acids from lymphocytes or from cell-free nucleic acids from a tissue, such as blood. Such portions may be referred to herein as "somatically rearranged regions." Somatically rearranged regions may comprise nucleic acids from developing or from fully developed lymphocytes, where developing lymphocytes are cells in which rearrangement of immune genes has not been completed to form molecules having (for example) full V(D)J regions. Exemplary incomplete somatically rearranged regions include incomplete IgH molecules (such as, molecules containing only D-J regions), incomplete TCRδ molecules as, molecules containing only D-J regions), and inactive IgK (for example, comprising Kde-V regions).

Amplification of Nucleic Acid Populations

In some embodiments, primer sequences of the first and second sets of primers may be selected in accordance with conventional multiplex polymerase chain reactions (PCRs). For example, guidance for selecting primers and for carrying out multiplex PCRs of nucleic acids encoding various immune receptor chains is found in the following references, which are in by reference: Faham and Willis, U.S. Pat. Nos. 8,236,503 and 8,628,927; Morley U.S. Pat. No. 5,296,351; Gorski, U.S. Pat. No. 5,837,447; Dan, U.S. Pat. No. 6,087,096; Van Dongen et al, U.S. patent publication 2006/0234234; European patent publication EP 1544308B1; Van Dongen et al, Leukemia, 17: 2257-2317 (2003); and the like, Guidance for multiplex PCRs may be found in Henegariu et al, BioTechniques, 23: 504-511 (1997), and like references. In some embodiments, primers are selected so that frequencies of amplified sequences in a final product are substantially, the same as frequencies, of the sequences in the starting reaction mixture. Such primer selection may include selection of primer lengths, primer binding sites and primer concentrations. As noted above, depending on the methods selected to generate sequence reads and attached sequence tags, the level of multiplexing may vary widely.

In some embodiments, a step of amplifying target nucleic acids includes linear amplification of target nucleic acids, such as, for example, by repealed cycles of annealing one set of primers (for example, a first set of "upstream" or "forward" primers), extending the primers, melting the extended strand from the template, so that the quantity of extended strands is amplified as a linear function of the number of cycles. In other words, a step of amplifying include copying a target polynucleotide (that is, at least one strand of a target polynucleotide) by repeated extensions of one set of primers. In some embodiments, such single or repeated extensions in one direction may be followed by steps of removing unextended primers and a single or repeated extensions of another set of primers in the other direction (for example, as second set of "downstream" or "reverse" primers).

The number of primer in a first set of primers and a second set of primers may vary widely depending on the number and type of immune receptor-chain nucleic acids are amplified in an assay. In some embodiments, consensus primers for various chains may be used. In other embodiments, specific primers may he designed for each different target polynucleotide amplified. Usually, both first set and second set of primers each comprise a plurality of primers. In some embodiments, the plurality of primers in the first set or the second set of primers is at least 50 primers; in other embodiments, the plurality of primers in the first set or the second set of primers is at least 100 primers; in other embodiments, the plurality of primers in the first set or the second set of primers is at least 150 primers; in other embodiments, the plurality of primers in the first set or the second set of primers is at least 200 primers; in other embodiments, the plurality of primers in the first set or the second set of primers is at least 250 primers. The number of primers in the first set may be the same or different than the number of primers are the second set.

In some embodiments, primers of the first set and the second set are selected so that the length of clonotypes are at least 30 nucleotides; in other embodiments, primers of the first set and the second set are selected so that the length of clonotypes are in the range of from 30 to 500 nucleotides; in other embodiments, primers of the first set and the second set are selected so that the length of clonotypes are in the range of from 30 to 400 nucleotides. In other embodiments, primers of the first set and the second set are selected so that the length of clonotypes are in the range of from 30 to 300 nucleotides; in other embodiments, primers of the first set and the second set are selected so that the length of clonotypes are in the range of from 30 to 200 nucleotides.

Exemplary PCR amplification protocols may be found in van Dongen et al, Leukemia, 17: 2257-2317 (2003) or van Dongen et al, U.S. patent publication 2006/0234234, which is incorporated by reference. Briefly, an exemplary protocol is as follows: Reaction buffer: ABI Buffer II or ABI Gold Buffer (Life Technologies, San Diego, Calif.); 50 μL final reaction volume; 100 ng sample DNA; 10 pmol of each primer (subject to adjustments to balance amplification as described below); dNTPs at 200 µM final concentration; $MgCl_2$ at 1.5 mM final concentration (subject to optimization departing on target sequences and polymerase); Taq polymerase (1-2 U/tube); cycling conditions: preactivation 7 min at 95° C.; annealing at 60° C.; cycling times: 30 s denaturation; 30 s annealing; 30 s extension. Polymerases that can be used for amplification in the methods of the invention are commercially available and include, for example, Taq polymerase, AccuPrime polymerase, or Pfu. The choice of polymerase to use can be based on whether fidelity or efficiency is preferred.

Real time PCR, picogreen staining, nanofluidic electrophoresis (e.g. LabChip) or UV absorption measurements can be used in an initial step to judge the functional amount of amplifiable material in a sample. In one aspect, multiplex amplifications of the invention are carried out so that relative amounts of sequences in a starting population are substantially the same as those in the amplified population, or amplicon. That is, multiplex amplifications are carried out with minimal amplification bias among member sequences of a sample population. In one embodiment, such relative amounts are substantially the same if each relative amount in an amplicon is within five fold of its value in the starting sample. In another embodiment, such relative amounts are substantially the same if each relative amount in an amplicon is within two fold of its value in the starting sample. In another embodiment, such relative amounts are substantially the same if each relative amount in an amplicon is within five fold of its value in the starting sample. As discussed more fully below, amplification bias in PCR may be detected and corrected using conventional techniques so that a set of PCR primers may be selected for a predetermined repertoire that provide unbiased amplification of any sample.

In some embodiments, amplification bias may be avoided by carrying out a two-stage amplification (for example, as described in Faham and Willis, cited above) wherein a small number of amplification cycles (for example, 2-5, or 2-10, or 2-15 cycles) are implemented in a first, or primary, stage using primers having tails non-complementary with the target sequences. The tails include primer binding sites that are added to the ends of the sequences of the primary amplicon that such sites are used in a second stage amplification using only a single forward primer and a single reverse primer, thereby eliminating a primary cause of amplification bias. Prior to initiation of the second stage amplification, non-extended primers of the first stage are removed from the reaction mixture, or are otherwise inactivated. In some embodiments, the primary PCR will have a small enough number of cycles (e.g. 2-10) to minimize the differential amplification by the different primers. The secondary amplification is then done with one pair of primers, which eliminates a source of differential amplification. In some embodiments, a small percent or portion, e,g, one percent of the reaction volume, of the primary PCR is taken directly to the secondary PCR reaction mixture. In some embodiments, a total of at least thirty-five cycles allocated between a first stage amplification and a second stage amplification.

In some embodiments internal standards may be combined with and amplified in the same reaction as recombined nucleic acids of a sample. Internal standard are nucleic acids with known sequences and known concentrations. For example, they may be cloned copies of a natural nucleic acid encoding portions of an immune receptor chain, or they may be synthetic nucleic acids. In some embodiments, the lengths and base compositions of the internal standards are selected to representative of the particular immune receptor chains being amplified. By monitoring changes in the relative concentrations of the internal standards after amplification, amplification bias may be detected, and conditions for non-biased amplification may be determined. For example, primer lengths, positions, and concentrations may be varied to minimize bias in the amplification product. In some embodiments, a plurality of internal standards are used in a reaction; in some embodiments, 2 to 50 different internal standards are used in a reaction; in other embodiments, from 2 to 25 different internal standards are used in a reaction; and in some embodiments, from 2 to 10 different internal standards are used in a reaction. In some embodiments, amplification bias is determined by measuring the relative, frequencies of the sequences of different target nucleotides (for example, all or selected clonotypes or internal standards) in an amplification product. In other embodiments, the presence, absence or level of amplification bias may be determined by real-time quantitative PCR of selected nucleic acids, such as two or more the internal standards. Internal standards may also be used to quantify the numbers of different clonotypes in the original sample. Techniques for such molecular counting are well-known, e,g. Brenner et al, U.S. Pat. No. 7,537,897, which is per QS incorporated herein by reference.

Generating Sentence Reads

Any high-throughput technique for sequencing nucleic acids can be used in the method of the invention. Preferably, such technique has a capability of generating in a cost-effective manner a volume of sequence data from which at least 1000 clonotypes can be determined, and preferably, from which at least 10,000 to 1,000,000 clonotypes can be determined. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring or the incorporation of labeled nucleotides during a polymerization step, polony sequencing, and SOLiD sequencing. Sequencing of the separated molecules has more recently been demonstrated by sequential or single extension reactions using polymerases or ligases as well as by single or sequential differential hybridizations with libraries of probes. These reactions have been performed on many clonal sequences in parallel including demonstrations in current commercial applications of over 100 million sequences in parallel. These sequencing approaches can thus be used to study the repertoire of T-cell receptor (TCR) and/or B-cell receptor (BCR). In one aspect of the invention, high-throughput methods of sequencing are employed that comprise a step of spatially isolating individual molecules on a solid surface where they are sequenced in parallel. Such solid surfaces may include nonporous surfaces (such as in Solexa sequencing, e.g. Bentley et al, Nature, 456; 53-59 (2008) or Complete Genomics sequencing, e,g. Drmanac et al, Science, 327; 78-81 (2010)), arrays of wells, which may include bead- or particle-bound templates (such as with 454, e.g. Margulies et al, Nature, 437: 376-380 (2005) or Ion Torrent sequencing; U.S. patent publication 2010/0137143 or 2010/0304982), micromachined membranes (such as with SMRT sequencing, Eid et al, Science, 323: 133-138 (2009)), or bead arrays (as with SOLiD sequencing or polony sequencing, e.g., Kim et al, Science, 316: 1481-1414 (2007)). In another aspect, such methods comprise amplifying the isolated molecules either before or after they are spatially isolated on a solid surface. Prior amplification may comprise emulsion-based amplification, such as emulsion PCR, or rolling circle amplification.

Of particular interest are approaches using sequencing by synthesis with reversible terminators, such as Solexa-based sequencing where individual template molecules are spatially isolated on a solid surface, after which they are amplified in parallel by bridge PCR to form separate clonal populations, or clusters, and then sequenced, such as described in Bentley et al (cited above) and in manufacturer's instructions (e.g. TruSeq™ Sample Preparation Kit and Data Sheet, Illumina, San Diego, Calif., 2010); and further in the following references: U.S. Pat. Nos. 6,090,592; 6,300,070; 7,115,400; and EP0972081B1; which are incorporated by reference. In one embodiment, individual molecules disposed and amplified on a solid surface form clusters in a density of at least $10^5$ clusters per $cm^2$; or in a density of at least $5 \times 10^5$ per $cm^2$; or in a density of at least $10^6$ clusters per $cm^2$. Solexa-based sequencing also provides the capability of generating two sequence reads from the same target sequence (or template) in a cluster, one sequence read each from opposite ends of a target sequence. In some embodiments, such pairs of sequence reads may be combined and treated as a single sequence read in subsequent analysis, or such pairs may be treated separately but taking into account that they originate from the same cluster. Sometimes the pair of sequence reads from the same template are referred to as "mate pairs," and the process of sequencing from both ends of a temple is referred to "bidirectional" sequencing. In some embodiments, a step of sequencing by synthesis using reversibly terminated labeled nucleotides includes the generation of a single sequence read for each cluster or clonal population of templates and the generation of a plurality of sequence reads (including but not limited to mate pairs) for each cluster or clonal population of templates. In still further embodiments, when a plurality of sequence reads are generated for each cluster or clonal population of templates, such plurality of sequence reads may be combined to form a single effective sequence read that is used in subsequent analysis, such as a coalescing step.

In one aspect, a sequence-based clonotype profile of a sample from an individual is obtained using the following steps: (a) obtaining a nucleic acid sample from T-cells and/or B-cells of the individual; (b) spatially isolating individual molecules derived from such nucleic acid sample, the individual molecules comprising at least one template generated from a nucleic acid in the sample, which template comprises a somatically rearranged region or a portion thereof, each individual molecule being capable of producing at least one sequence read; (c) sequencing said spatially isolated individual molecules; and (d) determining abundances of different sequences of the nucleic acid molecules from the nucleic acid sample to generate the clonotype profile. In one embodiment, each of the somatically rearranged regions comprise a V region and a J region. In another embodiment, the step of sequencing includes generating a plurality of sequence reads for each clonotype determined. In still other embodiments, the step of sequencing includes combining information or data from a plurality of sequence reads to form each clonotype. In some embodiments, such step of combining may be carried out by coalescing sequence reads as described in Faham and Willis, U.S. Pat. No. 8,628,927 (which is hereby incorporated by reference for this teaching) or by using sequence tags as described in Faham et al, U.S. patent publication 2013/0236895A1 (which is hereby incorporated by reference for this teaching). In another embodiment, the step of sequencing comprises bidirectionally sequencing each of the spatially isolated individual molecules to produce at least one forward sequence read and at least one reverse sequence read.

Further to the latter embodiment, at least one of the forward sequence reads and at least one of the reverse sequence reads have an overlap region such that bases of such overlap region are determined by a reverse complementary relationship between such sequence reads. In still another embodiment, each of the somatically rearranged regions comprise a V region and a J region and the step of sequencing further includes determining a sequence of each of the individual nucleic acid molecules from one or more of its forward sequence reads and at least one reverse sequence read starting from a position in a region and extending in the direction of its associated V region. In another embodiment, individual molecules comprise nucleic acids selected from the group consisting of complete IgH molecules, incomplete IgH molecules, complete IgK complete, IgK inactive molecules, TCRβ molecules, TCRγ molecules, complete TCRδ molecules, and incomplete TCRδ molecules. In another embodiment, the step of sequencing comprises generating the sequence reads having monotonically decreasing quality scores. In another embodiment, the above method comprises the following steps: (a) obtaining a nucleic acid sample from T-cells and/or B-cells of the individual; (b) spatially isolating individual molecules derived from such nucleic acid sample, the individual molecules comprising nested sets of templates each generated from a nucleic acid in the sample and each containing a somatically rearranged region or a portion thereof, each nested set being capable of producing a plurality of sequence reads each extending in the same direction and each starting from a different position on the nucleic acid from which the nested set was generated; (c) sequencing said spatially isolated individual molecules; and (d) determining abundances of different sequences of the nucleic acid molecules from the nucleic acid sample to generate the clonotype profile. In one embodiment, the step of sequencing includes producing a plurality of sequence reads for each of the nested sets. In another embodiment, each of the somatically rearranged regions comprise a V region and a J region, and each of the plurality of sequence reads starts from a different position in the V region and extends in the direction of its associated J region.

In one aspect, for each sample from an individual, the sequencing technique used in the methods of the invention generates sequences of least 1000 clonotypes per run; in another aspect, such technique generates sequences of at least 10,000 clonotypes per run; in another aspect, such technique generates sequences of at least 100,000 clonotypes per run; in another aspect, such technique generates sequences of at least 500,000 clonotypes per run; and in another aspect, such technique generates sequences of at least 1,000,000 clonotypes per run. In still another aspect, such technique generates sequences of between 100,000 to 1,000000 clonotypes per run per individual sample. In each of the foregoing, each clonotype per run is determined from at least 10 sequence reads.

The sequencing technique used in the methods of the provided invention can generate about 30 bp, about 40 bp, about 50 bp, about 60 bp, about 70 bp, about 80 bp, about 90 bp, about 100 bp, about 110 bp, about 120 by per read, about 150 bp, about 200 bp, about 250 bp, about 300 bp, about 350 bp, about 400 bp, about 450 bp, about 500 bp, about 550 bp, or about 600 bp per read.

Clonotype Determination from Sequence Data

Figure 4A:
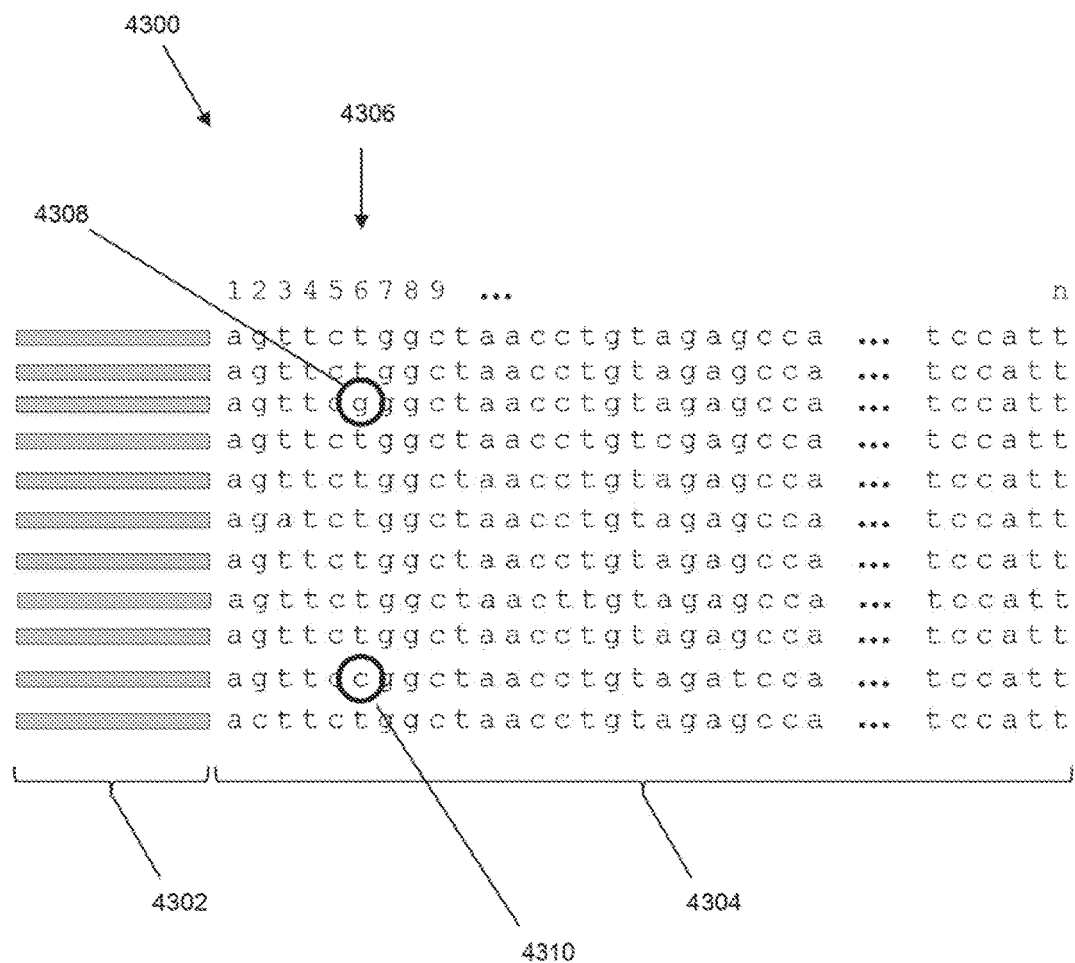
FIG. 4A illustrates the use of sequence tags for determining clonotype sequences from sequence reads.

In some embodiments of the invention, sequence tags are used to determine clonotypes and in other embodiments, sequence tags in combination with a sequence read coalescing step are used to determine clonotypes in embodiments in which a single unique sequence tag is attached to substantially every distinct target polynucleotide, clonotype determination using sequence tags is straight forward. In such embodiments, clonotypes of a sample are determined by first grouping sequence reads based on their sequence tags. Such grouping may be accomplished by conventional sequence alignment methods. Guidance for selecting alignment methods is available in Batzoglou, Briefings in Bioinformatics, 6: 6-22 (2005), which is incorporated by reference. After sequence reads are assembled in groups corresponding to unique sequence tags, then the sequences of the associated clonotypes may be analyzed to determine the sequence of the clonotype from the sample. FIG. 4A illustrates an exemplary alignment and method from determining the sequence (SEQ ID NO: 2) of a clonotype associated with a unique sequence tag. In this example, eleven sequence reads are aligned by way of their respective sequence tags (4302) after which nucleotides at each position of the clonotype portions (4304) of the sequence reads, indicated as 1, 2, 3, 4, . . . n, are compared. For example, nucleotides at position 6 (4306) are t, t, g, t, t, t, t, t, t, c, t: that is, nine base calls are t's, one is "g" (4308) and one is "c" (4310) (SEQ ID NO: 3 and SEQ ID NO: 4). In one embodiment, the correct base call of the clonotype sequence at a position is whatever the identity of the majority base is. In the example of position 6 (4306), the base call is "t", because it is the nucleotide in the majority of sequence reads at that position. In other embodiments, other factors may be taken into account to determine a correct base call for a clonotype sequence, such as quality scores of the base calls of the sequence reads, identities of adjacent bases, or the like. Once clonotypes are determined as described above, a clonotype profile comprising the abundances or frequencies of each different clonotype of a sample may be assembled.

Figure 4B:
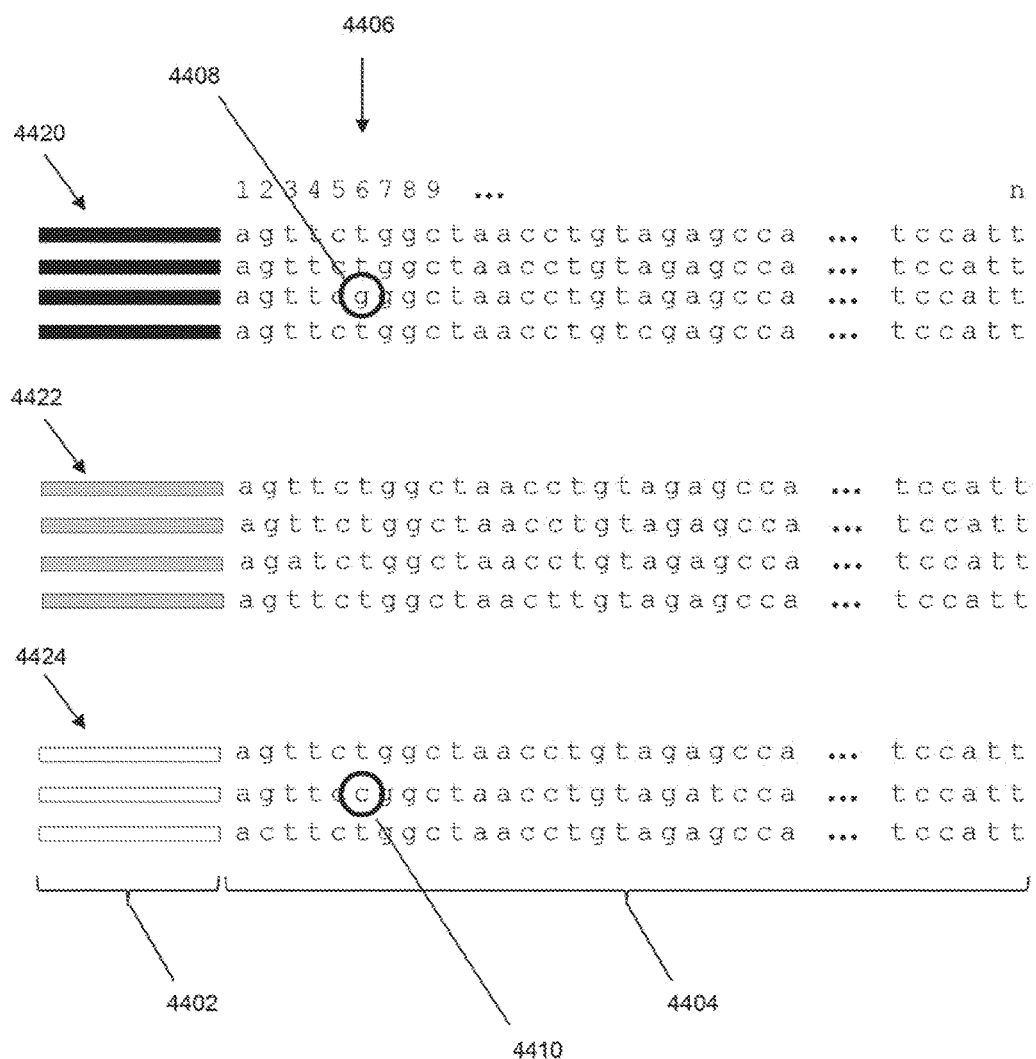
FIG. 4B illustrates the use of sequence tags in embodiments where multiple different sequence tags are attached to the same target polynucleotide or copies thereof.

In some embodiments, more than one extension step may be carried out using sequence-tag containing primers in order to increase the fraction of target polynucleotides in a sample that are labeled with sequence tags prior to amplification. In such embodiments, the more than one extension steps in the presence of sequence tag-containing primers results in a target polynucleotide and/or its copies being labeled with a plurality of different sequence tags. The size of the plurality depends on the number of extension steps carried out in the presence of the sequence tag-containing primers, the efficiency of the amplification reaction, whether only one or both the forward and reverse primers have sequence tags, and the like. In some such embodiments, the plurality is in the range of from 2 to 15, or in the range of from 2 to 10, or in the range of from 2 to 5. In some such embodiments, after amplification, copies of each target polynucleotide of a sample may be divided into a plurality of groups or subsets wherein members of each group or subset is labeled with the same sequence tag and members of each different group or subset is labeled with a different sequence tag; that is, members of the same group have the same sequence tag and members of different groups have different sequence tags. In other words, after amplification, in some embodiments, each copy of a target polynucleotide from a sample will be labeled with one of two different sequence tags; or in other embodiments, each copy of a target polynucleotide from a sample will be labeled with one of three different sequence tags; or in other embodiments, copies of a target polynucleotide from a sample will be labeled with one of four different sequence tags; and so on. In these embodiments, clonotypes may be determined by a combination of sequence tag alignment followed by coalescing steps for treating sequence reads within a group as originating from the same parent sequence based on a likelihood that common origin is true as a function of error rates, relative frequencies, and the like. FIG. 4B illustrates sequence reads from such an embodiment. In one approach, sequence reads are first grouped by common sequence tags (4402), which in the illustration results in three groups (4420), (4422) and (4424). In some embodiments, within each group, sequences (4404) are analyzed to determine a consensus sequence of the group; for example, as above, at each nucleotide position a base may be called as the majority base, or the highest frequency base, or the like. The group consensus sequences may then be coalesced with one another to determine clonotypes.

In some embodiments, the above aspect of the invention may be implemented in a method for profiling of virtually any population of nucleic acids in a sample. Such method may comprise the steps: (a) obtaining a sample comprising a population of nucleic acids; (b) attaching sequence tags to nucleic acids of the population to form tag-nucleic acid conjugates, wherein at least one nucleic acid of the population or copies thereof have different sequence tags attached; (c) amplifying the tag-nucleic acid conjugates; (d) sequencing the tag-nucleic acid conjugates to generate sequence reads having error rates and comprising a nucleic acid sequence and a tag sequence; (e) aligning sequence reads having like tag sequences to form groups of sequence reads having the same sequence tags; (f) coalescing sequence reads of groups to determine sequences of the nucleic acids, wherein groups of sequence reads are coalesced into different sequences whenever said groups of sequence reads are distinct with a likelihood of at least ninety-five percent; and. (g) determining the sequence profile of the population by determining the levels of the sequences. As applied to profiling a population of recombined nucleic acids, such method may be implemented by the steps: (a) obtaining a sample from an individual comprising T-cells and/or B-cells and/or cell-free DNA; (b) attaching sequence tags to recombined nucleic acid molecules of T-cell receptor genes or immunoglobulin genes from the sample to form tag-nucleic acid conjugates, wherein at least one recombined nucleic acid from the sample or copies thereof have different sequence tags attached; (c) amplifying the tag-nucleic acid conjugates; (d) sequencing the tag-nucleic acid conjugates to provide sequence reads having error rates and comprising a tag sequence and a recombined nucleic acid sequence; (e) aligning sequence reads having like tag sequences to form groups of sequence reads having the same sequence tags; (f) coalescing sequence reads of groups to determine clonotypes, wherein groups of sequence reads are coalesced into different sequences whenever said groups of sequence reads are distinct with a likelihood of at least ninety-five percent; and (g) determining the clonotype profile of the sample by determining levels of the clonotypes.

In the above embodiments, and other embodiments disclosed herein, the step of sequencing tag-nucleic acid conjugates comprises sequencing a sample of tag-nucleic acid conjugates from amplicon. Usually, such sample is a representative sample in that the relative frequencies of the target polynucleotides in the original sample (that is, the tissue sample, blood sample, or the like) are maintained in the sample of tag-nucleic acid conjugates from the product of an amplification reaction. In some embodiments in which population of recombined nucleic acids encoding immune receptor molecules are analyzed, a sample of tag-nucleic acid conjugates comprises at least $10^4$ tag-nucleic acid conjugates; in other embodiments, such sample comprises at least $10^5$ tag-nucleic acid conjugates; in other embodiments, such sample comprises at least $10^6$ tag-nucleic acid conjugates; in other embodiments, such sample comprises at least $10^7$ tag-nuclei acid conjugates.

Coalescing Sequence Reads

Figure 5A:
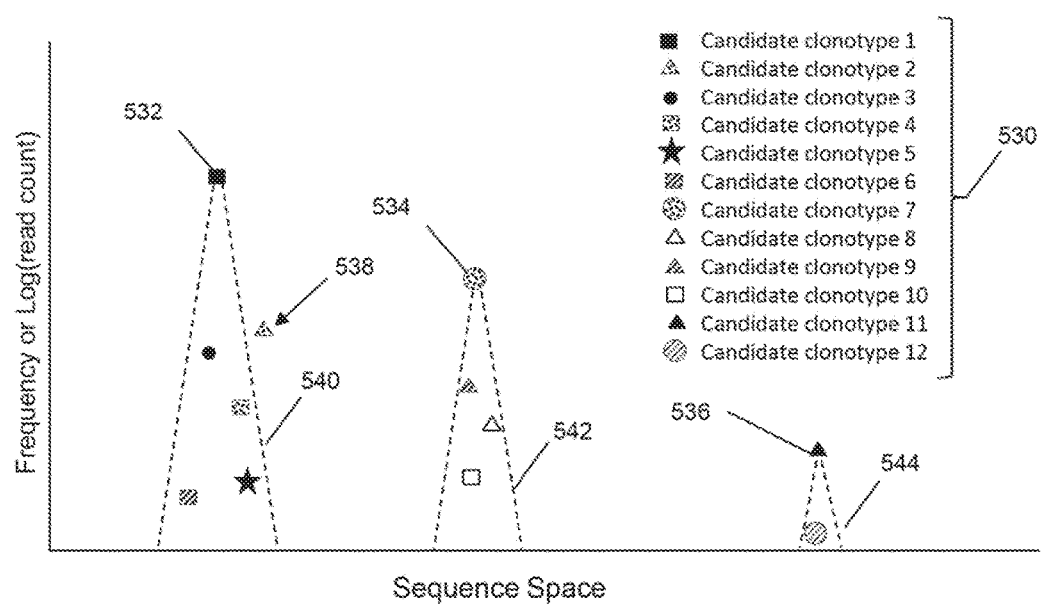
FIG. 5A illustrates concepts of clonotypes in sequence space and distances between closely related clonotypes.

In embodiments where multiple sequence tags are attached to an original recombined nucleic acid or copies thereof, a step of coalescing sequence reads (or consensus sequence reads from groups) may be carried out for determining clonotypes. Reducing a set of sequence reads for a given sample to a set of distinct clonotypes and recording the number of reads for each clonotype would be a trivial if sequencing technology was error free. However, in the presence of sequencing errors, each genuine clonotype is surrounded by a "cloud" of sequence reads with varying numbers of errors with respect to the its sequence. The "cloud" of sequencing errors drops off in density as the distance increases from the clonotype in sequence space. A variety of algorithms are available for converting sequence reads into clonotypes. In one aspect, coalescing of sequence reads (that is, merging candidate clonotypes determined to have one or more sequencing errors) depends on at least three factors; the number of sequences obtained for each of the clonotypes being compared; the number of bases at which they differ; and the sequencing quality score at the positions at which they are discordant. In some embodiments, a likelihood ratio may be constructed and assessed that is based on the expected error rates and a binomial distribution of errors. For example, two clonotypes, one with 150 reads and the other with 2 reads with one difference between them in an area of poor sequencing quality will likely be coalesced as they are likely to be generated by sequencing error. On the other hand two clonotypes, one with 100 reads and the other with 50 reads with two differences between them are not coalesced as they are considered to be unlikely to be generated by sequencing error. In some embodiments, the algorithm described below may be used for determining clonotypes from sequence reads. Sonic of these concepts are illustrated in FIG. 5A. In some embodiments of a coalescing step, sequence reads are first converted into candidate clonotypes. Such a conversion depends on the sequencing platform employed. For platforms that generate high Q score long sequence reads, the sequence read or a portion thereof may be taken directly as a candidate clonotype. For platforms that generate lower Q score shorter sequence reads, some alignment and assembly steps may be required for converting a set of related sequence reads into a candidate clonotype. For example, for Solexa-based platforms, in some embodiments, candidate clonotypes are generated from collections of paired reads from multiple clusters, e.g., 10 or more, as mentioned above.

The frequencies of candidate clonotypes may be plotted in sequence space, as illustrated in FIG. 5A, where such space is reduced to one dimension (the horizontal axis) for sake of illustration. The vertical axis gives the magnitude of each candidate clonotype's frequency, log (read count), or some like measure. In the figure, candidate clonotypes are represented by the various symbols (530). In accordance with one embodiment of the invention, whether two candidate clonotypes are coalesced depends on their respective frequencies or read counts (as noted above), the number of base differences between them (the more differences, the less likely is coalescence), and the quality scores of the bases at the locations where the respective sequences differ (higher quality scores makes coalescence less likely). Candidate clonotypes may be considered in the order of their respective frequencies. FIG. 5A shows candidate clonotype 1 (532), candidate clonotype 7 (534) and candidate clonotype 11 (536) as the three candidates with the highest three frequencies. Related to each such candidate clonotype are other candidate clonotypes that are close in sequence, but with lesser frequencies, such as (i) for candidate clonotype 1 (532) there are candidate clonotype 2 (538) and the candidate clonotypes 3, 4, 5 and 6 enclosed by cone (540); for candidate clonotype 7 (534) there are candidate clonotypes 8, 9 and 10 enclosed by cone (542); and (iii) for candidate clonotype 11, there is candidate clonotype 12 enclosed by cone (544). The cones represent likelihood boundaries within which a lesser frequency candidate clonotype would he coalesced with one of the higher frequency candidate clonotypes 1, 7 or 11. Such likelihood boundaries are functions of the frequency of the nearby candidate clonotypes (3, 4, 5 and 6 for 1; 8, 9 and 10 for 7; and 12 for 11) and their distances in sequence space from the respective higher frequency candidate clonotypes. Candidate clonotype 2 (538) is outside cone (540); thus, it would not be coalesced with candidate clonotype 1 (532). Again, the likelihood (of coalesce) boundaries are shown as cones because candidate clones with higher frequencies are more likely to be genuinely different clonotypes than those of lower frequencies and multiple differences at lower frequencies are more likely to be errors than multiple differences at higher frequencies.

The cloud of sequence reads surrounding each candidate clonotype can be modeled using the binomial distribution and a simple model for the probability of a single base error. This latter error model can be inferred from mapping V and J segments or from the clonotype finding algorithm itself, via self-consistency and convergence. A model is constructed for the probability of a given "cloud" sequence Y with read count C2 and E errors (with respect to sequence X) being part of a true clonotype sequence X with perfect read count C1 under the null model that X is the only true clonotype in this region of sequence space. A decision is made whether or not to coalesce sequence Y into the clonotype X according the parameters C1, C2, and E. For any given C1 and E a max value C2 is pre-calculated for deciding to coalesce the sequence Y. The max values for C2 are chosen so that the probability of failing to coalesce Y under the null hypothesis that Y is part of clonotype X is less than some value P after integrating over all possible sequences Y with error E in the neighborhood of sequence X. The value P is controls the behavior of the algorithm and makes the coalescing more or less permissive.

If a sequence Y is not coalesced into clonotype X because its read count is above the threshold C2 for coalescing into clonotype X then it becomes a candidate for seeding separate clonotypes (such as with candidate clonotype 2 (538) in FIG. 5A). An algorithm implementing such principles would also make sure that any other sequences Y2, Y3, etc. which are 'nearer' to this sequence Y (that had been deemed independent of X) are not aggregated into X. This concept of 'nearness' includes both error counts with respect to Y and X and the absolute read count of X and Y, i.e. it is modeled in the same fashion as the above model for the cloud of error sequences around clonotype X. In this way 'cloud' sequences can be properly attributed to their correct clonotype they happen to be 'near' more than one clonotype. Thus, going to FIG. 5A, if candidate clonotype 2 is deemed to be genuinely distinct from candidate clonotype 1 (532), then a special routine, or sub algorithm, would provide a rule for determining which of candidate clonotypes 1 (532) and 2 (538), candidates 4 and 5, between 1 and 2, should be coalesced to (if either).

In one embodiment, an algorithm proceeds in a top down fashion by starting with the sequence X with the highest read count. This sequence seeds the first clonotype. Neighboring sequences are either coalesced into this clonotype if their counts are below the precalculated thresholds (see above), or left alone if they are above the threshold or 'closer' to another sequence that was not coalesced. After searching all neighboring sequences within a maximum error count, the process of coalescing reads into clonotype X is finished. Its reads and all reads that have been coalesced into it are accounted for and removed from the list of reads available for making other clonotypes. The next sequence is then moved on to with the highest read count. Neighboring reads are coalesced into this clonotype as above and this process is continued until there are no more sequences with read counts above a given threshold, e.g. until all sequences with more than 1 count have been used as seeds for clonotypes.

As mentioned above, in another embodiment of the above algorithm, a further test may be added for determining whether to coalesce a candidate sequence Y into an existing clonotype X, which takes into account quality score of the relevant sequence reads. The average quality score(s) are determined for sequence(s) Y (averaged across all reads with sequence Y) were sequences Y and X differ. If the average score is above a predetermined value then it is more likely that the difference indicates a truly different clonotype that should not be coalesced and if the average score is below such predetermined value then it is more likely that sequence Y is caused by sequencing errors and therefore should be coalesced into X.

Successful implementation of the above algorithm for coalescing candidate clonotypes is dependent upon having an efficient way of finding all sequences with less than E errors (i.e. less than some sequence distance measure) from some input sequence X. This problem may be solved using a sequence tree. The implementation of such trees has some unusual features in that the nodes of the tree are not restricted to being single letters of the DNA sequences of the candidate clonotypes, as illustrated in FIG. 5D. The nodes can have arbitrarily long sequences, which allows for a more efficient use of computer memory.

All of the reads of a given sample are placed into the sequence tree. Each leaf nodes holds pointers to its associated reads. A unique sequence of a candidate clonotype retrieved by traversing backwards in the tree from the leaf to the root node. The first sequence is placed into a simple tree with one root node and one leaf node that contains the full sequence of the read. Sequences are next added one by one. For each added sequence either a new branch is formed at the last point of common sequence between the read and the existing tree or add the read to an existing leaf node if the tree already contains the sequence. Having placed all the reads into the tree it is easy to use the tree for the following purposes: 1) Finding the highest read count: sorting leaf nodes by read count allows one to find the leaf node (i.e. sequence) with the most reads, and successively lower numbers of reads; 2) Finding neighboring leafs: for any sequence all paths through the tree which have less than X errors with respect to this sequence are searchable. A path is started at the root and branch this path into separate paths proceeding along the tree. The current error count of each path as proceeding along the tree is noted. When the error count exceeds the max allowed errors the given path is terminated. In this way large parts of the tree are pruned as early as possible. This is an efficient way of finding all paths (i.e. all leafs) within X errors from any given sequence.

Figure 5B:
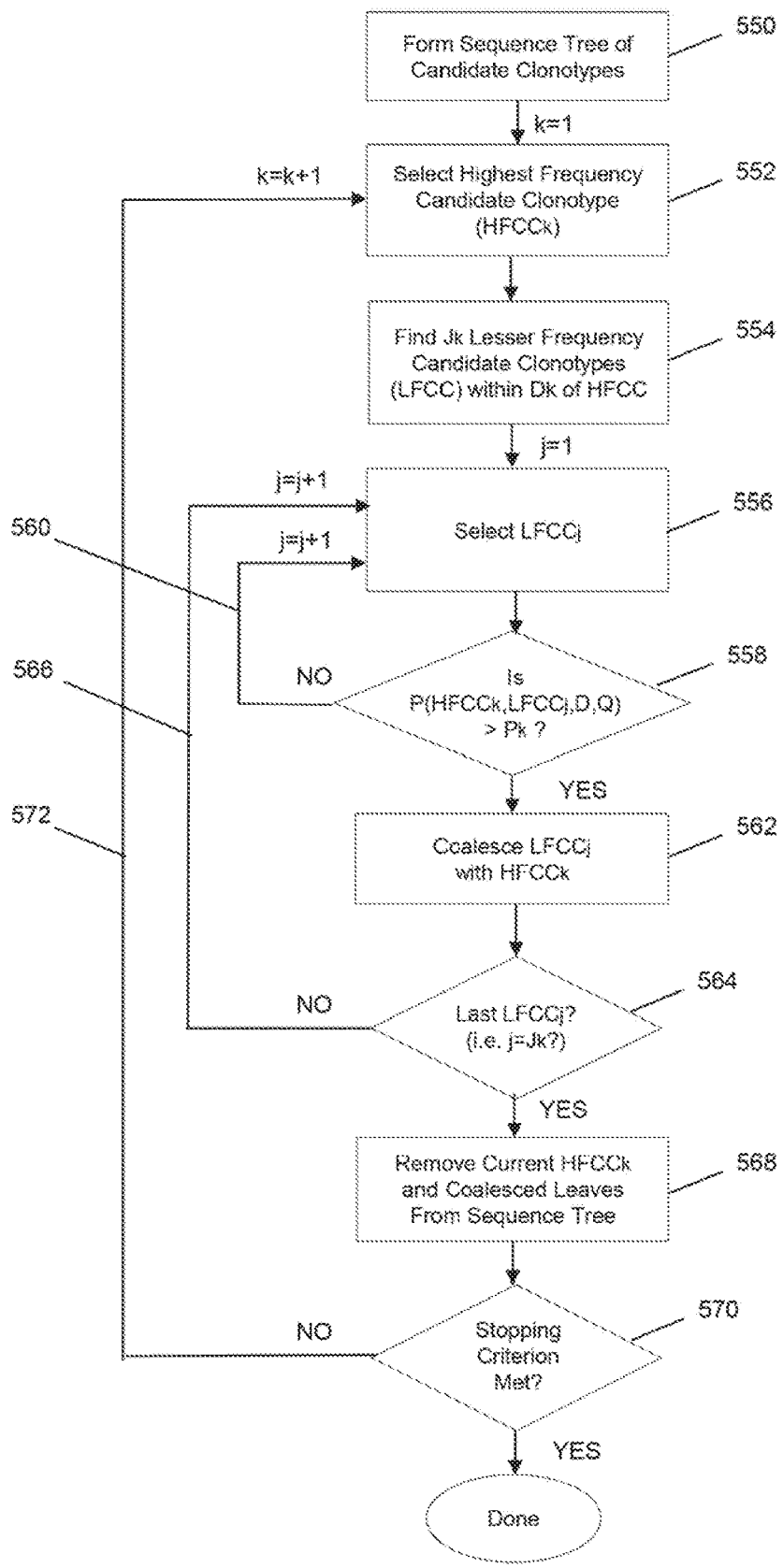
FIG. 5B is a flow chart illustrating one embodiment of a method for distinguishing genuinely different clonotypes from clonotypes that differ solely by sequencing errors (which should be coalesced).

Features of the above concepts are illustrated in more detail in the flow chart of FIG. 5B. A set of candidate clonotypes is obtained from sequence data obtained by sequencing recombined nucleic acids extracted from a sample of T cells or B cells. In one aspect, candidate clonotypes each include an NDN region and portions of V and J regions. These sequences are organized into a data structure (550) which may be a sequence tree. Not shown in FIG. 5B, as part of generating a set of candidate clonotypes, in one embodiment, sequence trees may also be constructed for known V regions and known J regions. Sequence reads making up a candidate clonotype may then be mapped, or aligned, to these known sequences via the sequence trees to efficiently determine the most likely known V and J sequences of the candidate clonotypes. Returning to FIG. 5B, once the candidate clonotypes are generated, a data structure, such as a sequence tree, is constructed for use in a method for distinguishing genuine clonotypes from candidate clonotypes that contain experimental or measurement errors, such as sequencing errors. The candidate clonotype that has the highest frequency of occurrence among the current candidate clonotypes ($HFCC_k$) is selected (552) from the data structure, for example a sequence tree; in other words, $HFCC_k$ is the candidate clonotype with the highest number occupies, or read counts in cycle k. Next, neighboring lesser frequency candidate clonotypes are identified (LFCCs) (554); that is, candidate clonotypes within a distance of $D_k$ are identified. In one aspect of the invention, this identification is carried out using a sequence tree which allows efficient sequence comparisons relatively short (<300 bp) sequences.

In one embodiment, the comparisons, or sequence alignments, are carried out using dynamic programming, e.g. as disclosed by Gusfield (cited above). In a further embodiment, such dynamic programming is banded dynamic programming where sequences that differ from the selected HFCC by more than a predetermined distance are not considered, which speeds the computation. The candidates $HFCC_k$ and $LFCC_j$ may be compared on the basis of many different criteria or properties. In one aspect, as mentioned above, candidate clonotypes are compared on the basis of at least two properties, (i) frequency or read counts and (ii) sequence differences. In another aspect, as mentioned above, candidate clonotypes are compared. On the basis of at least three properties: (i) frequency or read counts, (ii) sequence differences, and (iii) quality scores or measures of the bases where differences occur. In a one embodiment, sequence differences include base substitution; in another embodiment, sequence differences include base substitutions, deletions and insertions. The latter embodiment is especially applicable whenever sequence data is generated by sequencing-by-synthesis chemistries that do not employ terminators, such as 454 sequencers and Ion Torrent sequencers. Such sequencing approaches differentiate different sized homopolymer stretches by signal amplitude; thus, base-calling routines in such approaches are prone to insertion and deletion errors, because the difference in signal level from homopolymers differing by one nucleotide drops precipitously with increasing homopolymer size (that is, a 2-mer is readily distinguished from a 3-mer, but an 8-mer is almost indistinguishable from a 9-mer). In one aspect, comparisons of HFCCs and LFCCs may be implemented using a function (referred to herein as a "coalescence likelihood function"), such as $P(HFCC_k, LFCC_j, D, Q)$ shown in decision box (558), which depends on the quantities (i) through (iii) described above. Such a function may take many diluent forms, but generally the value of P changes with changes in (i), (ii) and (iii) as follows: The value of P preferably increases monotonically with the frequency of HFCC and the ratio of the frequency of HFCC to that of LFCC, such that the higher the ratio of the frequency of HFCC to that of LFCC, the higher the likelihood LFCC will be coalesced into HFCC. Likewise, the value of P preferably decreases monotonically with degree to which the sequences of HFCC and LFCC differ, so that the greater the difference between HFCC and LFCC (e.g. as measured by the minimal number of substitutions, insertions or deletions to change one to the other) the lower the likelihood LFCC will be coalesced with HFCC. Finally, the value of P preferably decreases monotonically with increasing quality scores of the locations where the sequences of HFCC and LFCC differ, so that for higher quality scores, the lower the likelihood LFCC will be coalesced with HFCC.

Figure 5C:
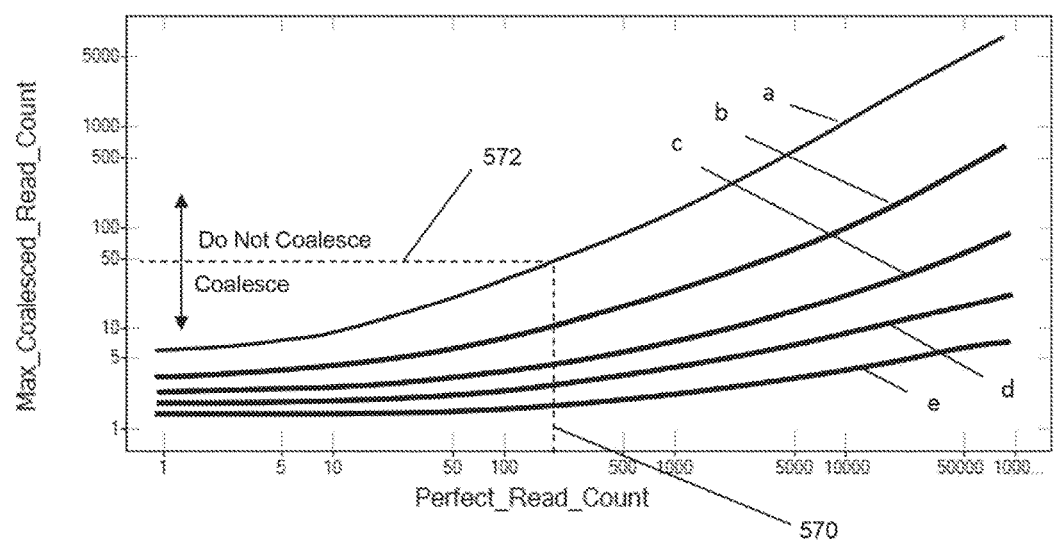
FIG. 5C illustrates the form of a numerical function used in one embodiment for determining whether or not to coalesce related clonotypes.
Figure 5D:
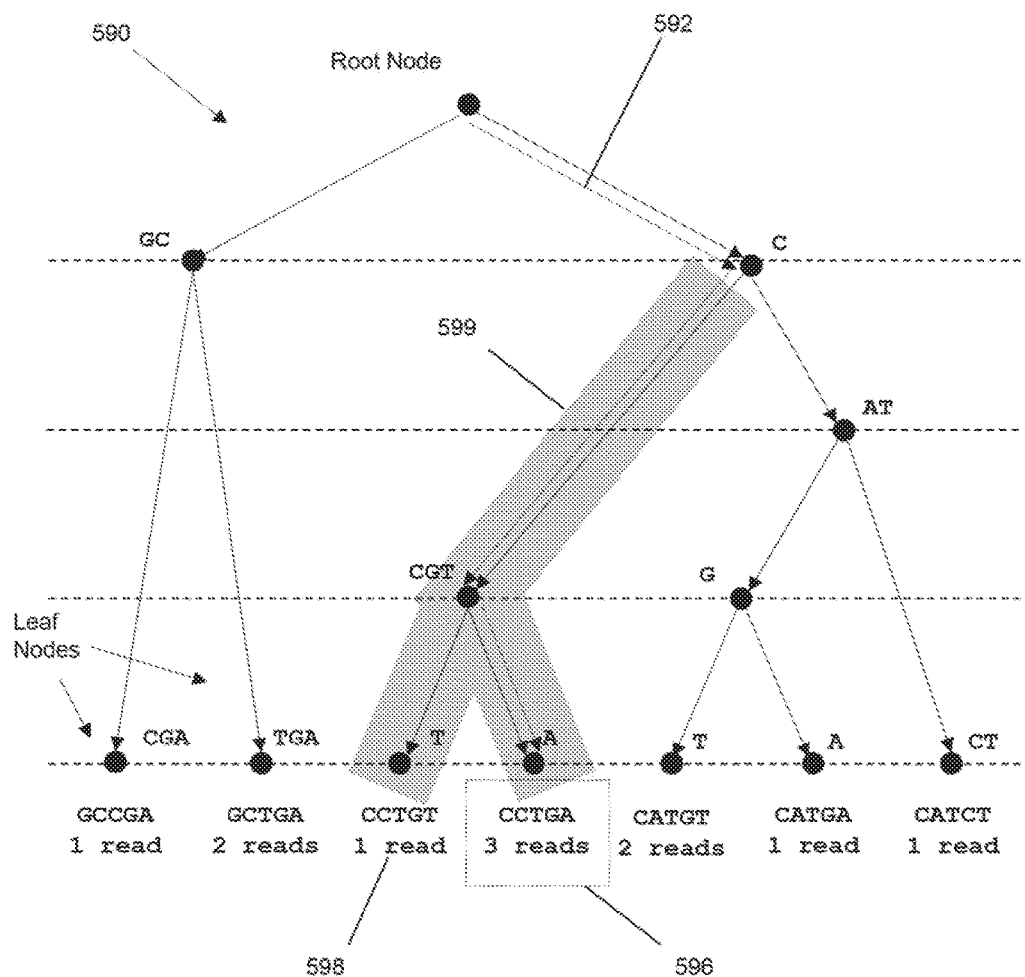
FIGS. 5D and 5E illustrate the use of sequence trees in a method of coalescing sequence reads.

When the sequences of HFCC and LFCC differ at more than one location, the quality scores a different locations may be combined in a variety of differ ways. In one embodiment, whenever there is a plurality of such differences, the plurality of quality scores is expressed as an average value, which may be either an unweighted average or a weighted average. FIG. 5C shows an exemplary function, P, computed for different quality values (curves a through c) for a given sequence difference. As illustrated in FIG. 5C, whenever HFCC is at a level of about 200 read counts (570), then if the quality scores are determined by curve (a), any LFCC with less than about 50 read counts (572) are coalesced into HFCC. The argument, D, of function P is a measure of the distance between the sequences $HFCC_k$ and $LFCC_j$ and its value may vary from cycle to cycle as an analysis progresses. (The indices "k" indicates that the values of constants with a "k" subscript may depend on the computational cycle, k.) In one embodiment, $D=D_k$, so that its value is a function of cycle number. In another embodiment, D=D(HFCC frequency), so that its value is a function of the frequency of HFCC, independent of cycle number. For example, as the frequency of HFCC decreases, then distance, D, of candidates to be compared decreases. In one embodiment, D is it Hamming distance between $HFCC_k$ and $LFCC_j$; however, other distance measures may be used. In one embodiment, $D_k$ is a non-increasing function of k; and in another embodiment, $D_k$ is a decreasing function of k. Decreasing the magnitude of D with increasing cycle number, or with decreasing frequency of HFCC, is advantageous in some embodiments because as a computation progresses to lower and lower frequency candidate clonotypes most such candidates are singletons, so that sequence distance (rather than frequency difference) becomes the predominant comparison. By lowering D as the computation progresses, unproductive comparisons to distant low frequency candidate clonotypes are reduced, thereby speeding up the computation. Function P may be a complicated expression depending on the number of factors being considered. FIG. 5C illustrates computed values for one embodiment of P which relates read count thresholds for coalescing an LFCC given a read count of an HFCC for different quality scores, as described above. Curves "a" through "e" represent the relationships for different quality scores (with curve "a" corresponding to the highest quality score).

Figure 5E:
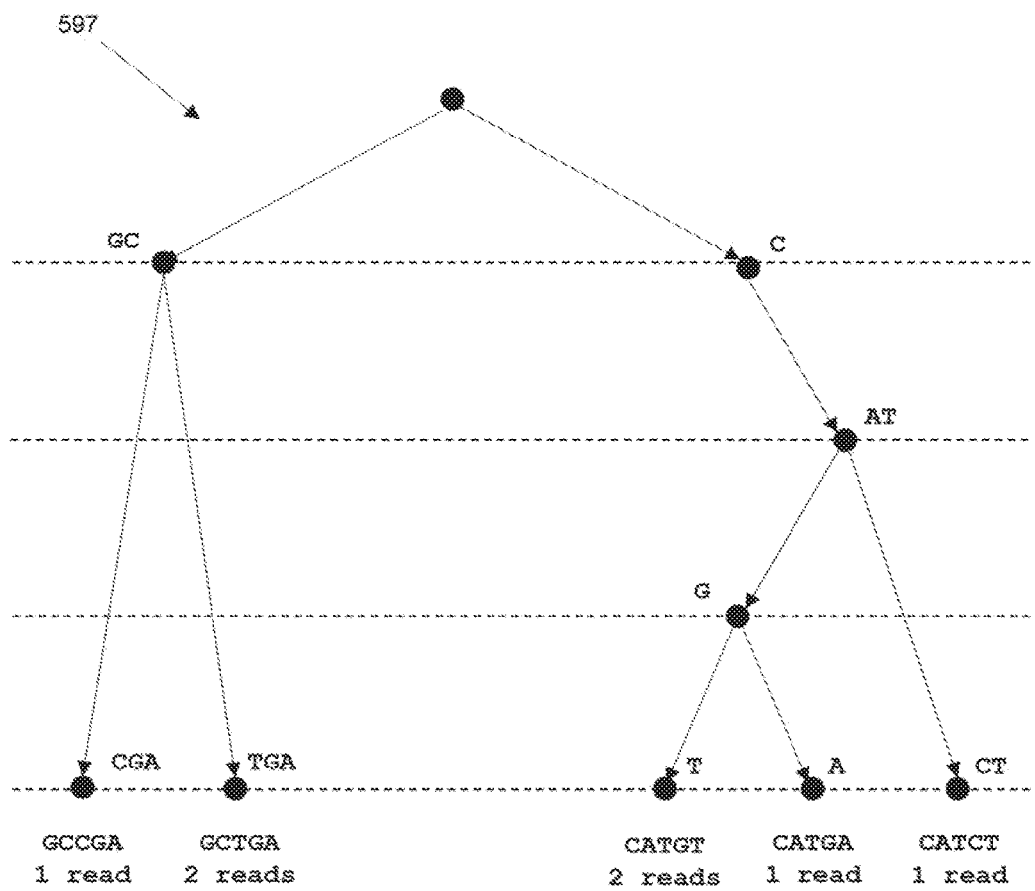

Returning to FIG. 5B, if $P<P_k$, then $LFCC_j$ is not coalesced with $HFCC_k$ and another LFCC is selected (560), if $P>P_k$, then $LFCC_j$ is coalesced with $HFCC_k$ (562), in which case another LFCC is selected (566), unless there are no more LFCC left to evaluate (564). If there are no more LFCC to evaluate (564), then the current $HFCC_k$ (including all of the LFCC's coalesced into it) is removed (518) from the data structure, such as the sequence tree. Such removal is illustrated in the simple sequence tree (590) of FIGS. 5D-5E. There, path (592) (indicated by dashed line) in sequence tree (590) corresponds to HFCC (596), which is coalesced with LFCC (598). After coalescence, the segment of path (592) in shaded area (599) is removed from sequence tree (590) to give reduced sequence tree (597) shown in FIG. 5E, which is used in subsequent computations to find neighboring LFCC (554). After such removal, clonotype determination is finished if a stopping criterion (570) is met. In one embodiment, stopping criterion (570) is whether the last non-singleton candidate clonotype has been processed (552). In another embodiment, stopping criterion (570) is whether the frequency or the read counts of the selected HFCC is below that corresponding to a single lymphocyte. In one aspect of the method of the invention, an amplification step may result in each lymphocyte in a sample being represented by multiple copies of the same clonotype; thus, in one embodiment, whatever HFCC has a number of read counts below the number corresponding to a single lymphocyte, then the computation is stopped. In some embodiments, such a number of read counts (or candidate clonotype copies) is at least 10; in another embodiment, such number is at least 20; in another embodiment, such a number is at least 30; in another embodiment, such a number is at least 40. If the stopping criterion is not met, then the next HFCC is selected (572). The analytical steps summarized in the flow chart of FIG. 5B may be implemented in any suitable programming language, such as C, C++, Java, C#, Fortran, Pascal or the like.

In accordance with one aspect of the invention, the above method for determining clonotypes and/or clonotype profiles comprises steps of (a) forming a data structure of recombined immune molecules from sequence reads obtained by high throughput nucleic acid sequencing, (b) coalescing with a highest frequency candidate clonotype any lesser frequency candidate clonotypes whenever such lesser frequency is below it predetermined frequency value and a sequence difference therebetween is below it predetermined difference value to form a clonotype, (c) removing the coalesced candidate clonotype from the data structure, and (d) repeating steps (b) and (c) until a clonotype profile is formed. In one embodiment, the data structure is a sequence tree.

In accordance with another aspect of the invention, the above method of determining clonotypes may be carried out by steps comprising: (a) providing a set of sequence reads from a repertoire of recombined immune molecules each having a V region, an NDN region and a J region wherein for each such molecule at least one sequence read encompasses at least a portion of the NDN region of such molecule; (b) farming from sequence reads encompassing at least a portion of an NDN region a sequence tree having leaves representing candidate clonotypes, each leaf and its corresponding candidate clonotype having a frequency; (c) coalescing with a highest frequency candidate clonotype any lesser frequency candidate clonotypes whenever such lesser frequency is below a predetermined frequency value and a sequence difference therebetween is below a predetermined difference value to form a clonotype having a sequence of the highest frequency candidate clonotype; (d) removing leaves corresponding to the coalesced candidate clonotypes from the sequence tree; and (e) repeating steps (c) and (d) until a highest frequency of a lesser frequency candidate clonotype is below a predetermined stopping value. In one embodiment, the step of forming further includes selecting a highest frequency candidate clonotype and identifying all said lesser frequency candidate clonotypes having a sequence difference therewith less than a predetermined difference value to form a coalescence subset. Thus, in such embodiment, one may limit the total number of LFCCs that must be compared for the coalescing operation (only ones within the predetermined difference value are considered). Such value is a process input depending on the application, e.g. the size of the repertoire, how much computing binge is used, and so on. As mentioned above, the function used for deciding whether to coalesce an HFCC with a LFCC can have a variety of forms. In one general aspect, for the step of coalescing, such a function may have the following properties. It depends on frequencies of HFCC, LFCC, the sequence difference therebetween (which may be expressed as a conventional string difference measure, such as a Hamming distance) and quality scores of the one or more nucleotide locations where the HFCC and LFCC differ; such that the function (i) monotonically increases with increasing ratio of frequency of HFCC and frequency of LFCC, (ii) monotonically decreases with increasing sequence difference between HFCC and LFCC, and (iii) monotonically decreases with increasing quality scores of the one or mare nucleotide locations. That is, in regard to property (iii), the surer one is that HFCC and LFCC are different (e.g., because there is a high level of confidence in the base calls), then the less likely they will be coalescenced.

In some embodiments, a coalescence likelihood function is selected so that sequence reads are coalesced into different clonotypes (or target polynucleotides, such as recombined nucleic acids) whenever such sequence reads are distinct with a likelihood or at least 95 percent; in other embodiments, a coalescence likelihood function is selected so that sequence reads are coalesced into different clonotypes whenever such sequence reads are distinct with a likelihood of at least 99 percent; in other embodiments, a coalescence likelihood function selected so that sequence reads are coalesced into different clonotypes whenever such sequence reads are distinct with a likelihood of at least 99.9 percent. As mentioned above, in some embodiments, a coalescence likelihood function depends on an error rate of a sequencing chemistry used, the amber of discrepant nucleotides in sequence reads being compared, and the relative frequencies of the sequence reads being compared; in another embodiment, a coalescence likelihood function depends on an error rate of a sequencing chemistry used, the number of discrepant nucleotides in sequence reads being compared, the relative frequencies of the sequence reads being compared, and the quality scores of the discrepant nucleotides. In the foregoing, selection of a predetermined frequency value and a predetermined difference value is a design choice that depend on particular applications. Factors affecting such choices may include details of the biology, speed of implementation, and the like.

Monitoring Applications

In one aspect, the invention is directed to methods for monitoring minimal residual disease by determining the presence, absence and/or level of nucleic acids in a sample that are characteristic or correlated with a disease. In some embodiments, such nucleic acids are somatically recombined nucleic acids, or clonotypes, which are correlated with a pre-cancerous or cancerous condition, such as a lymphoid or myeloid proliferative disorder, and which can be used to monitor the status of the disorder or condition. Such nucleic acids, and in particular clonotypes, are useful for monitoring minimal residual disease of a cancer after treatment, where the result of such monitoring is a key factor in determining whether to continue, discontinue or otherwise modify treatment. In many malignant lymphoid and myeloid neoplasms, a diagnostic tissue sample, such as a peripheral blood sample or a bone marrow sample, is obtained before treatment from which a clonotype profile is generated (a "diagnostic clonotype profile"). For lymphoid or myeloid proliferative disorders, it is usually not known prior to a diagnostic sample which immune receptor chain(s) are correlated to the lymphoid or myeloid clone of the disorder or condition. Consequently, under current practice many separate amplifications and sequencing must be carried out on different recombined nucleic acids encoding different candidate immune receptor chains in order to identify clonotypes correlated with a patient's disease or condition. One or more disease-correlated clonotypes (i.e. "correlating clonotypes") are identified in clonotype profiles resulting from such amplifications and sequencing efforts. Typically, the clonotypes having the highest frequencies in the clonotype profiles are taken as the correlating clonotypes. In one aspect of the invention, the number of separate amplifications and sequencing runs necessary to identify correlating clonotypes is greatly reduced by providing larger scale multiplex amplifications in a single reaction of portions of recombined nucleic acids encoding a plurality of difference immune receptor chains. In some embodiments, such plurality is in the range of from 2 to 4 separate immune receptor chains; and in other embodiments, such plurality is in the range of from 2 to 3 separate immune receptor chains. More particularly, in some embodiments, among BCR chains the following are amplified in a single multiplex reaction: recombined nucleic acids encoding IgH including at least a portion of the VDJ region, IgH including at least a portion of the DJ region, and IgK; and in other embodiments, among TCR chains the following are amplified in a single multiplex reaction: TCRβ, TCRδ and TCRγ.

After treatment, and preferably after attainment of as complete remission of the cancer, the presence, absence or frequency of such correlating clonotypes for nucleic acids is assessed periodically to determine whether the remission is holding or whether the neoplasm is returning or relapsing, based on the presence of, or an increase in the frequency of, the correlating nucleic acids or clonotypes (or related clonotypes) in a post-treatment clonotype profile or nucleic acid profile. That is, after treatment, minimal residual disease of the cancer is assessed based on the presence, absence or frequency of the correlating clonotypes or characteristic nucleic acids. As mentioned above, when such correlating clonotypes are common or correspond to a rearranged receptor segment that lacks sufficient diversity (so that non-cancerous cells may share the clonotype), the occurrence of such clonotypes in a post-treatment clonotype profile may give rise to a false positive indication of relapse.

Methods of the invention are applicable to monitoring any proliferative disease in which a rearranged nucleic acid encoding an immune receptor or portion thereof can be used as a marker of cells involved in the disease. In one aspect, methods of the invention are applicable to lymphoid and myeloid proliferative disorders. In another aspect, methods of the invention are applicable to lymphomas and leukemias. In another aspect, methods of the invention are applicable to monitoring MRD in follicular lymphoma, chronic lymphocyte leukemia (CLL), acute lymphocyte leukemia (ALL), chronic myelogenous leukemia (CML), acute myelogenous leukemia (AML), Hodgkin's and non-Hodgkin's multiple myeloma (MM), monoclonal gammopathy of undetermined significance (MGUS), mantle cell lymphoma (MCL), diffuse large B cell lymphoma (DLBCL), myelodysplastic syndromes (MDS), T cell lymphoma, or the like. In a particular embodiment, a method of the invention is particularly suited for monitoring MRD in ALL, MM or DLRCL.

In some embodiments, a patient sample, such as blood or bone marrow, is subjected to a diagnostic assay to identify which of a plurality of immune receptor chains may include the clonotype produced by a clone of a disorder (i.e., a correlating clonotype). Once the immune receptor chain of a correlating clonotype is determined, then subsequent monitoring assays may be specific for that particular immune receptor chain. For example, in some embodiments, a diagnostic assay may in the same reaction generate sequence-based clonotype profiles of a plurality of BCR chains, such as, IgH(VDJ), IgH(DJ) and IgK. If a correlating clonotype is an IgH(VDJ) chain, then subsequent monitoring assays may only generate IgH(VDJ) clonotype profiles. In some embodiments, the depth of sequencing in the diagnostic sample may be different than that of the monitoring sample. "Depth of sequencing" means the total number of sequence reads analyzed to construct clonotype profiles. For cancers, such as leukemias or lymphomas, since diagnostic assays are conducted on patient samples prior to treatment, the frequency or level of a correlating clonotype in the sample is typically high and readily identified, For example, any clonotype with a frequency over a predetermined level may be defined as a correlating clonotype. Such predetermined level may vary under with other patient indicators; however, often a predetermined level may be in the range of from 2 to 5 percent; or in some embodiments, five percent. Thus, in some embodiments, the depth of sequencing carried out is that which is necessary to reliably detect clonotypes present at a frequency of one or two percent or higher. In some embodiments, the depth of sequencing of a diagnostic sample produces at least 10,000 sequence reads; or in other embodiments, it is at least 100,000 sequence reads; in still other embodiments, the depth of sequencing of a diagnostic sample produces at least $10^6$ sequence reads. In some embodiments, the depth of sequencing or a monitoring sample is at least 10,000 sequence reads; in other embodiments, the depth of sequencing of a monitoring sample is at least $10^8$ sequence reads.

In some embodiments, a lymphoid proliferative disorder, such as a leukemia or lymphoma, in a patient may be monitored by generating clonotype profiles from successively obtained samples (or tissue samples) from the patient. Such clonotype profiles may be generated as described above. In some embodiment, such monitoring may be implemented by the following steps: (a) obtaining a sample from an individual comprising T-cells and/or B-cells and/or cell-free DNA; (b) attaching sequence tags to recombined nucleic acid molecules of T-cell receptor genes or immunoglobulin genes from the sample to form tag-nucleic acid conjugates, wherein at least one recombined nucleic acid or copies thereof have different sequence tags attached; (c) amplifying the tag-nucleic acid conjugates; (d) sequencing a sample of the tag-nucleic acid conjugates to provide sequence reads each having an error rate and each comprising a tag sequence and a recombined nucleic acid sequence; (e) aligning sequence reads having like tag sequences to form groups of sequence reads having the same sequence tags; (f) coalescing sequence reads of groups to determine clonotypes, wherein groups of sequence reads are coalesced into different recombined nucleic acid sequences whenever said groups of sequence reads are distinct with a likelihood of at least ninety-five percent; (g) determining the clonotype profile of the sample by determining levels of the clonotypes; and (h) determining the level of correlating clonotypes in the clonotype profile. In some embodiments, steps (a) through (h) may be repeated in the process of monitoring the patient to determine whether the level of correlating clonotypes is evidence of relapse of disease. In some embodiments, the steps of attaching and amplifying may comprise the following steps: (a) combining in a reaction mixture under primer extension conditions a first set of primers with a sample of recombined nucleic acids from immune cells expressing an immune receptor and/or cell-free DNA, wherein each primer of the first set has a receptor-specific portion such that the receptor-specific portion anneals to a different recombined nucleic acid at a predetermined location and is extended to form a first extension product, and wherein each primer of the first set has a 5'-non-complementary end containing a first primer binding site; (b) removing from the reaction mixture non-extended primers of the first set; and (c) adding to the reaction mixture under primer extension conditions a second set of primers, wherein each primer of the second set has a receptor-specific portion such that the receptor-specific portion anneals to the first extension product at a predetermined location and has a 5'-non-complementary end containing a second primer binding site, primers of the first set and/or primers of the second set comprising a sequence tag disposed between the receptor-specific portion and the first or second primer binding site, respectively, and wherein each primer of the second set is extended to form a second extension product, such that each second extension product comprises a first primer binding site, a second primer binding site, at least one sequence tag, and recombined nucleic acid encoding a portion of an immune cell receptor chain. In some embodiments, a step of coalescing recombined nucleic acids comprises coalescing sequence reads of different recombined nucleic acids whenever such sequence reads are distinct with a likelihood of at least ninety-nine percent; and in other embodiments, with a likelihood of at least 99.9 percent.

Methods of the invention are also applicable to monitoring minimal residual disease of a cancer in a patient, including a non-lymphoid or non-myeloid cancer which has an identifying pattern of mutations, for example, in a selected set of cancer genes. Such a pattern of mutations, that is, the presence, absence and/or level of genes containing such mutations, can indicate a likelihood of disease recurrence. In some embodiments, target polynucleotides for such monitoring may be exons, portions exons, selected introns and/or gene expression control regions, e,g. promoters, of a plurality of genes (referred to herein as "cancer gene molecules"). Cancer gene molecules may be isolated from a tissue sample using conventional techniques, such as exon aperture techniques, e.g. TruSeq™ exon enrichment kit (Illumina, San Diego, Calif.); Frampton et al, Nature Biotechnology, 31(11): 1023-1031 (2013); and the like. After such cancer gene molecules are obtained, sequence tags are attached to form tag-nucleic acid conjugate, tag-nucleic acid conjugate are amplified and sequenced in accordance with the invention.

Recent cancer genome sequencing studies have shown that there is significant heterogeneity in mutation patterns among different cancers, among different patients with the same cancer, among cells of the same tumor, and among cells of different metastatic sites in the same patient; however, within the same patient, the heterogeneous cancer cells typically evolve from a common ancestor, so that they share mutations and the evolutionary relationship among the cancerous cells may be discerned in a succession of measurements over time, e.g. Vogelstein et al, Science, 339: 1546-1558 (2013); Ding et al, Nature, 481(7382): 506-510 (2012); and the like; therefore, a pattern of mutations correlated with a cancer measured in a diagnostic sample provide a means to detect a recurrence of the same cancer or a clonally evolved version of it.

Cancer gene molecule may be selected from a wide variety of genes, including, but not limited to, the genes in Table I.

TABLE I

Exemplary Cancer Genes

| ABL1 | AKT1 | ALK | APC | ATM |
|---|---|---|---|---|
| BRAF | CDH1 | CSF1R | CTNNB1 | EGFR |
| ERBB2 | ERBB4 | FBXW7 | FGFR1 | FGFR2 |
| FGFR3 | FLT3 | GNA11 | GNAQ | GNAS |
| HNF1A | HRAS | IDH1 | JAK2 | JAK3 |
| KDR | KIT | KRAS | MET | MLH1 |
| MPL | NOTCH1 | NPM1 | NRAS | PGGFRA |
| PIK3CA | PTEN | PTPN11 | RB1 | RET |
| SMAD4 | SMO | SRC | STK | TP53 |
| VHL | | | | |

In some embodiments, the above method of monitoring a minimal residual disease of a cancer may comprise the following steps: (a) obtaining from an individual a tissue sample; (b) attaching sequence tags to each of a plurality of cancer gene molecules in the sample to form tag-nucleic acid conjugates, wherein at least one nucleic acid or copies thereof have different sequence tags attached and wherein the cancer gene molecules are characteristic of a cancer of the individual; (c) amplifying the tag-nucleic acid conjugates; (d) sequencing a sample of the tag-nucleic acid conjugates to provide sequence reads having error rates and comprising a tag sequence and a cancer gene sequence; (e) aligning sequence reads having like tag sequences to form groups of sequence reads having the same sequence tags; (f) coalescing cancer gene sequences of groups to determine sequences of cancer gene molecules, wherein groups of sequence reads are coalesced into different cancer gene molecules whenever said groups of cancer gene sequences are distinct with a likelihood of at least ninety-five percent; and (g) detecting in a profile of the cancer gene molecules the presence, absence and/or level of cancer gene molecules characteristic of the cancer of the individual. In some embodiments, a step of coalescing cancer gene sequences comprises coalescing sequence reads of different cancer gene molecules whenever such sequence reads are distinct with a likelihood of at least ninety-nine percent; and in other embodiments, with a likelihood of at least 99.9 percent.

Use of Sequence Tags to Detect Carry Over Contamination

Carry over contamination is a significant problem with techniques that include amplification of nucleic acids, e.g. Borst et al, Eur. J. Clin. Microbial. Infect. Dis. 23(4): 289-299 (2004); Aslanzadeh, Ann. Clin. Lab. Sci. 34(4): 389-396 (2004); and the like. Such contamination arises when traces of nucleic acid extraneous to a sample are unintentionally amplified in an assay of the sample and effect or impact a measured result. In a worse case, carry over contamination in a medical sample from a patient can result in a false positive interpretation of an assay result. The extraneous nucleic acid may conic from a source unrelated to a particular patient, for example, it may come from the sample of another patient. Or, the extraneous nucleic acid may come from a source related to a patient; for example, it may come from a different sample from the same patient handled in the same laboratory in the past or from an assay reaction on a different sample from the same patient which was processed in the same laboratory in the past.

Carry over contamination is especially challenging in setting when measuring highly complex populations of related nucleic acids, such as populations of recombined nucleic acids encoding immune molecules, such as T-cell receptors or immunoglobulins. The challenge arises because it is difficult to determine whether a sequence read or clonotype is part of the genuine diversity of an intended sample or whether they originate from an extraneous source of nucleic acid, such as another patient's sample or a prior sample of the same patient which are being processed in the same king of assay in the same laboratory. In one aspect of the invention, such carry over contamination may be detected by using sequence tags not only to determine clonotypes from sequence reads but also to determine whether a sequence tag originated in the current sample or from another sample. This is accomplished by maintaining a record of sequence tags determined from each patient sample, then whenever a subsequent measurement is made the sequence tags of the current measurement are compared to those of prior measurements. Such records of sequence tags associated with clonotypes are conveniently maintained as electronic records on mass storage devices because of the large number of tag from each measurement and the ease of searching and comparing electronic records using conventional algorithms. If a match is found then the most likely cause is carry over contamination, provided that the populations of sequence tags employed in the measurements are sufficiently large. The same exemplary ratios of the size of sequence tag population to a clonotype population for labeling by sampling discussed above are applicable for detecting carry over contamination. In one embodiment, such ratio is 100:1 or greater.

A is variety of search methods or algorithms may be used to carry out the step of comparing measured clonotypes to database clonotypes. Many conventional sequence alignment and searching algorithms are publicly available and have been described in the following references which are incorporated by reference: Mount, Bioinformatics Sequence and Genome Analysis, Second Edition (Cold Spring Harbor Press, 2004): Batioglou, Briefings in Bioinformatics, 6: 6-22 (2005); Altschul et al, J. Mol. Biol., 215(3): 403-410 (1990); Needletnan and Wunsch. J. Mol. Biol., 48: 443-453 (1970); Smith and Waterman, Advances in Applied Mathematics, 2: 482-489 (1981): and the like.

In some embodiments, the above methods for detecting and measuring contamination, such its carry-over contamination; in a sample from material originating from a different sample may comprise the following steps: (a) obtaining from an individual a tissue sample; (b) attaching sequence tags to cancer gene molecules or recombined nucleic acids to form tag-nucleic acid conjugates, wherein at least one nucleic acid or copies thereof have different sequence tags attached and wherein the cancer gene molecules are characteristic of a cancer of the individual; (c) amplifying the tag-nucleic acid conjugates; (d) sequencing a sample of the tag-nucleic acid conjugates to provide sequence reads each having an error rate and each comprising a lag sequence and a cancer gene sequence or recombined nucleic acid sequence; (e) comparing tag sequences to separately determined tag sequences from other tissue samples; and (f) determining the presence, absence and/or level of contamination by the identity of one or more tag sequences with any separately determined tag sequences from other tissue samples. Once tag sequences are determined in an assay, they may be compared to tag sequences in a database of tag sequences recorded from assays on other patients. Such steps of comparing may be implemented at the time of an assay, or such steps may be implements retrospectively, for example, at a time after the time of the assay. In one embodiment, sequence tags are attached to recombined nucleic acids in a tissue sample, such, as blood or bone marrow, from an individual suffering from a lymphoid proliferative disorder, such as a lymphoid cancer. In another embodiment, sequence tags are attached to cancer gene molecules, such as described above.

In further embodiments in which recombined nucleic acids are monitored form cross-contamination of tissue samples, the steps of attaching, and amplifying may be implemented as follows: (a) combining in a reaction mixture under primer extension conditions a first set of primers with a sample of recombined nucleic acids form T-cells and/or cell-free DNA, wherein each primer of the first set has a receptor-specific portion such that the receptor-specific portion anneals to a different recombined nucleic acid at a predetermined location and is extended to form a first extension product, and wherein each primer of the first set has a 5'-non-complementary end containing a first primer binding site; (b) removing from the reaction mixture non-extended primers of the first set; (c) adding to the reaction mixture under primer extension conditions a second set of primers, wherein each primer of the second set has a receptor-specific portion such that the receptor-specific portion anneals to the first extension product at a predetermined location and has a 5'-non-complementary end containing a second primer binding site, primers of the first set and/or primers of the second set comprising a sequence tag disposed between the receptor-specific portion and the that or second primer binding site, respectively, and wherein each primer of the second set is extended to form a second extension product, such that each second extension product comprises a that primer binding site, a second primer binding site, at least one sequence tag, and recombined nucleic acid encoding a portion of immune receptor chain; and (d) performing a polymerase chain reaction in the reaction mixture to form an amplicon, the polymerase chain reaction using forward primers specific for the first primer binding site and reverse primers specific for the second primer binding site.

Kits

The invention includes a variety of kits for carrying out methods of the invention. In some embodiments, kits comprise (a) a set of forward primers and a set of reverse primers for amplifying in a multiplex PCR recombined nucleic acids encoding a plurality of immune receptor chains wherein forward primers and/or reverse primers each have a target specific portion, a sequence tag and a common primer binding site, and (b) a primer removal element for removing after at least a first extension unincorporated primers non-extended primers) of the sets some embodiments, kits further comprise common primers specific for the common primer binding sites. In some embodiments, kits thriller comprise written instructions for using in components in a method of the invention. In some embodiments, kits further comprise forward and reverse primers specific for amplifying recombined nucleic acids encoding IgH(VDJ), IgH(DJ) and IgK. In some embodiments, kits further comprise forward and reverse primers specific for amplifying recombined nucleic acids encoding TCRβ, TCRδ and TCRγ. In some embodiments, kits further comprise internal standards comprising a plurality of nucleic acids having lengths and compositions representative of the target recombined nucleic acids, wherein the internal standards are provided in known concentrations. In some embodiments, kits include a single-stranded exonuclease as a primer removal element, such as $E.\ coli$ exonuclease I. In some embodiments, kits include a spin column capable of size selecting double stranded DNA as a primer removal element, While the present invention has been described with reference to several particular example embodiments, those skilled in the art will recognize that many changes may be made thereto without departing from the spirit and scope of the present invention. The present invention is applicable to a variety of sensor implementations and other subject matter, in addition to those discussed above.

Definitions

Unless otherwise specifically defined herein, terms and symbols of nucleic acid chemistry, biochemistry, genetics, and molecular biology used herein follow those of standard treatises and texts in the field, e.g. Kohlberg and Baker, DNA Replication: Second Edition (W.H., Freeman, N.Y., 1992); Lehninger, Biochemistry, Second Edition (Worth Publishers, New York, 1975); Strachan and Read: Human Molecular Genetics, Second Edition (Wiley-Liss, N.Y., 1999); Abbas et al, Cellular and Molecular Immunology, $6^{th}$ edition (Saunders, 2007).

"Aligning" means a method of comparing a test sequence, such as a sequence read, to one or more reference sequences to determine which reference sequence or which portion of a reference sequence is closest based on some sequence distance measure. An exemplary method of aligning nucleotide sequences is the Smith Waterman algorithm. Distance measures may include Hamming distance, Levenshtein distance, or the like. Distance measures may include a component related to the quality values of nucleotides of the sequences being compared.

"Amplicon" means the product of a polynucleotide amplification reaction; that is, a clonal population of polynucleotides. Which may be single stranded or double stranded, which polynucleotides are replicated from one or more starting sequences. The one or more starting Sequences may be one or more copies of the same sequence, or they may be a mixture of different sequences. Amplicons may be produced by a variety of amplification reactions whose products comprise replicates of the one or more starting, or target, nucleic acids. In one aspect, amplification reactions producing amplicons are "template-driven" in that base pairing of reactant, either nucleotides or oligonucleotides, have complements in a template polynucleotide that are required, for the creation of reaction products. In one aspect, template-driven reactions are primer extensions with a nucleic acid polymerase or oligonucleotide ligations with a nucleic acid ligase. Such reactions include, but are not limited to, polymerases chain reactions (PCRs), linear polymerases reactions, nucleic acid sequence-based amplification (NASBAs), rolling circle amplifications, and the like, disclosed in the following references that are incorporated herein by reference: Mullis et al, U.S. Pat. No. 4,683,195: 4,965,188, 4,683,202; 4,800,159 (PCR); Gelfand et al, U.S. Pat. No. 5,210,015 treat-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactant for performing a reaction, which may include, but not be limited to, buffering agents to maintain pH at a selected level during a reaction, salts, co-factors, scavengers, and the like.

"Clonality" as used herein meads a measure of the degree to which the distribution of clonotype abundances among clonotypes of a repertoire is skewed to a single or a few clonotypes. Roughly, clonality is an inverse measure of a clonotype diversity. Many measures or statistics are available from ecology describing species-abundance relationships that may be used for clonality measures in accordance with the invention e.g. Chapters 17 &, 18, in Pielou, An Introduction to Mathematical Ecology, (Wiley-Interscience, 1969). In one aspect, a clonality measure used with the invention is a function of a clonotype profile (that is, the number or distinct clonotypes detected and their abundances), so that after a clonotype profile is measured, clonality may be computed from it to give a single number. One clonality measure is Simpson's measure, which is simply the probability that two randomly drawn clonotypes will be the same. Other clonality measures include information-based measures and Mcintosh's diversity index, disclosed in Pielou (cited above).

"Clonotype" means a recombed nucleic acid of a lymphocyte which encodes an immune receptor or a portion thereof. More particularly, clonotype means a recombined nucleic acid, usually extracted from a T cell or B cell, but which may also be from a cell-free source, which encodes a T cell receptor (TCR) or B cell receptor (BCR), or a portion thereof. In various embodiments, clonotypes may encode all or a portion of a VDJ rearrangement of IgH, a DJ rearrangement of IgH, a VJ rearrangement of IgK, a VJ rearrangement of IgL, a VDJ rearrangement of TCR β, a DJ rearrangement of TCR β, a VJ rearrangement of TCR α, a VJ rearrangement of TCRγ, a VDJ rearrangement of TCR δ, a VD rearrangement of TCR δ, a Kde-V rearrangement, or the like. Clonotypes may also encode translocation breakpoint regions involving immune receptor genes, such as Bc11-IgH Bc11-IgH. In one aspect, clonotypes have sequences that are sufficiently long to represent or reflect the diversity of the immune molecules that they are derived from consequently, clonotypes may vary widely in length. In some embodiments, clonotypes have lengths in the range of from 25 to 400 nucleotides; in other embodiments, clonotypes have lengths in the range of from 25 to 200 nucleotides, "Clonotype profile" means a listing of distinct clonotypes and their relative abundances that are derived from a population of lymphocytes, where, for example, relative abundance may be expressed as a frequency in a given population (that is, a number between 0 and 1). Typically, the population of lymphocytes are obtained from a tissue sample. The term "clonotype profile" is related to, but more general than the immunology concept of immune "repertoire" as described in references, such as the following: Arstila et al, Science, 280: 958-961 (1999); Yassai et al, Immunogenetics, 61: 493-502 (2009); Kedzierska et al, Mol. Immunol., 45(3): 607-618 (2008); and the like. The term "clonotype profile" includes a wide variety of lists and abundances of rearranged immune receptor-encoding nucleic acids, which may be derived from selected subsets of lymphocytes (e.g. tissue-infiltrating lymphocytes, immunophenotypic subsets, or the like), or which may encode portions of immune receptors that have reduced diversity as compared to full immune receptors. In some embodiments, clonotype profiles may comprise at least $10^3$ distinct clonotypes; in other embodiments, clonotype profiles may comprise at least $10^8$ distinct clonotypes; other embodiments, clonotype profiles may comprise at least $10^5$ distinct clonotypes; in other embodiments, clonotype profiles may comprise at least $10^6$ distinct clonotypes. Such embodiments, such clonotype profiles may further comprise abundances or relative frequencies of each of the distinct clonotypes. In one aspect, a clonotype profile is a set of distinct recombined nucleotide sequences (with their abundances) that encode T receptors (TCRs) or B cell receptors (BCRs), or fragments thereof, respectively, in a population of lymphocytes of an individual, wherein the nucleotide sequences of the set have a one-to-one correspondence with distinct lymphocytes or their clonal sub populations for substantially all of the lymphocytes of the population. In one aspect, nucleic acid segments defining clonotypes are selected so that their diversity (i.e. the number or distinct nucleic acid sequences in the set) is large enough so that substantially ever T cell or B cell or clone thereof in an individual carries a unique nucleic acid sequence of such repertoire. That is, preferably each different clone of a sample has different clonotype. In other aspects of the invention, the population of lymphocytes corresponding to a repertoire may be circulating B cells, or may be circulating T cells, or may be sub populations of either of the foregoing populations, including but not limited to, CD4+ T cells, or CD8+ T cells, or other sub populations defined by cell surface, markers, or the like. Such sub populations may be acquired by taking samples from particular tissues, e.g. bone marrow, or lymph nodes, or the like, or by sorting or enriching cells from a sample (such as peripheral blood) based on one or more cell surface markers, size, morphology, or the like. In still other aspects, the population of lymphocytes corresponding to a repertoire may be derived from disease tissues, such as a tumor tissue, an infected tissue, or the like. In one embodiment, a clonotype profile comprising human TCR β chains or fragments thereof comprises a number of distinct nucleotide sequences in die range of from $0.1 \times 10^6$ to $1.8 \times 10^6$, or in the range of from $0.5 \times 10^4$ to $1.5 \times 10^6$, or in the range of from $0.8 \times 10^6$ to $1.2 \times 10^6$. In another embodiment, a clonotype profile comprising human IgH chains or fragments thereof comprises a number of distinct nucleotide sequences in the range of from $0.1 \times 10^6$ to $1.8 \times 10^6$, or in the range of from $0.5 \times 10^6$ to $1.5 \times 10^6$, or in the range of from $0.8 \times 10^6$ to $1.2 \times 10^6$. In a particular embodiment, a clonotype profile of the invention comprises a set of nucleotide sequences encoding substantially all segments of the V(D)J region of an chain. In one aspect, "substantially all" as used herein means every segment having a relative abundance of 0.001 percent or higher; or in another aspect, "substantially all" as used herein means every segment having a relative abundance of 0.0001 percent or higher. In another particular embodiment, a clonotype profile of the invention comprises a set of nucleotide sequences that encodes substantially all segments of the V(D)J region of a TCR β chain. In another embodiment, a clonotype profile of the invention comprises a set of nucleotide sequences having lengths in the range of from 25-200 nucleotides and including segments oldie V, D, and J regions of a TCR β chain. In another embodiment, a clonotype profile of the invention comprises a set of nucleotide sequences having lengths in the range of from 25-200 nucleotides and including segments of the V, D, and J regions of an IgH chain. In another embodiment, a clonotype profile of the invention comprises a number of distinct nucleotide sequences that is substantially equivalent to the number of lymphocytes expressing a distinct IgH chain. In another embodiment, a clonotype profile of the invention comprises a number of distinct nucleotide sequences that is substantially equivalent to the number of lymphocytes expressing a distinct TCR β chain. In still another embodiment, "substantially equivalent" means that with ninety-nine percent probability a clonotype profile will include a nucleotide sequence encoding an IgH or TCR β or portion thereof carried or expressed by every lymphocyte of a population of an individual at a frequency of 0.001 percent or greater. In still another embodiment, "substantially equivalent" means that with ninety-nine percent probability a repertoire of nucleotide sequences will include a nucleotide sequence encoding an IgH or TCR β or portion thereof carried or expressed by every lymphocyte present at a frequency of 0.0001 percent or greater. In some embodiments, clonotype profiles are derived from samples comprising from $10^5$ to $10^7$ lymphocytes. Such numbers of lymphocytes may be obtained from peripheral blood samples of from 1-10 mL.

"Complementarily determining regions" (CDRs) mean regions of an immunoglobulin (i.e., antibody) or T cell receptor where the molecule complements an antigen's conformation, thereby determining the molecule's specificity and contact with a specific antigen. T cell receptors and immunoglobulins each have three CDRs: CDR1 and CDR2 are found in the variable (V) domain, and CDR3 includes some of V, all of diverse (D) (heavy chains only) and joint (J), and some of the constant (C) domains.

"Clonotype Database" means a collection of clonotypes formatted and arranged for ease and speed of searching, comparing and retrieving. In some embodiments, a clonotype database comprises a collection of clonotypes encoding the same region or segment of an immune receptor. In some embodiments, a clonotype database comprises clonotypes of clonotype profiles hum a plurality of individuals. In some embodiments, a clonotype database comprises clonotypes of clonotype profiles of at least $10^4$ clonotypes from at least 10 individuals. In some embodiments, a clonotype database comprises at least $10^6$ in clonotypes, or at least $10^6$ clonotypes, or at least $10^9$ clonotypes, or at least $10^{10}$ clonotypes. A clonotype database may be a public database containing clonotypes, such as IMGT database (www.imgt.org), e.g. described in Nucleic Acids Research, 31: 307-310 (2003). Clonotype databases may be in a FASTA format, and clonotype database entries may be searched or compared using a BLAST algorithm, e.g., Altschul et al, J. Mol Biol., 215(3): 403-410 (1990), or like algorithm.

"Coalescing" means treating two candidate clonotypes with sequence differences as the same by determining that such differences are due to experimental or measurement error and not due to genuine biological differences. In one aspect, as sequence of a higher frequency candidate clonotype is compared to that of a lower frequency candidate clonotype and if predetermined criteria are satisfied then the number of lower frequency candidate clonotypes is added to that of the higher frequency candidate clonotype and the lower frequency candidate clonotype is thereafter disregarded. That is, the read counts associated with the lower frequency candidate clonotype are added to those of the higher frequency candidate clonotype and the higher frequency candidate clonotype and the lower frequency candidate clonotype are treated as the same that is, the observed difference between them is determined to be due to error (e.g. Sequencing error, amplification error, or the like). In some embodiments, the predetermined criteria is a likelihood function that depends on factors such relative frequencies of the candidate clonotypes being compared, the number of positions at which the candidates differ, the quality scores of the positions, and the like.

"Complementarily determining regions" (CDRs) mean regions of an immunoglobulin (i.e., antibody) or T cell receptor where the molecule complements an antigen's conformation, thereby determining the molecule's specificity and contact with a specific antigen. T cell receptors and immunoglobulins each have three CDRs: CDR1 and CDR2 are found in the variable (V) domain, and CDR3 includes some of V all of diverse (D) (heavy chains only) and joint (J), and some of the constant (C) domains.

"Contamination" as used herein means the presence in a tissue sample of one individual of nucleic acid from another individual. In one aspect, "contamination" means the presence of nucleic acid not originating from a patient which may affect the interpretation of a clonotype profile of the patient.

"Genetic identification" means a unique correspondence between an individual and a set of values (or states) of genetic markers from one or more genetic loci of the individual.

"Genetic, marker" mean a polymorphic segment of DNA at a genetic locus, which may be used to identify an individual. A genetic marker may be identified by its sequence or by adjacent or flanking sequences. Typically, a genetic marker can have a plurality of sequences, or values, in different individuals of a population. Exemplary genetic markers include, but are not limited to, short tandem repeats (STRs) single nucleotide polymorphisms (SNPs), and the like. The polymorphic segment of DNA may be genomic DNA or it may be reverse transcribed RNA. In one embodiment, the polymorphic segment is genomic DNA. In one embodiment, a genetic marker for use with the invention is identified by amplification and sequencing using conventional techniques. In another embodiment, genetic markers are amplified and sequenced together with immune molecules during the process for generating a clonotype profile.

"Internal standard" means a nucleic acid sequence that is processed in the same reaction as one or more target polynucleotides in order to permit absolute or relative quantification of the target polynucleotides in a sample. In one aspect the reaction is an amplification reaction, such as PCR. An internal standard may be endogenous or exogenous. That is, an internal standard may occur naturally in the sample, or it may be added to the sample prior to a reaction. In one aspect, one or more exogenous internal standard sequences may be added to a reaction mixture in predetermined concentrations to provide a calibration to which an amplified sequence may be compared to determine the quantity of its corresponding target polynucleotide in a sample. Selection of the number, sequences, lengths, and other characteristics of exogenous internal standards is a routine design choice for one of ordinary skill in the art. Endogenous internal standards, also referred to herein as "reference sequences," are sequences natural to a sample that correspond to minimally regulated genes that exhibit a constant and cell cycle-independent level of transcription, e.g. Selvey et at, Mol. Cell Probes, 15: 307-311 (2001). Exemplary internal standards include, but are not limited to, sequences from the following genes: GAPDH, $\beta_2$-microglobulin, 18S ribosomal RNA, and $\beta$-actin.

"Kit" refers to any delivery system for delivering materials or reagents for carrying out a method of the invention. In the context of methods of the invention, such delivery systems include systems that allow for the storage, transport, or delivery of reaction reagents (e.g., primers, enzymes, internal standards, etc. In the appropriate containers) and/or supporting materials (e.g., buffers, written instructions for performing the assay etc.) from one location to another. For example, kits include one or more enclosures boxes) containing the relevant reaction reagents and/or supporting materials. Such contents may be delivered to the intended recipient together or separately. For example, a first container may contain an enzyme for use in an assay, while a second container contains primers.

"Minimal residual disease" means remaining cancer cells after treatment. The term is frequently used in connection with treatment of lymphomas and leukemias.

"Lymphoid or myeloid proliferative disorder" means any abnormal proliferative disorder in which one or more nucleotide sequences encoding one or more rearranged immune receptors can be used as a marker for monitoring such disorder. "Lymphoid or myeloid neoplasm" means an abnormal proliferation of lymphocytes or myeloid cells that may be malignant or non-malignant. A lymphoid cancer is a malignant lymphoid neoplasm. A myeloid cancer is a malignant myeloid neoplasm. Lymphoid and myeloid neoplasms are the result of or are associated with, lymphoproliferative or myeloproliferative disorders, and include, but are not limited to, follicular lymphoma, chrome lymphocyte leukemia (CLL), acute lymphocyte leukemia (ALL), chronic myelogenous leukemia (CML), acute myelogenous leukemia (AML), Hodgkins's and non-Hodgkin's lymphomas, multiple myeloma (MM), monoclonal gammopathy of undetermined significance (MGUS), mantle cell lymphoma (MCL), diffuse large B cell lymphoma (DLBCL), myelodysplastic syndromes (MDS). T cell lymphoma, or the like, e.g. Jaffe et al, Blood, 112: 4384-4399 (2008); Swerdlow et al, WHO Classification of Tumours of Haematopoietic and Lymphoid Tissues (e. $4^{th}$) (IARC Press, 2008). As used herein, "B cell cancer" means a lymphoid or myeloid neoplasm involving B cells or cells developed therefrom, such as plasma cells. Likewise, "T cell cancer" means a lymphoid or myeloid neoplasm involving T cells or cells developed therefrom.

"Percent homologous," "percent identical," or like terms used in reference to the comparison of a reference sequence and another sequence ("comparison sequence") mean that in an optimal alignment between the two sequences, the comparison sequence is identical to the reference sequence in a number of subunit positions equivalent to the indicated percentage, the subunits being nucleotides for polynucleotide comparisons or amino acids for polypeptide comparisons. As used herein, an "optimal alignment" of sequences being compared is one that maximizes matches between subunits and minimizes the number of gaps employed in constructing an alignment. Percent identities may be determined with commercially available implementations of algorithms, such as that described by Needleman and Wunsch, J. Mol. Biol., 48: 443-453 (1970)("GAP" program of Wisconsin Sequence Analysis Package, Genetics Computer Group, Madison, Wis.), or the like. Other software packages in the art for constructing alignments and calculating percentage identity or other measures of similarity include the "BestFit" program, based on the algorithm of Smith and Waterman, Advances in Applied Mathematics, 2: 482-489 (1981) (Wisconsin Sequence Analysis Package, Genetics Computer Group, Madison, Wis.). In other words, for example, to obtain a polynucleotide having a nucleotide sequence at least 95 percent identical to a reference nucleotide sequence, up to five percent of the nucleotides in the reference sequence may be deleted or substituted with another nucleotide. or a number of nucleotides up to live percent of the total number of nucleotides in the reference sequence may be inserted into the reference sequence.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions or the following steps: (i) denaturing the target nucleic acid, (ii) annealing primers to the primer binding sites, and (iii) extending the primers by a nucleic acid polymerase in the presence or nucleoside triphosphates. As used herein, the terms "forward primer" and "upstream primer" are used interchangeably, and the terms "reverse primer" and "downstream primer" are used interchangeably. Also as used herein, if a double stranded target polynucleotide is displayed with its sense strand in a 5'→3' left-to-right orientation, a forward primer would bind to the antisense strand on the left and be extended to the right and a reverse primer would bind to the sense strand on the right and be extended to the left. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "TCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred μL, e.g., 200 μL. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517

(molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273:221-228 (1999)(two-color real-time PCR). Usually, distinct sets of primers are employed for each sequence being amplified. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences or internal standards that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobutin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, $2^{nd}$ Edition (Cold Spring Harbor Press, New York, 2003).

"Quality score" means a measure of the probability that a base assignment at a particular sequence location is correct, A variety methods are well known to those of ordinary skill for calculating quality scores for particular circumstances, such as, the bases called as a result of different sequencing chemistries, detection systems, base-carling algorithms, and so on. Generally, quality score values are monotonically related to probabilities of correct base calling. For example, a quality score, or Q, of 10 may mean that there is a 90 percent chance that a base is called correctly, a Q of 20 may mean that there is a 99 percent chance that a base is called correctly, and so on. For some sequencing platforms, particularly those using sequencing-by-synthesis chemistries, average quality scores decrease as a function of sequence read length, so that quality scores at the beginning of a sequence read are higher than those at the end of a sequence read, such declines being due to phenomena such as incomplete extensions, carry forward extensions, loss of template, loss of polymerase, capping failures, deprotection failures, and the like.

"Sequence read" means a sequence or nucleotides determined from a sequence or stream of data generated by a sequencing technique, which determination is made, for example, by means of base-calling software associated with the technique, e.g. base-calling software from a commercial provider of a DNA sequencing platform. A sequence read usually includes quality scores for each nucleotide in the sequence. Typically, sequence reads are made by extending a primer along a template nucleic acid, e.g. with a DNA polymerase or a DNA ligase. Data is generated by recording signals, such as optical, chemical (e.g. pH change), or electrical signals, associated with such extension. Such initial data is converted into a sequence read.

"Sequence tag" (or "tag") "barcode" means oligonucleotide that is attached to a polynucleotide or template molecule and is used to identify and/or track the polynucleotide or template in a reaction or a series of reactions. Each sequence tag has a nucleotide sequence which is sometimes referred to herein as a "tag sequence." A sequence tag may be attached to the 3'-5'-end of a polynucleotide or template or it may be inserted into the interior of such polynucleotide or template to form a linear or circular conjugate, sometime referred to herein as a "tagged polynucleotide," or "tagged template," or "tag-polynucleotide conjugate," "tag-molecule conjugate," or the like. Sequence tags may vary widely in size and compositions: the following references, which are incorporated herein by reference, provide guidance for selecting sets of sequence tags appropriate for particular embodiments: Brenner, U.S. Pat. No. 5,635,400; Brenner and Macevicz, U.S. Pat. No. 7,537,897; Brenner et al, Proc. Natl. Acad. Sci., 97: 1605-1670 (2000); Church et al, European patent publication 0 303 459; Shoemaker et al, Nature Genetics, 14: 450-456(1996); Morris et al, European patent publication 0799897A1; Wallace, U.S. Pat. No. 5,981,179; and the like. Selection of particular tag lengths and/or compositions my depend on several factors including, without limitation, the sequencing technology used to decode a tag, the number of distinguishable tags required to unambiguously identify a set of target polynucleotides, how different must rags of a set be in order to ensure reliable identification, e.g. freedom from cross hybridization or misidentification from sequencing errors, and the like. In some embodiments, sequence tags can each have a length within a range of from 6 to 100 nucleotides, or from 10 to 100 nucleotides, or from 12 to 50 nucleotides, or from 12 to 25 nucleotides, respectively. In some embodiments, sets of sequence tags are used wherein each sequence tag of a set has a unique nucleotide sequence that differs from that of every other tag of the same set by at least four bases; in other embodiments, sets of sequence tags are used wherein the sequence of each tag of a set differs from that of every other tag of the same set by at least five bases; in still other embodiments, sets or sequence tags are used where the sequence of each tag of a set differs from that of every other tag of the same set by at least ten percent of their nucleotides; or in other embodiments, at least twenty-five percent of their nucleotides; or in other embodiments, at least fifty percent of their nucleotides.

What is claimed is:

1. A method of detecting minimal residual disease in a patient being treated for cancer, the method comprising the steps of:
   (a) attaching sequence tags to each of a plurality of recombined nucleic acids in a sample containing T-cells and/or B-cells and/or cell free DNA or RNA obtained from the patient to form tag-nucleic acid conjugates, wherein at least one recombined nucleic acid or copies thereof have different sequence tags attached and are characteristic of the cancer of the patient, and wherein the attaching comprises:
      (i) combining in a reaction mixture under primer extension conditions a first set of primers with the sample, wherein each primer of the first set comprises a receptor-specific portion, a 5'-non-complementary end containing a first primer binding site and a sequence tag disposed between the receptor-specific portion and the first primer binding site, wherein the receptor-specific portion anneals to a different recombined nucleic acid at a first predetermined location and is extended to form a first extension product; and
      (ii) adding to the reaction mixture under primer extension conditions a second set of primers, wherein each primer of the second set has a receptor-specific portion, wherein the receptor-specific portion anneals to the first extension product at a second predetermined location, and wherein each primer of the second set is extended to form a second extension product, wherein each second extension product comprises a first primer binding site, sequence tag, and recombined nucleic acid encoding a portion of a T cell receptor chain or a B cell receptor chain;
   (b) amplifying the tag-nucleic acid conjugates;
   (c) sequencing a sample of the tag-nucleic acid conjugates to provide sequence reads each comprising a tag sequence and a recombined nucleic acid sequence;
   (d) aligning sequence reads having like tag sequences to form groups of sequence reads having identical sequence tags;
   (e) coalescing recombined nucleic acid sequences of groups to determine clonotypes, wherein groups of sequence reads are coalesced into different clonotypes whenever said groups of recombined nucleic acid sequences are distinct with a likelihood of at least 99.9 percent; and
   (f) detecting in a clonotype profile the presence, absence and/or level of clonotypes correlated with the cancer of the patient, thereby detecting the minimal residual disease in a patient.

2. The method of claim 1, wherein the amplifying comprises performing a polymerase chain reaction in the reaction mixture to form an amplicon, the polymerase chain reaction using forward primers specific for the first primer binding site and reverse primers specific for the second set of primers.

3. The method of claim 1, wherein the recombined nucleic acids comprise recombined nucleic acids encoding TCRβ, TCRδ and TCRγ chains, and wherein the primers of the first set and the primers of the second set comprise primers that flank regions of the recombined nucleic acids encoding VDJ regions of TCRβ and TCR and primers that flank VJ regions of TCRγ.

4. The method of claim 1, wherein the recombined nucleic acids comprise recombined nucleic acids encoding IgH and IgK and wherein the primers of the first set and the primers of the second set comprise primers that flank regions of the recombined nucleic acids encoding VDJ regions of IgH, DJ regions of IgH and VJ regions of IgK.

5. The method of claim 4, wherein the primers of the first set or the second set include at least one nested set of primers specific for a plurality of different primer binding sites in V regions of said IgH chains.

6. The method of claim 1, further comprising a step of removing from the reaction mixture non-extended primers of the first set and the second set.

7. The method of claim 6, wherein the step of removing comprises adding an enzyme with exonuclease activity to the reaction mixture.

8. The method of claim 1, wherein the annealing and extension of the primers of the first set is repeated after melting the first extension product.

9. The method of claim 1, wherein the annealing and extension of the primers of the second set is repeated after melting the second extension product.

10. The method of claim 1, wherein the sequence tags are mosaic tags, wherein the mosaic tags comprise alternating constant regions and variable regions.

11. The method of claim 1, wherein the first predetermined location is a V region.

12. The method of claim 11, wherein the receptor specific portion of each of the primers of the first set anneals to different non-overlapping positions in the V region.

13. The method of claim 1, wherein the second predetermined location is a J region or a C region.

14. The method of claim 13, wherein the receptor specific portion of each of the primers of the second set anneals to different non-overlapping positions in the J region.

15. The method of claim 13, wherein the receptor specific portion of each of the primers of the second set anneals to a single primer binding site in the J region.

16. The method of claim 2, wherein the forward primers and/or the reverse primers comprise a 5' non-complementary end comprising a sample tag.

* * * * *

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1
agttctggct aacctgtaga gcca                                          24

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
agttcgggct aacctgtcga gcca                                          24

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
agttccggct aacctgtcga gcca                                          24

<210> SEQ ID NO 4
<211> LENGTH: 22
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(22)
<223> OTHER INFORMATION: n is a, c, g, or t

<400> SEQUENCE: 4
nnnnnnnnnn nnnnnnnnnn nn                                            22

<210> SEQ ID NO 5
<211> LENGTH: 12
<212> TYPE: DNA
<213> ORGANISM: Artificial Sequence
<220> FEATURE:
<223> OTHER INFORMATION: primer

<400> SEQUENCE: 5
gtattttttt ct                                                       12

<210> SEQ ID NO 6
<211> LENGTH: 13
<212> TYPE: DNA
<213> ORGANISM: Artificial Sequence
<220> FEATURE:
<223> OTHER INFORMATION: primer

<400> SEQUENCE: 6
ttcagggggg gct                                                      13
```